US006983227B1

(12) United States Patent
Thalhammer-Reyero

(10) Patent No.: US 6,983,227 B1
(45) Date of Patent: Jan. 3, 2006

(54) VIRTUAL MODELS OF COMPLEX SYSTEMS

(75) Inventor: Cristina Thalhammer-Reyero, North Bethesda, MD (US)

(73) Assignee: Intertech Ventures, Ltd., North Bethesda, MD (US)

( * ) Notice: Subject to any disclaimer, the term of this patent is extended or adjusted under 35 U.S.C. 154(b) by 0 days.

(21) Appl. No.: 08/860,975

(22) PCT Filed: Jan. 17, 1996

(86) PCT No.: PCT/US96/00883

§ 371 (c)(1),
(2), (4) Date: Dec. 22, 1997

(87) PCT Pub. No.: WO96/22575

PCT Pub. Date: Jul. 25, 1996

Related U.S. Application Data

(63) Continuation-in-part of application No. 08/373,688, filed on Jan. 17, 1995, now abandoned, and a continuation-in-part of application No. 08/373,992, filed on Jan. 17, 1995, now Pat. No. 5,980,096.

(51) Int. Cl.
*G06G 7/48* (2006.01)
*G06F 9/455* (2006.01)

(52) U.S. Cl. .............................. 703/2; 703/11; 345/419; 715/700

(58) Field of Classification Search .................... 703/2, 703/11, 12; 715/700; 345/419, 335, 346, 345/349; 395/500.33, 500.32, 500.35; 706/11, 706/53, 4, 6, 10; 707/103, 10
See application file for complete search history.

(56) References Cited

U.S. PATENT DOCUMENTS

| 5,319,740 A | 6/1994 | Yamada et al. ............... 706/59 |
| 5,379,366 A | 1/1995 | Noyes ......................... 395/54 |
| 5,412,756 A * | 5/1995 | Bauman et al. ............... 395/50 |

(Continued)

FOREIGN PATENT DOCUMENTS

| EP | 0 367 544 | 5/1990 |
| EP | 0 367 544 | 9/1990 |
| WO | WO 91/06050 | 5/1991 |

OTHER PUBLICATIONS

Ackers, G.K. er al. (1997) Quantitative model for gene regulation by phage repressor. *Proc. Natl. Acad. Sci. USA*, 79, 1129–1133.

(Continued)

*Primary Examiner*—Thai Phan

(57) ABSTRACT

A computer based virtual models of complex systems, together with integrated systems and methods provide a development and execution framework for visual modeling and dynamic simulation of said models. The virtual models can be used for analysis, monitoring, or control of the operation of the complex systems modeled, as well as for information retrieval. More particularly, the virtual models in the present implementation relate to biological complex systems. In the current implementation the virtual models comprise building blocks representing physical, chemical, or biological processes, the pools of entities that participate in those processes, a hierarchy of compartments representing time-intervals or the spatial and/or functional structure of the complex system in which said entities are located and said processes take place, and the description of the composition of those entities. The building blocks encapsulate in different layers the information, data, and mathematical models that characterize and define each virtual model, and a plurality of methods is associated with their components. The models are built by linking instances of the building blocks in a predefined way, which, when integrated by the methods provided in this invention, result in multidimensional networks of pathways. A number of functions and graphical interfaces can be selected for said instances of building blocks, to extract in various forms the information contained in said models. Those functions include: a) on-the-fly creation of displays of interactive multidimensional networks of pathways, according to user selections; b) dynamic quantitative simulations of selected networks; and c) complex predefined queries based on the relative position of pools of entities in the pathways, the role that the pools play in different processes, the location in selected compartments, and/or the structural components of the entities of those pools. The system integrates inferential control with quantitative and scaled simulation methods, and provides a variety of alternatives to deal with complex dynamic systems and with incomplete and constantly evolving information and data.

119 Claims, 41 Drawing Sheets

U.S. PATENT DOCUMENTS

| | | | |
|---|---|---|---|
| 5,443,791 A | 8/1995 | Cathcart et al. | 422/65 |
| 5,657,255 A | 8/1997 | Fink et al. | 364/578 |
| 5,680,590 A | 10/1997 | Parti | 703/2 |
| 5,732,192 A * | 3/1998 | Malin et al. | 395/10 |
| 5,757,678 A | 5/1998 | Leeke | 703/6 |
| 5,801,942 A * | 9/1998 | Nixon et al. | 364/188 |
| 5,808,918 A | 9/1998 | Fink et al. | 364/578 |
| 5,835,758 A * | 11/1998 | Nochur et al. | 395/613 |
| 5,845,270 A * | 12/1998 | Schatz et al. | 706/11 |
| 5,914,891 A | 6/1999 | McAdams et al. | 703/11 |
| 5,930,154 A * | 7/1999 | Thalhammer-Reyero | 364/578 |
| 5,980,096 A * | 11/1999 | Thalhammer-Reyero | 364/578 |
| 6,038,540 A * | 3/2000 | Krist et al. | 705/8 |
| 6,051,029 A | 4/2000 | Paterson et al. | 703/22 |
| 6,069,629 A | 5/2000 | Paterson et al. | 345/808 |
| 6,078,739 A | 6/2000 | Paterson et al. | 703/6 |

OTHER PUBLICATIONS

Deville Y. et al. (2003) "An Overview of Data Models for the Analysis of Biochemical Pathways", *Brief Bioinform.* 2003 Sep;4(3):246–59.

Fadel F.G. (1994) "A Resource Ontology for Enterprise Modelling" in 3$^{rd}$ Industrial Engineering Research Conference Proceedings, 455–.

Foster R.O. et al (1973) "Short Term Glucose Homeostatis in Man: A Systems Dynamic Model" *J. of Dynamical Systems, Management abd Control, in Transactions of the ASME*, 308–314.

Fox, M. et al. (1993), "A Common Sense Model of the Enterprise", *Proceedings of the 2nd Industrial Engineering Research Conference*, pp. 425–429, Norcross GA: Institute for Industrial Engineers.

Galper A.R. et al. (1993) "Knowledge–Based Simulation of DNA Metabolism: Prediction of Action and Envisionment of Pathways", *Chapter 10 in Artificial Intelligence and Molecular Biology*, Ed. Hunter L., AAAI Press, 365–395.

Goldbeter, A. (1991) A minimal cascade model for the mitotic oscillator involving cyclin and cdc2 kinase. *Proc. Natl. Acad. Sci. USA*, 88, 9107–9111.

Grass G.M. et al (1993) "A Model to Predict Aqueous Humor and Plasma Pharmacokinetics of Oculary Applied Drugs", *35 Investigative Ophtalmology & Visual Science*, 2251–2259.

Gruninger, M., Fox, M.S. (1994), "An Activity Ontology for Enterprise Modelling", *Submitted to: Workshop on Enabling Technologies–Infrastructures for Collaborative Enterprises*, West Virginia University.

Ironi L et al., (1994) "A Framework for Building and Simulating Qualitative Models of Compartmental Systems" *Computer Methods and Programs in Biomedicine*, 233–254.

Iyengar S.S. (1992) Ed. "Structuring Biological Systems–A Computer Modeling Approach", *Chapter 7*, 210–226.

Jensen K. et al. (1985) "Self–Sustained Oscillations and Chaotic Behaviour in Kidney Pressure Regulation" in *1. Prigogine and M. Sanglier, eds., Laws of Nature and Human Conduct. Brussels: Taskforce of Research Information and Study on Science*, 91–109.

Karp P.D. (1993) "A Quantitative Biochemistry and Its Application to the Regulation of the Tryptophan Operon", *Chapter 8 in Artificial Intelligence and Molecular Biology, Ed. Hunter L., AAAI Press*, 289–324.

Kim, H., Fox, M.S., (1994), "Formal Models of Quality and ISO 9000 Compliance: An Information Systems Approach", *American Quality Congress (AQC) Conference, American Society for Quality Control*, Las Vegas NV.

Loomis W.F., Thomas S.R. (1976) "Kinetic Analysis of Biochemical Differentiation in Dictyostelium", *The Journal. of Biological Chemistry*, 251 (20) 6252–638.

Mavrovouniotis M.L. (1993) "Identification of Qualitatively Feasible Metabolic Pathways", *Chapter 9 in Artificial Intelligence and Molecular Biology, Ed. Hunter L., AAAI Press*, 325–364.

Mendes P. (1993) "GEPASI: a software package for modelling the dynamics, steady states and control of biochemical and other systems". *Comput Appl Biosci* 9(5):563–71.

Novak B., Tyson J.J. (1995). "Quantitative Analysis of a Molecular Model of Mitotic Control in Fission Yeast" *J. Theor. Biol.* 173:283–305.

Reed J.L., Palsson B. O. (2003) "Minireview –Thirteen Years of Building Constraint–Based In Silico Models of Escherichia coli" *J. Bacteriol.* 185(9): 2692–2699.

Riggs D.S. (1970) "*Control Theory and Physiological Feedback Mechanisms*", *The Williams and Wilkins Co. Eds.* 500–503.

Sauro H.M. (1993) "Scamp: a general–purpose simulator and metabolic control analysis program" *Comput Appl Biosci.Aug*; 9(4): 441–50.

Sturis J et al (1991) "Computer Model for Mechanisms Underlaying Utlradian Oscillations of Insulin and Glucose" *Am. J. Physiol.* 801–809.

\* cited by examiner

| a velocity-var , the velocity of a bioengine.E1.S2.I1 | |
|---|---|
| Options | do forward chain, do not backward chain |
| Names | none |
| Data type | float |
| Initial value | 0.0 |
| Last recorded value | no value |
| History keeping | keep history with maximum age of data points = 10 minutes |
| Validity interval | indefinite |
| Formula | none |
| Simulation details | no simulation formula yet, but has specific subtable |
| Initial value for simulation | default |
| Data server | G2 simulator |
| Default update interval | none |

<-1002
<-1003
<-1004
<-1005
<-1006
<-1007
<-1008
<-1009
<-1010
<-1015
<-1016
<-1017

1011

| simulation subtable for a velocity-var | |
|---|---|
| Names | none |
| Time increment for update | none |
| Simulation formula | |
| History keeping | keep history with maximum age of data points = 10 minutes |

<-1012
<-1013
<-1014

DISPLAY OF DYNAMICALLY CREATED INTERCONNECTED PATHWAYS

VIRTUAL MODELS OF COMPLEX SYSTEMS

PARENT CASES

Priority Claimed: This is a U.S. national stage filing under 35 CFR § 371 of International Application No. PCT/US96/00883, filed on Jan. 17, 1996, which was published in English under PCT Article 21(2) as WO 96/22575, and which claims the benefit as a continuation-in-part of the combined U.S. application Ser. Nos. 08/373,688 and 08/373,992, both filed Jan. 17, 1995. U.S. Ser. No. 08/373,688, now abandoned, was continued as Ser. No. 08/889,624, filed Jul. 8, 1997, and issued as patent U.S. Pat. No. 5,930,154 on Jul. 27, 1999. U.S. Ser. No. 08/373,992 issued as patent U.S. Pat. No. 5,980,096, on Nov. 9, 1999. Related patent EP 0821817, entitled "Control Systems Based on Simulated Virtual Models", was granted on Jun. 23, 1999. The preferred modeling, simulation, design and control systems, methods and interfaces of this invention are more fully disclosed in the specifications, drawings and appendixes of each of the above-referenced patent applications, which are incorporated herein by reference.

COMPACT DISC APPENDIX

The Tables 1–233 referenced in the specification are pseudo-code listings provided in the Compact Disc Appendix, which comprise one file with 213 pages.

TECHNICAL FIELD

The present invention in its broadest form relates to computer-based systems, methods and visual interfaces for providing an integrated development and deployment framework for visual modeling and dynamic simulation of Virtual Models of complex systems, which can be further integrated with monitoring and control devices to control the operation of the complex systems modeled and can be used for information retrieval. More in particular, the complex systems that are the focus of the exemplary embodiments of this invention are living organisms or subsystems or populations thereof, comprising any combination of biological and regulatory networks of genetic, biochemical and/or signal-transduction pathways, at the molecular, cellular, physiological or population levels.

COPYRIGHT NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND ART

Knowledge-Based and Model-Based System for Monitoring and Control

Process industries, including the pharmaceutical, biotechnology, chemical, food, environmental and others may save millions of dollars by using artificial intelligence for process optimization to control complex productions facilities. Using large-scale cultivation of microorganisms or mammalian cells are extreme cases in terms of complexity, when considering then as the individual manufacturing plants involved in complex chemical synthesis. Current systems monitor very general types of phenomena, such as gas pressure, pH, and in some occasions, the concentration of some product that correlates with cell growth or production, but those parameters are usually poor indicators of how much of the desired product is produced. Other methods for designing monitoring and control systems for laboratory and industrial applications have been described, such as the one described in the patent application published as EP 0 367 544 A2 (Int. Dev. Res. Center) 9 May 1990, which uses a graphical interface to graphically model the set of instruments and controllers of such monitoring and control systems and a natural language to allow the integration of the knowledge of experts into the automated control facilities. Most monitoring systems are concerned with the overall processes that occur within the physical constraints of given reactions tanks, but do not model the many compartmentalized subsystems contained in each of those tanks with biological systems, to more finely tune the productivity of those subsystems. Complex mixtures of chemical reactions can be finely controlled externally by modifying the types and amounts of inputs added, if one could predict what will happen by adding those inputs, which requires a good knowledge and a model of such system of reactions. This is particularly the case with biological cellular systems that have very sophisticated methods to transduce the signals provided by ligands in their external environment to the interior of the cell, resulting in the execution of specific functions. Such detailed and accessible mechanistic models of those pathways of reactions are not currently used for monitoring and control systems, but would be highly desirable.

Several knowledge-based systems for monitoring and control functions have been used to include the knowledge of experts into the automated control of production facilities. A knowledge-based system interprets data using diverse forms of knowledge added to the system by a human domain expert including: a) shallow knowledge or heuristics, such as human experience and interpretations or rules-of thumb; and b) deep knowledge about the system behavior and interactions. The systems that mainly based in the first type of knowledge are in general referred to as knowledge-based expert systems, and the logic is represented in the form of production rules. In the more advanced real-time expert systems, inferencing techniques are usually data-driven using forward chaining, but can also employ backward chaining for goal-driven tasks and for gathering data. The inference engine searches for and executes relevant rules, which are separate from the inference engine and therefore, the representation is intrinsically declarative.

Object-oriented expert systems allow a powerful knowledge representation of physical entities and conceptual entities. In those systems, data and behavior may be unified in the class hierarchy. Each class has a template that defines each of the attributes characteristic of that class and distinguish it from another types of objects. Manipulation and retrieval of the values of the data structures may be performed through methods attached to an object's class. Model-based systems can be derived from empirical models based on regression of data or from first-principle relationships between the variables. When sufficient information to model a process—or part of it—is available, a more precise and compact system can be built.

There is a number of commercially available shells and toolkits that facilitate the development and deployment of domain-specific knowledge-based applications. Of those, real-time expert-system shells offer capabilities for reasoning on the behavior of data over time. Each of the real-time object-oriented shells from various vendors offers its set of advantages, and each follows a different approach, such as compiled versus interpreted, and offers a different level of graphic sophistication. The specific shell currently selected for the implementation of this invention is Gensym Corporation's G2 Version 3.0 system, and in part Version 4.0, which is designed for complex and large on-line applications where large number of variables can be monitored concurrently. It is able to reason about time, to execute both time-triggered and event-triggered actions and invocations, to combine heuristic and procedural reasoning, dynamic simulation, user interface, database interface capabilities, and other facilities that allow the knowledge engineer to concentrate on the representation and incorporation of domain-specific knowledge to create domain-specific applications. G2 provides a built-in inference engine, a simulator, prebuilt libraries of functions and actions, developer and user-interfaces, and the management of their seamless interrelations. A built-in inspect facility permits users to search for, locate, and edit various types of knowledge. Among G2's Inference Engine capabilities are: a) data structures are tagged with time-stamp and validity intervals that are considered in all inferences and calculations, taking care of truth maintenance; and b) intrinsic to G2's tasks are managed by the real-time scheduler. Task prioritization, asynchronous concurrent operations, and real-time task scheduling are therefore automatically provided by this shell. G2 also provides a graphic user interface builder, which may be used to create graphic user interfaces that are language independent and allow to display information using colors, pictures and animation. Dynamic meters, graphs, and charts can be defined for interactive follow-up of the simulation. It also has debugger, inspect and describe facilities. The knowledge-bases can be saved as separated modules as ASCII files. The graphic views can be shared with networked remote CPUs or terminals equipped with X Windows server software.

Computer-Aided Physiological and Molecular Modeling and Artificial Intelligence in Molecular Biology Most computer-aided physiological and molecular modeling approaches have resulted in computer models of physiological function that are numerical mathematical models that relate the physiological variables using empirically determined parameters. Those models, which can become quite complex, aim at modeling the overall system.

Both molecular biology and medicine have been fields of previous activity in the application of artificial intelligence (AI). In molecular biology, although there were some early systems such as Molgen and Dendral, the activity has intensified recently as a consequence of the explosion in new technologies and the derived data, mostly related with the Human Genome project and the handling of large amounts of sequence data generated, relating to both DNA and proteins. There has also been an increased interest in computer methodologies in 3D structural models of molecular interactions. For a current state of the art, see the topics covered in symposia such as the recent Second International Conference on Intelligent Systems for Molecular Biology, 1994, Stanford University, CA. (its Proceedings are here included by reference). Here, only two projects will be mentioned that have some common objectives with the system that is the object of this invention. Discussions over other previous approaches are also included in those references.

The Molgen group at Stanford University has studied scientific theory formation in the domain of molecular biology, as reported by Karp, P. D. and Friedland, P. (included here by reference). This project relates to the system of this invention in that both "are concerned with biochemical systems containing populations of interacting molecules . . . in which the form of knowledge available . . . varies widely in precision from quantitative to qualitative", as those authors write. The Ph.D. dissertation of P. D. Karp (included here by reference) "developed a qualitative biochemistry for representing theories of molecular biology", as he summarizes in an abstract in AI Magazine, Winter 1990, pp 9–10. He developed three representation models to deal with biochemical pathways, each having different capabilities and using different reasoning approaches. Model 1 uses IntelliCorp's KEEframes to describe biological objects and KEE rules to describe chemical reactions between the objects, which he recognizes to have serious limitations because is not able to represent much of the knowledge available to biologists. The objective of Model 2 is to predict reaction rates in a given reaction network, incorporating a combination of quantitative and qualitative reasoning about state-variables and their interdependencies. The drawbacks are that this model is not able to incorporate a description of the biological objects that participate in the reactions, and it does not have temporal reasoning capabilities, representing just a static description of the state variables and their relationships. The third model, called GENSIM and used for both prediction and hypothesis formation, is an extension of Model 1 and is composed of three knowledge-bases or taxonomical hierarchies of classes of a) biological objects that participate in a gene-regulation system, b) descriptions of the biological reactions that can occur between those objects, and c) experiments with instances of those classes of objects. The GENSIM program predicts experimental outcomes by determining which reactions occur between the objects in one experiment, that create new objects that cause new reactions. Characteristics of the GENSIM program that may be relevant, although different, for the system of this invention are: a) chemical objects are homogeneous populations of molecules, objects can be decomposed into their component parts, and identical objects synthesized during a simulation are merged; b) chemical processes represent reactions between those populations as probabilistic events with two subpopulations, one that participate in the reaction and one that does not. Those processes can create objects and manipulate their properties, but cannot reason about quantitative state variables such as quantities. In his words, "processes . . . specify actions that will be taken if certain conditions hold", and in that sense are like production-rules; c) restrictions are specified in the form of preconditions for chemical reactions to happen; and d) temporal reasoning is not available, resulting again in static representations and simulating only behavior in very short time intervals.

The system of this invention integrates a variety of forms of knowledge representation, some of them totally novel, while some of these forms may have been treated by other authors similarly in some aspects. However, upon integration into a totally new approach, that treatment becomes a part of a novel representation and innovative system. Regarding the semi-quantitative simulation component this invention, L. E. Widman (1991) describes a semi-quantitative simulation of dynamic systems in a different domain, with the assumption that " . . . questions can be answered in terms of relative quantities rather than absolute quantities . . . model parameters that are not specified explicitly are given the implicit, default values of 'normal' (unity) . . . ". As it will become clear from the detail descriptions in the following sections, the innovative tools and methods used in the present implementation a requite different. For example, while he assumes that " . . . the default, or implicit, value of 'normal' maps onto unity for parameters and onto zero for variables . . . . " the assumption in the prebuilt modular components in the current implementation differs in that the default value of 'normal' may map onto values other than unity and zero, with those values being defined based on expert knowledge.

DISCLOSURE OF INVENTION

This invention describes an integrated computer-based system, methods and visual interfaces for providing a development and deployment framework for visual modeling and dynamic simulation of Virtual Models of complex systems, which can be further integrated with monitoring and control devices to monitor and control the operation of the complex systems modeled, based on the real-time simulation of those Virtual Models. The system of this invention can be used by scientists to build the Virtual Models, which in turn are to be used by scientists or process engineers to design, monitor and control a variety of processing units. The Virtual Models can also be used for information retrieval, by using the set of visual interfaces provided to perform a variety of tasks. The available information and data about those complex models is stored into modular, modifiable, expandable and reusable knowledge structures, with several layers of encapsulation that allow to hide or display the details at the desired level of complexity. More particularly, the Virtual Models in the present invention describe visual models of biochemical complex systems, comprising sets of icons representing processes and their participants linked into multidimensional pathways, further organized in a hierarchy of icons representing discrete time and space compartments, wherein such compartments may contain other compartments, and wherein those modular icons encapsulate in different layers all the information, data, and mathematical models that characterize and define each Virtual Model.

Some process industries use large-scale cultivation of microorganisms or mammalian cells, which are extreme cases in terms of complexity when considering those cells as the individual manufacturing plants involved in complex chemical synthesis. Microorganisms are the preferable systems for producing natural substances that have a multitude of uses, such as drugs, foods, additives, biodetergents, biopolymers, and other new and raw materials. Mammalian cells are the preferable systems for producing potent active substances for therapeutic and diagnostic uses. The ultimate level of complexity is using a whole animal as the live factory for continuous production for important secreted proteins. However, the current systems only monitor very general types of phenomena, such as gas pressure, pH, and in some occasions, the concentration of some product that correlates with cell growth or production. For example, for controlling the production of a particular secreted protein that is produced in very low amounts in relation to other proteins, the total protein amount of protein is measured, which is a very poor indicator of how much of the desired protein is produced. Complex mixtures of chemical reactions could be finely controlled externally by modifying the types and amounts of inputs added, if one could predict what will happen by adding those inputs, which requires a good knowledge and a model of such system of reactions. This is particularly the case with biological cellular systems that have very sophisticated methods to transduce the signals provided by ligands in their external environment to the interior of the cell, resulting in the execution of specific functions. Such detailed and accessible mechanistic models of those pathways of reactions are not currently used for monitoring and control systems, but would be highly desirable. This invention provides the system and methods that allows scientists to visually build detailed mechanistic models of the complex systems involved, and to further develop and use inference methods to integrate the simulation of those Virtual Models with inputs from monitoring devices to allow for the intelligent control of the operation of the complex system.

The accuracy and validity of knowledge-based systems correlates not only with the quality of the knowledge available to the developers but also with their ability to understand, interpret and represent that knowledge. Because of the complex interrelationships driving the biochemical processes within and between cells, it is necessary to provide the many options for knowledge representation required by those systems. This invention presents a hybrid dynamic expert system that combines: a) the inheritance and encapsulation features characteristic of an object-oriented modeling approach, b) the procedural and rule-based inference capability of an expert system, and c) a model-based simulation capability. It is an objective of this invention to provide a framework that: a) allows domain-experts to directly enter their knowledge to create visual models, and to modify them as needed based on additional experimentation, without the need of knowledge engineers as intermediaries, and b) provides a knowledge-base having a well defined structure for representing knowledge about entities, populations of entities, processes, pathways and interacting networks of pathways, providing a visual interface and associated methods capable of dealing with incomplete and constantly evolving information and data. The data structures and domain-specific knowledge-base are independent of application-specific use, allowing the application-specific knowledge-bases to expand without affecting the basic operation of the system. Specific applications can be quickly built by using the prebuilt building blocks and the paradigm of "Clone, Link, Configure, and Initialize". The structure of the domain-specific knowledge-base serves also as the infrastructure provided to store additional information about new objects and models. The innovations of this invention include but are not limited to the specific design, generation, integration, and use of the libraries of building blocks, access panels, and their associated methods, that allow for representation, interpretation, modeling and simulation of different types of entities and their states, their relations and interactions, the pools of each of those entities in different compartments, the processes in which those pools of entities participate, and their discrete compartmentalization in time and space, as well as the concepts that make the simulation of this very complex systems possible. A large Virtual Model can be built as a set of modules, focusing each on different subsystems. Each of the modules can be run on top of the repository module that contain the class definitions and associated methods, and they can be dependent or independent of each other, or they can be maintained in separate CPUs and seamless integrated by the Shell's supervisor.

Such libraries provide the prebuilt building blocks necessary for visually representing the vast breath of knowledge required for building Virtual Models of complex systems in general, and of biological systems in particular. The building blocks are classified in palettes that can be selected through system menus. The descriptive information, data, and the mathematical models are all encapsulated within the modular components, in the form of attributes or in the form of component icons, with a plurality of methods associated with each of the icons. The visual models are built by interconnecting components of each reservoir icon to components of the one or several process icons in which their entities participate as inputs or outputs, or by interconnecting components of each process icon to components of the one or several reservoir icons that provide inputs or receive outputs to that process icon, resulting in complex networks of multidimensional pathways of alternating layers of reservoir icons and process icons, which may be located in the same on in different compartments. The time compartment icons, the reservoir icons, and the process icons or their components comprise sets of quantitative variables and parameters, and a set of associated methods that permit real-time simulations of the models created with those modular components. The system of this invention combines a number of programming paradigms, integrating the visual interface to define and constrained objects represented by icons, with procedural and inferential control and quantitative and semi-quantitative simulation methods, providing a variety of alternatives to deal with complex dynamic systems.

Of importance in simulating the behavior of complex systems is the need to model the different quantities and states at which the entities can be found in particular locations at different points in time, and also to model the events that cause the transitions from one state to another, or the translocation from one location to another, or the progress to the next phase in the time sequence. Teachings of this invention comprise: the representation of those states, transitions, and locations; the methods to implement their graphic modeling; and the methods to dynamically simulate the dynamics of the pools of entities in each state, location, or phase. In the particular domain implemented to illustrate this invention, there are several major types of states and transitions to be considered, depending of whether the entity to be considered is a biological system, organ, cell, cellular compartment, molecule or any other of their components. We are providing here with just a few examples considered in the currently preferred embodiment of this invention.

The architecture of the system of this invention allows various bioProcesses to simultaneously compete for the contents of a bioPool while also allows one bioPool to participate in various bioProcesses in different capacities, with different units within a bioPool behaving in different ways, as determined by the class of bioReactant to which they are distantly connected via the bioPosts. With this implementation, all bioEngines that input units into a given bioPool and all the bioEngines that get input units from that bioPool are integrated. At the same time, all bioPools that input units into a given bioEngine and all the bioPools that get input units from that bioEngine are also linked. The result is a very complex multidimensional network of composite bioObjects, which provides the matrix for further reasoning and simulation by the program. For example, the formulas that provide the values for the encapsulated sets of variables and parameters refer to linked bioObjects, both graphically or distantly, providing the capability of concurrently and dynamically compute as a large number of processors arranged both in parallel and in series within that matrix.

The modeled system's behavior is defined by mathematical components, represented by a set of model differential and algebraic equations that provide the values of the system's variables and describe their behavior, together with the set of associated parameters that control the behavior of the variables and the system as a whole. The system's variables and parameters are embedded and distributed throughout the system of connected structures, encapsulated within the subcomponents that define the system's architecture. The model can then be viewed as a set of embedded block diagram representations of the underlying equations that can be used for dynamic numerical simulation and prediction of the effects of perturbations on the system, and to ask what-if type questions.

The compartmentalized bioModels, and the methods attached to them, encode knowledge that enables the program to reason about the containment of different parts of the model in several compartments, while the architecture of the network of linked bioObjects of diverse types is transparently maintained, regardless of the transfer of the bioObject icons to different locations. They also comprise quantitative variables and parameters, some relating to quantities and rates translocation, distributed either within the corresponding reservoirs and process or relating to time intervals that may be associated with the time compartments, all of which have associated simulation formulas to compute their values. In addition, the modeler can define expert rules to monitor the values of any of those variables while the simulation is running, and to either set other values or control the course of the simulation in a variety of ways. The expert rules can also reason about time or about events resulting from the simulation, and Inference using those types of knowledge may direct further actions to be executed by the system.

The visual interface further provides quick access to several automated methods for compiling, retrieving, and displaying the modular components of the visual models as well as the information and data they contain. The system integrates inferential control with quantitative and semi-quantitative simulation methods, and provides a variety of alternatives to deal with complex dynamic systems and with incomplete and constantly evolving information and data. A number of functions and visual interfaces can be selected from the menus associated with each of those icons or their components, to extract in various forms the information contained in the models build with those building blocks, such as:

a) methods to create and display of interactive networks of pathways, by programmatically integrating the components of the Virtual Model into multidimensional networks of interacting pathways, including branching and merging of pathways, cross-talk between pathways that share elements, and feed-back and forward loops;

b) methods to perform complex predefined queries that combine criteria related to the structural composition of the bioEntities involved, the position of bioPools downstream or upstream of the bioPool taken as reference, the role that those pools of entities play in processes, the location of those pools and processes in the discrete time and space compartments, or any combination of them;

c) methods to dynamically simulate their continuous interactions, modifications and translocations to other compartments, and the time-dependency of such interactions, optionally using the encapsulated absolute-valued or scaled-valued parameters and variables.

The examples provided to document the current implementation of this invention focus on modeling biochemical regulatory processes that are relevant for intracellular or intercellular signaling. This is however one of the many potential applications of the system of this invention, and it should not be construed to limit the applicability of this system to the numerous other applications that involve complex systems in any other domain, which can be developed by minor modifications or additions of the system using the methodology here presented.

There are numerous other uses of the core system, methods and visual interface of this invention, in addition to the monitoring and control applications described here. Of particular interest is the modeling and simulation of disease specific conditions and the testing the effects—both desired and unwanted side effects—of potential therapeutic agents. This invention also allows to analyze disturbances such as potential environmental or biological inducers of disease in both physiological and pathophysiological models. The methods included in this invention can in a similar way be used in a variety of applications, including but not limited to: simulation and prediction of experimental results; interactive drug design; study of drug side-effects and multiple drug interactions; simulation of interactive causes in the induction and progression of disease, including both biological and environmental factors; diagnostics and clinical decision support; therapy planning; theoretical research; and numerous other applications.

The foregoing and additional objectives, descriptions, features, operations and advantages of the present invention will be understood from the following detailed description of the preferred embodiments in combination with the accompanying figures.

BRIEF DESCRIPTION OF DRAWINGS

FIG. 10 is the table of attributes of a complex variable structure that allows the integration of measured values and the simulated values that facilitates the implementation of this invention.

BEST MODE FOR CARRYING OUT THE INVENTION

Figure 1:
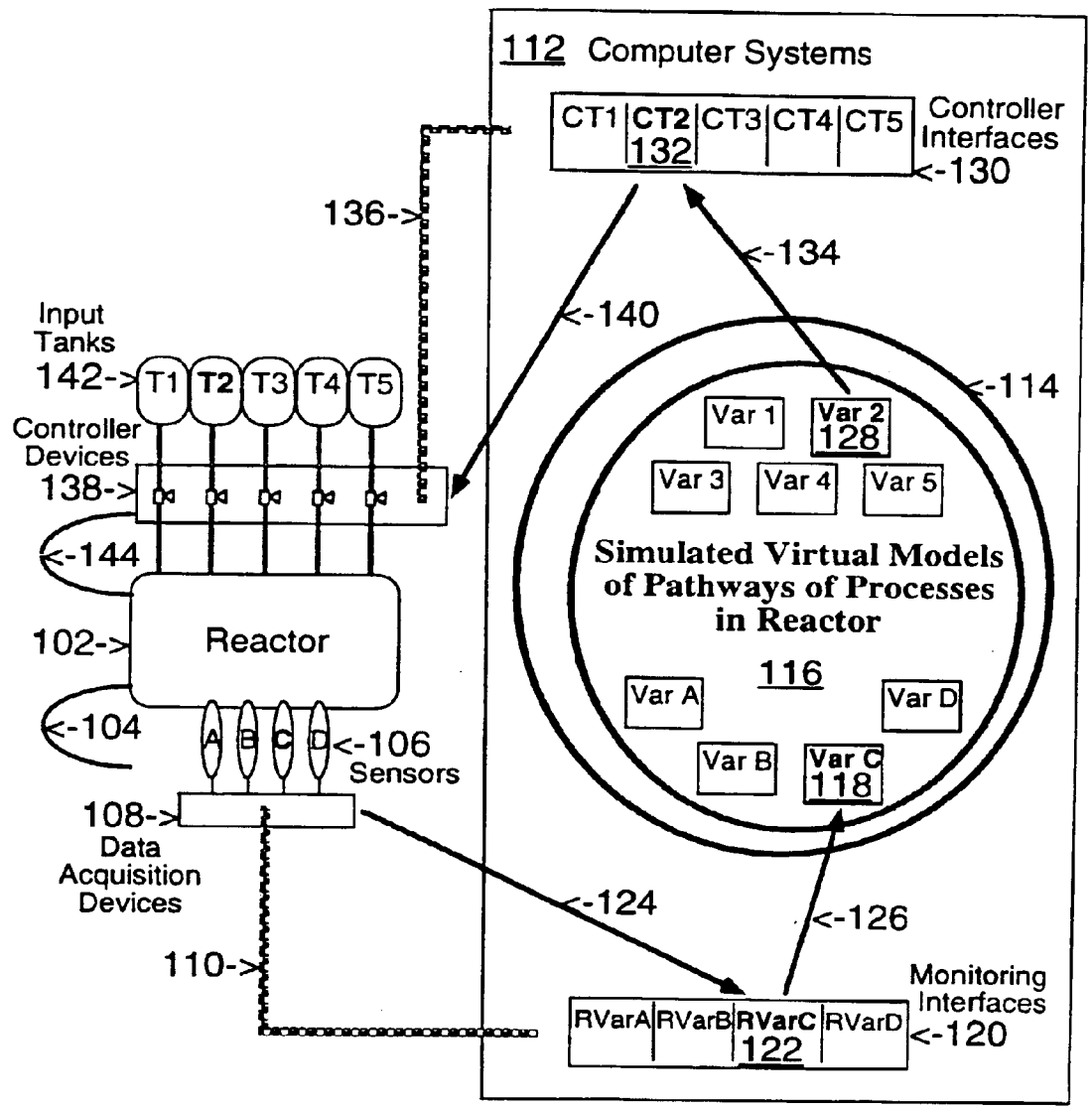
FIG. 1 is a high-level illustration of the various components integrated in the system of this invention to use the Virtual Models for control functions.

Notes: The body of the present application has sections that may contain some discussion of prior art teachings, intermingled with discussion of innovative and specific discussion of the best mode to use that prior art in this invention as presently contemplated. To describe the preferred embodiments, it is necessary to include in the discussion the capabilities offered by the shell used as development and deployment framework for this invention (hereafter referred to as "the Shell"). The applicant specifically notes that statements made in any of those sections do not necessarily delimit the various inventions claimed in the present application, but rather are included to explain how the workings of an existing set of tools is used to illustrate the preferred embodiments of the new tools and applications claimed in the claims section. The currently preferred embodiment of this invention, as described in the present application, is based on the definitions of a particular Shell: Gensym Corp.'s G2 Expert System. There are several other attributes that relate to the Shell's built-in performance and formatting capabilities, which are not shown in those examples. Some information included within the body of this application was extracted from various sources describing the characteristics of G2, including user manuals (included here by reference), and some of this material is subject to copyright protection.

Monitoring and Controlling the Operation of a Reactor using a Simulated Virtual Model The system object of this invention is a hybrid combination of model-based methods describing the explicit mechanistic reference behavior of the production system with the input from process sensors that monitor the state of the production system, triggering event-based control flow of operations characteristic of each system. The system implements rules that wait for events to happen. Such events may be complex combinations of individual events, such as selected measured values reaching certain predefined or simulated values, or be within certain predefined ranges, including the implementation of fuzzy-logic within those rules. Such rules may fire other rules or invoke inference procedures or cause certain control actions to take place. This system can detect the current status of the production system, and when the selected monitored variables reach certain values specified by the simulated values of those variables, then certain control action take place. This system incorporates monitoring capabilities with the knowledge-based model to provide expert control of the operation of the production system or biofermentor. This control system provides simultaneous supervision of any number of operating variables (such as intermediary or end-products, which in the case of cellular systems can be intracellular or secreted), and compares them with the simulated values of those variables resulting from the encapsulated mathematical models and, depending on the dynamically monitored behavior of the production system, the control system is able to compensate by feeding components at different rates, feeding additional components, or stop feeding some of the previous components.

Because of the user friendly and intuitive interface, the bench scientists can participate in the design of the production system by editing the knowledge-base and the visual models themselves, incorporating information and data obtained in their own experimental research or that from other published resources. It allows the direct incorporation of research into the scale-up operations. The scientists can rapidly build models by selecting any desired building block from the many palettes provided, clone it and drop it on desired compartment, link it to other building blocks in the model, configure it by entering values of desired attributes, and initialize it to establish relationships with other building blocks in the model. The information and data is entered into the system as attributes of objects, either as user inputs, or directly from measuring devices using and interface between said measuring devices and the computer system.

The system provides a graphical computation and control language, where the objects communicate through the links established between them. Some of those linkages are built in within the composite prebuilt building blocks, while the modeler establishes other links between appropriate components from different building blocks. Other information, such as the name, description, references, or the values of parameters specific for each component are entered by the modeler. Variables in this system are themselves objects, and maybe of two major classes: a) one-valued variables have only one value, which may be either provided during a simulation by a simulation formula or procedure, or inferred by any other means, such as rules or general formulas defined by the modeler; and b) two-valued variables have two values: the simulated-value as before, and the measured-value is provided in real time through an external sensor mapped to said variable. The one-valued variables are used by default because of their smaller footprint, and their values are provided by default by generic simulation formulas that are specific for each class of variable. However, the modeler can replace them with the equivalent subclasses of two-valued variables for each instance of a component where the variable is mapped to an external sensor, and when both the measured valued and the simulated value of such variable is desired. The modeler can also write specific formulas for any desired instance of a variable, which then overrides the default generic formulas. It is possible, through any of the inference mechanisms to compare the measured value and the simulated-value, either the current values or the values mapped at some time point in the past, since the system is able to keep a time-stamped history of both types of values, and take specified actions when the inference criteria are met, such as: causing a valve for a component feed to be more or less open or closed, or activating or deactivating whole branches of the model pathways being simulated. Such actions can alternatively be invoked as a result of comparing either the measured-value or the simulated-value to any predefined constant value or range of values, or the value of any other variable or parameter in the system. Or the action or set of actions could result from inferences involving any number of comparisons between measured-values or simulated-values for any number of variables, or any number of parameters, or any predefined constant values.

As shown in FIG. 1, a system of this invention is composed of:

a) a reactor (102), which may comprise any combination of reaction tanks, fermentors, bioreactors, or other processing units;

b) one or more data acquisition devices (108), which may comprise any combination of hardware and software devices, such as sets of sensors (106) that measure the amounts of selected chemicals in the reactor, signal transducers, filters, amplifiers, data acquisition boards, appropriate device drivers, or any other required devices;

c) one or more computer systems (112) comprising CPU, memory, storage device, display, user input device, linked (110) to the data acquisition devices (108);

d) one or more computer programs (114) and one or more computer Virtual Models (116) of pathways of chemical interactions and other processes in the reactor (102), wherein the computer programs (114) and the Virtual Models (116) are used to quantitatively or semi-quantitatively simulate in real-time the Virtual Models (116), wherein the Virtual Models encapsulate one or more variables (118) that represent the quantities of certain monitored entities in the reactor (102) and one or more variables (128) that represent the quantities of certain entities or certain events, which, when reaching certain values during the simulations of the Virtual Models (116) by the computer programs (114), trigger certain control actions that affect the operation of the reactor (102), and wherein both the computer programs (114) and the Virtual Models (116) are loaded in the memory of one or more of the computer systems (112);

e) one or more monitoring interfaces (120) loaded in the memory of one or more of the computer systems (112), which act as bridges (122) or software interfaces between the data acquisition devices (108) and the computer programs (114) and allow passing of values (124, 126), such as the values of the amounts of certain entities in the reactor (102), as measured (104) by the corresponding sensors (106), to the corresponding variables (118) embedded in the Virtual Models (116) that represent said amounts;

f) one or more controller devices (138), which regulate the operation of the reactor (102), such as controlling the flow of certain inputs (142) to the reactor (102), wherein the controller devices (138) are linked (136) to the computer systems (112);

g) one or more controller interfaces (130) loaded in the memory of one or more of the computer systems (112), which act as bridges or software interfaces between the computer programs (114) and the controller devices (138) and allow passing of control signals generated by the computer programs (114) as a result of the values of any combination of any number of variables (128) embedded in the Virtual Models (116) reaching certain values.

Depending on the application requirements, the interfaces may provide bridges to Supervisory Control and Data Acquisition (SCADA) systems, Distributed Control Systems (DCS) or Programmable Logic Controllers (PLCs), with the adequate protocol drivers, as well as to relational databases, object-oriented databases, ASCII files, as well as to a number of other connectivity applications, allowing the program to send or receive values over said interface.

The knowledge-based Virtual Models include model-based reasoning that models the dynamic behavior of processes on the reactor. This mechanistic approach may involve any number of variables to be monitored, including those measured and monitored in the reactor and those simulated and monitored in the Virtual Models. The Virtual Models provide a visual qualitative and quantitative description of processes that happen inside of the reactor, as well as a description of the participants in those processes. The system of this invention separates the representation of the physical systems as Virtual Models from the monitoring and control aspects, allowing to integrate the same Virtual Models with different combinations of monitoring an d control designs, to solve different production needs.

FIG. 1 also shows the directions of flow of data and control in the system of this invention. The amounts of certain entities, which are specific for each particular process design, are captured (104) by the corresponding set of biosensors (106) and, through the data acquisition devices (108), those values are passed (124) to the monitoring interface variables, which in turn pass those values (126) to the corresponding variables (118) in the Virtual Models (116) that represent those values. Those variables (118) are integrated with many other variables and parameters embedded in the Virtual Models (116) during the real-time simulation of the Virtual Models (116), including other variables (128) embedded in the Virtual Models (16) that represent quantities, rates, or other events, and which are monitored by the programs (114) during the simulation. Whenever during the simulation the values of any combination of any number of said monitored simulated variables (128), which are specific for each particular process design, reach certain values, then the programs (14) pass control signals (134), through the appropriate control auxiliary structures (132) in the controller interfaces (130), which are forwarded (140) to the controller devices (138), which in turn control the flow of inputs (142) and regulate (144) the operation of the bioreactor (102), which is being monitored (104) in a continuous manner.

Depending on the application requirements, the interfaces may provide bridges to Supervisory Control and Data Acquisition (SCADA) systems (such as the HP's RTAP SCADA or others), Distributed Control Systems (DCS) (such as Honeywell TDC3000 DCS or others) or Programmable Logic Controllers (PLCs) (such as Allen-Bradley's PLC3/PLC5 families, or others), with the adequate protocol drivers, as well as to relational databases, object-oriented databases, ASCII files, as well as to a number of other connectivity applications, allowing the program to send or receive values over said interface. The program (114) and the interfaces (120, 130) are separate processes, which may be located on one or more host computers. In the later case, a communications link, such as a TCP/IP or DECnet protocols based link and port, is required. The program can also use various interfaces simultaneously, linked to different types of devices. The interface serves as a bridge between selected variables embedded in the objects of the Virtual Models and their corresponding mappings in one or more external systems. Functions defined in the interface can be invoked by remote procedure calls (RPCs) defined in the program, and viceversa.

The ideal system for the intelligent control of biotechnological processes must posses a large set of features reflecting the real-time aspects of the control system, as well as the specific characteristics of the biochemical processes involved. There are a variety of new sensor technologies that may be used to provide the monitoring capabilities external to the Virtual Models. Furthermore, the system of this invention allows to integrate a variety of real-time control options with the ability to use mechanistic models to drive the automatic decision making support for process control.

The knowledge-based Virtual Models include model-based reasoning that models the dynamic behavior of processes on the reactor. This mechanistic approach may involve any number of variables to be monitored, including those measured and monitored in the reactor and those simulated and monitored in the Virtual Models, which are both used as inputs for the inference engine to be compared against each other or against other specified values, and which meeting the specified conditions trigger actions that result in control operation on the reactor. The Virtual Models provide a visual qualitative and quantitative description of processes that happen inside of the reactor, as well as a description of the participants in those processes. In some cases, the reactor may contain chemicals in solution or bound to other structures, such as carriers or membranes. In other cases, the reactor may contain less defined mixtures resulting from cell extracts. Yet in other cases, the reactor may contain cells of one or more types, interacting with each other and with their environment, the culture medium, where each of such cells is an reactor itself that interact with other cell reactor. The system of this invention provides capabilities to produce more or less detailed Virtual Models of any of those types of reactors, or Virtual Models of subsystems within such reactors.

The program provides a domain-specific framework for continuous and discrete process modeling and simulation, which combines a hierarchical object-oriented representation to provide facilities for hierarchical systems modeling to handle multi-dimensional information, model-based and knowledge-based reasoning, temporal inferencing, and dynamic real-time monitoring and control. Furthermore, the system of this invention separates the representation of the physical systems as Virtual Models from the monitoring and control aspects, allowing to integrate the same Virtual Models with different combinations of monitoring and control designs, to solve different production needs.

The present invention also refers to a domain-specific, application-independent, knowledge-based and model-based, object-oriented, iconic, real-time computer system capable of being used by scientists as a framework to construct specific and interactive information, modeling and simulation applications in the chemical and biochemical domains. It provides a variety of domain-specific, application-independent tools, graphical interfaces and associated methods to provide users the capability to extract, interactively or automatically, the integrated knowledge contained in those applications or models build by the modeler, and to further use those models, among other uses, to navigate through the pathways of processes and explore those processes and their participants, or for quantitative real-time dynamic simulations. The computer system comprises a plurality of methods, hereinafter called "the methods" and diverse sets of objects, some of them representing either entities or concepts, hereinafter called bioObjects, and other representing other auxiliary structures, which in general are referred as tools. Objects are arranged in object-class hierarchies and workspace hierarchies. Methods may be associated with a class of objects, an individual instance of a class, or a specified group of instances within a class. Libraries of prebuilt knowledge-based generic bioObjects are provided as the building blocks that can be combined in prescribed ways to create diverse and new knowledge structures and models.

In the description of this invention, the following clarifications should be noted:

a) a person using the underlying Shell to define the domain-specific application-independent but knowledge-based classes of objects, their associated methods, and the prebuilt knowledge-based building blocks is hereinafter referred to as a "developer", while the person using those building blocks to build application-dependent models, or expanding the libraries of prebuilt bioObjects, is hereinafter referred to as "modeler", and the person that extracts and uses the accumulated knowledge and runs simulations, is hereinafter referred to as a "user";

b) text expressions are case insensitive, and what is referred in the description as bioObject or bioProcess, may be referred to in the code as bio-object or bioprocess, or the names may appear in the code in low case or all capitalized;

c) a window refers to a display of the program on a computer screen, while a workspace refers to one of the many containers of objects that may be displayed within a window, and the subworkspace of an object is the workspace (only one) that may be associated with that object and may encapsulate the components of that object (composite object);

d) the selection of a menu option is equivalent to clicking on that option, and both expressions are used in the following description of this invention;

e) expressions similar to "selection of option A displays B" is a short form meaning something similar to "selection of option A causes the invocation of the action or procedure specified in the definition of option A and, as a result of the execution of such action or procedure, B is displayed in the window from which option A was selected."

Figure 18:
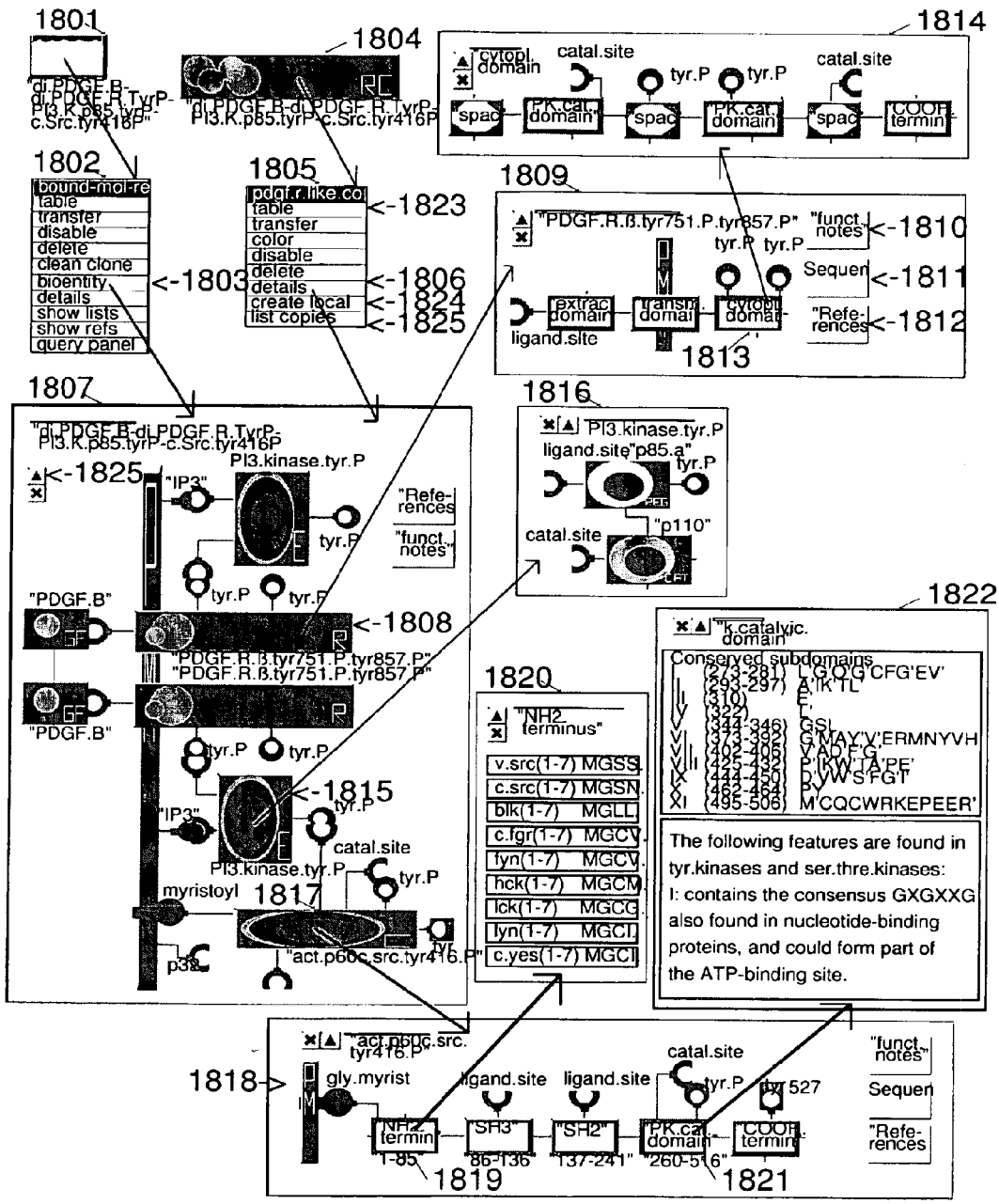
FIG. 18 shows an example of a complex molecular structure built with the prebuilt molecular components.
Figure 20:
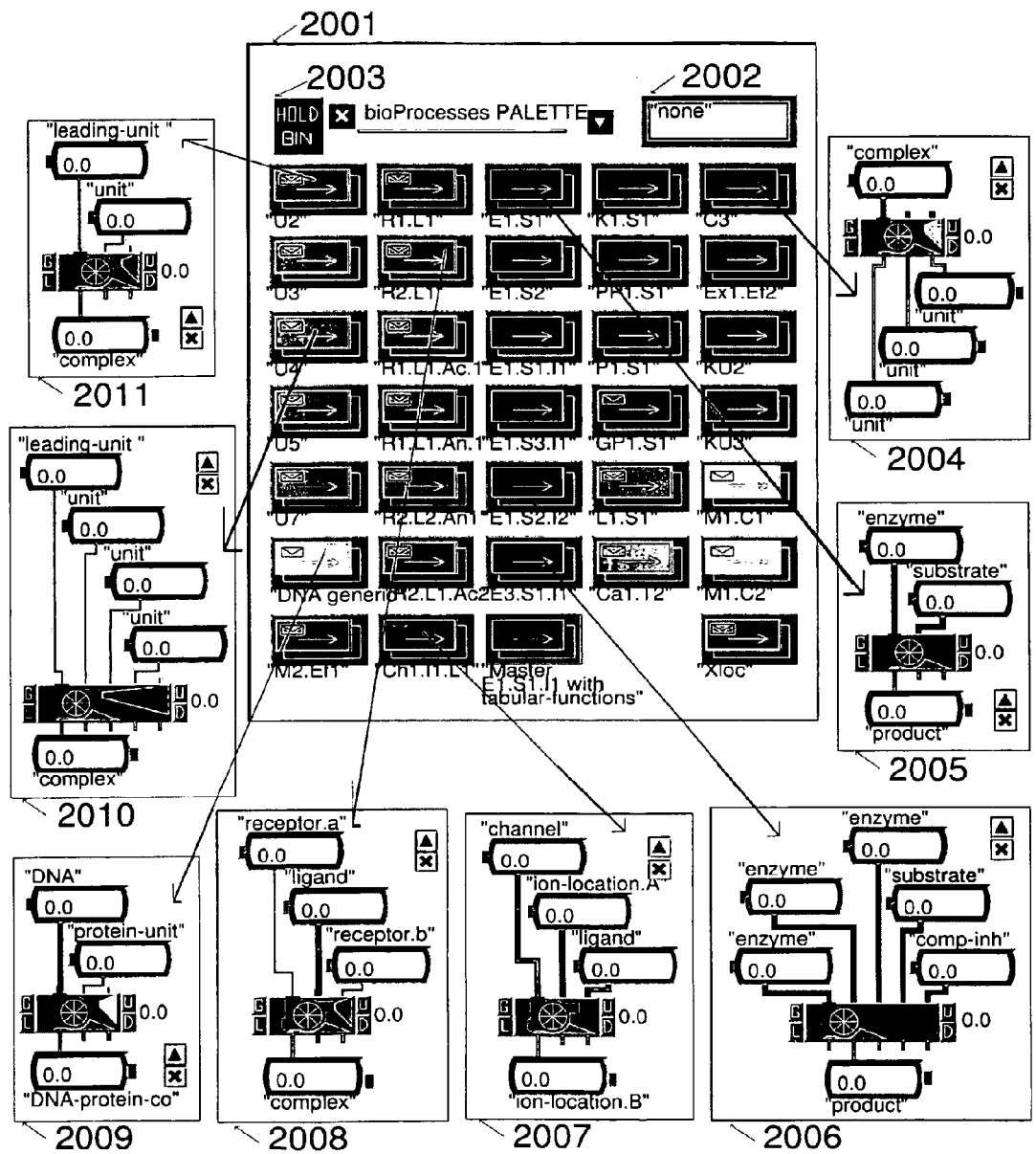
FIG. 20 shows a palette with examples of prebuilt composite processes.
Figure 23:
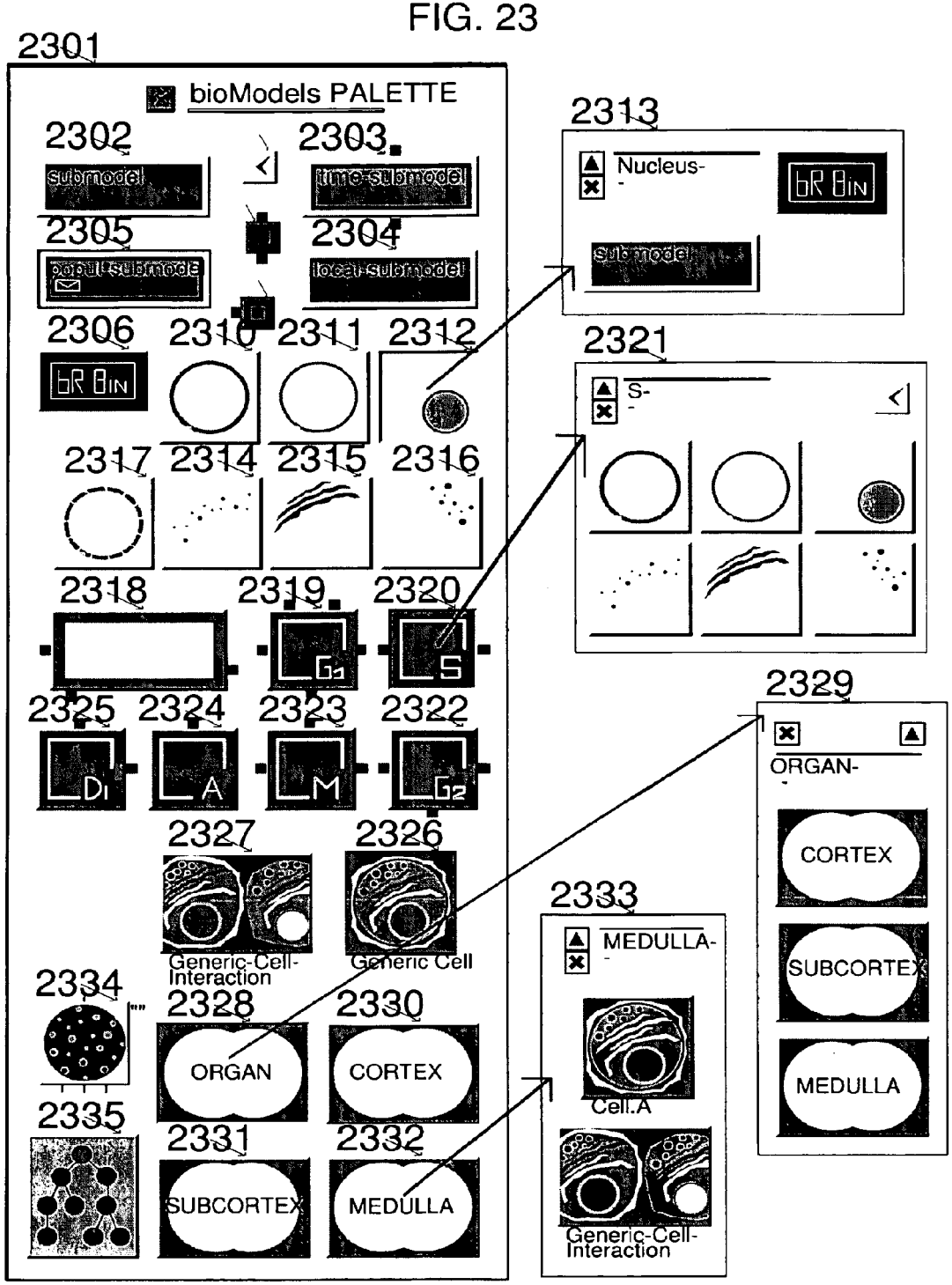
FIG. 23 shows a palette with examples of prebuilt composite domain-specific compartments.

The preferred embodiment of this invention integrates a variety of knowledge representation techniques, as required for creation of virtual models of complex systems. The accuracy and validity of knowledge-based systems correlates not only with the quality of the knowledge available to the modelers but also with their ability to understand, interpret and represent that knowledge. The object-oriented approach provides a powerful knowledge representation of physical entities (such as organs, cells, DNA, enzymes, receptors, ligands, mediators, or ions) and conceptual entities (such as processes and cellular interactions, quantities and rates). In this system, data and behavior are unified in the objects. Two characteristics of object-oriented environments, encapsulation and inheritance, are very important for the design and implementation of the system of this invention. Objects are defined following class hierarchies in which the definition of each class specifies the types of attributes characteristic of all subclasses and/or instances of that class. Encapsulation permits to hide the details behind each object, and encapsulation is implemented in two different forms: a) at the attribute level, is the standard form of encapsulation of object-oriented approaches; and b) at the workspace level, a less common form of encapsulation related more to the iconic approach. Multiple levels of workspace encapsulation are supported (FIGS. 18 and 24), allowing modules with a multilayered structure with increasing levels of detail. Since the subworkspace is not inherited through the class hierarchy, neither are the components. However, once a generic instance for a class is completed with components in its subworkspace, it can be added to the corresponding palette (FIGS. 18, 20, 23)

as a prebuilt building block, and the resulting composite object can be cloned, in which case all encapsulated levels of subworkspaces are also cloned. The interpreted domain-specific framework approach is easy to use and allows rapid building of iconic models. The domain-expert knowledge is represented in an easy to understand declarative from, separated from the methods that specified how that knowledge is used by the program. The iconic approach allows the user configuration for building of models to consist primarily of connecting iconic objects and filling out their tables of attributes. The visual framework enables reasoning about the interactions between objects and their compartmentalization. This graphical programming capability is particularly important because it allows the continuous expansion and modification of the system, necessary for this type of applications, by scientist modelers with no programming skills. Its modularity allows to delete, modify or create parts of the system without affecting the operation of the rest of the system. The knowledge can also be extended and reused under different contexts, and in different new applications. The same hierarchic architecture used to develop the bioObjects can be extended by the modeler to expand the libraries of bioObjects, creating new objects or by cloning, configuring and modifying existing ones. With its iconic format, the system can be easily browsed and understood by the user.

The principle followed in the design and implementation of this invention is the breaking down of the knowledge about entities, processes and pathways down to smaller functional units, to a level where the following requirements can be met: a) allowing their repeated use as building blocks in a variety of situations; b) allowing access to the structures and processes that are susceptible to control and regulation; and c) keeping the number of units manageable. The functional units, hereinafter called composite bioObjects, are further broken down into operational and standardized knowledge and data structures. These generic but domain-specific iconic objects add flexibility and allow the user to open tables of individual instances to input data, modify existing bioObjects, or create new types of bioObjects. Following such principle, the system of this invention comprises a variety of domain-specific knowledge structures, all encoded as objects, with further components, such as: a) other iconic bioObjects on their subworkspaces, b) standard graphic user interface objects such as buttons to request data displays or input panels, c) non-iconic objects, which might be pointed to as attributes of other objects, such as domain-specific variables, parameters, lists or arrays, or d) methods refering to the bioObjects, their attributes or their components, such as actions, formulas (Tables 83–88), relations (Tables 75 and 218a, rules (Tables 76–81) and procedures (various Tables), and which can be invoked interactively by the user from either the bioObjects or their components or from the standard graphic user interface objects or domain-menus, or invoked programmatically by other rules or procedures, and which are hereinafter referred to as the associated methods. It is an object of this invention the manner in which the combination of those types of knowledge structures encode, in a distributed form, the data and the knowledge that enables the system to compute and to reason about conditions and events defined by the developer, the modeler, any other external source, and/or generated during a dynamic simulation. Based on those conditions, the knowledge structures are used by the Shell to infer or simulate different behaviors, while data, information and/or control are propagated and actions are executed. As can be observed by comparison with the prior art previously discussed with the description in the sections to follow, the form of knowledge representation in the iconic models, libraries of composite bioObjects, graphical interface and associated methods, and the overall organization of the system object of this invention offer a very different and innovative approach that not only integrates the qualitative and quantitative description of chemical and biochemical objects with a set of state and dependent variables, such as amounts and rates, but also incorporates temporal reasoning and generates dynamic simulations.

Figure 8:
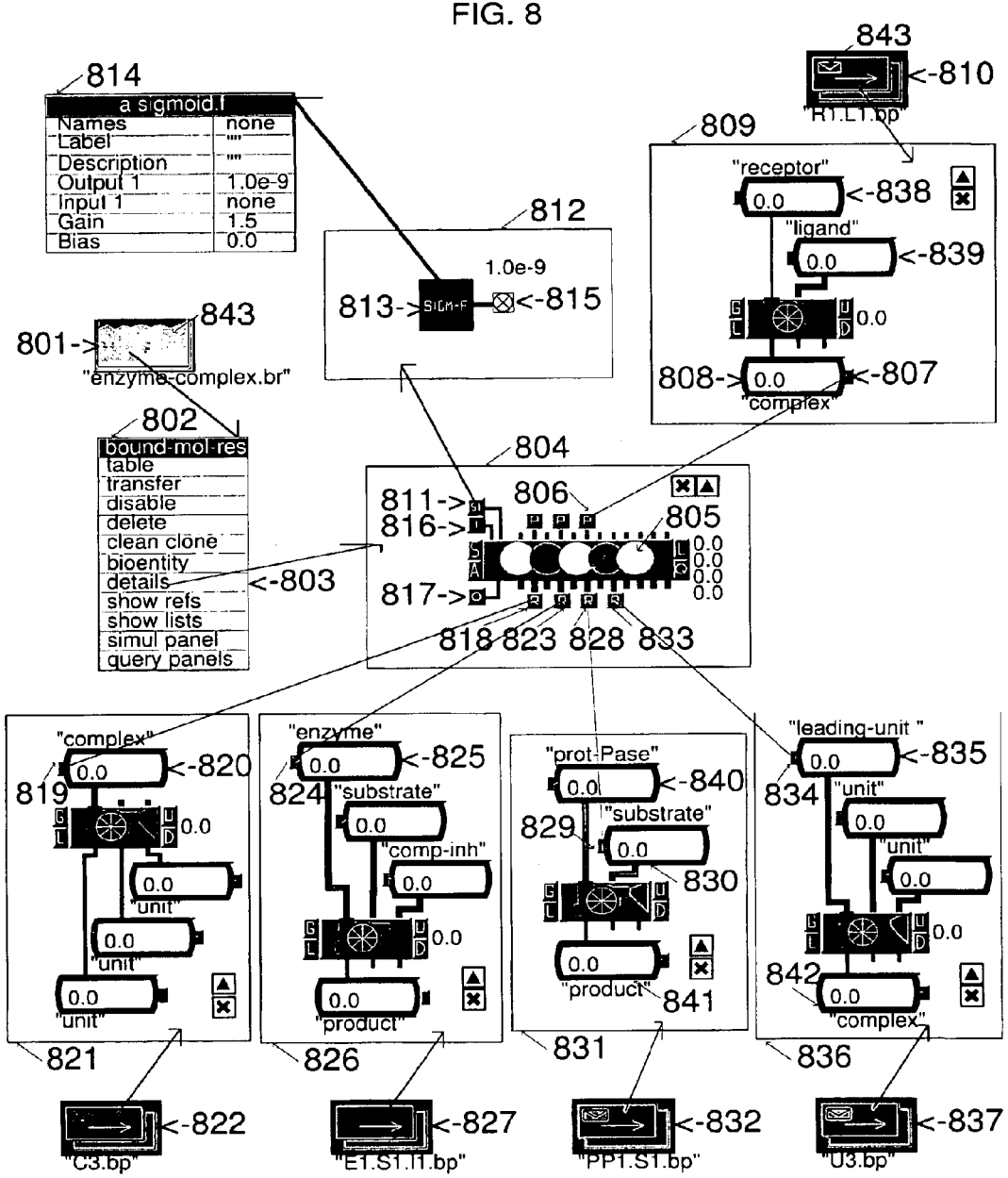
FIG. 8 is a detailed representation focusing on the iconic components of a pool of entities and its inputs and outputs.
Figure 24A:
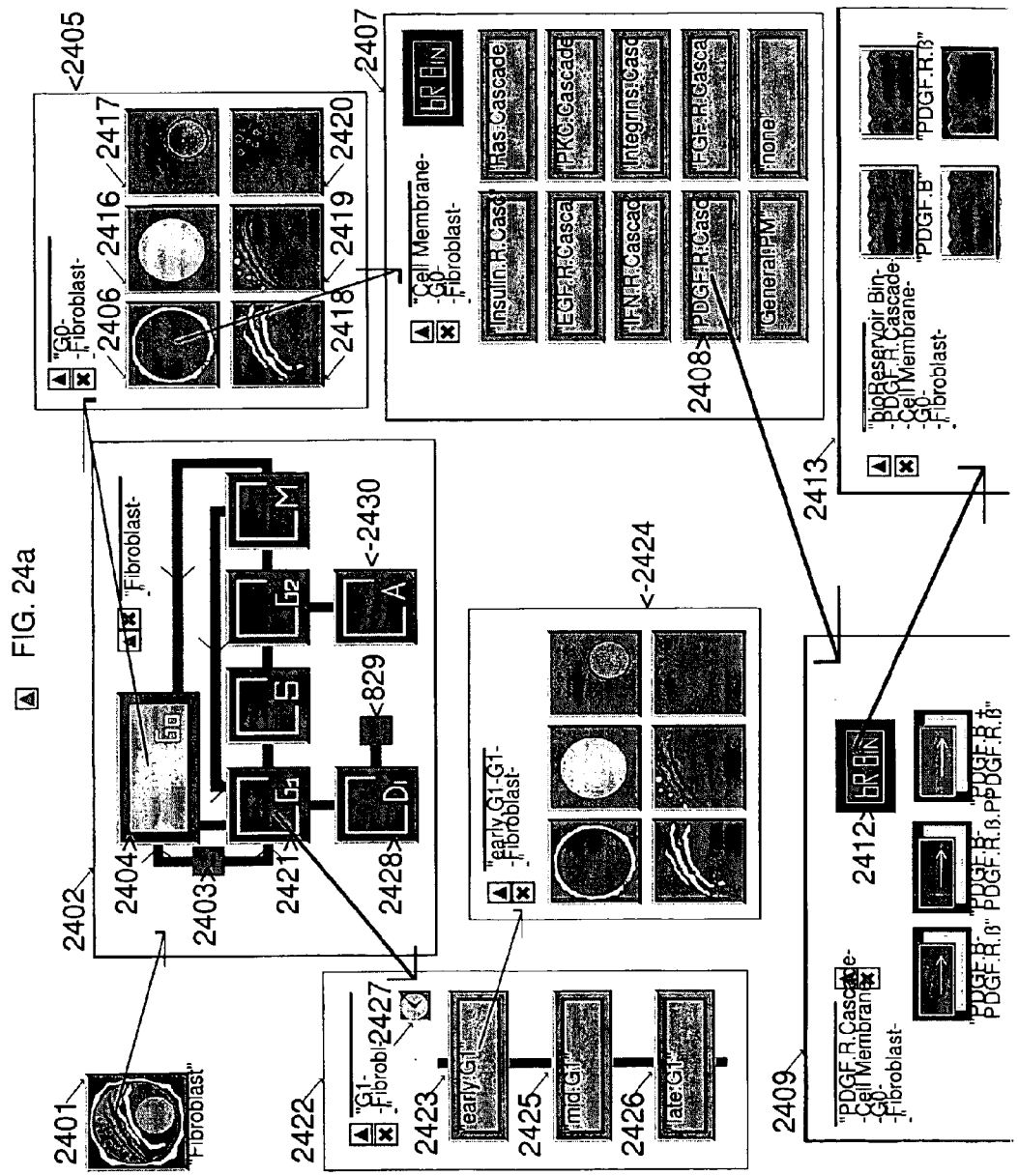
FIG. 24a and FIG. 24b describe a domain-specific compartmentalization of the components of a Virtual Model, in this case focusing on the sequential phases of a cell's cycle and on its subcellular compartments.
Figure 24B:
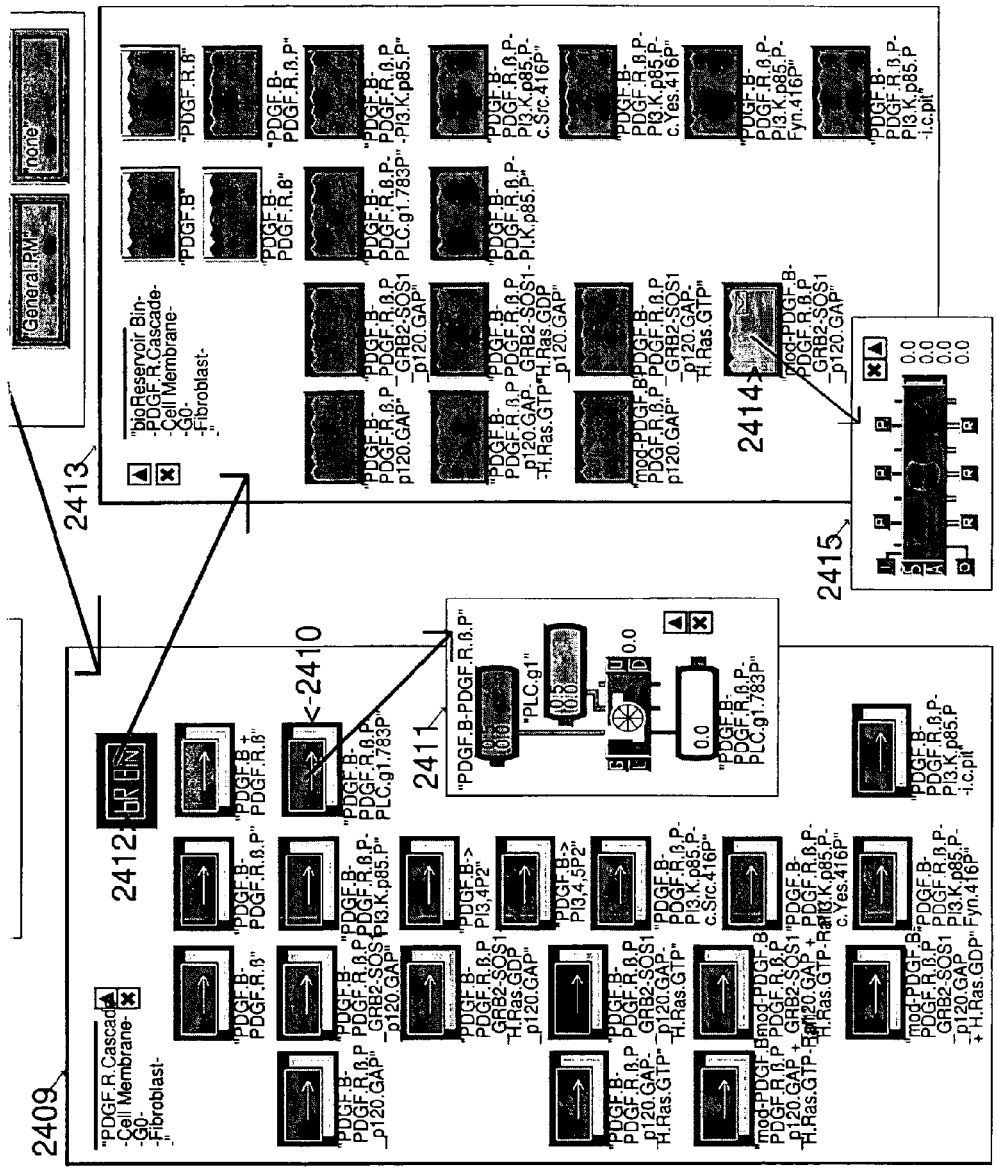

Therefore, one innovation of the present invention is the iconic interface and associated methods used to partition the domain knowledge into modular and interactive knowledge structures represented as iconic objects, the connections, interactions and relations between those structures, and their behavior, incorporating declarative and procedural information. Each independent functional iconic building block, a composite bioObject, comprises a set of iconic bioObjects and other objects and represents either:

a) the descriptive characterization of single units of molecular entities, molecular subcomponents, or molecular complexes, hereinafter called in general bioEntities (FIG. 18);

b) the description of a number of units with the same characteristics, defined as a population of such molecular entities or molecular complexes in specific states, hereinafter called a bioPool, which together with the potential inputs to and outputs from such bioPool is encapsulated in what is hereinafter called a bioReservoir (FIG. 8);

c) the interactions between fractions of different such populations of molecular entities or molecular complexes, or their transitions from one molecular state or discrete compartment to another over time, hereinafter called bioProcesses (FIG. 7); or d) the organization and integration of networks of pathways composed of sets of linked bioReservoirs and bioProcesses (FIGS. 7, 8) organized in compartments, hereinafter called bioModels (FIG. 24). Low level bioModels can be further organized in discrete location and time compartments, representing the subcellular organelles and the phases of the cell cycle respectively, which are themselves components of higher level compartments representing single cells. All those types compartments are themselves bioModel subclasses at different levels of complexity and detail in a hierarchy of subworkspaces.

BioObject, a subclass of the class objects provided by the Shell, is the superclass at the top of various hierarchies of classes of objects such as the class hierarchies of bioEntity, bioReservoir, bioProcess, bioModel, and others. Each instance of a class is characterized by the set of attributes defined for the class, which can be inspected in the table of attributes attached to each object by selecting it with the mouse. Some attributes define configuration information, while other attributes describe the composition and characteristics of the object, and still others hold dynamic state information, such as the current value(s), data histories, and status. The value of some attributes of an object, such as the variables and parameters, can be dynamically modified at runtime.

The knowledge-based modeling and simulation system of this invention interprets the information and data contained in the BioObjects' data structures, based on additional knowledge contained in the form of rules, formulas or procedures. Model-based knowledge is integrated and encapsulated in the structural, functional and behavioral models represented by the virtual iconic models or bioModels. Those virtual models are defined qualitatively (FIG. 24) by the locations, connections, and relations of their components, and quantitatively by their encapsulated mathematical models (FIGS. 12–15). The constants, parameters and variables that define those models are distributed through the different types of bioObjects, defined as their attributes, and the corresponding formulas and functions relate those data structures to others and characterize the particular system. The system integrates propagation of values, inference and control throughout the pathways. Model-generated results are used as input information for the inference engine, and dynamic models can also reason about the historic values of its variables as well as projecting values of variables into the future. All those different types of knowledge are added by human domain experts to incrementally build an integrated Virtual Model.

In the current implementation of this invention, the variables embedded in the model that are set to get values from the sensors (such as the concentrations of the corresponding bioPools) inherit their properties from two parent classes: a class of float-variable and a class of interface-data-service. One of the attributes of the later class is Interface, which value defines the interface that will provide the current value for such variable. The value for such variable, the same as for any other variable in this system, can be set to be evaluated at set intervals, or it can be set to its value having a value that expire after a set validity interval. When the inference engine seeks the value of said variable, either at the preset update intervals or when such value is needed but has has expired, a request if set to the specified interface to provide a value. Such variables are registered in the interface. After the interface is set-up, when the start_interface function is called by the program and the connection established between the interface (107) process and the computer program (115) process, the functions executed by the interface comprise: initialize_context (initializes the connection between the program and the interface), pause_context, resume_context, shutdown_context, receive_registration (called when the program seeks to map for the first time a variable to an external data point); receive_deregistration, poll for data (checks periodically which registered variables need updating, retrieved data values available, packages the data into the data structure used by the return functions, and sends the data back to the program (115); get_data (called when the program requests data service for one or more registered variables); set_data (called when the program executes one or more set actions within a rule or procedure, it sends a request to the interface to set the external data point to which the registered variable is mapped, it also may call interface return functions to change the value of the registered variable after its corresponding value in the external system has been changed). The interfaces perform also many other functions related to passing objects and messages, checking data types, and several other API functions.

In the current implementation of this invention, methods such as procedures, rules, formulas and relations, defined in a structured natural language, may apply to a single instance or a group of instances, or to a class or a group of classes, and they may include references to connections and to connected objects. Methods may refer or apply to the values of attributes at different time points or to the behavior of variables or parameters over time. They can perform in response to: a) given events or conditions, b) at predetermined time intervals, or c) upon request from other rules or procedures. Methods can be executed in real-time, in simulated time, or as fast as possible, implementing different strategies concurrently and over extended periods of time. Arithmetic and symbolic expressions can be used independently or combined, and dynamic models may include from non-linear differential equations to logic expressions to simulate both analytic and/or heuristic behavior.

Figure 32:
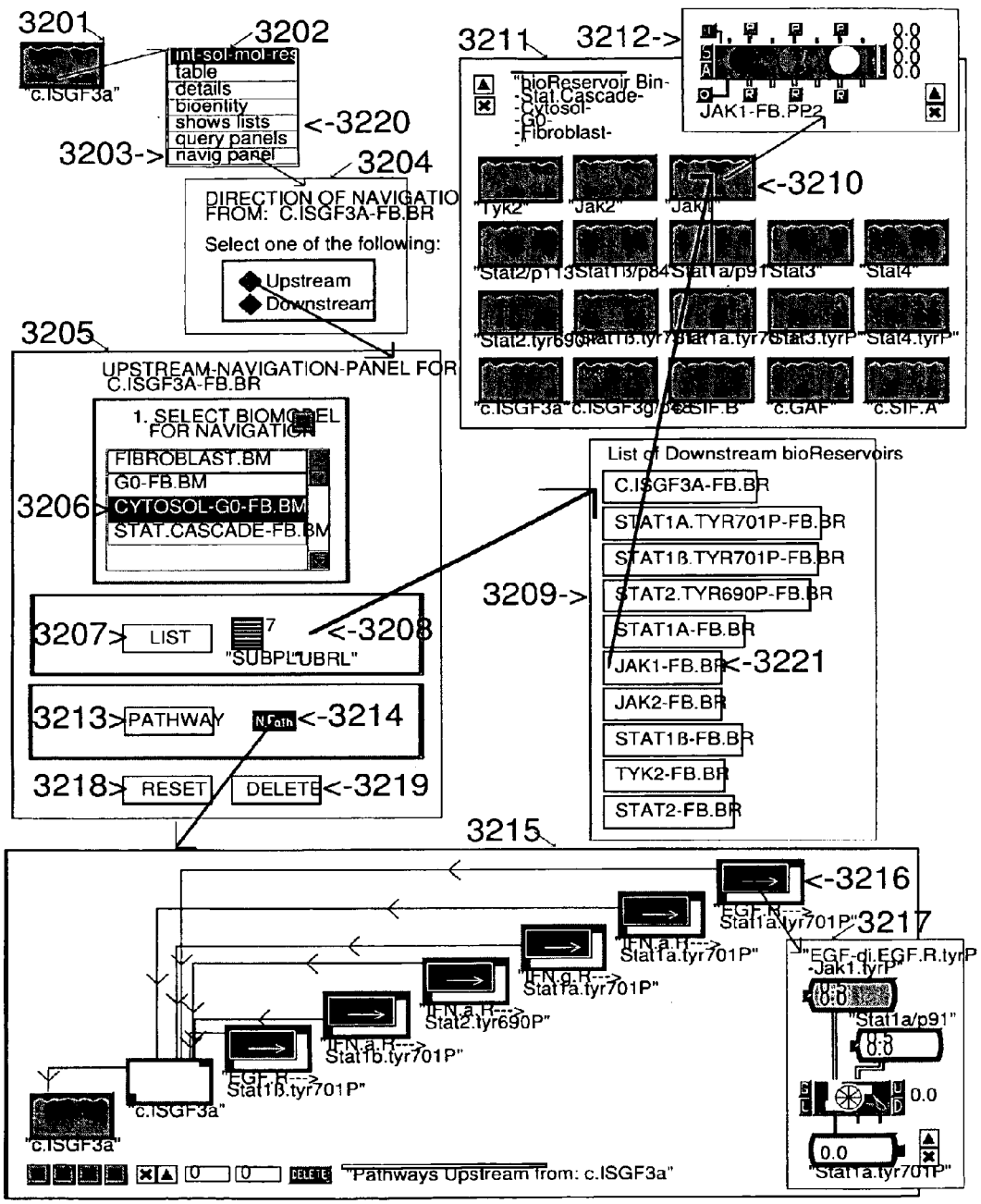
FIG. 32 describes an example of the predefined Navigation Panels that the user can request from any reservoir within the Virtual Model for the dynamic generation of constrained pathways of all the processes that are either upstream or downstream from that reservoir, but which are contained within a compartment selected by the user.
Figure 33:
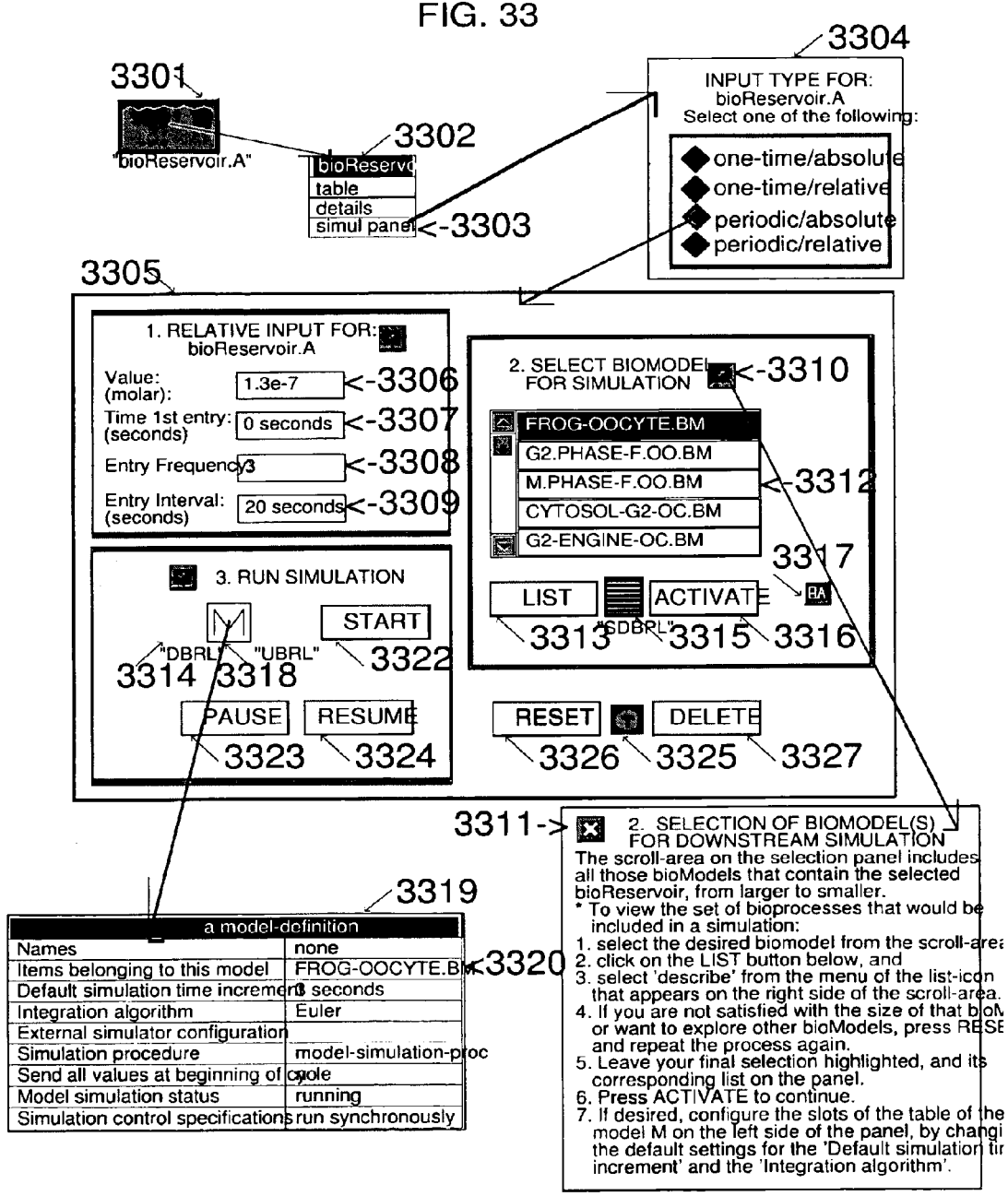
FIG. 33 describes an example of the predefined Simulation Panels that the user can request from any reservoir within the Virtual Model the dynamic generation of constrained pathways and for the control of the dynamic simulation of the kinetics of those pathways.
Figure 34:
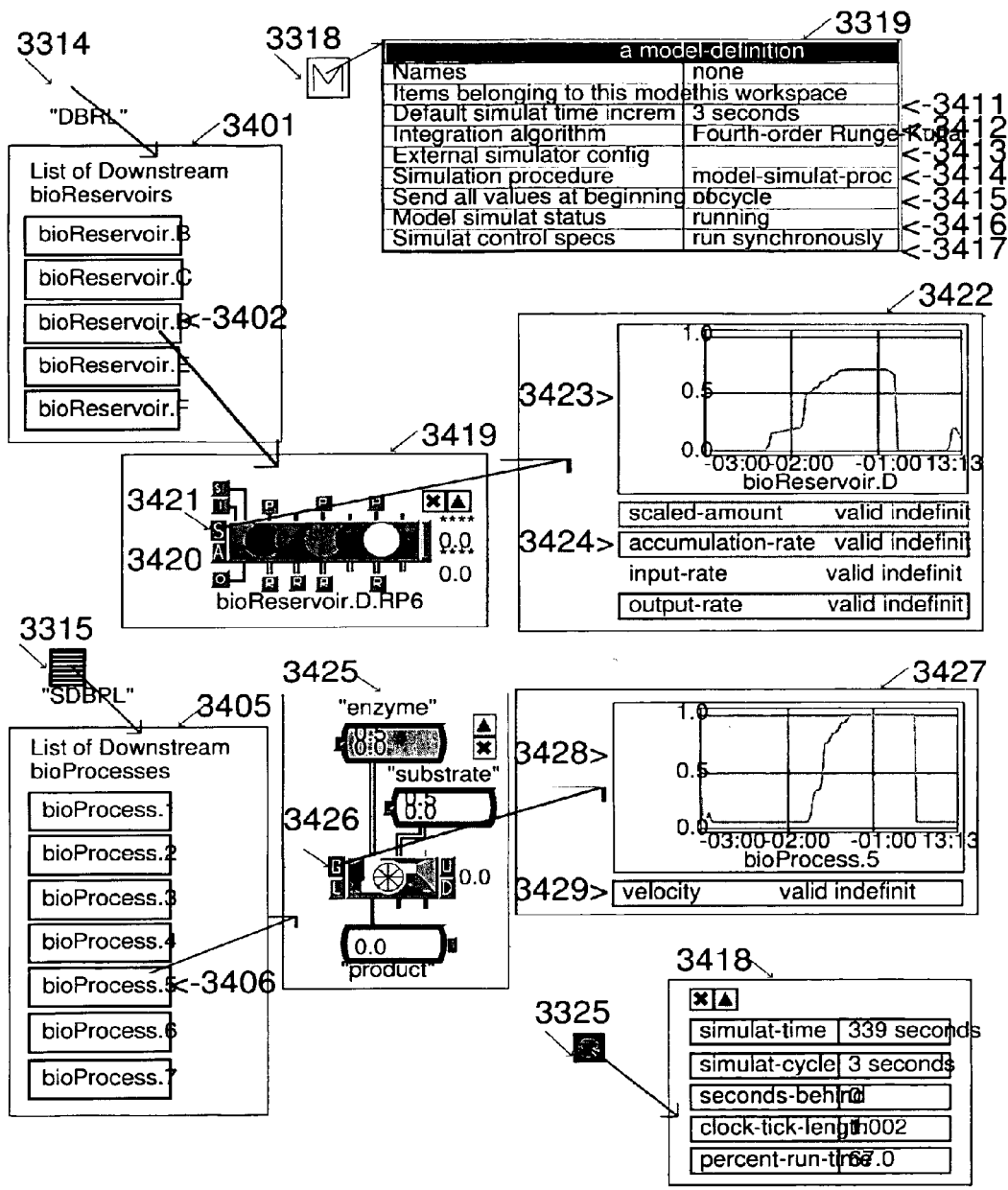
FIG. 34 describes how such simulation can be followed by plotting the time-series of any of the quantitative values of any reservoir and process in the subsystem being simulated.

The following sections will also discuss various of the innovative teachings of this invention that refer to methods and tools used to retrieve and display the stored information and data, encapsulated in graphic and interactive models of complex molecular mechanisms and pathways, allowing to:
  a) interactively navigate through those pathways (FIGS. 31, 32, 35, 36);
  b) perform queries that refer to:
    i) the functional modular structure of the bioEntities involved,
    ii) the position of bioPools downstream or upstream of the bioPool taken as reference,
    iii) to the location in cellular compartments of the processes in which those bioPools of bioEntities participate, or
    iv) any combination of the previous three (FIG. 30); and
  c) dynamically simulate the kinetic interactions between the bioReservoirs and bioProcesses, to mimic the regulation and function of cellular systems (FIGS. 33, 34).

The system of this invention can be implemented layered on top of any advanced real-time object-oriented expert-system development environment or shell that support the methodologies described throughout this application, or it can also be developed in total or in part from scratch, parting from any combination of hardware and software platforms, either already existing or developed for this or other purposes, that provides the capabilities and means required for this implementation. In particular, and for the purpose of illustrating a preferred embodiment of this invention, this system is currently implemented on the Version 3.0 or Version 4.0 of G2 Real-Time Expert System (G2) shell, an object-oriented development and deployment system produced by Gensym Corp. of Cambridge, Mass., and hereinafter referred to as the "Shell", which supports dynamic simulation and temporal reasoning. While many of the underlying capabilities referred to below are common to other static or real-time expert-system development environments, some capabilities may be currently specific for G2, but equivalent capabilities can be expected to be developed by others. This Shell currently runs on several UNIX-based platforms, and it is being extended to Windows NT. For detailed information about the underlying capabilities of this system, Gensym Corp. should be consulted. Among the generic, domain-independent, tools and capabilities provided by the Shell, are:
  a) a proprietary structured natural language, supported by a pop-up text editor, for encoding the object definitions as well as rules, procedures, functions, relations, formulas and values;
  b) a graphical language, supported by an icon editor, based on a visual representation of connected icons, and the capability to associate workspaces with objects, which allows the organization of knowledge at different levels of detail in objects within objects, each represented by icons. The Shell also allows to reason about those iconic objects, their connections, and their locations in the workspace hierarchy. Distant connections (611) can be also maintained, and reasoned about, between objects in different workspaces (602, 603);

c) an inference engine, which interprets relations, functions, rules and procedures;

d) a simulator, which may compute the values for three types of linear or non-linear systems: dependent variables or parameters, from algebraic equations; discrete-state variables or parameters, from difference equations; or continuous-state variables or parameters, from differential equations;

e) a supervisor, which controls operations, such as task prioritization, asynchronous concurrent operations, and real-time task scheduling. Other real-time features include time stamping and validity intervals for data, history-keeping, and real-time data interfaces;

f) a set of predefined generic object classes;

g) several inference methodologies, such as data-driven, event-driven, goal-driven or time-driven capabilities;

h) a graphic user interface development environment to create: user controls such as action buttons, radio buttons, check boxes, and type-in boxes; and graphic displays such as readout-tables, graphs and charts;

i) dynamic messages, to pass information to the developer and user;

j) an inspect facility, with various capabilities used in this invention to allow developers and users to: a) show on a workspace the class hierarchies of any specified class, or all the members of any specified class, as well as the workspace hierarchy of any specified object, or the module hierarchy; b) go to any specified object in the knowledge-base, displaying that object in the center of the screen; c) search for a set of objects that fit a set of specified characteristics; d) highlight or replace any word or expression within any specified class; and e) write to a file the text of the table of attributes of any named item, or of all the items upon a named workspace;

k) a describe facility allows, through the "describe" option of any object to find out the relations between objects or the elements of dynamic lists, making possible to go to the icon of each element of the list, which provides a very useful facility to navigate to objects selected following desired criteria used to fill the list;

l) a tracing and debugging facility facilitates such developer's tasks;

m) the capability of breaking an application into a hierarchy of dependent modules;

n) the message board manage text messages generated by the system, such as configuration error messages, prompts generated at run-time, or explanations requested by the user. The system of this invention also use those facilities to generate messages that show up on the screen to indicate a wide variety of abnormal conditions appearing during modeling or simulation, such as all those expressions used in many procedures listed in the tables as: inform the operator that " . . . "; and o) support for distributed applications by allowing different knowledge-base modules to be located in several workstations. Communication between distributed modules is handled transparently by the Shell's built-in network protocols. A simulation application can be distributed among several workstations when the knowledge-base is distributed as well, allowing computer resources to be adjusted to achieve the necessary performance.

The Shell also provides a predefined object class, called "object-definition", which iconic instances have a table of attributes that provide frames or templates to define the attributes of new classes of objects, such as: a) the names, types and default values for new attributes for that class, which are added to, or overriding, the set of attributes inherited from the superior class; b) an icon specific for that class, which can also be inherited; and c) the stubs that define the types of connections specified for that class. Instances of the so defined classes can be created: a) programmatically, in which case they are transient when created, but can be transferred to a workspace and them be made permanent; or b) by selecting the "create-instance" option from the menu of the object-definition, which creates an iconic instance of that class that sticks to the mouse-pointer and can be dropped by clicking on a workspace. Additional instances can be also created by selecting the "clone" option from the menu of a previously created instance. G2 provides an inference engine that operates on information from different sources, such as: values compiled in the knowledge-base, simulated values, and values received from the user, sensors or other external sources, and responds to events from the user, simulator, or external data servers.

Each variable has an attribute called data-server, which value determines how said variable receives its value. Options are the inference engine (the system gets the value from an specific formula, a generic formula, or a data seek, in that order), the simulator (the system gets the value from an specific simulation formula or a generic simulation formula, in that order), or interfaces to external monitoring devices, databases, or file systems. By default, in he current implementation of this invention, the variables are simulation variables, which means that their data-server is the simulator. A simulation variable may have two values: the current value may be optionally provided by inference engine or one of the interfaces, while the simulated value is provided by the simulator. Or it may have the current value provided by the simulator, in which case it has that such value. In those particular instances where the variables correspond to substances that are being monitored in the reactor, the variables are then set to receive two values, the current measured value, provided by the external sensors through the appropriate interface, and the simulated value. The non-simulated values may be set to expire after a desired period of time, so that the inference engine seeks a new value when needed. Different part of the simulation may run at different times, as desired. The time interval for a simulation may be specified at 4 different levels, in the following order of priorities: each variable may have its own update time; each generic simulation formula may have it own time increment, which applies to the group of variables to which said generic formula applies; the simulation-model has its update interval, which applies to all the variables included in said model; and finally, the whole knowledge-base has a default simulation time increment that applies when none of the other have been specified.

The current implementation of this invention also allows the inclusion of fuzzy-logic statements, such as if (y<6 (+−3))/=(z>4(+−2)). Fuzzy truth expressions are available only in the inference engine, rules, and procedures, while the simulator only uses discrete values. Fuzzy operators comprise: is more true than, is less true than, is not more true than, is not less true than, =, and /=. The fuzzy truth-values are assigned to expressions with a fuzzy truth band in parenthesis, such as: the concentration of receptor1>0.8 (+−0.2). The truth-threshold is set for the inference-engine as a whole. For example, if said threshold is set to 0.7, for the antecedent of a statement to be true it must be greater than or equal to 0.7.

The current implementation of this invention improves the control of the sequential addition of inputs to the reactor, at times and in amounts that are appropriate for the status of the biochemical processes within the reactor. In the example below, it is expected that the concentration of receptor1 expressed on the cell surface, which is available for detection by the receptor1-sensor, is induced at some point by some internal events that happen inside of the cell. Such internal events are the result of complex interactions, induced by the occurrence of some combination of previous events, including those events induced as a result of some previous addition of some other ligand, or any other chemical or combination of chemicals, controlled by one or more other pumps controlling inputs to the reactor. This fine control based on the knowledge about the mechanisms involved, avoids, for example, to add costly ligand1 to the reactor at a time when the cells are not ready to use it, with the likelihood that it will be destroyed by other enzymes, and the risk that it will not be anymore active when the cells become ready to make use of it at a later time. It also could prevent that ligand1 exerts damaging effects to the cells when provided when cells are in the wrong state, as it has been demonstrated for various compounds that induce programmed cell death when signal from said compounds are transmitted to the cell in the absence of other required signals.

An example of such control statement using fuzzy-logic is: "if the average over the last 3 minutes of the concentration of receptor1>0.8 (+−0.2) and the average over the last 3 minutes of the concentration of ligand1<0.5 (+−0.1) and the average over the last 3 minutes of the flow-of-pump-L1=the flow-of-pump-L1 then conclude that the flow-of-pump-L1=the flow-of-pump-L1*1.2 and call adjust-flow-of-pump (flow-of-pump-L1)", wherein: a) the concentration of receptor1 and the concentration of ligand1 are variables coupled to the corresponding sensors for those substances in the reactor, which are monitoring devices external to this system; b) the statement "the average over the last 3 minutes of the flow-of-pump-L1=the flow-of-pump-L1" prevents additional changes in the flow for an specified period of time, to allow the system to adjust to the last changes; and c) adjust-flow-of-pump (flow-of-pump-L1) is a remote procedure call that activates the external device that controls the pump controlling the delivery of ligand1, while passing the value of the variable flow-of-pump-L1 to it.

In an alternative implementation, the bioPools of the components that regulate critical cellular events, or of those that are monitored in the reactor, may have an additional attribute defined as a fuzzy logic parameter, which value can then be accessed by different monitoring/control statements. Fuzzy values may take values from −1.000 true (certainty of being false) to 1.000 true (certainty of being true). The value of said parameter could be provided by a rule, or by a generic or specific formula defined by the modeler, which is dependent on either the measured or simulated value of the corresponding concentration variable, as preferred. For example, said fuzzy attribute may be called "availability", and its value could be provided by a rule, such as: "if the concentration of any substrate S>the Michaelis-constant of S/2(+−the Michaelis-constant of S/2) then conclude that the availability of S is true".

This means that whenever the concentration of any given substrate is greater than or equal to 85% of its Michaelis-constant, with the truth-threshold set to 0.7, then said substrate is considered to be available (availability is 0.7 true) under this setting. If the concentration of said substrate is smaller than 85% of its Michaelis-constant then it is considered to be not available (availability is less than 0.7 true), and if the other conditions have been met, it would cause the flow-of-pump-S to be increased. For example, the monitoring/control rules could then refer to such fuzzy logic variables being true or false, and would allow the modeler to modify the rules for single or groups of bioReservoirs, without the need to modify the control rules, such as: "if the average over the last 3 minutes of the availability of receptor1 is true and the average over the last 3 minutes of the availability of ligand1 is not true and the average over the last 3 minutes of the flow-of-pump-L1=the flow-of-pump-L1 then . . . "

The current implementation of this invention also allows to:
a) use the simulated Virtual Model to entirely take control of when and how the inputs are added to the reactor, (or the outputs, such the culture medium or cells, removed); or
b) synchronize the simulated model to the processes in the reactor, by allowing certain critical measured values from the reactor to provide the values for their corresponding variables in the simulated model, which are then used by other dependent variables and propagated down the simulated model. Such synchronized simulated model is the used as described in a).

The Virtual Model: Domain Specific Knowledge Representation

The computer system, methods, and interfaces that are the objects of this invention can be applied to visually model and quantitatively simulate any type of complex system involving any type of processes and their participants. The set of palettes of prebuilt building blocks provided should reflect the needs of the particular domain in order to facilitate the tasks of the modeler, permitting the basic paradigm of "Clone, Link, Configure and Initialize" and other automated methods. A library of prebuilt Query Panels and other panels, such as Navigation, Simulation and Experiment Panels facilitate the tasks for users to rapidly extract and dynamically use the knowledge and data contained in each specific application. The description that follows is based on one particular domain, that of biochemistry, to illustrate one of the implementations of such computer system, methods, and interfaces. However, similar computer systems, methods, and interfaces can be implemented in a similar manner for domains other that of biochemistry. For example, in a business domain, what in this description is called bioEntities can be substituted with different types of entities, such as employees or projects, and bioProcesses can be substituted with the different activities in which both interact, the bioReactants with the roles they play in such activities, which frequently may involve other participants. Employees are like enzymes, with the more capable having higher rate-constants. Projects are like the substrates, and employees may have higher affinities for some projects, with a likelihood that they will interact in a process in which a quantifiable measure of the outcome, such as quantity or level of quality, will depend on quantifiable measure of the employee, lets say amount of time put on that project and level of specific experience. The bioPool of each employee could represent his/her time, and the max-amount could be set to a day, a month, a year, or any other amount. The Contribution to each project would be the amount of time invested in that role, while the different activities will compete for the time left available.

In the remainder of the description of this invention, the focus will be on biochemical systems, which are complex, hierarchical, heterogeneous and non-linear systems, involving an interplay between the processes of transport, reaction and conformational change. They are regulated by cybernetic flows of information. The system object of this invention uses a kinetic approach to model these chemical and biochemical systems, rather than a thermodynamic interpretation, although thermodynamic variables are also included to allow modification of the behavior of the kinetic system. The current approach, which focus on the amounts of entities, such as concentrations, densities, scaled-amounts, or other quantities of each bioReservoir's bioPool of cells, molecules, or molecular complexes, in a particular state, a; a continuous function of time, and on specific coefficients or rate constants that, in conjunction with the current values of those amounts, define the velocity of a bioProcess's bioEngine, and the rates of consumption of certain bioReactants that participate in such bioProcess or the rates of production of its bioProducts, which are dependent on such velocity and specific stoichiometric coefficients, and which are equivalent to the rates at output and input from their connected bioPool, respectively. This kinetic approach is closer to the way of thinking of biochemists and molecular biologists.

Figure 2:
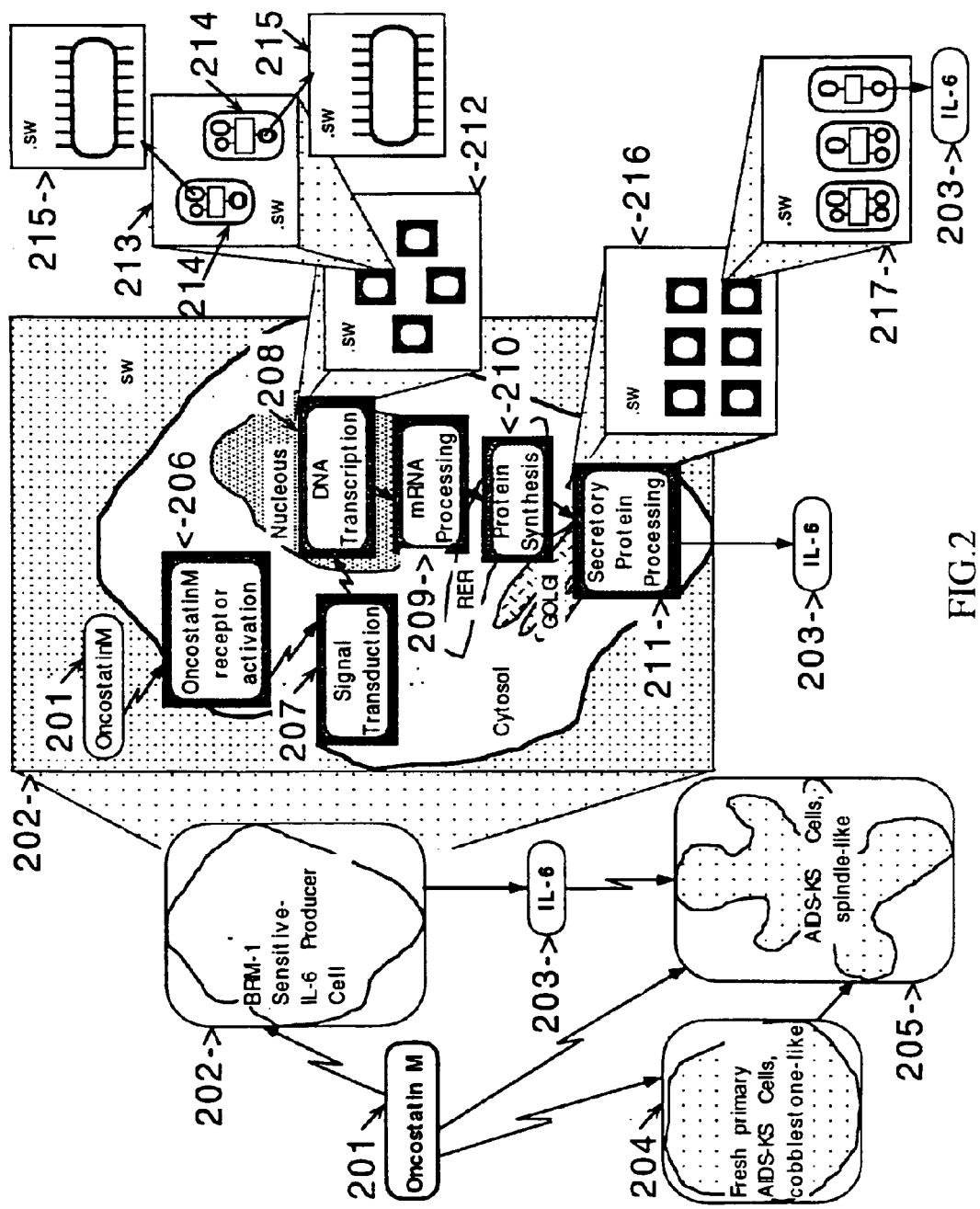
FIG. 2 is a schematic representation of the organization in the system of this invention of the components of the Virtual Models in the domain of cell biology.

The cellular representation in this invention aims to reproduce the fact that function is not inherent in any one component of the cell, but rather emerges from the cooperation of many components, which depend on compartmental organization and functional relationships, and deals with multiple levels of biological and biochemical structural complexity, such as physiological systems, organs and their compartments, cells, subcellular organelles, and molecules. The schematic representation on the left side of FIG. 2 shows an abstraction of the types of molecular and cellular relationships and interactions that are modeled and simulated, with unlimited levels of encapsulation being an important feature exploited by this system, allowing to start dealing with a topic with a high-level representation, and then successively "clicking" into objects of interest, to show the next level of detail. This high-level example, at a low-level of detail, can be summarized by what a biomedical expert could describe as "Oncostatin M (201) is a biological response modifier that induces different responses on different cell types: a) it induces certain classes of cells (202) to secrete the cytokine IL-6 (203); b) it induces differentiation of primary, cobblestone-like AIDS-KS cells (204) into mature spindle-like AIDS-Ks cells (205), which are capable of long-term growth in agar when both Oncostatin M and IL-6 are present". This statement and its graphic representation combine knowledge at very different levels of detail, equivalent to the way human mind can abstract knowledge. For instance, it deals with both molecules and cells as entities as if they were similar types of structures, when in reality that is very far away from the reality. Cells are composed of thousands of different types of molecules. In some cases, an overall pathway within the cell can be known to some extent while in others the mechanism of a biological response may be totally unknown.

Figure 29:
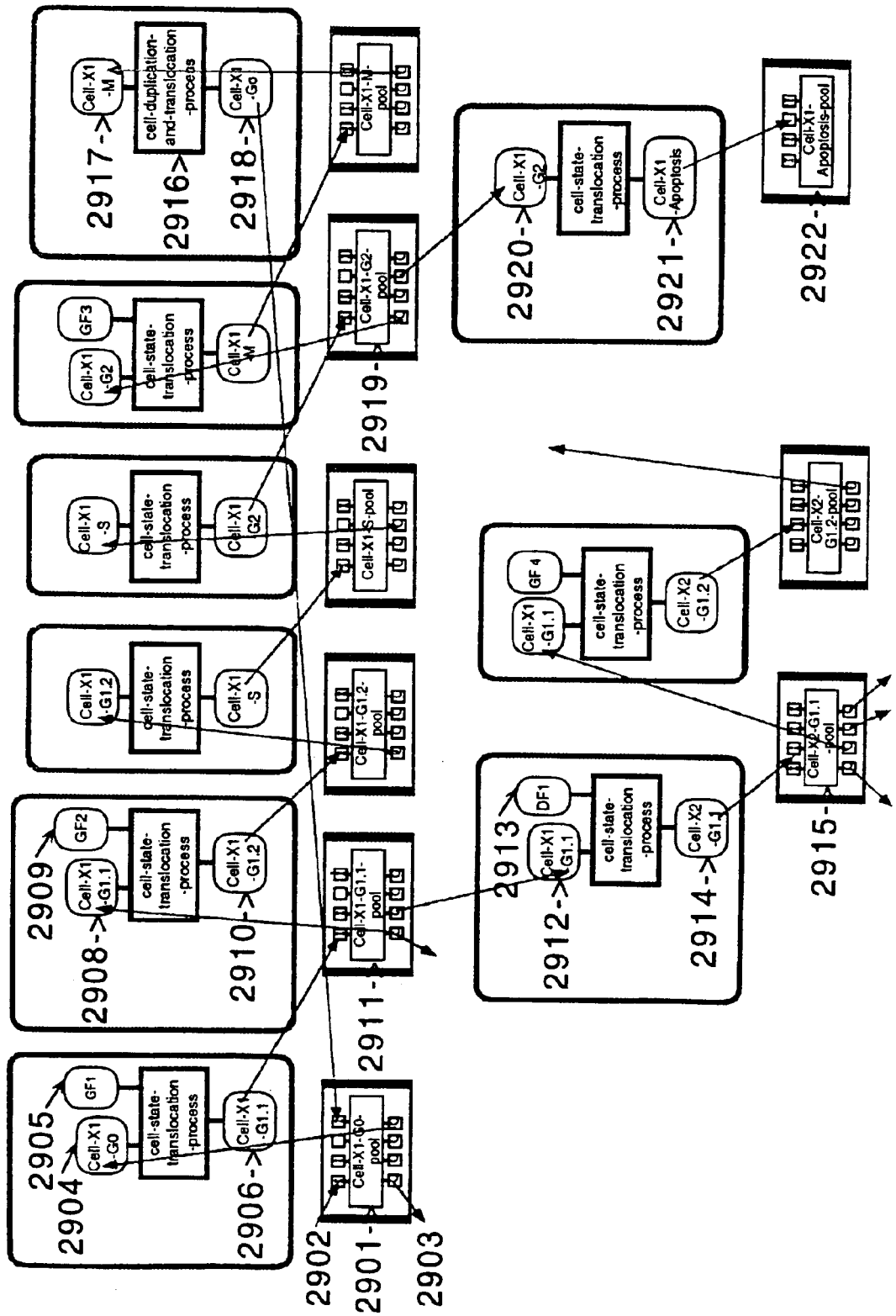
FIG. 29 is a detailed representation of how in this invention pools of cells interact with pools of molecules as reactants of processes, which products are either molecules or cells in a different state.

The system of this invention can be described in very similar terms. On the one side, bioPools of cells and molecules can interact with each other, in any combination in a variety of bioProcesses, as shown in FIG. 29 and described in more detail later. On the other side, as schematically shown on the right side of FIG. 2, the components of each type of cell can be modeled and analyzed at increasing levels of detail, as encapsulated in various layers of bioModels (202–212, 216, 217), until at the end of the layer hierarchy (213) the single bioProcesses (214) are represented, and their associated bioReservoirs (215), which point to their associated bioEntities. In general, the signals transmitted bed the cellular signaling or regulatory pathways progress within each cell in repeated cycles, driven by external and internal events, and sometimes time in a synchronous way, and they may extend from cell to cell, some times activating the producer cell as well. An typical but simplified high-level example of a cellular signaling pathway driven by a certain agonist, such as Ortcostatin M, is shown in FIG. 2 as: agonist (201)->receptor activation (206)->signal transduction (207)->gene transcription (208)->mRNA processing (209)->protein synthesis (210)->secretory protein processing (211)->transport->(receptor activation). By clicking again and again on objects at each level, one can focus on specific areas at the desired level of complexity. In the one example shown in FIG. 2, this multiple encapsulation process has been abstracted. It illustrates a cell-bioProcess in which, after a cell (202) has been activated by Oncostatin M (201), the secretion of interleukin IL-6 (203) is induced, but only after the sequential activation of numerous biological processes (bioProcesses) (214), involving numerous pools (bioPools) (215) of biological entities (bioEntities), contained in bioReservoirs, which are encapsulated in this simplistic example within lower-level bioModels, each representing one the major group of steps of the pathway mentioned earlier (206–211). Clicking on any of these bioModels, such as DNA-transcription (208) or secretory-protein-processing (211) displays their subworkspaces (212 and 216 respectively), which may contain a set of other bioModels (such as those superior to 213 and 217), and the process can be repeated any number of times, until reaching bioModels composed of sets of bioProcesses (214), and their related bioReservoirs (215).

To represent biochemical systems it is necessary to refer to the characteristics and current state of single entities, and at the same time to refer to populations of entities with similar properties. In a small application for molecular genetics, Karp (1989) was only able to represent and implement the overall system either as a network of molecules interacting in a pathway or as a network of variables quantitatively representing the processes in a pathway, as separated systems, but he was not able to integrate both, the description of participating entities and the quantitative processes. This integration is one the teachings of this invention. Furthermore, contrary to the system of this invention, his representation was static and did not include temporal reasoning, having all processes represented as instantaneous reactions.

Figure 3:
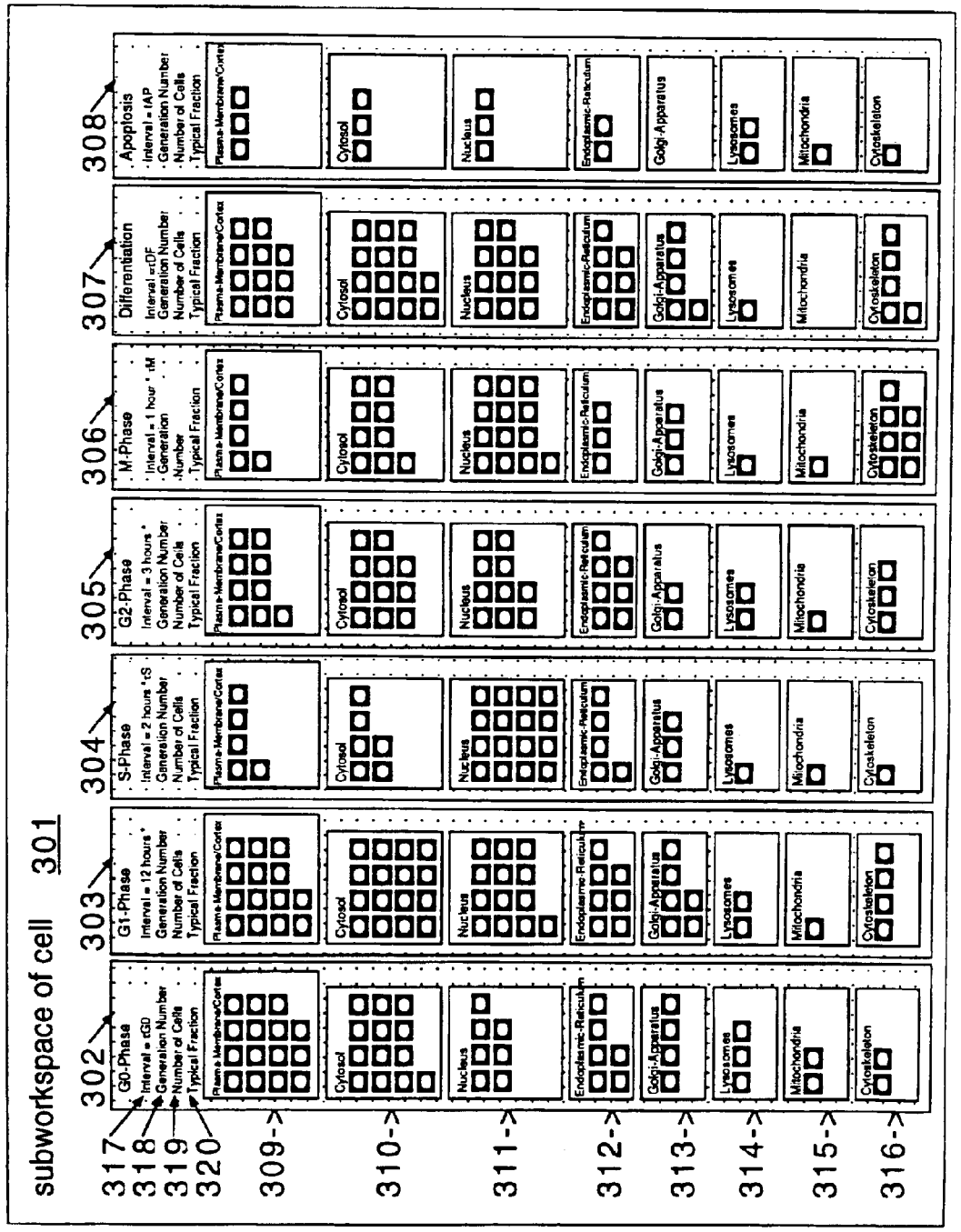
FIG. 3 is a schematic representation of the organization of domain-specific processes in discrete space compartments and time compartments.
Figure 4:
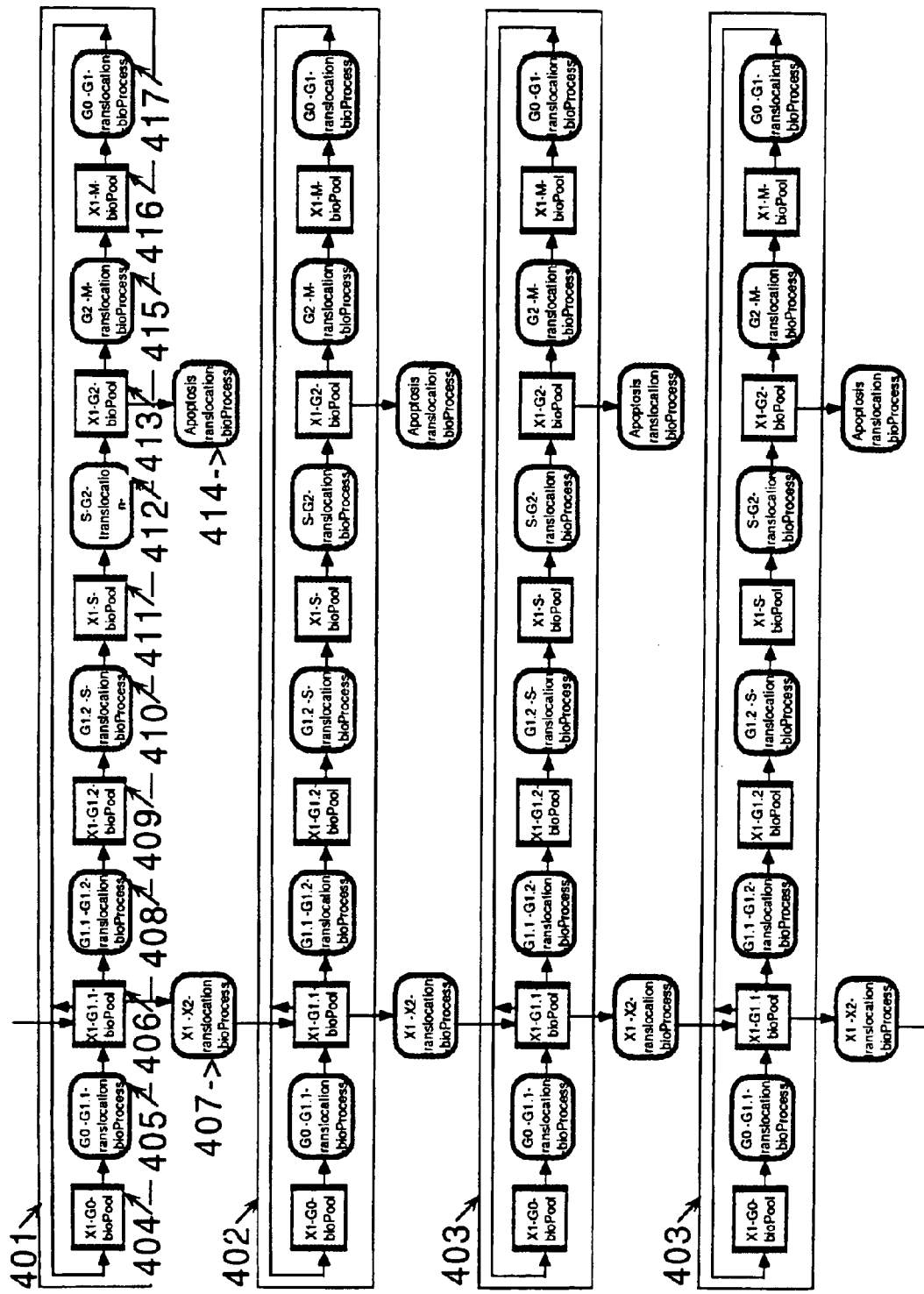
FIG. 4 is a schematic representation of the handling of the dynamics of the progression of populations of cells through different states by means of the sets of pools of cells and processes characteristic of this invention.

FIG. 3 shows how the intermediate submodels are preferentially organized in two types of superior compartments (301) of a cell represented by the different subsequent cell states represented by the cell-phases (302–308), and within each of those the cell-compartments (309–316) that represent the different cell organelles. Each of the cell-phases contain a detailed description of large numbers of components, encapsulated in the different sublayers, and a set of characteristic parameters and time-variant attributes (317–320) that can be used to model the progression of a population of cells through those compartments. That concept is schematically represented in FIG. 4, where some of the cells of that population X1 may keep cycling through those phases (401), as represented by the bioPools of cells in each phase: Go (404), G0.1 (406), G1.2 (409), S (411), G2 (413), and M (416), if some specific and required conditions are met, as specified by their corresponding transitions represented here by the translocation-bioProcesses (405, 408, 410, 412, 415, and 417), or they can exit the cycle if other set of conditions are met (407) and differentiate to another related cell type characterized ty different functions and therefore a different cell cycle (402, 403) or if yet other set of conditions are met (407) they may dye by programmed cell death or apoptosis (414).

A cell-bioModel is represented as a set of bioReservoirs and bioProcesses, systematically organized in the subworkspaces of other bioModels contained in such cell-bioModel, which represent each a separate compartment in time and location, and within those, sets of biologically related processes or pathways. At higher levels of organization, bioProcesses connected to bioReservoirs of cells or cell-interactions are organized into bioModels that represent organ compartments, which are organized into organs, and which are organized into physiological systems. Different cell-bioReservoirs encapsulate zither populations of different cell subsets or populations of the same cell subset in different stages or in different locations. Each of those cell-bioReservoirs makes reference to a predefined cell-bioModel, which has a characteristic phenotype representative of the population of cells encapsulated in that cell-bioReservoir. The different phenotypes may characterize: a) different cell lineages, b) different stages of differentiation within the same cell lineage, or c) cyclical changes in the cell characteristics over time, within the same differentiation stage. Phenotypes are sets of characteristics measurable on intact cells, and the transition of cells from one phenotype to another are represented in the present embodiment of this invention as a translocation of a fraction of the cells from the cell-pool of the former subset to the cell-Pool of the later subset. The events that trigger those transitions may be unknown, but they may be recognized by changes in measurable or functional markers, such as the appearance of a new receptor, the synthesis of DNA, the secretion of specific interleukins, or mitosis, and the relative time in which they appear or disappear may be known, in which case those transitions are time-driven. More specifically, a cell-bioEntity, which is a high-level external representation or description of a cell, may make reference to a cell-bioModel, which as described above is internally characterized by its components and mechanisms, represented by the pathways of bioReservoirs and bioProcesses.

Figure 5:
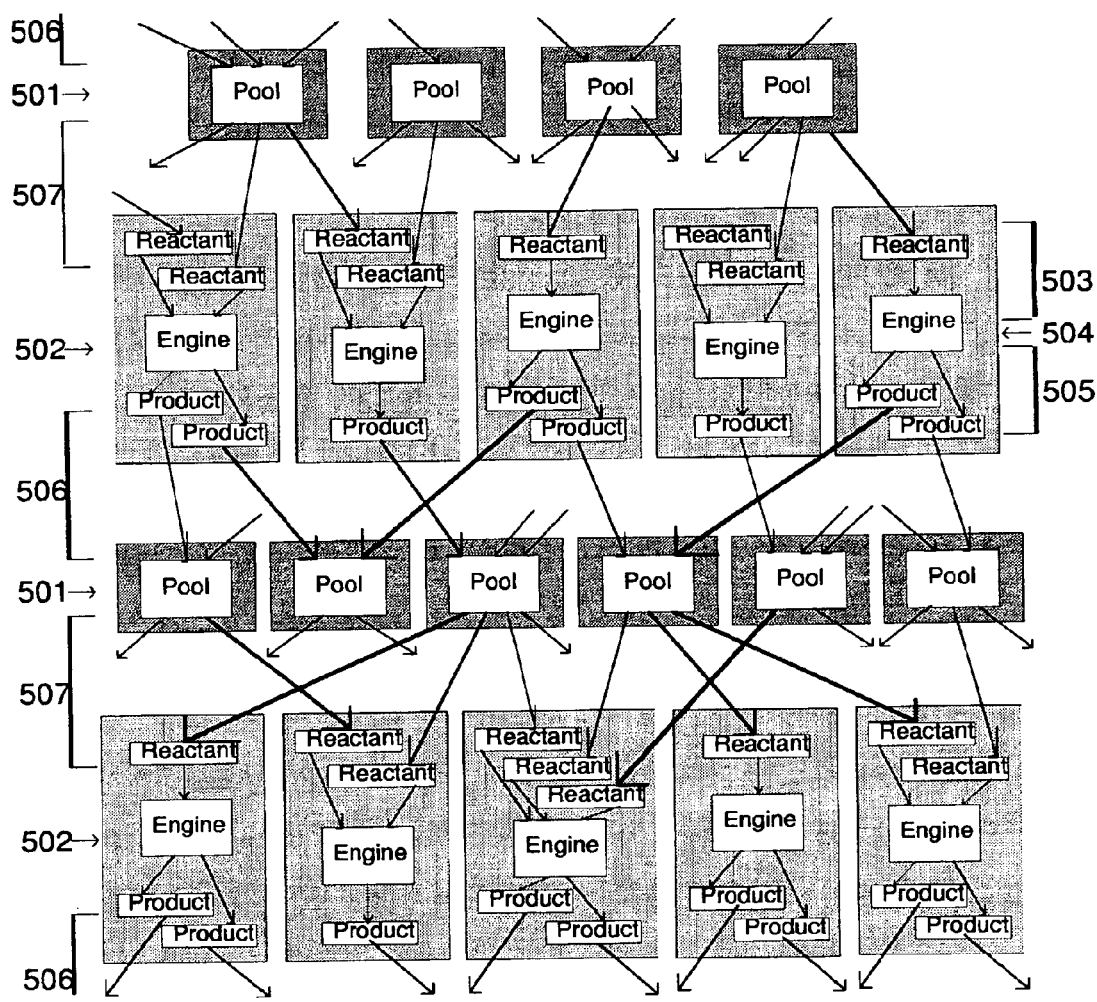
FIG. 5 is a schematic representation of the multiple layers of linked pools of entities and processes the result in the multidimensional pathways characteristic of this invention.

FIG. 5 is a diagrammatic introduction to important concepts upon which much of the processing and reasoning of the current invention is based, where the different layers of arrows represent the direction of flow of information and data. In this system, pathways refer to sets of alternating layers of bioReservoirs and bioProcesses connected to each other to indicate participation of the populations or pool of chemicals represented by the bioReservoirs in the processes represented by the bioProcesses, and to further indicate that the processes represented by the bioProcesses provide inputs to the pool of chemicals represented by the bioReservoirs. The result of those specific connections is a multidimensional network of interconnected biochemical pathways that determines the basic architecture of this system. That basic architecture also defines the resulting network of parameters and variables, and the specific arguments for the generic formulas that provide the values for those variables are determined by those connections. A bioReservoir (501) is an iconic knowledge-structure that encapsulates a bioPool, which refers to a population of a single type of molecule or complex contained within an imaginary space. A chemical process is represented as a bioProcess (502), an iconic knowledge-structure that encapsulates various components, including a bioEngine (504) that controls the Velocity at which the input(s) of the bioProcess, the bioReactant(s) (503), are consumed and the output(s), the bioProduct(s) (505), are produced. BioReactants can also be said to represent the participation of certain number of units of a bioPool as the input to a given bioProcess, and more specifically, the role that such number of units of the bioPool play in such bioProcess. BioProducts can also be said to represent the participation of certain units of a bioPool as output from a given bioProcess Both types of knowledge-structures integrate bioProcesses with bioReservoirs in a complex architecture that allows to model the kind of complex systems and multidimensional pathways that are characteristic of the domain of this invention. In such integrated system, units from the bioPool of a consumable bioReactant are transferred to the bioPool(s) represented by one of its bioProduct(s), at a dynamically computed rate. The term upstream is used hereafter to indicate those bioReservoirs, bioProcesses, or pathways that affect the inputs to a given bioReservoir or bioProcess, while the term downstream is used hereafter to indicate those bioReservoirs, bioProcesses, or pathways that are dependent upon the outputs to a given bioReservoir or bioProcess.

The fast and short-term regulation, such as the temporary inhibition or activation of enzymatic activity is modeled through separate bioPools of the more active and less active (or inactive) forms. Each modification of molecules or complexes that results in qualitative or relevant quantitative changes in their activity or function is represented as transfer of units between those different bioPools. Examples of those modifications include post-translational modifications of proteins, including allosteric changes, such as phosphorylation, isoprenylation, and so on. The slower, long-term, regulation of enzymatic activity is modeled by induction or depression of protein synthesis, which optimizes its concentration for the newly required function. Constitutive enzymes and receptors are considered to be synthesized and degraded at a constant rate, resulting in a constant steady-state level. In regulated molecules environmental signals, such as the extracellular availability of a hormone or growth factor, for instance, may cause the rate of synthesis or expression of new surface receptors to increase X-fold. If the rates of outputs are not concurrently and equally regulated by the same factor, then a new steady-state level will be reached, which may or may not return back to normal after the activating signal ceases. Examples of those modifications include: a) gene mutations and other modifications, b) DNA transcription, c) post-transcriptional splicing and other modifications of RNA, and d) translational regulation.

BioPools, bioReactants, bioEngines, and bioProducts are classes of basic bioObjects that further encapsulate a variety of knowledge structures, including quantitative attributes, parameters and variables, which values, provided by simulation formulas, can be dynamically simulated in real-time. The amount of such units comprised in a bioPool, represented by a variable such as Concentration or other appropriate amount, is dynamically computed at run time, parting from an initial value or basal-amount set by the modeler, or in its absence, from a default value set by the developer. The arguments of the variables of these basic knowledge structures are the output values of certain other variables and/or parameters that are attributes of either: a) the same bioObject instance or b) instances of connected bioObjects of different classes. For instance, an argument for the Consumption-Rate of some bioReactants (503) and for the Production-Rate attribute of any bioProduct (505) is the value of the Velocity attribute of the connected bioEngine (504), while the values of the Contribution attribute of each bioReactant may be arguments of the Velocity attribute of the bioEngine. Furthermore, the Production-Rate (506) of some bioProducts and the Consumption-Rate (507) of some bioReactants are arguments for the Input-Rate and the Output-Rate attributes, respectively, of the bioPool to which they are distantly connected, while the argument of the Contribution of any bioReactant (503) may be the value of the Concentration attribute of the connected bioPool. Told in a different way, note that: a) the flow of data between the bioPool and a bioReactant is bi-directional, involving two variables in the bioPool and two in the bioReactant, b) the flow of data between a bioReactant and the bioEngine is bi-directional, involving two variables in the bioReactant and one in the bioEngine, c) the flow of data between the bioEngine and a bioProduct is unidirectional, involving one variable in the bioEngine and one in the bioProduct, and d) the flow of data between a bioProduct and the bioPool is unidirectional, involving one variable in the bioProduct and one in the bioPool. The reversibility of any binding can be represented in two alternative ways: a) implicitly reflected in the output of a single process, which is the balance in the predominant direction (as represented by the specific or global kinetic parameters), or b) explicitly modeled as two separated processes in the forward and reverse directions.

Figure 11:
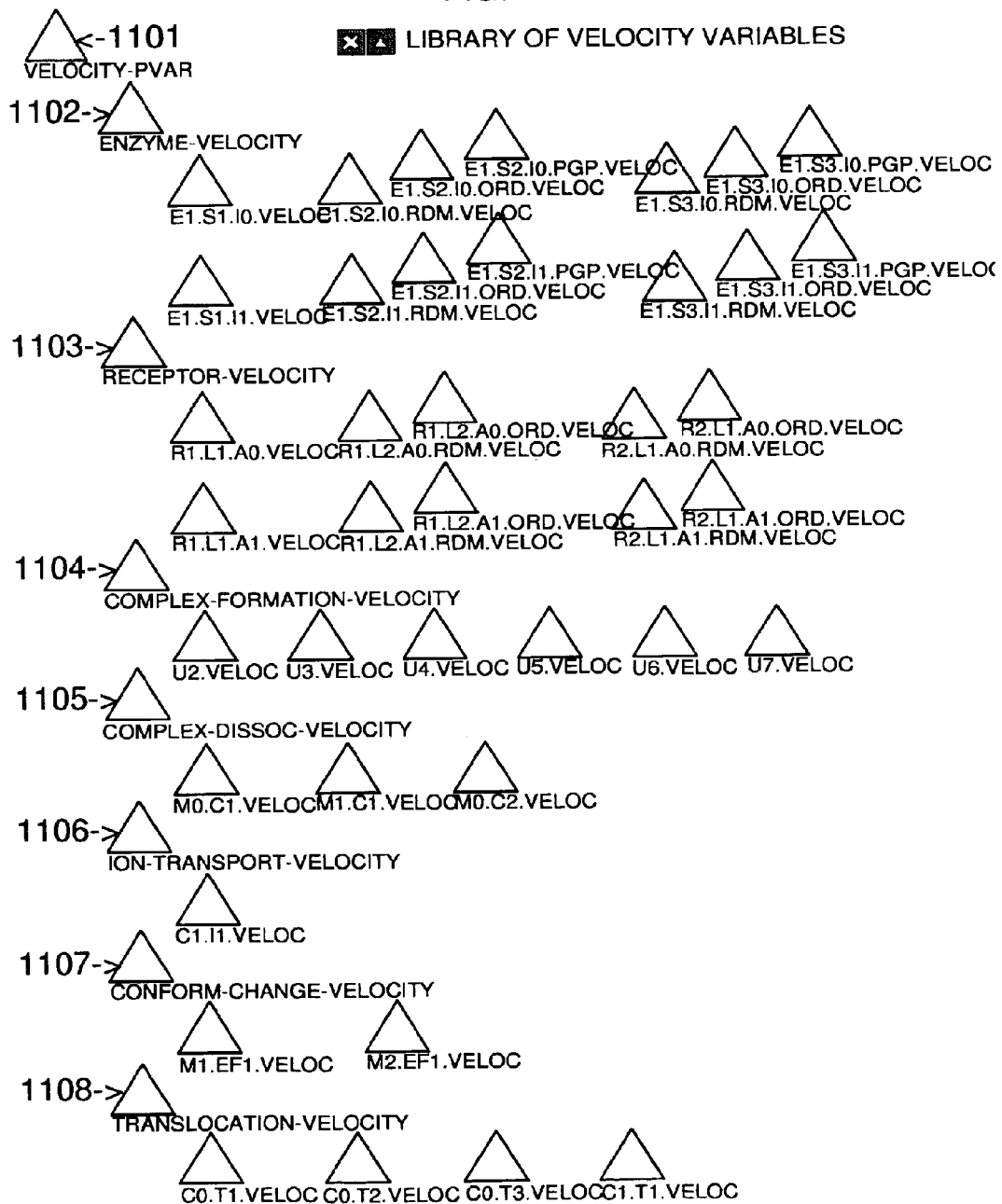
FIG. 11 is a library of predefined classes of variables with associated generic simulation formulas associated with each class available to the modeler virtual models for a specific domain.

The value for the basal-concentration, basal-density or basal-scaled-amount parameters of each population reflects the physiological steady-state value, when the rate of change is equal to 0 or equivalently when the sum of the inputs equals the sum of the outputs. The bioPools representing synthetic agonists, antagonists or inhibitors, such as drugs or toxic substances, have a basal-concentration of 0.0, have no modeled inputs other than the user-entries, and therefore the $\Sigma$ inputs=entry value, at the compartment where it is first introduced. However, it can have several modeled outputs, including the participation in modification-processes and translocation-processes, in addition to the decay term that represents diffusion, degradation and dilution. It is farther constrained in that the $[As]*(m+\Sigma \text{ outputs}) \leq [\text{entry}]$. Concentrations are used in general within classes of bioPools representing soluble entities. However, as it is found empirically in biological systems, most entities are associated with membranes, with large polymerized structures such as the cytoskeleton or the extracellular-matrix, or associated with one or more other macromolecules forming complexes. This means that the concentration of those bound entities is less relevant than the actual amount of those molecules that are available in the appropriate compartment at a given time, and therefore the term density is used to represent units per compartment. Furthermore, most simulations of biological systems are more meaningful in terms of relative amounts or ratios among the quantities of interacting or regulatory molecules, and therefore the alternative variable called scaled-amount is provided for each bioPool, which is dimensionless and does not require units. The values of the Velocity of the generic bioEngines, as provided in the Palettes, are computed using the default generic simulation formulas associated with the subclass of parameter or variable associated with it, which by default are dependent on the values of a set of scaled variables and parameters. The user can however replace them with instances of other velocity-pvar subclasses from the library provided (FIG. 11), each with its associated generic simulation formula based on absolute values (Table 85), depending on the subclass.

Life and growth depends upon closed cycles of mutually dependent interactions. In a constant environment, the proportions of the various constituents settle down to constant values and a steady-state is reached. The steady-state correspond to an optimum state, since the lack of such balanced state would lead to rate-limiting steps. When the environment changes, those proportions move towards new values to achieve again optimum growth in the new environment. The principle underlying this system's dynamic modeling is the network of a combination of state and dependent variables, encapsulated within the structure of the bioObjects contained in the specified bioModel. The bioObjects provided are programmed by default for steady-state modeling. A dynamic simulation is initiated after the introduction of desired perturbations or initial conditions by the user, and the input data initiates a forward chaining, which involves both control and data flow from bioReservoirs to its connected downstream bioProcesses, and from these to their connected downstream bioReservoirs, moving along the bioModel's pathways. Inputs from external control systems or databases can be also forward-chained during run-time. A variety of methods are then used to compute or infer new values for the variables or parameters, derive conclusions and pass on control signals, and trigger action sequences, each as appropriate. The forward and backward associations between bioObjects for runtime execution are either inherent in the connections between the bioObjects or are explicitly configured through the model-blocks. The required integration of dataflow and sequential control mechanisms is accomplished in the currently preferred embodiment while taking advantage of the intuitive capabilities provided by the graphical architecture, where the bioObjects encapsulate the data to which related methods apply, and the parameters and variables are hidden but their values can be displayed. The specific way the bioObjects are connected specify both data flow and control flow, representing sequential or concurrent ordering of procedure execution, and the information needed to execute an algorithm is provided by or inferred from the architecture. The evaluation methods of the bioObjects involved in the simulated pathways execute in parallel during forward chaining, passing along the arguments to the posterior bioObjects, while the arguments of the anterior bioObjects are passed to them.

There are other parameters and variables defined in the system of this invention, which are also involved in the dynamic quantitative simulations of the visually modeled systems, and which can be incorporated in two distinct and alternative forms of simulation reasoning, absolute or scaled, as will be described in more detail under the heading Simulation Mode. For example, the factors that affect and define the transformation rates, such as the catalytic, binding or transfer rate of a bioProcesses (here preferably encapsulated as the Velocity attribute of its bioEngine), are distributed as attributes of the various connected bioObjects and comprise:

a) the quantities of the bioReactants of different types, such as enzymes, substrates, inhibitors, and activators, or receptors, agonists and antagonists, or components of a complex (here preferably encapsulated as the Concentration, Density, or Scaled-Amount attribute of the bioPool connected to each bioReactant, which values can be directly incorporated into the equation that gives the value of such Velocity, when using the absolute reasoning; or indirectly incorporated into the equation that gives the value of the Contribution attribute of each bioReactant, which holds an intermediary scaled value that is incorporated into the equation that gives the value of such Velocity, when using the scaled reasoning);

b) the values of specific kinetic parameters characteristic of each type of bioReactant (here preferably encapsulated as: the Effective-binding-sites attribute of enzymes and receptors, and the Michaelis-constant, Equilibrium-dissociation constant, or equivalent attribute of substrates, ligands, or other bioReactants, respectively, which values can be directly incorporated into the equation that gives the value of such Velocity, when using the absolute reasoning, or, alternatively, the Scaled-Michaelis.k, Scaled-equil.dissoc.k, or equivalent attribute of substrates, ligands, or other bioReactants, respectively, when using the scaled reasoning), or, alternatively, a global kinetic parameter specific for that bioProcess that replaces and represents the combination of the specific parameters of each of the bioReactants of that bioProcess (here preferably encapsulated as the Rate-constant-sec attribute of its bioEngine);

c) the stoichiometric coefficients (here preferably encapsulated as the Stoichiometric-coeff attribute of bioProducts and bioReactants); and d) the effects of environmental conditions such as temperature and pH are also specifically defined as attributes, and can be integrated into the simulation within the appropriate equations.

Chemical and biochemical reactions are continuous processes, within the time intervals that are dependent on the type of reaction and the environmental conditions, with the balance of the reaction favoring in general the forward direction. The strategy used in the system of this invention is to forward chain from inputs values from the user-interface or from databases. In the preferred embodiment of this invention, the specific way the BioObjects are connected specify the sequential or concurrent ordering of data flow, and the parameters of model equations are included as object attributes. Model-generated results may be used as input data for other simulated equations or as events to be used by the inference engine. These dynamic models can also reason about the behavior of variables in the past and project the behavior of variables into the future. Integrating the activities of the different parts of a model system requires the simultaneous solution of a set of non-linear ordinary differential equations and a set of dependent algebraic equations. In this invention, this system takes advantage of the two methods of explicit integration supported by the Shell: either the first-order Euler scheme or the quadratic fourth-order Runge-Kutta scheme, depending of the desired accuracy of the computation. The updates of the different variables may be synchronous or asynchronous, as a result of the variables having equal or different update intervals. The dynamic values of variables or parameters may be displayed in both digital and graphic forms.

The default values and equations provided with the preferred embodiment of this invention, represent an steady-state modeling approach, since biochemical systems are better represented by steady-state than by equilibrium situations. The value for the Basal-Concentration of each population reflects the physiological normal steady-state value, when the rate of change is equal to 0 or equivalently when the sum of the inputs equals the sum of the outputs. Enzymes that are constitutively abundant and in their active form have no effect on the steady-state, since they are not rate limiting. However, regulated enzymes, such as kinases and phosphatases among others, may be constitutive only in their inactive form, and their Concentration influence the Production-Rate of the active form in the same way as the Concentration of a substrate controls its consumption rate. In the system of this invention, the activation-process of an enzyme (u other bioEntity) means consuming units of the bioReservoir of the inactive form and producing units of the bioReservoir of the active form, and therefore it is the same treatment as for any other substrate and product. The regulation of enzymatic activity is modeled through separate bioProcesses that represent forward or feedback inhibition or activation processes or pathways. Each modification of molecules or complexes that results in relevant qualitative or quantitative changes in their function is represented as separate bioEntities, which are represented in separate bioPools and bioProcesses. Examples of those modifications comprise: a) gene mutations and other DNA modifications; b) post-transcriptional splicing and other modifications or degradation of RNA; c) post-translational modifications of proteins, including allosteric changes, phosphorylation, isoprenylation, and so on, and degradation; and d) modifications and degradation of other molecules. Synthesis and degradation, as well as allosteric changes or other modifications, may also be implicitly modeled within the parameters that affect the Velocity of a bioProcess, or as separate mathematical model-blocks connected to to bioPools as inputs or outputs.

The types of inhibitions in which a reversible or irreversible complex is formed, such as the binding of an antagonist to a cell-receptor, and the feedback activation or inhibition by secreted products, are all modeled as separate receptor-processes or complex-formation-processes that compete in the background for the amount of cell-receptor available in the common bioPool, according to their respective affinities and concentrations. The reversibility of any binding is usually not explicitly modeled, unless the complex is a target for regulation, and it is implicitly included in the output that is the balance in the predominant direction (as represented by Ks vs. k1 and k−1).

In fast growing cells or organisms, the dilution factor resulting from cell growth is represented by a parameter m, while in slow growing cells direct enzyme degradation is more important, since the levels of many enzymes in animal cells is controlled bed the balance between enzyme synthesis and degradation, called turnover. The synthesis of an enzyme is represented differently, depending on the available information or the level of detail desired, as a zero-order process or as a first-order or higher-order kinetics, proportional to the concentration of other enzymes or regulators that participate in the complex processes of, while the degradation may have a first-order kinetics proportional to the concentration of enzymes, or or higher-order kinetics, depending also on the concentration of other enzymes or regulators that participate in the regulated degradation process. The total response associated with any particular population of receptors is represented as the maximal activity of a single receptor in the activated state times the receptor density, or scaled-amount, of the bioPool representing that particular compartment.

The system of this invention deals with the "incomplete information" characteristic of biological systems by integrating the scaled or semi-quantitative values with the absolute values, as discussed in later sections. The scaled-valued variables, such as scaled-amount, have values within the 0.0 to 100.0 scale to normalize the diverse ranges of magnitudes involved in the system. The default initial values of the scaled-basal-amounts vary within this range to best represent the knowledge about the physiological steady-state conditions. As a way of examples: a) a value of 100.0 may model an constitutive abundant enzyme, receptor, or complex-subunit in their inactive form, while this value may decrease at run-time as the value(s) of their active or other derivative(s) increase, so that the total remains 100.0; b) a value of 50.0 may model the normal steady-state catalytic concentration for a constitutive regulated active state of an enzyme, or the steady-state concentration of a substrate, binding protein or ligand, or c) a value close to 0.0 may model any highly regulated induced molecule.

Temporal reasoning is important to model and describe the causal mechanisms that drive biological systems. Temporal reasoning is achieved in the system of this invention in several ways:

a) In general, temporal reasoning is implicit in this real-time system during a simulation, when the values of the variables and many of the parameters vary over lime.

b) Entire contents of BioModels, such as those representing the successive phases of the cell cycle, and other time-submodels within those phases, can be activated and deactivated over time by activating or deactivating the subworkspace of such bioModels, as specified within procedures and rules, at pre-specified simulation time intervals, or based on events generated at runtime, such as a certain variable reaching a threshold value, or a combination of both.

c) The subworkspaces of specific bioProcesses can be also programmed to be activated for a specified period of time after their activation, as given by its active ation-hold-interval attribute. This attribute can be a default value or a value entered by the user or as modified at runtime. This is an alternative to having the control of the inactivation of such subworkspace based on another event. It can also be reasoning by a combination of a given time interval or a given event, whatever comes first, or by events triggering the change of the value of the activation-hold-interval attribute in a pre-specified manner. One such option is to provide a tabular function such as by looking.

In the currently preferred embodiment of this invention, a unit of a given chemical entity, referred to as a bioEntity that describes the characteristics and state of a single molecule or complex, is considered a separated knowledge structure, which is referred to as an attribute of a bioReservoir and can be accessed from the menu choices of this and other bioObjects, such as a bioReactant connected to its bioPool, which refers to a population of molecules with the characteristics described for such bioEntity. The information about the characteristics of particular functional states of a given molecule or complex is encoded as separate instances of classes of bioEntity, as will be described in detail in later sections. Different behaviors of each bioEntity are then explicitly defined through the mechanisms represented by the bioProcesses in which bioReactants that make reference to such bioEntity participate. In other words, it can also be said that bioProcesses represent the interactions of a bioPool of such bioEntity with bioPools of other bioEntities, as defined visually through their connected bioReactants or bioProducts. Furthermore, in the present invention, a single molecule can be described in more detail by and ordered and connected set of instances of more elemental bioEntities, referred to as bioEntity-components, which represent molecular functional components such as subunits, domains, motifs, active sites, regulatory sites and mutation sites. The additional levels of detail are implemented in this invention through the encapsulation of subworkspaces. In a similar way, sets of simple molecules can be components of other bioEntities representing a complex, or of a heter-mol-complex. Since unlimited levels of encapsulation are allowed, it is possible to start dealing with a topic with a very general visual overview, and then successively "clicking" into objects of interest, to show the next level of detail.

As will be described in the following sections, in the system of this invention, the methods used to process the application-specific knowledge are separated from the application-specific knowledge itself. The domain-specific but application-independent knowledge is encoded in at least four different forms, characterized by: a) the selection, combination and specific connections of the simple knowledge structures that contain the variables and parameters that quantitatively define this system, within the subworkspace of a prebuilt composite bioObject; b) the selection and design of those simple structures and their interactions as components of the composite structures, which provide for the resulting transparently interconnected architecture underlying this system; c) the selection and definition of the specific attributes of each of those types of structures, which describe and characterize the potential behavior of those structures; and d) the methods in the form of procedures, rules, formulas, functions and relations that together provide for the monitoring, control and execution of the system. On the other hand, the application-specific knowledge is incorporated in at least two different ways: a) the selection, combination in different ways and connections of those prebuilt composite bioObjects and predefined structures; and b) the configuration of the values of the predefined attributes of those selected structures.

Operating Facilities for Developing, Modeling, Navigating, Queering, and Simulating the Virtual Models The following descriptions of objects, tasks, procedures, and the complex processing that follows only highlights some features, and is not meant to substitute for the more detailed descriptions shown by the pseudo-code listings provided as Tables at the end, as referred to within the text when appropriate.

Developer Mode: Definition of the Building Blocks
Domain-Menus

Figure 9:
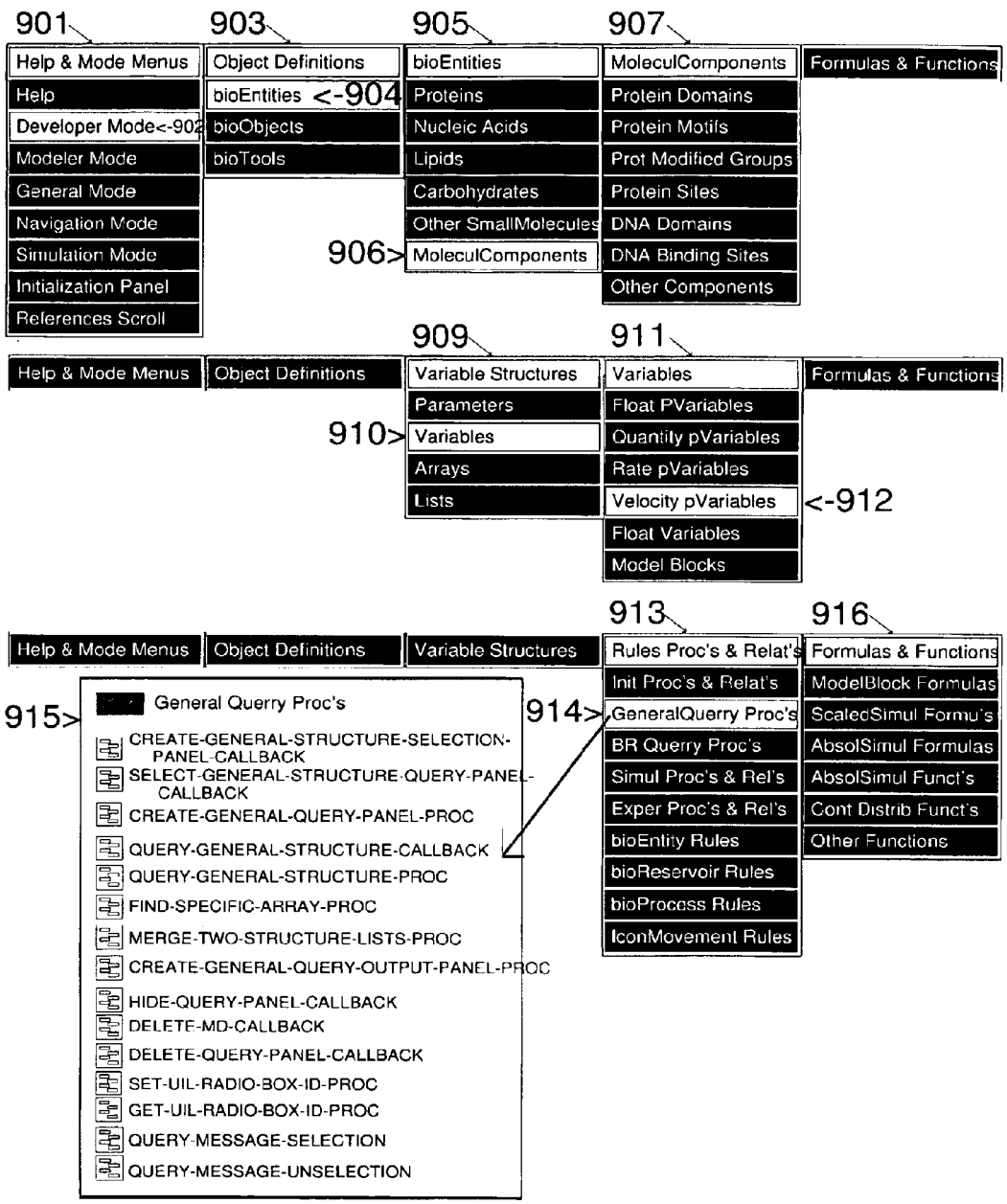
FIG. 9 shows domain menus that allow different types of access to different types of capabilities, for the purpose of modeling or using the virtual models, here focusing on the developer mode that allows developing additional tools.

The Developer Mode can be restricted to only those users with development rights. FIG. 9 shows the domain-menus associated with this mode in this invention, which are shown here in an expanded way to facilitate the discussion of the organization of the definitions of object classes and methods. Selecting the "Help & Mode Menus" head (901) pulls down a set of options, each causing upon selection specific actions, including displaying named workspaces or subworkspaces of named objects, such as panels, palettes or libraries, or generating other walking menus for the window from which it is selected. Selecting Developer Mode (902) displays the additional menu heads: "Object Definitions" (903) with pull down options pointing to major groups of object classes, "Variable Structures" (909), "Rules Proc's & Relat's" (913), and "Formulas & Functions"(916). Domain-menus include walking menus, and whenever an option has additional suboptions then a new pull-down menu is created and displayed in the next adjacent menu slot. For example, selecting "bioEntities" (904) displays the pull-down menu headed by "bioEntities" (905), which options refer to different subclasses of the class bioEntity, and further selecting "MoleculComponents" (906) displays the one headed by "MoleculComponents" (907), and further selecting "Protein Motifs" (908) displays a workspace that contains the definitions of the class protein-motif and all its subclasses. In a similar way, selecting "Variable Structures" (909) and further "Variables" (910) displays the menu headed "Variables" (911), and further selecting "Velocity pVariables" (912) displays the workspace shown in FIG. 11 containing the definitions of the class velocity-pVar and its various layers of subclasses. In other cases options bring directly to a workspace, such as for "Rules Proc's & Relat's"-

>"GeneralQuery Proc's" (914), which directly displays the workspace (915) that contains the definitions of some of the procedures needed for the processing of General Queries.

General Groups and High-Level Classes

The classification and definitions of the object classes is now described. Table 1 shows the different classes of objects and groups of tools and methods comprised in this invention, which are all knowledge structures implemented as objects. Those tools and methods are preferably organized into major groups, each comprising several object classes, which may each further comprise several levels of more specific subclasses, to be discussed in more detail in the following sections. The class bioTool (Table 21), a subclass of the class object defined within the Shell, is defined to include a variety of auxiliary iconic structures used in this invention, and has no additional attributes. Each top class of those groups is a subclass of one of the generic classes of objects defined within the Shell, from which they inherit a set of attributes and capabilities. Several of those capabilities may be proprietary technology specific for that Shell. For further details, the reader is referred to the G2 Reference Manual Version 3.0 or Version 4.0 and other documentation produced by Gensym Corp., which are here included by reference. In this filing, only those Shell-defined attributes that are necessary to describe this invention will be considered, and these attributes or their equivalents may be common to other development environments. Other attributes and capabilities not mentioned here may, however, facilitate the development tasks and improve the performance of this invention. In the following discussion, attention will be focused mainly on those attributes incrementally defined for each subclass.

There are several other basic classes defined within the Shell that the system of this invention uses without relevant modifications. One of those are workspaces, which are items used to hold and display other items, and which attributes include names, user restrictions, margin, border, background, and module assignment. Workspaces can be independent higher-level workspaces, or subworkspaces subordinated to objects. Subworkspaces may also have the capability of being activatable, if so defined in their superior object, which means that the objects upon them are only active and accessible to the inference engine and the simulator when such subworkspace is activated. Other capabilities of the Shell, such as flashing of the icons, changing colors, or rotation of specific patterns can be used to animate a simulation and to indicate relevant events, such as showing the bioObjects that are activated, or which variables' values are out of range, and many other applications.

The object class definitions listed in the Tables include only those attributes which provide new and relevant information, such as: a) Class name, b) Superior class, and c) and Attributes specific to class. Other attributes are mentioned only when relevant or modified, following the following rules:

"Capabilities and restrictions" describes which additional capabilities or restrictions apply to all the instances of all the subclasses of that class The Shell-defined capabilities used in the current implementation of this invention comprise: "activatable-subworkspace", for the classes bioReservoir, bioProcess, time-compartment, and hold-bin; and "subworkspace-connection-post" for the class model-box.

"Class restrictions" defines which menu options and other non-menu choices are available or disallowed, or which attributes are visible in the table, in each particular user mode for all the instances of all the subclasses of the class for which they are defined. The Shell-defined non-menu choices include: "move-object", . . . The Shell-defined menu choices include: "table", "name", "transfer", "create-subworkspace", "change-size", "describe", "disable", "delete", "rotate-reflect", . . .

"Inherited attributes" are usually not be listed in the Tables, since they can be deduced by adding up the listings of "attributes specific to class" of each of the superior classes. On occasions, however, inherited attributes may be listed for the purpose of summarizing disperse definitions. When an attribute is defined in more than one object-definition, the most proximal (or lower-level) definition overrides the others.

"Menu option" refer to whether the name of the object class appears as an option within the new-object selection from the menu of workspaces, or with other words, whether the class can have instances (if the value of this attribute is "a final menu choice") or whether the class is only a superior to other subclasses (if the value of this attribute is "not a final menu choice"). This attribute will be only listed for those high-level classes that are "not a final menu choice", and it is otherwise assumed that the class is "a final menu choice."

"Stubs" define each of the connection stubs for that class and their position on the class' icon, and optionally the direction of flow and/or the name of the connection port. The stubs can be inherited from superior classes, in which case the value of this attribute will be inherited, or the class may have no defined connections and the value is none, and in either case this attribute may not be listed. If it is not listed and the superior class has defined stubs, then it is assumed that the stubs are inherited, and if the superior class has no defined stubs, then it is assumed that the value of this attribute is none.

"Icon description" defines the iconic appearance of the icon characteristic of all the instances of the class. The icon can be inherited or be specific for that class, and usually contain differently colored layers, or color-regions, which color may change dynamically at run-time, to visualize the state of the objects, such as selected, or of their subworkspaces, such as activated. The detailed description of the icons is not included in the Appendix to save space, and in most occasions it will be simply referred to as the <name of the class>-pattern, followed by its dimensions (to have a reference for the stubs), and by the color-regions, which may be referred to by rules and/or procedures.

In addition to an attribute table and sometimes a subworkspace, each iconic object has an associated menu with a set of options. Some of those menu options, and options defined within the Shell, perform standard tasks common to all objects, such as: change-size, clone, color, delete, describe, disable, go-to-subworkspace, move, and name. Many of those tasks are self-explanatory and will not be further described. Other novel and domain-specific menu options are defined in this invention as user-menu-choices to provide interactive access by the user to automatic or semi-automatic tasks related to the configuration of the knowledge structures and to requests diverse forms of processing and display of such knowledge. User-menu-choices are defined for the specific class named in its applicable class attribute, as in the example shown in Table 25. They appear as options in the menu associated with the icon of every instance of every subclass of said applicable class, unless a class restriction is defined for any of those classes to exclude that option from the menu in any particular user mode. Selecting any particular options triggers one or more actions. All those domain-specific tasks provide a highly interactive user-interface and are important teachings of this invention. Those options and the methods invoked upon their selection will be discussed in later sections. Here we will focus on the definitions of all object classes and on the description of their attributes.

Variable Structures:

Variables and Parameters:

In the present invention, the quantitative attributes of object classes may be defined as simple attributes, or as instances of subclasses of parameters or variables. The values of simple attributes can be modified through rules, procedures, or other actions of the inference engine. The values for the variable and parameters may be provided from different sources. The Shell's simulator is used in the current implementation to compute the simulated values of variables and parameters that are integral parts of the bioReservoirs and bioProcesses, as described later, including state variables. Those values are preferentially provided by generic simulation formulas, although modelers may also provide specific simulation formulas for specific variables. Users can also input values for the simulator through the input-panels described below, and the program can also update values based on values received from other sources, so that values from different sources are integrated. To standardize the units used during a simulation, the absolute values are preferentially entered in Molar, M/sec, moles/liter, or seconds, as pertinent.

There are large number of subclasses of parameters and variables involved in this system, as defined in Tables 2 through 15. Only a few of them are used as independent parameters or variables represented by their icon, and usually they have auxiliary functions, such as the x-pos and y-pos (Table 3) used to aid in the graphic drawing of pathways on a workspace. In this invention, most parameters and variables are implemented as attributes of the various classes of bioObjects, or other objects such as model-blocks (FIG. 19, Table 22) or inference blocks (Table 23), as well as attributes of other variables. Aside from the high-level classes, most of the other subclasses do not have additional specific attributes, but many have distinctive default settings, as specified in their listed definitions. The separated subclasses allow to attach specific methods to each class, either in the form of formulas, or by referring to all members of the class in rules, procedures or other actions. Since it would be tedious and repetitious to discuss each subclass of parameter and variable that are referred to in the system of this invention, listed definitions of other objects, their definitions are instead listed in lumped groups by similarities, and only a few that are representative or important to the understanding of the operation of the overall system will be discussed in the relevant section.

In the currently preferred embodiment, domain-specific variables and parameters are subclasses of various subclasses of the Shell's class parameter, such as float-parameter, integer-parameter or symbolic-parameter, text-parameter or truth-parameter. Those that represent parameters in this domain are grouped under the domain subclasses int-par (Table 3) or float-par (Tables 48), depending on their value types. Those that represent variables in this domain are grouped under the domain subclass float-pvar (Tables 9–12), which are subclasses of float-parameter. The reason for these discrepancies is that In the Shell's classes "parameter" and "variable" do not fully correspond to the common concepts of variables and parameters and are simply two different data structures with different constraints and capabilities. This invention also defines a set of subclasses of float-var (Tables 13–15), a subclass of the Shell's class float-variable, as an alternative for domain attributes such as Concentration, Density and Velocity (which by default are represented by pVars, as discussed in more detail in the next paragraph) or parameters such as a variety of kinetic constants (which by default are represented by simple float attributes).

The Shell's "variables" have capabilities important for the implementation of this invention, such as: a) allowing the user to set a desired instance, lets say the concentration or density attribute of a bioPool representing an entity the quantity of which is monitored in a reactor, to receive a measured value from the external monitoring sensor while its simulated value is being simulated in parallel, based on the Virtual Model specifications, and then by using inference rules to monitor either value or both values, and to compare them to a specified threshold or range or to each other, and to initiate some control actions to regulate the reactor system monitored by the sensor; and b) allowing the user to define simulation or general formulas specific for a particular instance of a variable by writing the formula directly in the corresponding slot for the formula in the instance's simulation subtable. Because the Shell's variables are larger structures that require more memory space, this invention uses by default subclasses of the Shell's parameter as attributes of bioObjects. However, alternative but equivalent subclasses of variables are also provided, allowing the user to delete the default parameter and replace it with the equivalent variable, allowing the user to then write any customized specific simulation (values provided by the simulator) or general (values provided by the inference engine) formula to model that particular variable. Differences between the Shell's parameters and variables include: a) parameters do not have slots for specific formulas but can receive values from generic formulas that apply to instances of a class; and b) a variable may have an initial value and two current values, the inferred and the simulated values, while a parameter have only one value that can be either inferred or simulated; c) the inferred value of a variable can be set to expire after a time interval and therefore a variable may have no value (it should not expire when the value is used by the simulator), while a parameter always has a value; c) variables can backward-chain to seek its values, while parameters cannot; and d) variables cannot be directly referenced by procedures. When using a different Shell with parameters and variables with different attributes and capabilities, some modifications may be necessary. Examples of default instances are shown in FIGS. 13 through 17 (and their definitions in the indicated Tables) for variables such as: velocity-var (1301, Table 13), model-block-output-var (1428, Table 14), and model-block-var (1430, Table 14), and for parameters such as: basal-density-par (1506, Table 7), scaling-density-par (1508, Table 6), density-entry-pvar (1510, Table 9), scaled-entry-pvar (1512, Table 9), input-rate-pvar (1514, Table 11), density-pvar (1518, Table 10), basal-conc-par (1522, Table 7), conc-pvar (1524, Table 10), contribution-pvar (1615, Table 10), consum-rate-pvar (1617, Table 11), binding-rate-pvar (1706, Table 11), time-delay-par (1711, Table 8), ph-par (1713, Table 5), ph-factor-par (1715, Table 5), and produc-rate-pvar (1723, Table 11).

The details of a variable are here discussed in reference to FIG. 10, where the attribute table (1001) of velocity-var shows the attribute slots provided to enter specific information to define and control each particular instance, such as the methods of inference allowed (1002); its name (1003); data type allowed (1004); optional initial value (1005); last recorded value (1006); the number of data points or the time period for keeping the values of the most recent history of that variable, together with the time stamps at which those values were collected (1007); the period of time for which each value is valid (1008); the formula slot where the user may optionally write a specific formula for the inferred value of that particular instance (1009); details about its optional simulated value (1010), which may include an additional simulation subtable (1011), which contains slots that allow the user to optionally control the simulation of that particular instance, such as the time increment for update (1012), a specific simulation formula (1013), and the number of data points or the time period of values to be stored (1014); the main table also provides for the initial value for simulation (1015); whether its value is provided by the inference engine, any simulator or external interfaced sources, such as sensors or databases (1016), and the default update interval (1017).

To add a variable or parameter of the desired class as an attribute of a bioObject, the modeler can select the "add subtable" from the menu that appears when clicking on the slot of the value that attribute, and then navigate through successive menus to follow the hierarchy of subclasses of variable or parameter, in this case of float-variable, until the desired subclass can be selected, which results in the creation of an instance of that subclass that gives the value to the attribute from which slot it was requested. To replace an existing variable or parameter for another, the existing one is first deleted, and then the sequence above is followed. To define the specific simulation formula the same process has to be followed. Some examples of such attributes comprise:

Another example of why and how specific instances of the default parameters are to be substituted when needed for the larger variables is discussed here. The Velocity attribute (1705) of an instance (1701) of a subclass of bioEngine is an instance (1701) of a subclass of rate-pvar, binding-rate-pvar, which value is simulated according to a generic-simulation-formula that refers to such subclass (example in Table 83) and represents a mathematical model for all reactions of such type. The Velocity attribute is allowed more flexibility in this invention because there are not only many types of processes, depending on the participants in each case, but there are also many opinions about what is the most fitting equation to compute the Velocity of each type. In addition, there are two types of simulation provided by the system of this invention, as discussed under the Simulation Mode heading. One is semi-quantitative, using scaled (dimensionless) variables, and the other uses variables with absolute values. The currently preferred embodiment of this invention is defined by default with a matching set of scaled variables, each with its associated simulation formula. For the Velocity attribute, depending on the bioEngine subclass, different subclasses of rate-pvar (Table 11) are used, such as: catalytic-rate-pvar, binding-rate-pvar, dissociation-rate-pvar, modification-rate-pvar, or transfer-rate-pvar, with such scaled-values based formulas. However, the modeler can substitute those with an appropriate instance of an alternative set of more specific subclasses of velocity-pvar (Table 12), such as those shown in FIG. 11 with more specific absolute value based formulas. Each subclass of velocity-pvar (1101), such as: enzyme-velocity (1102), receptor-velocity (1103), complex-formation-velocity (1104), complex-dissoc-velocity (1105), ion-transport-velocity (1106), conform-change-velocity (1107), and translocation-velocity, (1108), has more specific subclasses, and each of those subclasses has its associated more specific absolute value based simulation formula. The nomenclature used for naming each subclass indicates all the participating components and the reaction type. For example, 1E.2S.1I.ORD.velocity is meant for a bioengine. 1E.2S.1I, which means that its icon has at the top four specific stubs connected to one enzyme.r, two substrate.r and one inhibitor.r, and the formula for that instance reflects the fact that the reaction happens in an ordered fashion, that is substrate1.r binds before substrate2.r, and the inhibitor is a competitive inhibitor of the first substrate. The subclasses of velocity-pvar, and their associated simulation formulas, represent only the more typical cases, but they are only a fraction of all possible cases that user may need to represent. Therefore, another alternative is provided for the modeler to write the simulation formula that most appropriately fits the system to be modeled, substituting with an instance of the class velocity-var described above.

The system of this invention utilizes the history keeping capability for the values of relevant parameters and variables, as specified in their listed definitions, to graph the time-line or to reason about those historic values. The user can decide to display those values in charts or other display forms. The historic values, as well as their maximum, minimum, average values, or rates of change over time can be not only be displayed, but also used by the user in different ways, such as storing them in external files or databases, allowing the values to be further analyzed.

Arrays and Lists

Arrays and lists are structures that hold a number of items or values in an ordered way. The subclasses of arrays (Tables 16 and 17) and lists (Tables 18–20) have all the characteristics of their parent classes, as defined in the Shell, and they may have additional attributes within the system of this invention, as specified in their definitions. Arrays are indexed, and therefore each of its elements can be directly referred to by referring to its index, while lists may be indexed or not. The length of arrays has to be predetermined, before additional values are added, while the length of lists increase automatically, as more elements are added. However, the current implementation of this invention uses arrays to permanently store the transient values of its elements by setting the initial-values attribute of an array equal to the desired values to be stored, separated by commas, which may be the current values of the elements of that particular array at any point in time, or the elements of an auxiliary list, as described in the section describing the methods for queries.

One of the classes of arrays used in the current invention is query-array (Table 16), a subclass of symbol-array, which instances are created by the query initialization procedures. For example, one of the uses of a set of query arrays is for storage in each of all the instances of each class of molecular components in the Virtual Model (Table 16), as described later. The instances of references-array (Table 17), a subclass of text-array, refer to sets of instances of the class reference-block (Table 34) and may be attributes of instances of bioEntities, bioReservoirs or bioProcesses, or bioModels, being used as described below. Furthermore, instances of the Shell's class float-array can be used to store all the values of a desired parameter or variable during a monitoring session or a simulation run, which can then be stored to a file or passed to another external program or device for further analysis or processing.

Bioitem-list (Table 20) is a subclass of the Shell's class item-list with no additional attributes. The different subclasses of bioitem-list (Table 20) are restricted to instances of particular classes of objects, such as experiment-selections, bioReservoirs, and bioProcesses. This invention uses lists in various ways, including: a) as transient auxiliary structures to process information at run-time, not visible to the users, such as instances of query-list (Table 18), a subclass of symbol-list, are used as auxiliary structures in the creation of query-arrays, and instances of scroll-text-list (Table 19), a subclass of text-list, are used as auxiliary structures in the creation of scroll-areas; and b) as auxiliary structures with their icons upon a workspace, which in addition to be used to process information at run-time they are available to the user for inspection, such as those shown in FIGS. 31 through 35 listing upstream and downstream bioReservoirs and bioProcesses, in reference to the bioObjects from which they where requested. Clicking on those icons by the user causes the display of the elements of the list, providing direct access to the objects listed and to the attribute table of the objects listed.

BioTools

Class Model-Block

Figure 19:
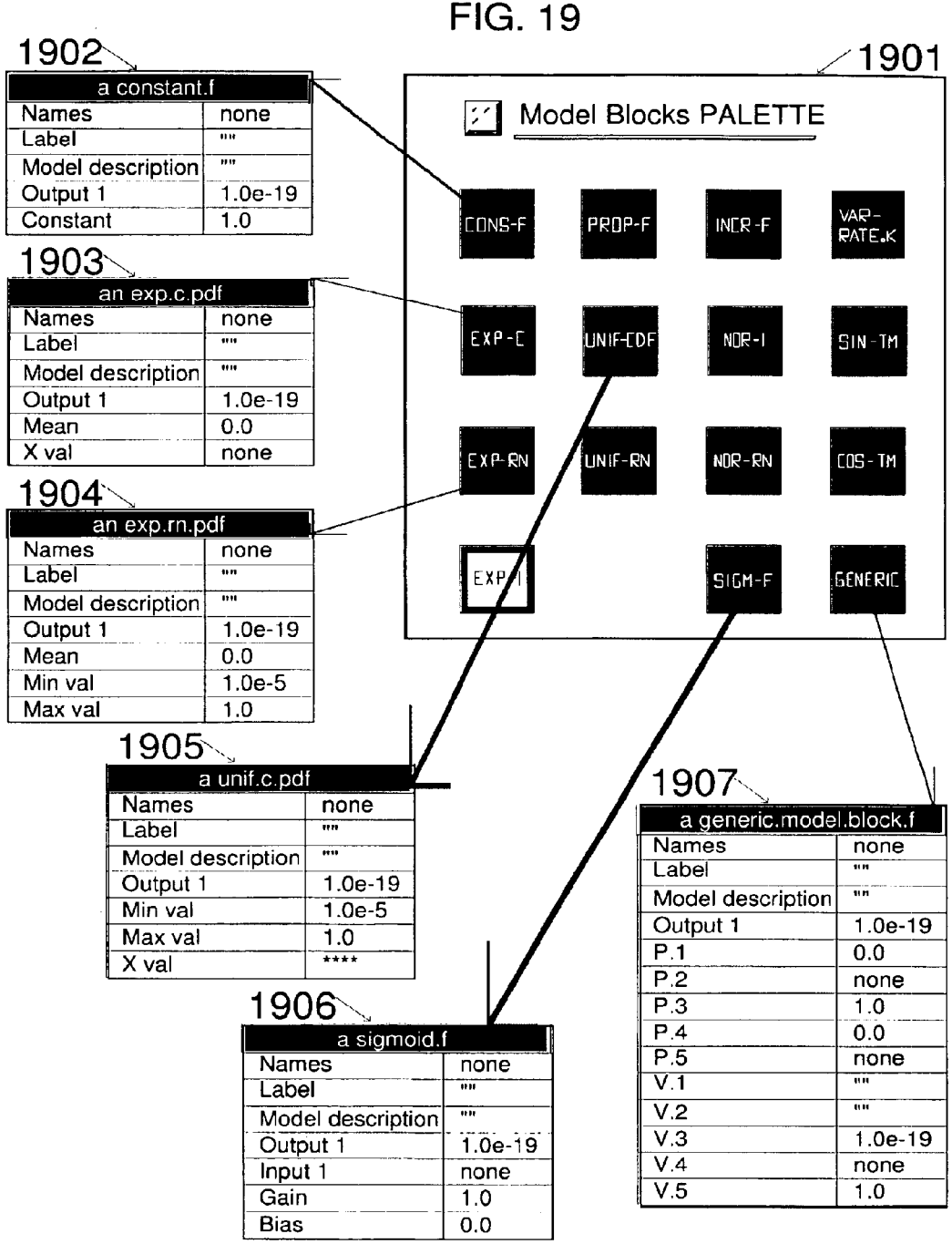
FIG. 19 shows a palette with examples of prebuilt model-blocks.

The class model-block (Table 22), a subclass of the class bioTool, may have as many subclasses as needed to represent the different mathematical models needed by the domain modeler, and some representative subclasses are shown in FIG. 19 as examples. Some examples of generic simulation formulas used to compute the value of the outputs for those subclasses are shown in Table 87. Also included is a generic-model-block, to be further defined by the modeler, which is a placeholder for new parameters and/or variables to be added, and for specific general or simulated formulas for those newly added variables. The additional attributes for the class model-block includes Output.1 and each subclass have additional specific attributes that are simple attributes, parameters or variables, and which vary in number and type (Table 22). A model-block is an iconic object, preferentially used upon the subworkspace of a model-box, which encapsulates the components of a mathematical model, as defined by its attributes, where the value of one or more of those attributes, the outputs, are dependent on the values of inputs, which may be constant or may changed at run time. The inputs may be have any type of origins, including: a) one or more other attributes of the model-block; b) one or more attributes of other objects in the Virtual Model; c) one or more values originating from any external source interfaced with the system, such as external sensors, databases, or external simulators; d) any auxiliary independent constant, parameter, or variable; e) any timer or meter; or f) any combination of the above.

Figure 12:
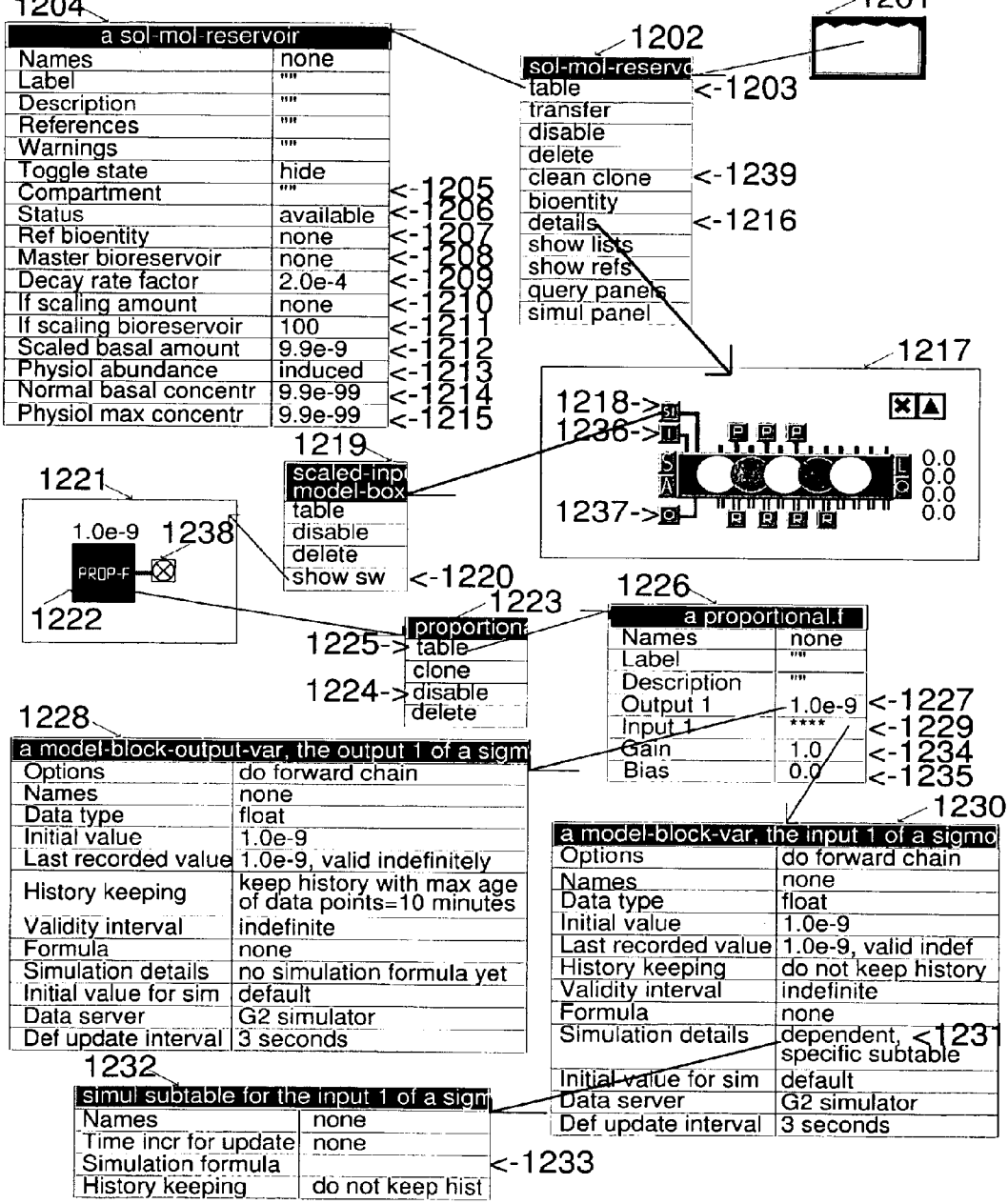
FIG. 12 describes the sets of attributes of the components of a reservoir, focusing on the variables and parameters of its model-block component.

As shown in FIG. 12, clicking on an instance of model-block (1222) displays its menu (1223). The "disable" option (1224) is used when a set of alternative model-blocks is configured for a given bioPool to disable those not currently in use. The "table" option (1225) displays the table of attributes (1226) and provides access to its variables. Two classes of variables defined to be used as attributed of model-blocks: model-block-var and model-block-output-var Table 12) differ in the default settings: only the former has by default a simulation subtable and only the latter keeps history of its value, while both have an initial value and indefinite validity interval, so that they always have a value, and therefore can be used by the simulator. Clicking on the slot (1227) of the attribute Output.1 displays its subtable, the attribute table of an instance of model-block-output-var (1228). Although the predefined model blocks classes have associated generic formulas to compute the value of their output.1, the modeler may want to override it by requesting, by clicking on the slot of its simulation details attribute, the addition of a simulation subtable. The subtable of the attribute Input.1 (1229) shows the table of an instance of model-block-var (1230), and clicking on the slot of the attribute Simulation-details (1231) displays its simulation subtable (1232) with additional attributes, among them one (1233) to hold the simulation formula to be written by the modeler. The particular subclass selected in this example, a proportional.f, is defined with two additional attributes given by simple float attributes with default values of 1.0 for Gain (1234) and 0.0 for Bias (1235), which represent what their names indicate.

Class Inference-Block

The class inference-block (Table 23), a subclass of the class bioTool, may have as many subclasses as needed to represent the different inference models needed by the domain modeler, and some representative subclasses are shown (Table 23) as examples. Some examples of generic simulation formulas used to compute the value of the outputs for those subclasses are shown in Table 88. The additional attributes for the class inference-block includes Outcome, given by an outcome-par, and each subclass have additional specific attributes that are simple attributes, parameters or variables, and which vary in number and type (Table 23). An inference-block is an object, preferentially used as an attribute of bioObjects, such as time-compartments, which represents an inference model, as defined by the methods providing the value of its Outcome, which is dependent on the values of some inputs. The inputs may be have any type of origins, including: a) one or more other attributes of the inference-block; b) one or more attributes of other objects in the Virtual Model; c) one or more values originating from any external source interfaced with the system, such as external sensors, databases, or external simulators; d) any auxiliary independent constant, parameter, or variable; e) any timer or meter; or f) any combination of the above.

Class Button The class button (Table 24) is a subclass of bioTool, which additional attributes include Toggle-state. A subclass of button is action-button (Table 24), which additional attribute, action-proc-name, holds the name of the specific procedure invoked when that button is selected by the user. Clicking an action-button triggers its "select" option (Table 25), which invokes the button-handler-callback, which invokes the procedure defined as attribute of each subclass, such as the one example shown for hide-sup-ws-callback (Table 26) for a HIDE button. Action-buttons play a supportive role in this invention by controlling the display, and in some cases the activation, of workspaces, allowing the interactive navigation through the entire Virtual Model. Other subclasses of button, named tracers, initiate important interactive tasks to create and display pathways, lists, or graphs from a point of view within the Virtual Model relative to the bioReservoir or bioProcess from which they are selected.

The class change-mode-button (Table 27) is a subclass of action-button with the additional attribute Mode, which upon selection starts the change-mode-callback (Table 27). A set of these buttons on a panel, with the Mode and Label attributes of each button of the set equal to each of the possible values of the user-mode attribute of the window, allows the user to interactively change from one user mode to another, for the particular window displaying the panel. The optional behaviors of many types of objects in this system are user mode specific, as defined within the Class-restrictions attribute of the object-definitions of the corresponding classes, such as the actions invoked when selecting their icons (Tables 20, 24, 28, 30, 32, 34, 47, 52, 53, 54, 65, 66), the options that appear on their menus, or the visible attributes.

The following classes are subclasses of the class button with no additional attributes, but have subclasses with specific methods associated with them: a) the class path-tracer's (Table 28) "show" option starts the path-tracer-handler-proc (Table 29), which calls the configure-tracer-proc (Table 29) and one of three optional procedures, depending on the class of the path-tracer, as described in later sections related to bioProcesses, Navigation Panel, Simulation Panel, and Experiment Panel, where they play a support role by controlling the dynamic creation and display at run-time of interactive pathways of either bioReservoirs or bioProcesses or both; b) the class lists-tracer's (Table 30) "show" option starts the list-tracer-handler-proc (Table 31), which calls the configure-tracer-proc (Table 29) and one of three optional procedures depending on the class of the lists-tracer, as described in later sections related to bioReservoirs and bioProcesses, where they play a support role by controlling the dynamic creation and display at run-time of lists of either bioReservoirs or bioProcesses that are either upstream or downstream of the bioReservoir or bioProcess where the lists-tracer is located; and c) the class graph-tracer's (Table 32) "show-plot" option starts the graph-tracer-handler-proc (Table 33), which calls the configure-graph-tracer-proc and one of three optional procedures, depending on the class of the graph-tracer as described in later sections related to bioReservoirs and bioProcess, where they play a support role by controlling the dynamic creation and display at run-time of graphs that plot the values over time of key variables or parameters of those bioObjects. The actions performed by these procedures are similar, creating first a display with a graph and each a different set of predefined complex variables and then establishing relationships among those variables and the graph.

Group of Operating/Display Tools

The classes query-panel and entry-panel (Table 37) are both subclasses of the class uil-tailored-dialog, as defined in G2 Version 3.0, from which they inherit several attributes used for run-time processing. The different types of query-panels and entry-panels are designed as partially built master structures, which are dynamically cloned and completed at run-time, upon requests from the user. The dynamically created Entry Panels (FIGS. 32, 33 and 35) are used to interactively set-up and start constrained navigations, simulations, and experiments, and for selection of monitoring/control components. The dynamically created Query Panels (FIG. 30) are used to interactively perform predefined complex queries, based on functional modular structure, relative position within the pathways, function (roles as bioReactants), or location in subcellular compartments.

Scroll-areas are structures provided by the Shell. In this invention, Scroll-areas are created dynamically and used extensively (FIGS. 30–35) to list and provide direct access named instances of different types of bioObjects. For example, a scroll-area is created upon request from an Experiment Panel (FIG. 35) by selecting the BIORESERVOIRS button (3506), listing in a scrollable fashion all named instances of bioReservoirs in the Virtual Model and providing direct access to them. The scroll-messages that form the scrollable components of the scroll-area, and which refer to the objects of interest, can be ordered alphabetically or in other ways.

Connections and bioPosts

Connections are used to connect visualObjects (FIGS. 6 and 7) upon a workspace (601, 602) and are established graphically, by the union of the stubs (608, 609) attached to the bioObjects involved (605, 606, 607) or by extending a stub of a bioObject and attaching it directly to another bioObject, if the latter allows manual connections. Several domain-specific connections are subclasses of the Shell's class connection, and represent different abstract concepts such as inputs, outputs, links, relationships, or information passed between objects. Stubs are handles (716, 718, 720) on the icons of objects that are clicked and dragged to create the connections (608, 609, 717, 719). The definitions of the subclasses of bioEntity, bioPool (610), bioEngine (605), bioReactant (606), bioProduct (607) and bioPost (703, 704, 711, 712) prescribe the class of connections that are allowed at each port of their icons, as defined in their stubs slot. Direction of flow may also be specified in such definitions. Stubs are color and pattern coded to represent the different types. The stubs are inherited, and those stubs that are not used can be graphically removed.

Figure 6:
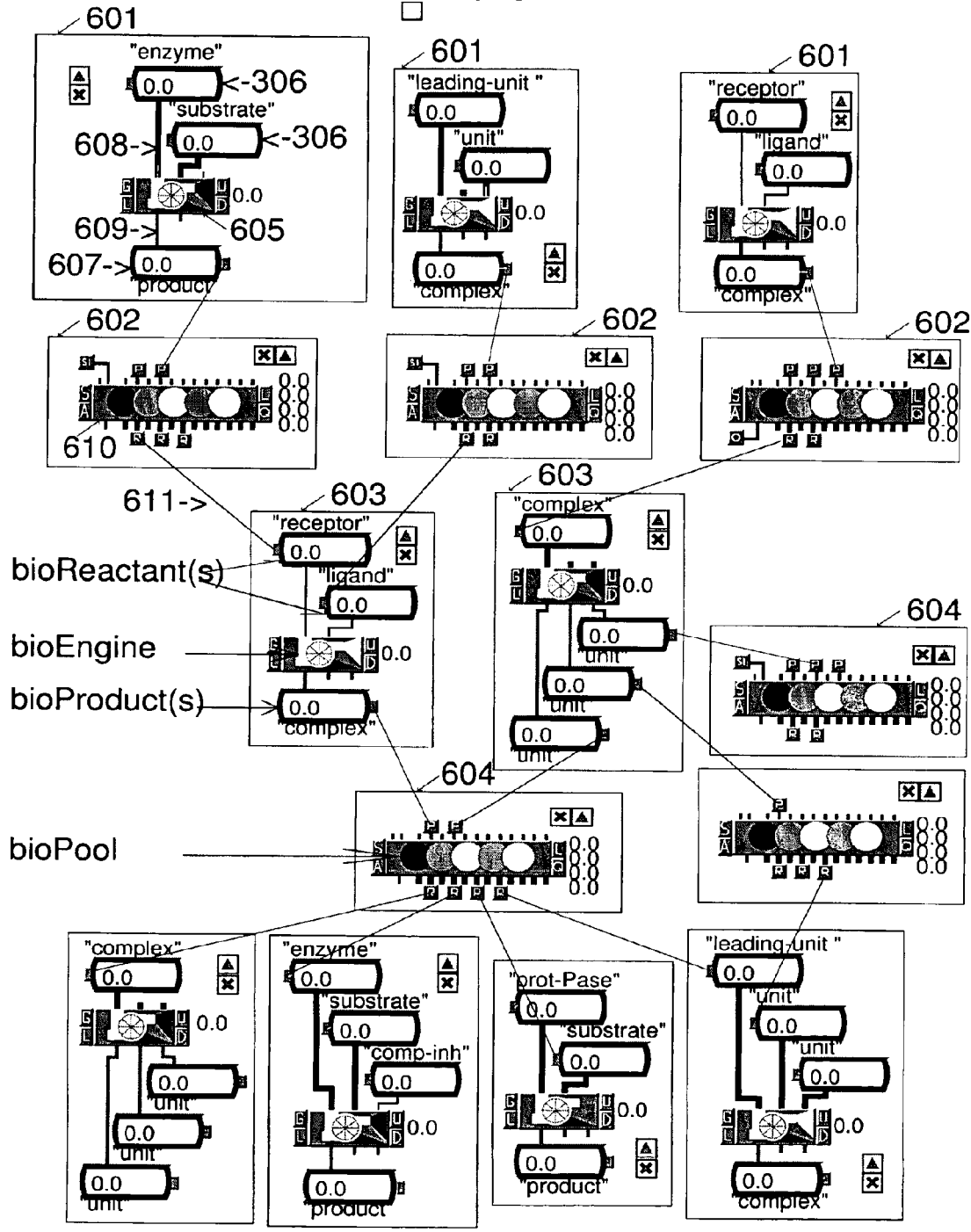
FIG. 6 is a more detailed representation of how the various iconic components encapsulated in the icons representing the pools of entities and processes are linked in the current implementation of this invention.
Figure 7:
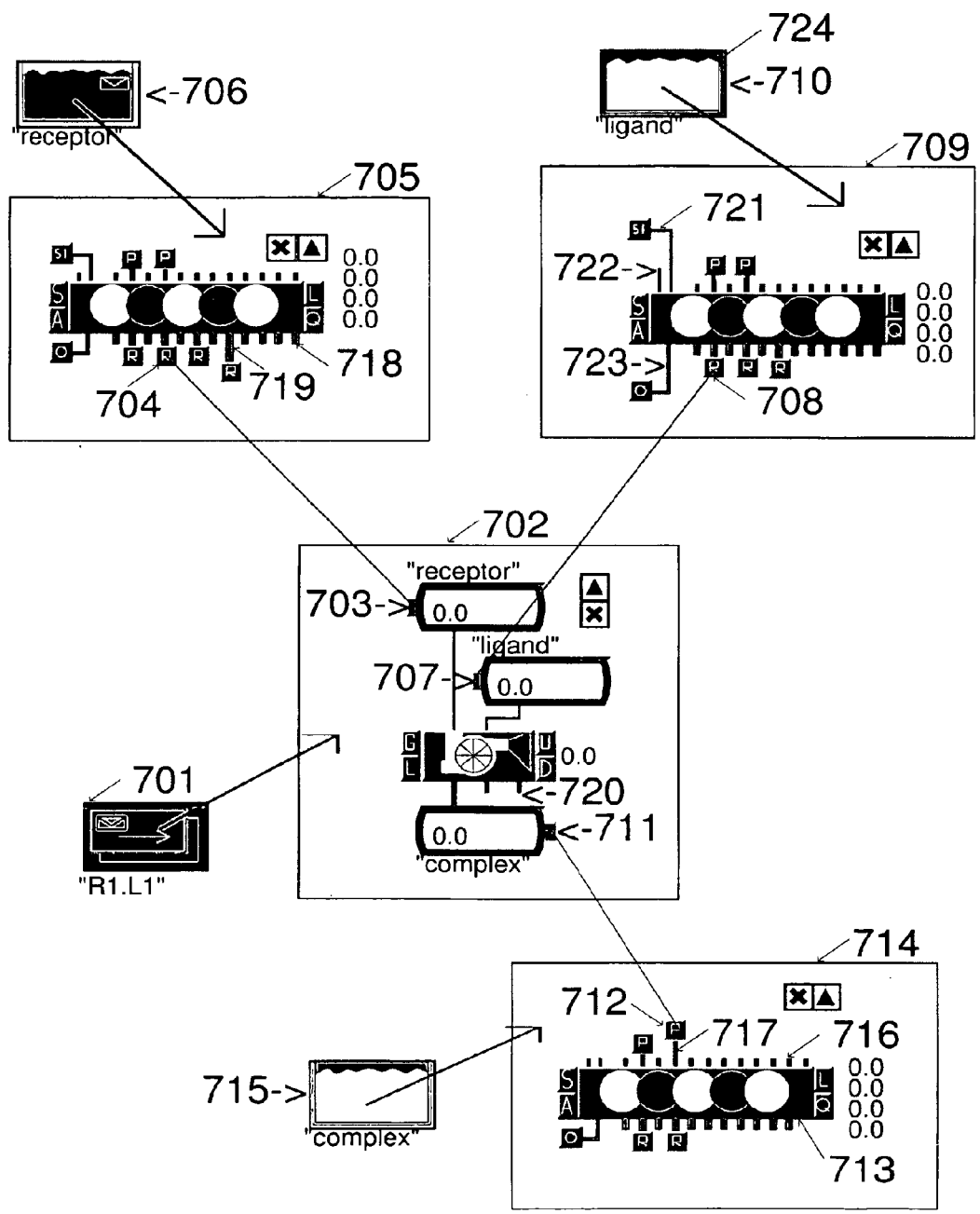
FIG. 7 is a detailed representation focusing on the iconic components of a process and their relations to its sources of inputs and the targets for its outputs.

The definitions of connection subclasses, some of which are shown in Table 38, include the descriptions of the Cross section pattern, that provide each with characteristic pattern and color to facilitate visualization and modeling tasks, and a predefined Stub length. Each of those classes is specific for connecting particular combinations of objects, as described below (FIGS. 6 and 7). Stubs of different classes or subclasses are not allowed to connect to each other, to prevent the modeler from making erroneous connections. Connections comprise the following major classes:

the class p-connection represents a bioProcess input to a bioReservoir, and more specifically a bioProduct's input to a bioPool, in terms of both unidirectional material flow and data flow. Several stubs for p-connections are defined at the top (716) of the class bioPool, which may graphically connected (717) to the one stub defined at the bottom of each biopool-p-post (712). Also several stubs for p-connections are defined at the bottom (720) of the class BioEngine, which may graphically connected (609) to the one stub defined at the top of each bioProduct (607).

the class r-connection represents a bioReservoir's input to a bioProcess through a bioReactant, in terms of both unidirectional material flow and bi-directional data flow. An r-connection may connect (719) a biopool-r-post to the bottom of a bioPool, or may connect (608) a bioReactant to the top of a BioEngine. Several stubs for r-connections are defined at the bottom (718) of the class bioPool. In addition, the class r-connection has many subclasses, which differ in their characteristic cross section color pattern, and each connects a different class of bioReactant to a matching stub of the same subclass defined at the top of a bioEngine. The definition of each subclass of bioReactant specifies within the stubs attribute the specific subclass of r-connection, and the definition of each subclass of bioEngine specifies within the stubs attribute a set of specific subclasses of r-connections and their locations. The purpose of this implementation is to prevent users from making the wrong connections, while directing the user to make the appropriate connections by matching the color pattern.

the class model-box-connection has three subclasses, scaled-input-box-connection (721), input-box-connection (722), and output-box-connection (723), used (FIG. 8) to graphically connect instances of scaled-input-model-box (811), input-model-box (816), and output-model-box (817), respectively, to predefined corresponding ports of a bioPool. The stubs for these specific connections are defined for each subclass of model-box, and for each subclass of bioPool at named ports, and these subclasses are color coded to guide the modeler to match the color pattern when making the connections.

the class link defines the connections between the component bioEntities (1819, 1821) of other bioEntities (1817), representing the continuity of an ordered sequence of structural components.

the class icon-wire is a tool used to connect a biorole-post (703, 707, and 711) to its bioRole-Object. The class graph-link is a tool used to connect either a bioEngine to various types of tracers (3105, 3110, 3117, 3426) or a bioPool to various types of tracers (3421). After the connection is made, these connections are made invisible by either a rule at run-time or by a procedure invoked at initialization time.

The class BioPost (Table 39) is a subclass of the Shell's class connection-post. Connection-posts are like extensions of connections that permit to physically interrupt a graphic connection and continue it on another workspace, but without interrupting the flow. A teaching of this invention is the design, uses, and methods associated with the different subclasses of bioPost, each referring to an iconic structure (703 or 711) that may be distantly connected to another bioPost of a complementary subclass (704 or 712, respectively). BioPosts are components located on the subworkspaces of bioReservoirs and bioProcesses and, since they are located upon different subworkspaces, they are distantly connected by receiving the same name. These structures integrate bioReservoirs and bioProcesses, wherever they are located. There are several restrictions built into the system of this invention to prevent users from making the wrong connections, or to warn them that wrong connections have been made, such as when a bioReactant-post is given the same name as a bioPost that is not a biopool-r-post, or when a bioproduct-post is given the same name as a bioPost that is not a biopool-p-post. The various subclasses of bioPost (Table 39) will be further described below, within the overall description of bioReservoirs and bioProcesses.

BioObjects

The class bioObject (bio-object, Table 40) is a subclass of the Shell's class object, with various subclasses and various restrictions when in different modes, as listed. BioObject comprises all the classes of knowledge structures used to represent the biochemical systems characteristic of this domain. These object classes are characterized by their defined attributes, which can be: a) simple attributes of various types, such as text, symbols, integers, floats or truth values; or b) other previously defined objects, including parameters and variables of any of those types, or lists and arrays of those types of elements. The values for the parameters and variables can be provided by any of a variety of sources, such as the user-inputs, interfaced on-line sensors, or dynamically by the inference engine (for instance, through specific or generic formulas, rules or procedures), or a simulator (for instance, through specific or generic simulation formulas or simulation procedures), reflecting the changing values of the attributes defined within the knowledge structures and in the context selected by the user.

All bioObjects have at least three common attributes: a) Names, a Shell-defined attribute that binds one or more unique symbols to an object; b) Label, a text attribute that allows to identify bioObjects that may not have a unique name; and c) Description, an optional text string for any additional information. While names are required in the current implementation for some bioObjects to be integrated into the pathways, such as bioReservoirs, bioProcesses, and bioPosts, labels are preferred for identification in other cases, because they require less memory than symbols, do not have to be unique, their syntax is less restrictive, and offer more attractive options for display.

Among the major bioObject's subclasses, which further subclasses are described in later sections, are:

Class bioNode-Object: (Table 40): inherits all attributes and icon from bioObject and have no specific attributes, and can only have subclasses, not instances. However, there are methods that refer to this class, and therefore, like with many other classes throughout this system, the differentiation between classes may not appear in their definitions but rather on their behavior, through methods that applied to them.

Class bioView-Object: (Table 40): inherits all attributes and icon from bioObject, and can only have subclasses, not instances. A option "details" defined for this class upon selection by the user starts the procedure go-to-view-proc, which takes among its arguments the instance from which it was invoked and the current window and, depending on the value of the instance's Toggle-state attribute of hide or show, it causes the instance's subworkspace to be displayed or hidden, it toggles such value to the other value, which is an event that fires a rule that causes the instance's icon to be configured to its pressed or depressed appearance. New attributes defined for this class comprise:

References, defined for several subclasses of bioObject, is an optional text that makes reference to the sources of information and data used to construct and configure that instance of any subclass of bioObject for which it is defined. This attribute may be defined as: a) a simple text attribute, which the user may consult to perform independent searches, or using this invention search facilities, such as the Master-Reference-Panel; or b) a reference-array (Table 17) in combination with the option "show-references", which when selected by the user starts the show-references-of-array-proc (Table 126), which displays dynamically created copies of the instances of reference-block (Table 34) referred to by the values of that array.

Warnings is an optional simple text attribute, the value of which is set by the modeler to warn the user about any abnormalities or data included, such as, for a bioReservoir, when that particular pool of molecules have not yet been observed experimentally, but can be assumed to exist by analogy to similar systems, or when the pool has been observed but the quantitative data has been assumed. This attribute is used in conjunction with a design (723, 843) in the icons defined for all those classes and their subclasses as a separated color-region, called flag-color, that is changed to yellow to make the user aware of the existence of warnings, or back to any appropriate color. Those changes are automatically executed by procedures invoked during initialization, or at run-time by a set of rules.

Toggle-state is an attribute also defined for objects for which their icons' appearance change upon selection by the user, depending on the value of this attribute, which alternatively switches between show and hide when the user clicks on the icon.

BioEntities

Figure 30:
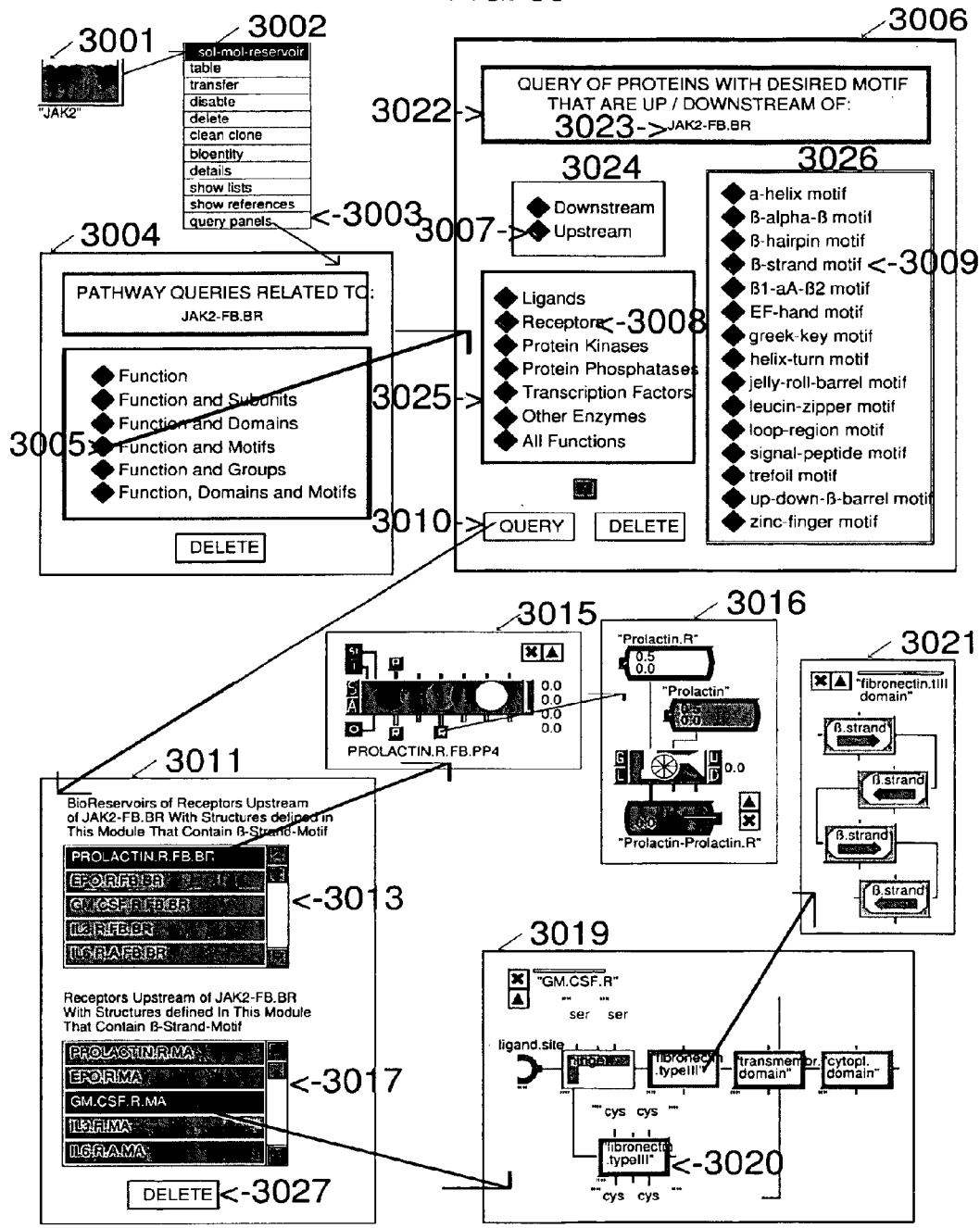
FIG. 30 describes an example of the predefined Query Panels and their use.

A bioEntity is an iconic knowledge structure that represents any biochemical entity or their components, at different levels of structural complexity. Each bioEntity may have information encoded in various ways, including: a) information and data stored in its table of attributes, and b) each bioEntity may have a subworkspace upon which the components that represent its functional modular structure are visually defined. As shown in FIG. 30, selecting from a bioEntity icon's (3004) menu (3005) the "details" option (3006) displays its structure (3007), which may have several layers of detail (3008–3022). In the current implementation, functional components represent structural components that are relevant for the bioEntity's function and regulation, that allow the user to visualize the structural composition. The iconic composition is also used in the inference for processing of queries that involve the structure, which refer to bioEntities that have certain components in their subworkspace. Each functional component of a bioEntity belongs itself to a bioEntity class, either molecule or bioEntity-component or any of its hierarchy of subclasses.

The class bioEntity (Table 42), a subclass of bioObject, has numerous subclasses, organized in a hierarchical structure with different levels, according to the way a biochemist would classify different molecules, by taking into consideration their commonalities in chemical composition in the upper levels of the hierarchy, such as protein, nucleic acid, or lipid, followed by a reference to their function, such as, within the class protein, active-polypeptide, receptor, or enzyme. Table 41 shows a partial listing of such hierarchy, with some examples of the subclasses at different levels. Additional attributes include References, described above.

There are two major subclasses of bioEntity:

The class simple-bioEntity (Table 43) includes all the subclasses with simple structures that are not further visually described in the current implementation, and they do not generally have subworkspaces with additional components. This class has two subclasses (Table 43), protein-site, and protein-modified-group, each with its additional subclasses: Additional attributes include:

Id is a simple attribute that is used to hold a text to identify the instance instead of using a unique name;

Position is a simple text attribute to indicate the position of that component within the molecule when applicable, such as the position of an Aminoacid in the sequence of a protein, and is usually displayed; and Superior-bioEntity is a simple indexed attribute that holds the name of the first superior bioEntity in the workspace hierarchy that has a name, if any, a value that is computed by the program within the query reasoning and, as explained later, this mechanism is provided to avoid repetition of structures that are shared by various instances of the same family or of other families that share regions of homology.

The class complex-bioEntity (Table 44) includes all those subclasses that can be further described by their components in their subworkspaces. As shown in FIG. 30, selecting from icon's (3004) menu (3005) the "details" option (3006) displays its structure (3007), which may have several layers of detail (3008 through 3022). Additional not previously described attributes include:

Master-bioEntity is a simple indexed attribute that may hold the name of a bioEntity that is displayed when the user selects the "details" option. This value is set by the program upon cloning an existing named bioEntity using the "create-local" option, as described later. BioEntities with no names and which its Master-bioEntity names another bioEntity, the master bioEntity, can be considered as only a copy or pointer to the subworkspace, or Master-details, of the master bioEntity, but it can also hold additional information in its table of attributes or in its own subworkspace, or Local-details.

The major subclasses of complex-bioEntity, defined to deal with multiple levels of biochemical structural complexity, include:

the class bioEntity-component and its subclasses (Table 44) represent he lower-level molecular functional components such as: dna-component and its subclasses, such as dna-domain, promoter, operator, and so on; protein-component and its subclasses, such as protein-domain, protein-motif, and so on; and membrane and its subclasses. The subclasses of this class may have 4 stubs of the class link used to link different bioEntity-components, allowing for branching, and those stubs that are not used can be dragged away. Additional attributes include: Superior-bioEntity and Position, defined above; and Size.

the class molecule (Table 45) and its successive level of subclasses such as those of protein (Table 45), nucleic-acid, and so on, represent the next level of complexity. For example, ss shown in FIG. 30, a protein may have a set of domains or motifs, or a combination of both, and it may have in addition one or more protein-sites, or protein-modified-groups, connected to the domains and or motifs at approximate locations, with the more accurate position displayed in the Position attribute. A protein-domain may also have in its SW a set of smaller domains or motifs, or a combination of both, and it may have in addition one or more protein-sites, or protein-modified-groups, including copies of those connected to the icon of the domain.

the class heter-mol-complex and its subclasses, such as nucleosome or, tf-dna-complex, represent a higher level of complexity. A heter-mol-complex or a complex-molecule may be composed of other molecules. For example, a tf-dna-complex may have a dna or a gene icon in association with one or more icons of specific transcription-factors. In turn, the structure of a simple molecule is represented by an ordered set of bioEntities of the class bioEntity-component in its sub-workspace.

the class membrane and its subclasses, are used to represent interactions of several types of cellular membranes with other molecules.

Figure 13:
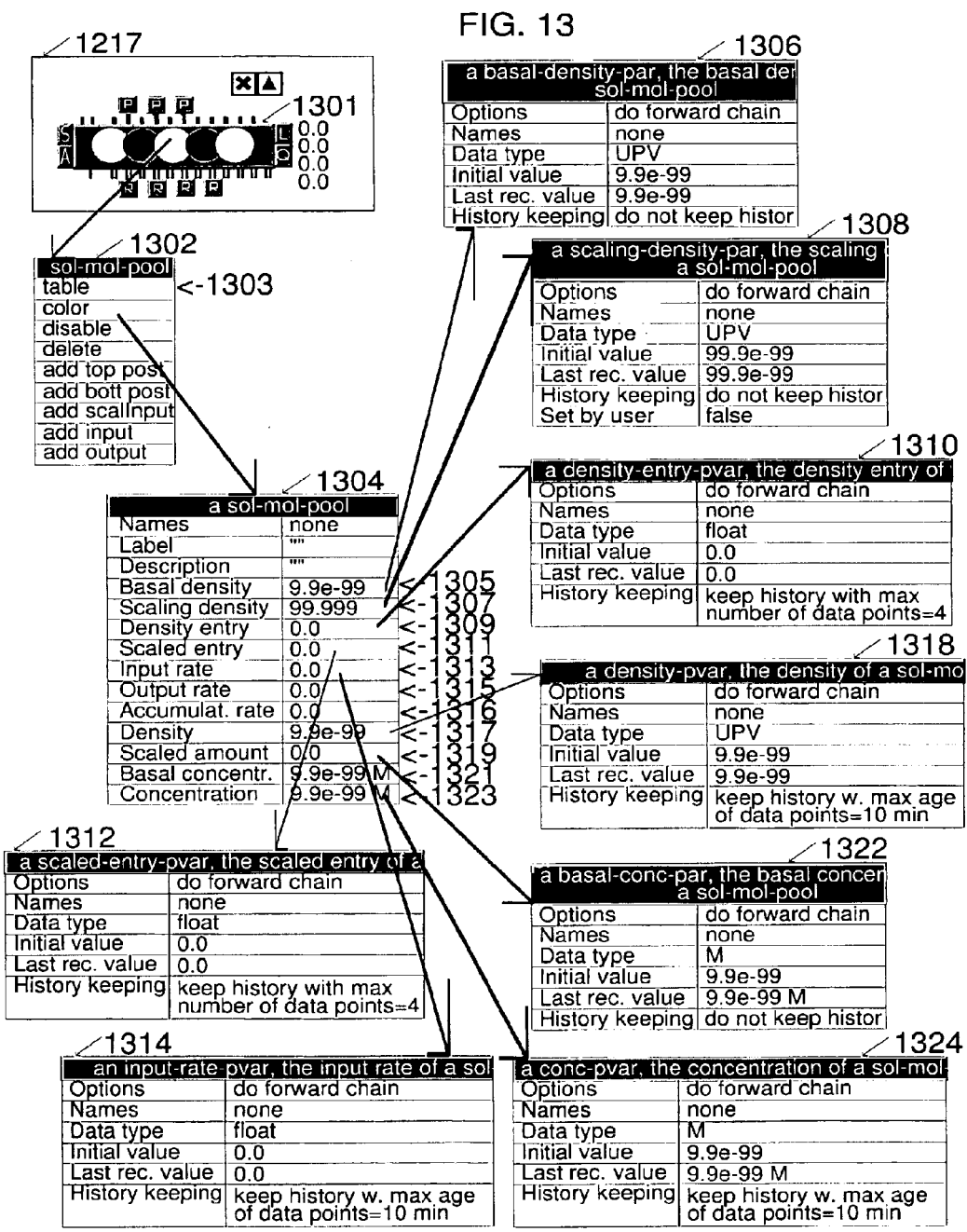
FIG. 13 describes the sets of attributes of the components of a pool of entities, focusing on its variables and parameters.

Additional information about an instance of bioEntity can be stored in its table of attributes, such as the example shown for a default instance of the subclass p.tyr.kinase (Table 45). The inherited attributes shown are successively added through the hierarchy of its superior classes, such as molecule, protein, and enzyme, and include:

Synonyms is a simple text attribute to list the different names by which a molecule or complex may be known;

In-species is a simple text attribute to list the species or common name of living organisms in which that molecule or complex has been found, such as all, human, mouse, *Drosophila, C. elegans, S. cerevisiae*, and so on;

In-tissues is a simple text attribute to list the tissues in which that molecule or complex has been found;

InCells is a simple text attribute to list the cell types in which that molecule or complex has been found;

InOrganelles is a simple text attribute to list the organelles within a cell in which that molecule or complex has been found, and it may take values such as plasma-membrane, cytosol, nucleus, and so on;

Cas-number is a simple text attribute to indicate the CAS number assigned to that molecule, which is indexed to allow for faster searches and has a default value to indicate the preferred format;

Mol-weight is a simple integer attribute to indicate the molecular weight of a single molecule or complex, preferably expressed in Daltons;

Isoelectric-point is a simple float attribute to indicate the isoelectric point of the molecule or complex;

Sequence is a simple text attribute to contain information about the sequence of a molecule, if relevant;

Substrates-info is a simple text attribute to contain information about the known specific substrates or groups targeted by the enzyme;

Inhibitors-info is a simple text attribute to contain information about the known specific inhibitors of the enzyme;

Ligands-info is a simple text attribute to contain optional information about any other ligand that may bind to the enzyme;

The class bioEntity-notes, (Table 46), a subclass of bioTool, comprise auxiliary structures located the subworkspace of a bioEntity, that serve as iconic containers for different types of specific information about the bioEntity, which can be displayed by selecting the "details" option.
BioReservoirs
Class bioReservoir As shown in FIGS. 8 and 12, a bioReservoir (801, 1201) is an iconic object that represents an imaginary container of a population of similar molecules or molecular complexes, represented by a bioPool (805, 1301). A bioReservoir has several operational functions and encapsulates several forms of knowledge (FIGS. 8, 12, 13). A bioReservoir's menu (802, 1202) provides access to a variety of tasks to be discussed in sections below. Here we will define some of the components involved. The "table" option (1203) displays its table of attributes (1204), which holds values set by the modeler that, in addition to provide useful quantitative or qualitative information to the user, may be used by the program to set the initial conditions before a simulation is run. The values of some of the attributes of a bioReservoir characterize the system and are stored as part of the permanent database. The values of other parameters and variables (1305–1324) pertaining to a bioReservoir that are computed when a simulation is run, but which do not usually require to be set by the modeler, are hidden for convenience as attributes of the bioPool encapsulated in each bioReservoir, as described below, but they could as well be implemented as attributes of the bioReservoir.

The class bioReservoir (Table 47) is a subclass of bioView-Object and its subclasses (Tables 47 and 48) include: bound-mol-reservoir (801), sol-mol-reservoir (1201), cell-reservoir, exp-cell-reservoir, genet-mol-Reservoir, some with further subclasses. All instances of all subclasses of bioReservoir have an activatable-subworkspace, which means that any object upon such subworkspace are not recognized by the inference engine or the simulator unless the subworkspace is activated, and therefore any of the tasks associated with their icons are not functional when inactivated. When the application is started, all those subworkspaces are deactivated, and in the current implementation of this invention they are activated when the general initialization procedures are invoked, as described below. In FIG. 12 is shown a table of attributes (1204) of an instance not yet configured, shown here with its default values. The unlikely default value of 9.9e–99 given to some of those attributes, which provides a) a signal for the user that an adequate value has not been entered yet by the modeler, and b) a branching criteria for the inference engine. Attributes newly defined for this class and its subclasses not previously described include:

Compartment (1205) is an simple attribute optionally set by the modeler to represent the physical boundaries of the encapsulated bioPool;

Status (1206) is a symbolic attribute, which value is set and used at run time by the simulation and other procedures, as an aid in the activation of pathways and in the creation of interactive pathway displays. It can take any of the values specified in the definition table and it is not visible to the modeler or other users.

Ref-bioentity (1207) is an optional attribute optionally set by the modeler to point to the bioEntity instance that describes the structure of a unit representative of those populating that bioReservoir. This value is used by the program when the user selects the "bioEntity" option from the menus of either the bioreservoir itself or any of the bioReactants and bioProducts distantly connected to its bioPool, and that option appears on those menus only when the value of this attribute is not the default value none;

Master-bioreservoir (1208) is set only by the program when copies of named bioReservoirs are made, such as those used in the creation of interactive pathway displays, and is used by the program to display the subworkspace of the bioReservoir referred to by the value of this attribute, when the "master-details" option is selected by the user. This attribute is not visible to the modeler or other users.

Decay-rate-factor (1209) is a parameter, which value may be entered by the modeler or can be modified at run time by rules or procedures. Its default value is 2.0e–4, a value small enough not to cause dramatic changes, but in line with some experimental observations in the domain of this invention, but it should preferably be modified by the modeler to better reflect individual cases.

If-scaling-amount (1210) is a simple attribute set by the modeler to indicate to the program the value to be used to interconvert between the absolute-valued and the scaled-valued variables or parameters of bioPools and their connected bioReactants. The complex methods used for these conversions differ, depending on the classes of bioPools and bioReactants involved, as discussed in more detail under the Simulation Mode heading. Its default value of 100 is used if not modified by the modeler, if the value of the if-scaling-bioreservoir attribute is none.

If-scaling-bioreservoir (1211) is a simple attribute, which value may optionally be set by the modeler to indicate to the program that the value of the if-scaling-amount should be taken from the bioReservoir named by this attribute. This value is only required or used when the value of the if-scaling-amount attribute is the default, otherwise, the later value is used and this attribute is ignored. This and the previous attribute are not visible in General Mode.

Scaled-basal-amount (1212) is a float simple attribute set be the modeler that represents the scaled value of the amount of units in the encapsulated bioPool under normal or basal conditions, equivalent to a fraction of the maximum amount that this bioPool can reach under optimal physiological conditions. Since in many occasions in the domain of this invention neither the basal nor the maximum amounts can be measured or known with certainty, this value represents in such occasions the best estimated guess, and it is an important semi-quantitative knowledge component. The default is the unlikely value of 9.9e–99.

Physiol-abundance (1213) is a symbolic attribute, which value is set by the modeler to indicate the physiological level of abundance of the entity in the compartment represented by that bioReservoir. It is a symbolic replacement of the previous attribute when the 9.9e–99 has not been modified by the modeler. The values allowed for this attribute in this invention are: highest, abundant, steady-state, low-induced or only induced, which currently correspond to the scaled values of 1.0, 0.9, 0.5, 0.1, and 1.0e–9, respectively. However, this default scale can be changed to different values, and additional symbols and values can be added to the scale. As and alternative, fuzzy-sets can be defined for the values of this attribute, and fuzzy-logic can then be applied to those values. The reasoning for using the values of either the previous or this attribute, in conjunction with one or more of the following attributes, are discussed in more detail under the Simulation Mode heading.

Normal-basal-concentration (1214) is a float simple attribute set be the modeler that represents the physiological average value of the concentration of the entity represented by a sol-mol-reservoir.

Normal-basal-density (instead of 1214) is a float simple attribute set be the modeler that represents the average value of the density of the entity represented by a bound-mol-reservoir.

Physiol-max-concentration (1215) is a float simple attribute set be the modeler that represents the physiological maximum value of the concentration of the entity represented by a sol-mol-reservoir.

Physiol-max-density (instead of 1215) is a float simple attribute set be the modeler that represents the physiological maximum value of the density of the entity represented by a bound-mol-reservoir.

Selecting the "details" option (803) displays the subworkspace (1217,804), which contains the components that characterize a bioReservoir. The classes of those components that are using in the modeling process are defined below, while other auxiliary structures are described in later sections. The descriptive qualitative, structural, and functional information of a bioEntity is kept in this invention separated from the configurable additional quantitative information that characterizes each bioReservoir, allowing the Ref-bioentity (1207) of several bioReservoirs, representing populations of the same type of entity in different locations or points in time, to point to the same bioEntity to reduce the size of the Virtual Model.

Class bioPool

The class bioPool (Table 49) is a subclass of bionode-object and comprises several subclasses, such as sol-mol-pool, bound-mol-pool, ..., including those defined in Tables 50 and 51. A bioPool (805, 1301) is defined with a characteristic icon with two sets of stubs of two classes of connections: a set of p-connection stubs at the top of the icon, and a set of r-connection stubs the bottom of the icon. Each p-connection stub is to be connected to a biopool-p-post (806) and each r-connection stub is to be connected to a biopool-r-post (818, 823, 828, 833) on the subworkspace (804) of the bioReservoir (801), which allow to establish distant connections to bioProducts (808) and bioReactants (820, 825, 830, 835), respectively, and allow bi-directional flow of data and control between them. As shown in FIG. 13, every instance of bioPool (1301) has an associated menu (1302), and selecting the "table" option (1303) displays its table of attributes (1304). Several of the attributes of a bioPool are variables or parameters (1305–1324), which include a density-related set and a concentration-related set, which values do not have to be set by the modeler (with the exception of the basal quantities, which are preferably set by the modeler if known but they are not required, since they can be computed from the set values of other attributes of the bioReservoir, or their default values), since they are inferred or simulated, as described under the Simulation Mode heading. The units of all the parameters and variables of all bioPools connected to the same bioProcess have to be appropriately matched. Newly defined attributes of bioPool comprise:

Basal-Density (1305) is given by a basal-density-par (1306). The subclass sol-mol-pool has additionally a Basal-Concentration (1321) given by a basal-conc-par (1322). The values of either of these attributes may be set by the modeler to indicate: a) the normal physiological steady state density or concentration, or any other appropriated measured or assumed value, for physiological molecules or complexes, or b) 0.0 for pharmacological or other molecules that are added to the system from an external environment. This value is required for any bioReservoir that participates in a simulation, and if its default value has not been overridden by the user with a new value, the program sequentially pursues other sources of the Basal-Density value, as determined by a generic basal-density-procedure that is called during the activation process of a simulation, only for those bioReservoirs that have been activated for a simulation.

Scaling-Density (1307) is given by a scaling-density-par (1308), which value is inferred by a procedure invoked at initialization, as discussed in more detail under the Simulation Mode heading. This value is used by simulation formulas to interconvert scaled values and absolute values.

Density-Entry (1309) is given by a density-entry-pvar (1310). It takes the value of a user-input at a time, or different times intervals, during simulation as defined by the user in an input-panel, during the simulation set-up process. It has a default value of 0.0, and a new value may be inferred and set by a procedure called when the simulation is started, and, after the new inferred value has been propagated, it reverts back to the default value of 0.0. This value is an argument to the Accumulation, where it is summed to other inputs and outputs.

Scaled-Entry (1311) is given by a scaled-entry-pvar (1312), and it is the scaled equivalent of the Density-Entry, with its value set and used in a way similar to that described above;

Input-Rate (1313) is given by a input-rate-pvar (1314), which value is given by a simulation formula that sums all the visually defined inputs, including: a) the current values of the Production-Rate of all the bioProducts connected to the biopool-p-posts of the bioPool, if any;

and b) the input modeled by means of a model-block encapsulated in any connected input-model-box (or scaled-input-model-box), if any;

Output-Rate (1315) is similarly given by a output-rate-pvar, which value is given by a simulation formula that sums all the visually defined outputs, including: a) the current values of the Consumption-Rate of the consuming bioReactants connected to the biopool-r-posts of the bioPool, if any; and b) the output modeled by means of a model-block encapsulated in any connected output-model-box, if any;

Accumulation (1316) is given by an accumulation-pvar, a time variant and continuous state variable that represents a quantity in the classical systems dynamics sense, which, given an initial value, here set to be equal to the basal-amount (or scaled-basal-amount), as discussed under the Simulation Mode heading, integrates the input-rate, the output-rate, the input entered by the user through an input-panel, if any, and the decay term, which is a function of the current value of the Concentration or Density as given by the decay-rate-factor of the bioReservoir (a decay rate constant in $sec^{(-1)}$), which represents a variety of outputs not modeled visually or through a model-block, including the degradation and diffusion components). Since at steady-state the overall rate of output is equal to the overall rate of input, then, by definition, the Accumulation should approach 0.0 in a closed system, in the absence of additional external disturbances, such as user-inputs or inputs modeled by model-blocks.

Density (1317) is given by a density-pvar (1318), which value represents the number of molecules, complexes, or cells per liter, or any other unit of volume, such as the volume of the reaction mixture in a reactor. The subclass sol-mol-pool has the additional attribute Concentration (1317) given by a scaling-density-par (1318), which value in M (Molar) represents moles per liter. In the implementation used to illustrate this invention, simulations operate by default based on the Density of the bioPools involved. In the case of sol-mol-pool, where the quantities used by scientists may be most commonly given as Concentrations, the second set of concentration related variables is defined to facilitate user-input, but those quantities are preferably transformed into density-related variables by the program, using Avogadro's number (6.023e23 molecules per mol), before integration with other quantities. However, several other types of quantities could be used as well, with conversions to other units of measure, such as activity (X-units times Y-unit), amount (X-units), or others types of densities (such as X-units per Y-unit). The same concepts and the same type of formulas, rules and procedures, apply to other-quantities, and a variety of units may also be allowed for entries from the user or other external sources, by providing lookup-tables or any other standard methods for automatically converting any of those units to the desired target units. Hence, the modeler has the option to design and define a system totally or partially based on a different quantity measurement, as long as proper care is taken to maintain consistency throughout the system. In those cases, the quantities entered by the modeler in the attribute slots of the bioReservoir that refer to physiological levels would also have to reflect those different sets of units.

Scaled-Amount (1319) is given by a scaling-density-par (1320), which value represents an scaled, dimensionless, alternative to Density, Concentration, or any other absolute-valued quantity. This attribute is used in the default scaled reasoning, which is the preferred method when dealing with biological systems, when absolute quantitative data is incomplete, and much of the data available is from relative measurements. The Scaled-Amount can be converted into a Density, and vice versa, by using the value of the Scaling-Density of the bioPool.

Class bioPool-Post

The class bioPool-post (Table 52) is a subclass of bioPost and has two subclasses: biopool-p-post (712, 806), which is to be connected (717) to an input p-connection at the top of a bioPool's icon, and its name is to be given to one bioproduct-post (711, 807) to establish a distant connection; and biopool-r-post (704, 708, 818, 823, 828, 833), which is to be connected to an output r-connection at the bottom of a bioPool's icon, and its name is to be given to one bioReactant-post (703, 707, 819, 824, 829, 834) to establish a distant connection. BioPool-posts are located upon the subworkspace of a bioReservoir and connected to a bioPool, which function in combination with bioRole-posts is to connect the bioPool to one or more bioEngines. The additional attributes for these classes include:

Id is a simple text attribute used as a unique identifier, instead of the unique name, in some types of processing, such as in the alternative simulation procedures described in that section;

Ref-bioprocess is a pointer to the bioProcess instance that encapsulates the bioProduct or bioReactant to which the biopool-p-post or biopool-r-post, respectively, are distantly connected. The value is interactively set by selecting the "set-refs" option of the bioproduct-post or bioReactant-post to which it is distantly connected; and it is used by the program for interactive navigation through bioReservoirs and bioProcesses, as described below.

Class Model-Box

As shown in FIG. 12, a model-box is an iconic object (1218, 1236, 1237) located upon the subworkspace (1217) of a bioReservoir (1201) and connected to its bioPool, which function is to hold and connect the optional model-blocks (1222) on its subworkspace (1221) to the bioPool. The class model-box (Table 53) is a subclass of bioTool and has three subclasses, each playing a different role as their name indicates: scaled-input-model-box (1218), input-model-box (1236), and output-model-box (1237). Model-boxes are created by selecting a menu (1302) option of the closest bioPool, as described below. An instance of model-block is connected to the connection-post (1238), which comes with the subworkspace of a model-box. The superior connection of such connection-post is that defined by the stub of the model-box that contains it, and therefore, the model-block (1222) connected to it is distantly connected to the bioPool to which the model-box (1218) is connected. The menu options available for all subclasses of model-box depend on the user mode. Clicking on a model-box (1218) in any of the user modes bypasses its menu (1219) and selects the "show-sw" option (1220), which causes its subworkspace (1221) to be displayed.

BioProcesses

Class bioProcess

Figure 14:
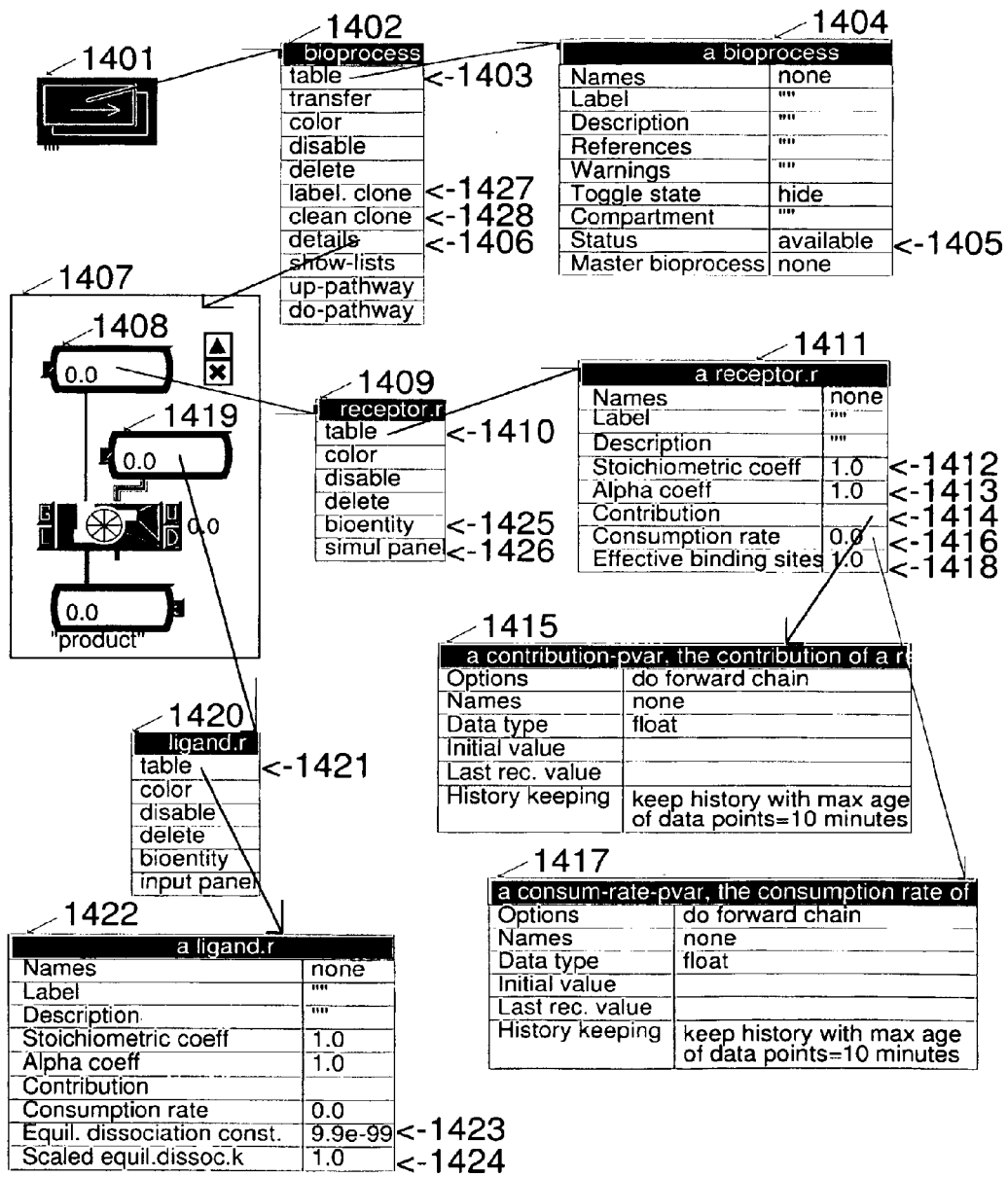
FIG. 14 describes the sets of attributes of the components of a process, focusing on the variables and parameters of its reactants.
Figure 15:
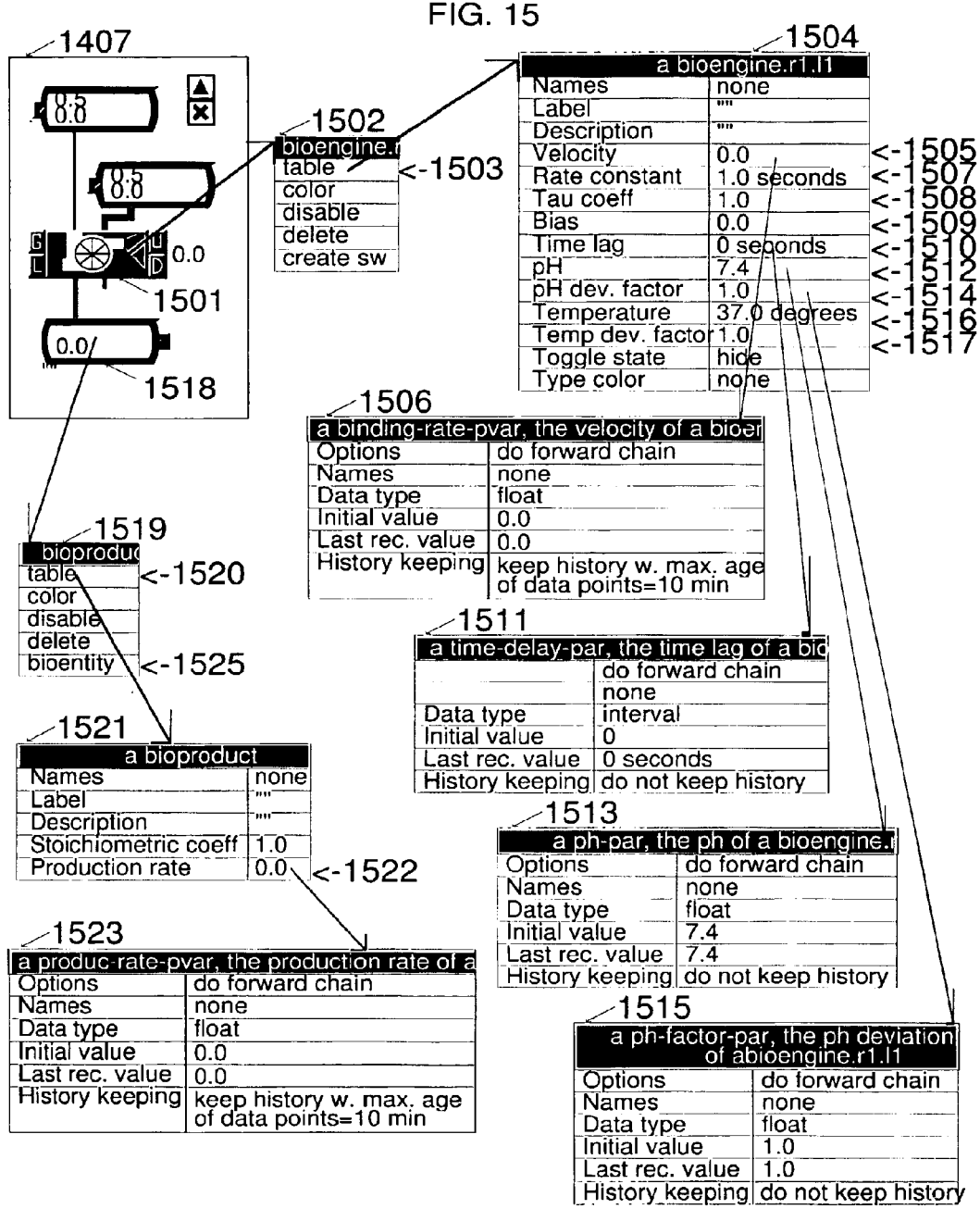
FIG. 15 describes the sets of attributes of the components of a process, focusing on the variables and parameters of its engine and products.

The class bioProcess (Table 54) is a subclass of bioViewObject, and comprises the subclass cell-bioProcess. As shown in FIGS. 7, 14 and 15, a bioProcess is an iconic object (701), which subworkspace (702) contains components that visually represent the preconditions (bioReactants, 1408, 1409), the process engine (bioEngine, 1501) and the effects (bioProducts, 1518) of a process as connected objects with encapsulated variables and parameters that describe the process qualitatively and quantitatively. The subworkspace of bioProcesses is activatable, allowing to control the availability of its components by activating or deactivating the subworkspace. In the current implementation those subworkspaces are activated with the general initialization procedures, as described under the General Mode heading. The many different types of bioProcesses are all instances of that class or its subclass, and differ mainly in the iconic components upon their subworkspace. The different types are also visually distinguished by different colors for the type-color region of their icon, which is changed programmatically to be the same color as the color of the type-color region of the bioEngine they encapsulate.

A bioProcess has several operational functions, encapsulates several forms of knowledge (FIGS. 7, 14, 15), and has a menu (1402) that provides access to a variety of tasks to be discussed in sections below. Here we will define some of the components involved. The "table" option (1403) displays its table of attributes (1404) that holds various attributes, some of which have values that are set by the modeler and provide information for the user, and others are auxiliary attributes hidden from modelers and users, which values are set and used only by the program at run-time. Most attributes specific for this class have been previously described for other classes. Newly described attributes include:

Master-bioprocess (1405) is set by the program when copies of a named bioProcesses are made, such as those used in the creation of interactive pathway displays, and is used by the program to display the subworkspace of the bioProcess referred to by the value of this attribute, when the "master-details" option (visible only when the attribute has a non-default value) is selected by the user. This attribute is not visible to the modeler or other users.

The "details" option (1406) displays the subworkspace (702, 1407) with all its visual components. In addition to other auxiliary structures to be discussed below, the main components comprise a single bioEngine (1501), which represents the interactions between the inputs represented by the bioReactants (1408, 1419) where the bioProduct(s) (1518) are generated.

As described below (FIG. 29), a cell-bioProcess may encapsulate bioReactants and bioProducts that represent pools of cells, in addition to encapsulating bioReactants and bioProducts that represent pools of chemicals. So it is possible to have bioProcesses where molecules interact with molecules, as well as cell-bioProcesses where molecules (2905) interact with cells (2904), or cells interact with cells. In addition, there may be pools of pairs of interacting-cells.

Other type of bioProcesses represent translocation processes between location compartments, where the bioReactant represents a fraction of a given bioPool in a given compartment that is removed from that bioPool and transferred, with a time-lag if so desired, to the target bioPool that is connected to the bioProduct, and which represents a different pool the same entity in a different compartment. Additional types of bioProcesses represent transfer of cells from a bioPool (2901) representing one state of those cells to another bioPool (2911) representing a different state of those cells. Each of these types of bioProcesses encapsulates the appropriate subclasses of bioEngines. There are many other types of bioProcesses defined in this invention and, in addition to those examples already mentioned, some others are discussed with the modeling approaches below. Many more types of processes can be represented by composing additional types of bioProcesses by a modeler skilled in the art.

Class bioEngine

The class bioEngine (Table 56) is a subclass of bionode-object and comprises a hierarchy of subclasses. A few examples, of which incremental definitions are shown in Tables 56 through 58, are: amplifier-bioengine, binding-bioengine, lumped-bioengine and cell-bioEngine. Each bioEngine's icon (605, 1501) has a number of stubs of different types of r-connections at the top, to be connected (608) only to bioReactants (606), and a number of stubs of p-connections at the bottom, to be connected (609) only to bioProducts (607). The number and class of defined specific r-connections specify the different classes of bioReactants to be connected, such as enzyme.r, substrate.r, inhibitor.r, receptor.r, agonist.r, antagonist.r or unit.r (FIG. 20). The bioEngines of the class lumped-bioengine, including those with two or more enzymes, represent lumped models of two or more reactions in series, and are used to model stretches of pathways the detail of which is either not desired or not known, and only the rate limiting reactions are represented.

The major subclasses of bioEngine (Table 55) are arranged according to the type of reaction or process they represent, indicated by their names. The next level of classes usually refers to the type of activity of the members of the class and is usually characterized by the class of the variable that defines its Velocity attribute. Further subclasses of each of those classes are defined according to the number and type of their defined stubs, which determines the number and classes of connected bioReactants, and further by color coding the icons to show further specialization, such as using different type-color for different types of enzymes, such as protein-kinases, protein phosphatases, and so on. Further differentiation between particular instances can be generated by selecting as the value of their Velocity attribute an instance of different subclasses of velocity-pvar. The nomenclature used for each subclass refers to the defined bioReactants, such as:

a) bioengine.E1.S2.I1 is an enzyme-bioengine that represents an enzymatic reaction and which icon has at the top four stubs: one for the enzyme.r, two for substrate1.r and substrate2.r, and one for an inhibitor.r;

b) bioengine.R1.L1.An1 is a receptor-bioengine, which icon has at the top three stubs: one for the receptor.r, one for ligand.r, and one for an antagonist.r;

c) bioengine.M1.Ef1.An1 is a conform-change-bioengine that represents an induced conformational change process and which icon has at the top three stubs: one for modifier.r, one for effector.r, and one for an antagonist.r;

d) bioengine.U2 is a complex-formation-bioengine (2011) that represents the formation of a complex from two previously independent bioEntities (which may themselves be complexes) and which icon has at the top two stubs: one for unit1.r and one for unit2.r;

e) bioengine.C1.M1 is a complex-dissoc-bioengine that represents the dissociation of one complex induced by a mediator into two or more independent bioEntities (which may themselves be complexes) and which icon has at the top two stubs for complex.r and mediator.r;

f) bioengine.ch1.i1.L1 is a channel-bioengine (2007), which icon has at the top three stubs: one for channel.r, one for ion-Input.r, and one for ligand.r; or g) bioengine.C1.In1 is a translocation-bioengine that represents a translocation between different compartments and which icon has at the top two stubs: one for carrier.r and one for input.r.

As shown in FIG. 15, a bioEngine (1501) is located upon the subworkspace (702, 1407) of a bioProcess and represents the action of any process, such as synthesis, modification, complex-formation, translocation, diffusion, degradation, and so on. Selecting the "table" option (1503) from the menu (1502) of a bioEngine displays its table of attributes (1504), in this case with the default values. Attributes not previously described include:

Velocity (1505) is an attribute, specific for each subclass, which value is an instance of any of the subclasses of rate-pvar, described above, which for the receptor-bioengine shown is a binding-rate-pvar (1506). The values for this dependent variable are provided by generic simulation formulas that model the rate of the interactions of the bioReactants connected to the bioEngine. Its arguments may be the Contributions of each of its bioReactants, when using the scaled set of variables and formulas, or the bioReactant's kinetic-coefficients and the Densities, Concentrations or other quantities of the bioPools connected to the bioEngine through the bioReactants. Its output is an argument for the Consumption-Rate and Production-Rate of the connected bioReactants and bioProducts, respectively. Therefore, this attribute may take as arguments either a set of scaled-valued variables and/or parameters, in which case this attribute would be also scaled-valued, or a set of absolute-valued variables and/or parameters, in which case this attribute would be also absolute-valued.

Rate-constant-sec (1507) is a simple float attribute, which value may optionally be set by the modeler to provide the rate-constant in seconds for the overall process. This value is used, in combination with the Contribution, by the set of generic simulation formulas that use the scaled set of variables, which is currently the default mode of operation. The default value is used if no other value is set by the modeler.

Tau-coeff (1508) is by default a simple float attribute, which value may optionally be set by the modeler to modify the rate-constant-sec by such factor, allowing for testing the effects of a modification of such parameter on the simulation of the system without having to change the value of such parameter that may have been obtained experimentally. This value is incorporated by default in the generic formulas provided, and if not configured by the modeler, multiplying by its default value of 1.0 has no effect on the system.

Bias (1509) is a simple float attribute, which value may optionally be set by the modeler to modify by a constant amount the rate-constant-sec, for testing purposes, without having to change the value of the later attribute. This value is incorporated by default in the generic formulas provided, and if not configured by the modeler, adding its default value of 0.0 has no effect on the system;

Time-lag (1510) is an optional time-interval attribute that may be useful for certain instances of bioEngines, which value, given by a time-delay-par (1511), is optionally set by the modeler to indicate the period of time by which the forwarding of the computed output of the Velocity of a bioEngine is delayed. It represents a time delay, equivalent to holding an amount from a bioPool for the specified period of time, which is returned after that time has elapsed. An example of its use is when a bioReactant and a bioProduct of this process are both connected to the same bioPool, and the forwarding of the output value of the Velocity is delayed. The value of this attribute may also be modified at run time, as a result of dynamic events related to this or other processes, and may be simulated or inferred by means of modeler-defined formulas, rules, or procedures;

pH (1512) and Temperature (1516) are optional float attributes, which values are given by a ph-par (1513) and a temperature-par and which, as their name indicate, represent the environmental conditions under which the process takes place. The values of these parameters may vary at run time, as a result of dynamic events related to this or other processes, and may be simulated or inferred by means of modeler-defined formulas, rules, or procedures;

pH-deviation-factor (1514) and Temp-deviation-factor (1517) are optional float attributes, which values are given by a ph-factor-par (1515) and a temp-factor-par and which are used in conjunction with pH or Temperature, respectively, and represent a correction factor that either accelerates or decelerates the process when the values of either the pH or the temperature deviates from their defined default values. If used, the values of these parameters may remain constant or may vary for different values of the pH or temperature, as defined by a tabular function similar to a look-up table.

Class bioRole-Object

The class bioRole-Object (Table 59) is a subclass of bioObject, and has two subclasses: bioReactant and bioProduct. A bioRole-Object is an iconic object that represents the role that units from a bioPool plays in a bioProcess, either as a different types of bioReactants (FIG. 21), such as: enzyme.r, substrate.r, inhibitor.r, subunit.r, receptor.r, agonist.r, antagonist.r, carrier.r, and so on, each representing the specific roles of the inputs that different bioReactants provide to the bioEngine, or as a bioProduct.

As shown in FIG. 14, a bioReactant (1408, 1419) is connected by an input r-connection at the top of a bioEngine, and represents the material contribution from a bioPool to the bioEngine to which it is connected. To be operational, the bioReactant-post (703, 707) connected to a bioReactant must have the same name as one of the bioPool-r-posts (704, 708) connected at the bottom of a bioPool. The two bioReactants shown are representative examples of a pair of two interacting molecules or complexes with complementary roles or functions: a receptor and its ligand. Many other combinations of two, three or any other number of interacting participants are possible, to represent other types of processes, such as combinations of enzyme and substrate(s), units that form a complex, and so on. These combinations may also include antagonists or inhibitors, which may alternatively be represented as competing in a separate process, the latter being the preferred alternative in the default implementation using the scaled set of variables and simulation formulas.

The class bioReactant (Table 61) comprises a hierarchy of subclasses, such as: amplifier-bioreactant, source-bioreactant, leading-bioreactant, binding-bioreactant, inhibitor-bioreactant, single-bioreactant, cellReactant, cell-receptor, extracell-ligand, and their subclasses. A few examples of their incremental definitions are shown in Tables 61 through 64. There are several attributes common to all subclasses of bioReactant, while each subclass has one or two specific attributes. Every bioReactant (1408, 1419) has its menu (1409, 1420), and selecting its "table" option (1410, 1421) displays its table of attributes (1411, 1422), in this case showing the default values for their attributes. New and not previously described attributes specific for any of the subclasses include:

Stoichiometric-coeff (1412) is a simple float attribute of all subclasses of bioReactant and bioProduct, which constant value represents the characteristic stoichiometric coefficient of that participant in that particular bioProcess. In other words, the set of the stoichiometric-coeff of all bioReactants and bioProducts of a particular bioProcess indicates the relationship between the number of units of each bioProduct produced per number of units of each bioReactant;

Alpha-coeff (1413) is a simple float attribute, which value may optionally be set by the modeler to modify by a factor the Contribution, which value is computed by the program. This is of interest for testing the effects of a global modification of such variable on the simulation of the system. This value is incorporated by default in the generic formulas provided, and if not configured by the modeler, multiplying by its default value of 1.0 has no effect on the system. Alternatively, the modeler may delete the alpha-coeff-par and provide instead a simple float value Contribution (1414) is an attribute of every subclass bioReactant, which value is given by a contribution-pvar (1415), which value is dynamically computed while a simulation is running. The meaning and use of this attribute is a novel teaching of this invention, designed to meet some of the challenges posed by the domain of this invention, where both qualitative and quantitative knowledge is frequently scattered and incomplete. This attribute represents the Contribution of each bioReactant to determining the overall rate of the transformation in that bioProcess, as represented by the Velocity of its bioEngine. The contribution is a variable that can take values from 0.00 to 1.00, and represents a dimensionless scaled concentration (or other equivalent quantity variable). The scaling of the concentration is done at the bioReactant level, rather than at the bioPool level, to allow for additional flexibility. In this way, the absolute concentration can be scaled differently for each bioEngine, centering around the specific constant that characterized the molecular interactions between each specific pair of bioReactants. The type of constant may be different for different bioReactants representing the same BioPool depending on the role played by each bioEntity in a given bioEngine, such as a Km for each substrate, the Ki for an inhibitor, the Ks for ligands or complex-subunits. The default values for all types of contribution are equal to: a) 0.5 for normal steady-state physiological conditions (for that particular compartment); b) 0.0 for bioPools of inducible proteins or non-physiological molecules; or c) 1 for constitutive and repressible proteins. The user can either directly override a relative value or leave the default values. A generic formula specific for each of the bioReactant classes determines how the value of each contribution class is computed.

Consumption-Rate (1416) is an attribute of every subclass of bioReactant, which value is given by a dependent consum-rate-pvar (1417), which value is dynamically computed while a simulation is running, and indicates the rate of consumption of units of the connected bioPool in such bioProcess. Its arguments are the bioReactant's stoichiometric-coeff and the Velocity of the bioEngine, and its value is an argument for the Output-Rate of the connected bioPool. For those classes of bioReactants that are not consumed in a reaction, the value of this attribute remains 0.0. In this invention, an enzyme.r or an inhibitor.r are preferably not consumed in the enzyme-processes. However, they may be retained, by modeling them with a time-delay-var with its specific formula. Note that the connected bioReservoir may be configured for the quantity of the bioPool to decay dynamically, representing their degradation and diffusion components, and it also may be consumed in other bioProcesses;

Effective-binding-sites (1418) is a simple float attribute of the subclasses of bioReactant that refers to molecules or complexes that have binding activity, such as all the subclasses of amplifier-bioreactant and leading-bioreactant, and its value is set by the modeler to indicate the number of effective binding sites per unit.

Kinetic-parameters are by default simple float attributes specific for some subclasses of bioReactants, which values are optionally set by the modeler to indicate the value of the kinetic parameter characteristic for that particular instance. A set of two attributes is provided for each of such subclasses, one to hold the absolute value and the other to hold a scaled value of such kinetic parameter, which are used by the set of absolute generic simulation formulas in conjunction with the absolute-valued variables, or by the currently default set of scaled generic simulation formulas in conjunction with the scaled-valued variables, respectively. Alternatively, in cases where the value of the kinetic-parameter is time-variant and dependent on other variable values, the modeler may choose for individual bioReactants to define for that attribute an instance of kinetic-parameter-var (Table 13), in which case the modeler has to define the specific simulation formula to provide the value for that particular instance, as previously described (FIG. 10). Examples:

Equilibrium-dissociation-constant (1423) and Scaled-equil.dissoc.k (1424) for the subclasses of binding-bioreactant (Table 98) indicate the absolute or a scaled value, respectively, of the Ks characteristic of that agonist or complex-subunit;

Catalytic-constant and Scaled-catalytic.k for the subclasses of enzyme.r (Table 95) indicate the absolute or a scaled value, respectively, of the characteristic kp of that enzyme, where kp is the equivalent of the units of activity per catalytic center, or $kp=Vmax/[E]t$ $(t^{-1})$;

Michaelis-constant and Scaled-michaelis.k for the subclass substrate.r (Table 96) indicate the absolute or a scaled value, respectively, of the Km characteristic of that substrate, where Km is the dynamic constant equivalent to the substrate concentration that yields half-maximal velocity, or $Km=(k-1+kp)/k1$. This attribute may optionally be considered to represent the Ks, where Ks represents the intrinsic dissociation-constant, or $Ks=[E][S]/[ES]=k-1/k1$ $(M)=1/Keq$, may be used when the system modeled is under rapid equilibrium conditions, which is usually not required because of the dynamic nature of the simulation system of this invention, which may be used in a formula in conjunction with the catalytic-constant or scaled-catalytic.k, respectively, of the interacting enzyme.r; or Inhibition-constant and Scaled-inhibition.k for subclasses of inhibitor-bioreactant (Table 99), which values are optionally set by the modeler to indicate the absolute or a scaled value, respectively, of the Ki characteristic of that inhibitor or antagonist (where the factor $(1+[I]/Ki)$ may be considered as an [I]dependent statistical factor describing the distribution of enzyme between the E and EI forms).

The class bioProduct (Table 60) has the subclass cell-bioProduct. As shown in FIG. 15, a bioProduct (1518) is connected to an output p-connection at the bottom of a bioEngine (1501), and represents the material contribution from a bioEngine to the bioPool to which it is connected. To be operational, the bioProduct-post (711) connected to a bioProduct must have the same name as one of the bioPool-p-posts (712) connected at the top of a bioPool (713). Every instance of bioProduct (1518) has its menu (1519), and selecting "table" (1520) displays its table of attributes (1521), which in this case shows the default values for its attributes. Not previously described attributes specific of this class include:

Production-Rate (1522) is given by a produc-rate-pvar (1523), which value indicates the rate of production of the units that will be added to the connected bioPool, which is dependent on the bioProduct's Stoichiometric-coeff and the Velocity of the bioEngine, and is an argument for the Input-rate of the connected bioPool.

Class bioRole-Post

Figure 22:
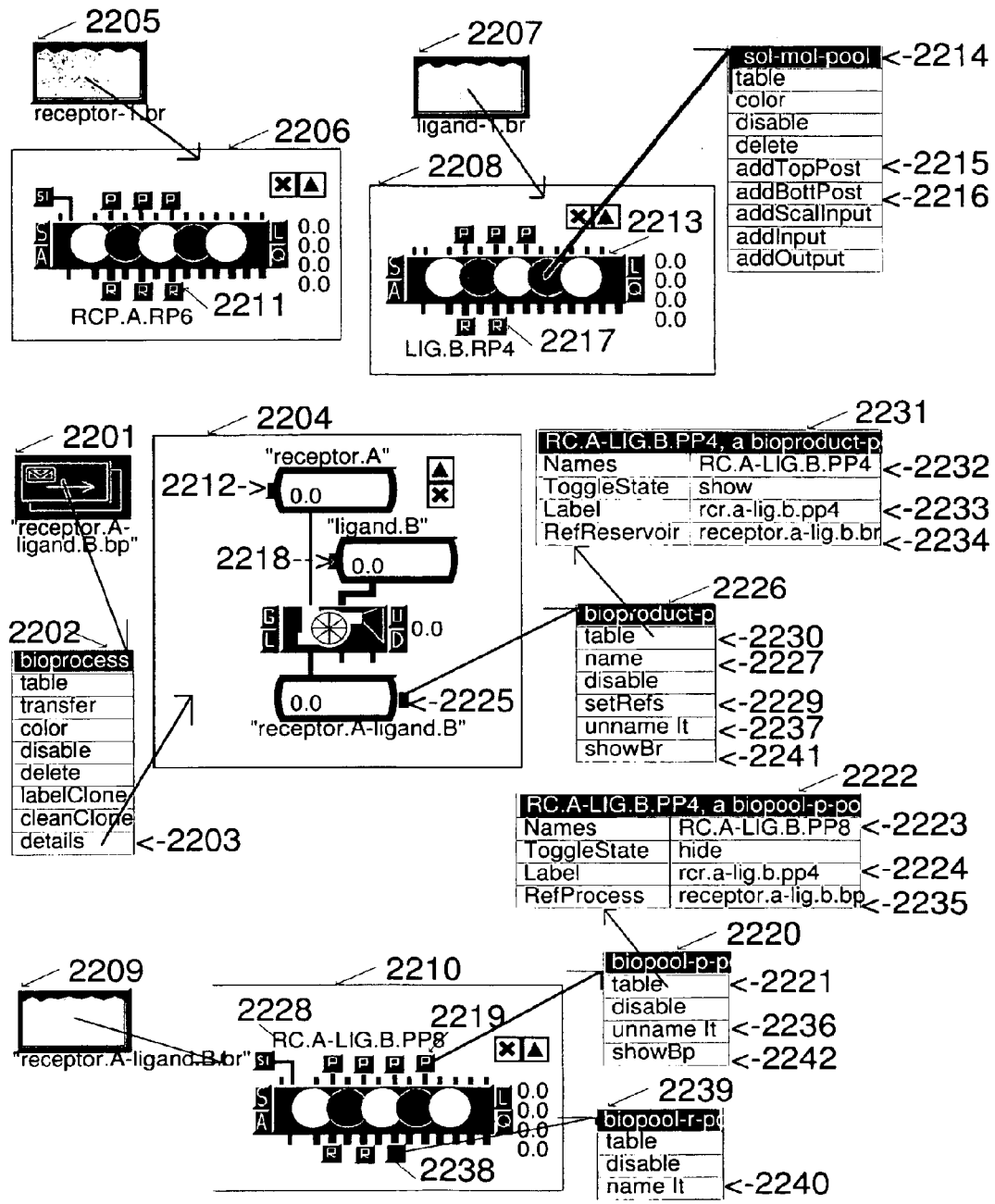
FIG. 22 describes the tools for interactively establishing links between components that result in multidimensional pathways.

A bioRole-post is located upon the subworkspace of a bioProcess and its function is to connect a bioRole-Object to a bioPool through a bioPool-post. The class bioRole-post (Table 65) is a subclass of bioPost, from which it inherits all its capabilities, and has two subclasses: bioReactant-post (703, 707), which together with a biopool-r-post (704, 708) distantly connects a bioReactant to a bioPool; and bioProduct-post (711), which together with a biopool-p-post (712) distantly connects a bioProduct to a bioPool. The new attribute defined for these classes is:

Ref-bioreservoir (2234) is a pointer to the bioReservoir instance (2209) that encapsulates the biopool-r-post or biopool-p-post to which it is distantly connected. The value is interactively set by selecting the "set-refs" (2229) option, and it is used by the program for interactive navigation through bioReservoirs and bioProcesses, as described below (FIG. 22).

BioModels

In this invention, a bioModel means an iconic knowledge structure, which, depending on the subclass, encapsulates in its subworkspace a set of interrelated composite bioObjects, such as bioReservoirs, bioProcesses or other bioModels. BioModels are used to partition the Virtual Model into a modular hierarchy of subworkspaces of bioModels, and can be also described as subsystems or fragments of a larger network of pathways, which can be reused as modules of desired degrees of complexity to be combined in a variety of ways to build larger and diverse systems. BioModels are objects represented by icons (FIG. 23), and the constants, parameters, and variables that quantitatively model the system are distributed throughout their component building blocks, which function as distributed parallel processors. The dynamic aspect of a bioModel is determined by a system of algebraic and differential equations that provide the values for the encapsulated dependent and state variables. BioModels represent empirical biological models derived from experimental descriptive information and semi-quantitative or quantitative data. Very complex bioModels can be built by connecting component parts of an unlimited number of other bioModels by means of connection-posts. The icon of some bioModels, such as sequential time-compartments (2303, 2318 through 2322), may contain stubs to allow connection to other bioModels.

The class bioModel (Table 66) is a subclass of bioView-Object and have no additional defined specific attributes, but inherit the attributes Names, Label, Description, References, Warnings, and Toggle-state. It comprises various subclasses (only some examples of which are listed in Tables 66 through 73), which represent any physiological system at different levels of structural complexity, such as organ (2328), tissue (2332), cell-interaction (2327, 2501), cell (2326, 2602), or subcellular organelle (2310–2316, 2406, 2416–2420), or any other intermediate compartment within those compartments, such as: submodel (2302–2305, 2408), bioReservoir-Bin (2306, 2412, 2413), and On-Hold-Bin.). A submodel schematically represents a portion of any size of the network of pathways of a larger structure, such as a cell-bioModel. The subworkspace (1630, 2409, 2520) of a submodel contains a set of related bioProcesses and also a bioReservoir-Bin (2412), which encapsulates (2414) a set of related bioReservoirs connected to those bioProcesses. However, the bioReactants and bioProducts of any bioProcess that is a component of a bioModel may be connected to bioPosts of bioReservoirs that may be located in the same or in other bioModels. As the submodel becomes larger, it may be broken down into smaller submodels by simply cloning a new submodel and transferring to its subworkspace the desired bioProcesses and to the subworkspace of its bioReservoir-bin the corresponding bioReservoirs. The connectivity of the pathways is transparent to movements of bioObjects from one bioModel to another, since they are directly connected among them through the structures upon the subworkspaces of bioReservoirs and bioProcesses.

This architecture results in a hierarchy of bioModels encapsulated within other bioModels (FIG. 24), which ultimately encapsulate bioProcesses (2410) and bioReservoirs (2414), which encapsulate bioReactants, bioEngines and bioProducts (2411), or bioPools (2415), respectively. Although this topology may appear complex, at run-time each of the variables depend on the variables of only those bioObjects directly connected, and therefore the system operates as a set of processors concurrently computing in parallel. The distant connections between bioProcesses and bioReservoirs, established through the bioPosts anywhere in the knowledge-base, interconnect the different bioModels into a dynamic multidimensional network of any unlimited complexity. This architecture facilitates the implementation of feedback and forward loops, interactions between components of different pathways, elements that are shared by different pathways, and connections between segments of pathways that are built as separate reusable modules. When one bioPool participates in feedback-loops in two or more pathways, this bioPool may be able to 'switch' one pathway to the other at a given point, as a result of continuously varying functions, such as different velocities or diffusion rates.

The class On-Hold-Bin (2003) is characterized by having an activatable-subworkspace, which is usually maintained deactivated. The instances of On-Hold-Bin are used to store within a submodel bioReservoirs and/or bioProcesses that are either substitutions for the bioReservoirs and/or bioProcesses encapsulated in such submodel, or additional bioReservoirs and/or bioProcesses to extend the pathway represented by such submodel, which are appropriately connected, but which the user wants to exclude from a simulation or other uses. By having the subworkspace deactivated, all those structures are ignored by the inference engine and the simulator. The user may have those structures included or excluded from a simulation or other uses at will, as described under the Modeler-Mode heading. The table of attributes of each instance of an On-Hold-Bin allows to store and access additional information. All instances of On-Hold-Bin have either one of two alternative menu options: a) if the subworkspace of the On-Hold-Bin is activated, then the "deactivate-sw" is available, which upon selection by the user deactivates such subworkspace; or b) if the subworkspace of the On-Hold-Bin is deactivated, then the "activate-sw" is available, which upon selection by the user activates such sub-workspace.

Some of those subclasses of bioModels, such as the sequential time-compartments, can be independently activated and activated by the program during a simulation run. The efficiency of large-scale simulation applications can also be significantly improved using that mechanism, by having whole branches of the model that are not relevant at some point in time deactivated and activated when required, driven by events generated as a result of the simulation itself, or at given time intervals.

The class cell-bioModel (2326, Table 68) is used to represent a cell as observed from the inside (FIG. 24). It is a container of subcellular compartments that may encapsulate different layers of submodels until at the end of the compartment hierarchy, the bioReservoirs and bioProcesses are encapsulated. Cell-bioModels are used for modeling prototypic cells of interest in a very detailed way through their functional structural components, which at the end encapsulate variables and parameters that allow to quantitatively simulate those models, or more realistically, constrained submodels within the cell, which can be selected by selecting any of the compartments at any desired level. The hierarchical encapsulation allows not only to display different levels of detail to focus only those parts of the system that are relevant to the user at any given time, but also allow to expand the model adding additional levels of detail whenever desired. Each cell-bioModel or any of its encapsulated bioModels can be used as modules to build other bioModels with increasing degree of complexity. This modular and reusable building block structure gives the system great flexibility and transparency, while allowing to build very complex cell-entities.

As shown in FIG. 24, each cell-bioModel (2401) has a subworkspace (2402) upon which are represented the characteristic phases of the cell cycle (2421), that follow a repeated cyclic pathway, or the cell differentiate into a different stage (2428), or may go into apoptosis (2430), a terminal stage. The cell-phases (2318–2322, 2404, 2421, 2428, 2430)) are subclasses of the class cell-phase, the main defined subclass of the class time-compartment (Table 69), but other types of compartmentalization are also possible by means of instances of the class time-submodel (2303, 2423, 2425, 2426). Instances of the class biomodel-post (2403, 2429), ant its associated methods (Table 70) allow to connect those cell-phases with another cells-phases upon other cell-bioModel, and to display them.

The G0-compartment (2404) in cell biology represents resting-cells. In this invention, this compartment also represents the background processes of resting-cells, but in addition it also contains all those background bioProcesses that are not specific for any other phase of the cell-cycle or which cross-over the boundaries of several of those phases. This compartment is frequently the starting point of a simulation and its bioPools are usually modeled by the default "normal" steady-state values of the variables and parameters of interest.

The G1-compartment (2421) represents a state of cells after they have been activated by external factors, and may be further compartmentalized into two or more time-compartments. For example: the G1.1-compartment represents activated-cells or early-G1-phase-cells which have recently entered the G1-phase of the cell cycle, as characterized by transcription of early-response genes, expression of new receptors; while the G1.2-compartment or late-G1-phase-cells, is characterized by transcription of late-response genes or increased secretion of specific cytokines or other signaling factors.

The S-compartment (2320) represents the state of cells in S-phase, characterized by DNA synthesis.

The G2-compartment (2322) represents cells in the G2-phase, characterized by double DNA content and before entering mitosis.

The M-compartment (2323) represents cells in the M-phase, during the mitotic process.

The Di-compartment (2325, 2428) represents cells entering a new differentiation stage, when a different set of activated early-response and/or late response genes induce permanent changes in the types of genes expressed. This layer is followed, depending on the combination and strength of signals provided by simulation events, by either the G0-compartment or both this and the G1-compartment of the next cell type in the differentiation pathway.

The Ap-compartment (2324, 2430) for apoptotic cells, when cells in the G2-layer do not receive the appropriate signals to enter the M-layer. This is a terminal layer which only effect is to reduce the size of the total cell population. (Note that the total cell population size is increased at the transition after every M-layer, by an amount equal to the size of the population in that M-layer. The non-specifically-modeled overall cell death is represented by a decay parameter, set to fit the experimental data.

The default time-duration (317) of each of these temporal layers is set according to experimentally obtained knowledge of such duration, under specified "normal" conditions. A layer-rate-constant t1, is constrained to values $-1>t1>1$ and initially set to 0. When the effects of different combinations and strength of signals on the duration of any of the layers are measured, then the value of t1 is adjusted to fit the target values of the experimental set-->tT=tO (1+t1).

Each time-compartment (2404, 2423) encapsulates (2405, 2424) several spatial compartments that run in parallel to each other, and which represent the clearly defined subcellular compartments, called cell-Compartments (Table 67), such as the cell-membrane (2406), cytoplasm (2416), nucleus (2417), endoplasmic-reticulum (2418), Golgi apparatus (2419), endosomes (2420), mitochondria, and so on. It also encapsulates a timer (Table 70, 2427) with an activation time attribute given by an elapsed-simul-time-par, which can be used in the control of the deactivation of the subworkspace that contains it by inference methods based on such value. The connections between the time compartments belong to the class cycle-path (Table 38) and encapsulate a number of parameters and variables to hold the values of the rate-constant and the progression rate that can be used when developing quantitative models for simulation purposes. A number of other variables and parameters that describe among others: a) the size related attributes of the cells, and b) quantities related to population dynamics, such as those shown in FIG. 3 (317–320), which are attributes of the cell-phases, are defined in Tables 3 through 11. A collection of inference blocks (Table 23) may also be used to control (Table 77) the activation and deactivation of the time compartments, at intervals that are predefined or dynamically computed depending on simulated variables are also defined. Table 88 lists as an example a set of simulation formulas for state variables that can be used to compute the dynamic changes in cell numbers that are accumulated in each of the cell-phases, when using these graphic structures in combination with a population dynamics approach. Furthermore, Table 78 lists a set of rules that can be alternatively used to control the progression through those cell-phases, when using the mechanistic approach. As the reader may realize, there are a number of different alternatives, encapsulated within those graphic building blocks, to model the complex systems at different levels, as discussed in the modeling section.

Figure 28:
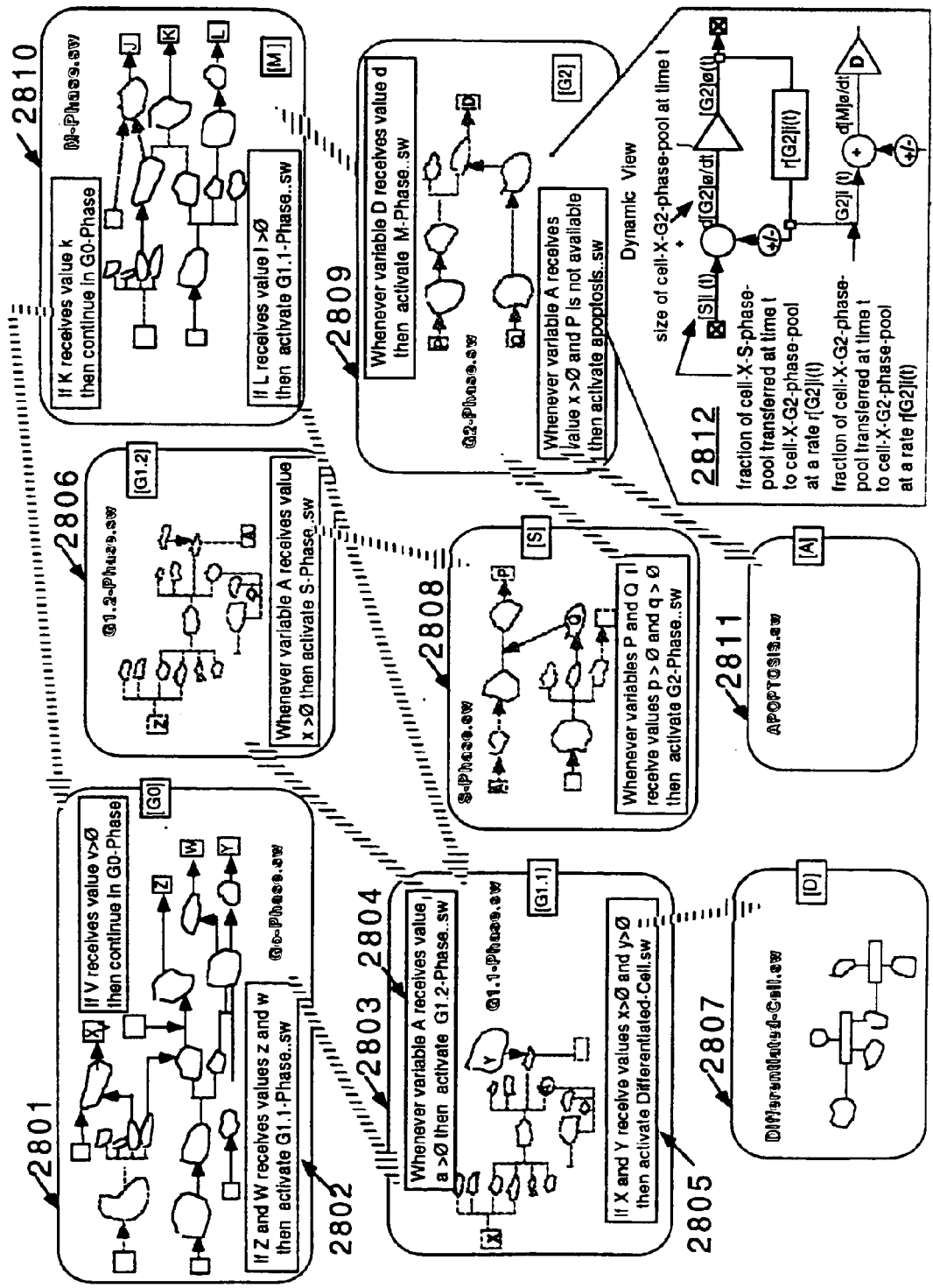
FIG. 28 is a schematic representation of the combination of the inference and simulation capabilities used in this invention to simulate Virtual Models of complex systems.

FIG. 24 shows the major states considered in the currently preferred embodiment of this invention, following the classical nomenclature and concepts generally accepted in the scientific community, the resting state is defined as the Go phase. Each of the values of the Cell-phase attribute of a cell-bioModel indicates which of those phases is currently activated, if any in addition to the G0-phase. While at Go, if the cell is activated by a growth factor, antigen or any other activating stimulus, the cell enters the activated state or G1, from which it can follow to other phases of the cell cycle or the differentiating states, depending on the signals received. G1 is bounded by the progression signal or cell birth and the initiation of DNA replication, and characterized by sequential expression of additional genes, protein synthesis and cell growth. S is bounded by initiation and completion of DNA synthesis. G2 is bounded by the completion of DNA synthesis and the initiation of mitosis, and characterized by further cell growth and/or protein secretion. M is bounded by initiation of mitosis and completion of cell division, usually represent about 2% of the total. Although the cell cycle is a continuous one, it can be compartmentalized into functional cycle intervals whenever it is deemed useful to better represent the dynamic simulation of the system. As shown in FIGS. 4, 28, and 29, there are switching points (406, 2803, and 2911) at early G1 where the cell has to decide between the differentiation and the cyclic pathways resulting in a variety of different patterns that depend on both the internal stage of the cells and other components in the system, external to the cells. A typical pattern results in: a) cells in the resting stage, when the steady-state conditions are assumed, then after activation by specific external signals, switching through the cycling phases one or more cycles, or back to resting, then after activation by specific external signals during one of those stages, switching to one of the next nodes in the tree, committing themselves to that branch of the tree in the longitudinal pathway, then once at the new node they may go back to a) for a period of time, in a resting stage during which the new steady-state conditions are assumed, or, if activated by specific external signals they may go back to b) with the new steady-state conditions as the base-line.

Each of the cell-Compartments comprises a subworkspace (2407), which may contain various submodels (2408). Other local-submodels (2304) are also provided for other types of spatial compartmentalization. The subworkspace (2409) of a submodel may contain other submodels, and submodels may also contain bioProcesses (2410) or bioReservoirs. In the current embodiment, the bioReservoirs (2414) are preferentially hidden in a bioReservoirs-bin (2412) that belongs to that submodel.

Figure 25A:
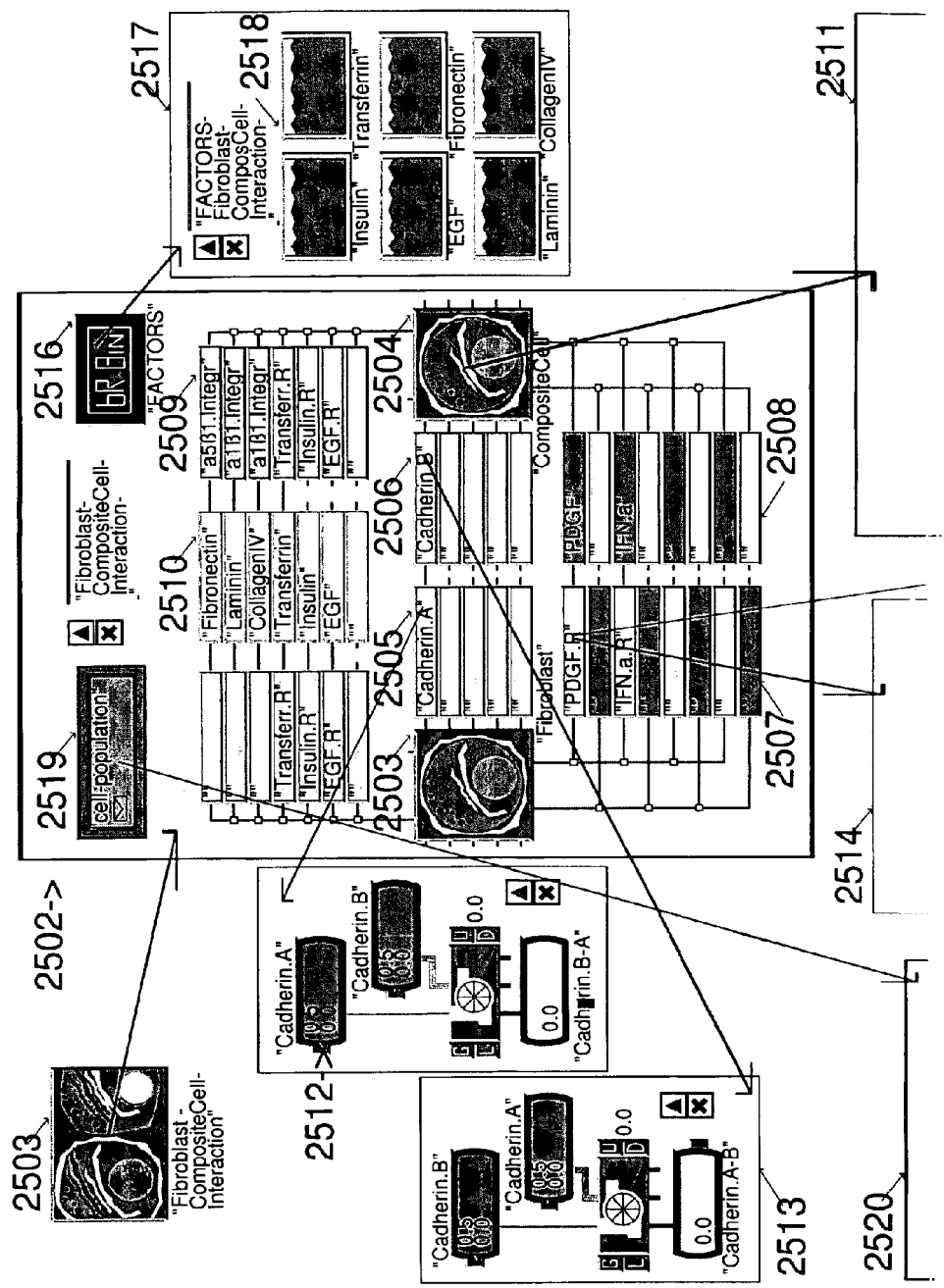
FIG. 25a and FIG. 25b describe a domain-specific implementation of compartmentalized model of two cells interacting with each other and with the external environment.
Figure 25B:
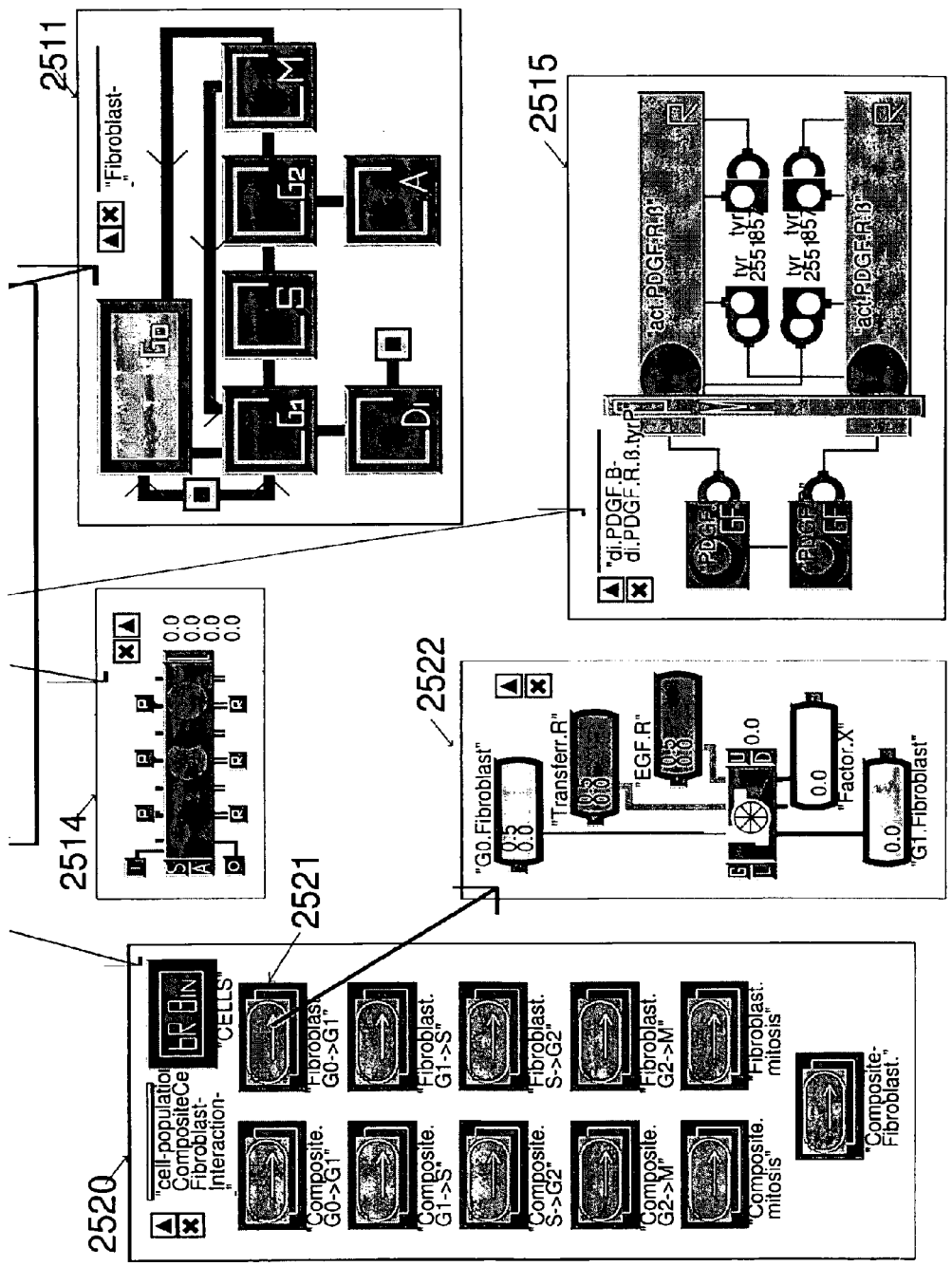
Figure 26:
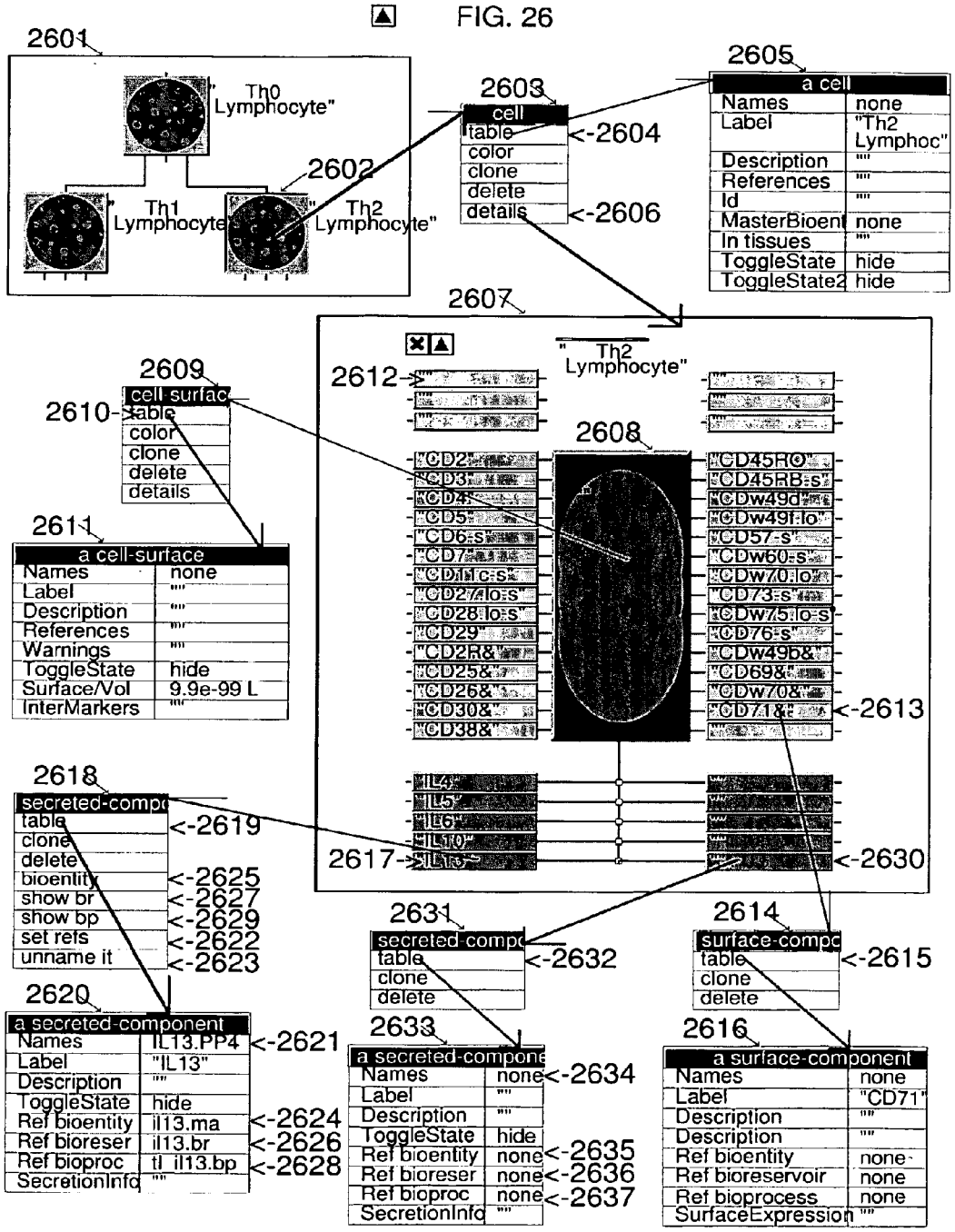
FIG. 26 describes a domain-specific characterization of the compartmentalized model from an external point of view.

As shown in FIG. 25, instances of the class cell-interaction (Table 72, 2327, 2501) encapsulate in their subworkspace (2502) the interaction of two cells (2503 and 2504), that use the graphic extracellular-components (Table 72a) to interact with each other directly by means of surface-components (2505, 2506); through the components that one secretes, the secreted-components (2507), for which the other has specific receptors, the surface-components (2508); and both interact with their environment through specific receptors (2509) for systemic-components (2510). As shown in FIG. 26, each of those components has a table of attributes (2616, 2620, and 2633), referring to an specific bioEntity (2624), bioReservoir (2626) and bioProcess (2628) within the cell-bioModel, and are connected to the internal mechanistic pathways. Clicking on those icons displays their menus (2614, 2618, 2631) from which options the user can select the display of the associated structures, as specified in the attributes. The different menu options and their associated procedures are listed in Tables 72c, d, and e). Tables 72b and f list functions that allow the modeler to automate the task of establishing the distant connections to those graphic structures. The interacting-cells (2503 and 2504, Table 72) in this interface do not encapsulate a mechanistic model of its components, but rather refer to and display another cell-bioModel that store those mechanistic models. In this way, this structure is used as an interface to design interactions between other cell-bioModel, and new cells and other connections to bioProcesses or bioReservoirs can be established. The external components (2612), such as serum or incubation media, or single or lumped toxic-byproducts, for which there are specified or lumped receptors are represented by a set of bioReservoirs, such as serum-Pool, are connected to a bioProcess with a receptor-engine that has at least one bioProduct connected with one of the bioReservoirs within the cell. The function of the bioEngine is to compute the consumption an exhaustion of nutrients at a rate proportional to m, the specific growth rate. The byproduct-Pool's concentration is used to modify the value of m by multiplying it by a parameter $0<m<1$.

Figure 27:
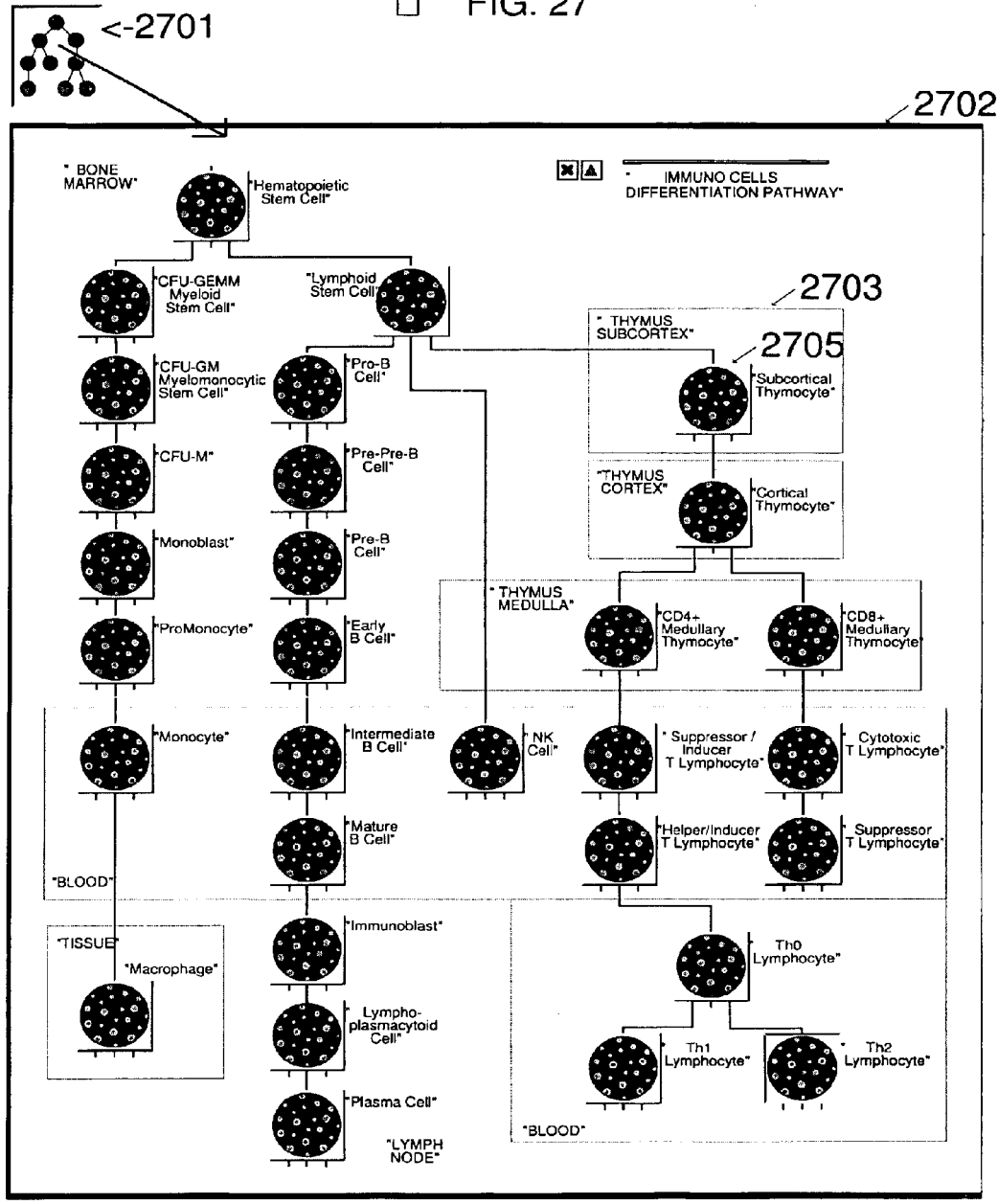
FIG. 27 describes a domain-specific implementation of an evolutionary tree representing the alternative successive states that a compartmentalized model may follow depending on the events that depend on their internal processes responding to the environment, from an external point of view.

Cells are represented in this invention in two different ways: as the class cell-bioModel (2401) composed of cell-Compartments, as described above, and as the class cell (2602) used to represent a cell as observed from the outside and including any defined, mostly external, characteristic markers (2607), as shown in FIG. 26, that can be used to assigning that cell to one type of cells and to distinguish it from cells of other types. The instances of class cell (2602, 2705), with sets of stubs on the top and bottom of their icons, are used to classify cells according to a branching differentiation tree, as shown in FIG. 27, to define the many nuances between them that differentiate them from each other, particularly when following the almost continuous differentiation process. As an example, a Th2-lymphocyte (2607) is shown in FIG. 26. An instance of cell may correspond to an instance of cell-bioModel, but it is expected that there are many more intermediary stages represented by the lighter cells, which represent the much lower level of detail most frequently available. BioReservoirs representing cell populations may refer in their Ref-bioentity attribute to a named instance of cell. One of the menu options for this class is "biomodel", which, upon selection, displays the subworkspace of the bioModel referred to by one of its attributes, Ref-biomodel, if any, and that option is only visible when such attribute has a value. The class differentiation-pathway (2335, 2701, Table 73) provides structures that allow the modeler to manually build differentiation trees, such as the one shown in FIG. 27, which are based on expert-knowledge to represent the sequential progress from one stage of differentiation to the next. The different stages through which a cell lineage goes through is a continuous process, which can be simplified with the representation used in this system consisting of discrete stages that represent different stages of differentiation, defined by characteristic and measurable phenotype, that follow a tree like longitudinal pathways. The cells in those pathways are of the class cell (2602, 2705) and further encapsulate detail as shown in FIG. 26. A cell contains information in a table of attributes (2605) and in its sub-workspace where the different icons include a cell-surface (2608), since this is a representation of the cells from the outside, and a set of components that allow that cell to display characteristic markers and receptors that allow them to interact to the outside world.

Inference and Simulation Structures

Functions are statements, which define a sequence of operations that are performed when the function's name and arguments appear as part of an active expression. The tabular-function-of-one-argument (Table 74), a class defined within the Shell, has an important use in the domain of this invention by allowing to deal with situations when the algebraic relationship between two variables is not known, but the experimental data is available, and straight-line interpolation is optional. Tabular functions can also be used in other expressions, such as the rule: if the [Product1] ([Substrate1]) decreases then inform the operator that "[Substrate-1] may be inhibitory at high concentrations".

Relations are defined associations between two items, which can be dynamically concluded and reasoned about, and in the current implementation of this invention, they represent physical and abstract relationships between objects, such as a-downstream-bioReservoir-of, or the-downstream-BR-list-of. After being defined by the developer, relations are established transiently at run-time by the inference engine. The dynamic reasoning used for query, navigation, and simulation depend heavily in the use of relations, in addition to the graphical connections. The existing relations for a particular object can be also be listed using the "describe" option. Most of the relations are created during the initialization set of procedures, while others are created at run-time.by the sets of procedures used during query, navigation, and simulation. The creation and breaking of relations are treated as events that are forward chained to rules that refer to the relations in their antecedent. Relation definitions are shown in Tables 75 and 218a.

Domain-specific rules (Tables 76 through 81) are used to conclude or to respond to the changing conditions in the world defined by the domain-specific knowledge structures. In the current embodiment, a rule has, in addition to its body that encodes the rule itself, a set of attributes that can be configured to establish its mode of operation and to define its restrictions, such as: whether it can be invoked by forward chaining and backward chaining, whether it may cause data seeking or forward chaining, focal classes and focal objects, priority, and its scan interval. Different types of rules may lack some of those capabilities. For example: a) whenever rules have no focal objects or classes, and cannot be invoked by forward or backward chaining, being only event driven. Such events may be a relation being established or broken, or moving the icon by the user, which is frequently used in this application to either trigger the automatic configuration of the value of some attribute, or the appearance of the icons, or the position of the icons; and b) initially rules are first and only invoked when a knowledge-base is started, or when a subworkspace is activated. Therefore, the situations to which those rules applied, and the conditions under which they can be invoked, can be very much constrained by the generic and specific sets of options and attributes of each particular instance.

Formulas (Tables 82–88) in this system can be defined as expressions that define the relationships of a variable or parameter to other variables or parameters, in a way that when one variable or parameter changes the formula predetermines in which way other variables or parameters will be changed, either by the inference engine, in the case of general formulas, or by the simulator, in the case of simulation formulas. Generic simulation and general formulas provide values for a whole class or group of bioVariables or bioParameters, in contrast with the specific simulation and general formulas, which are attached to the definition of one variable and apply only to that variable. The definitions of generic simulation formula for sets of scaled-valued variables (Tables 83 and 84), mixed-type variables and absolute-valued variables (Table 86) will be discussed under the Simulation Mode heading.

Modeler Mode: Creating the Virtual Models

Menus, Palettes and Libraries

The Modeler Mode is made available to those users who have rights to build or modify applications. The modeler's tasks are all based on the basic paradigm of "Clone, Connect, Configure and Initialize", and consist of building and configuring graphical models of the structure of bioEntities, as well as to design and build graphical models of complex networks of cross-talking pathways, which result from the modeler's actions of cloning, connecting and configuring sets of bioProcesses, bioReservoirs, and bioEntities. To facilitate the modeler's tasks, the Modeler-Menu provides a way to organize and access the different components of the system.

Figure 16:
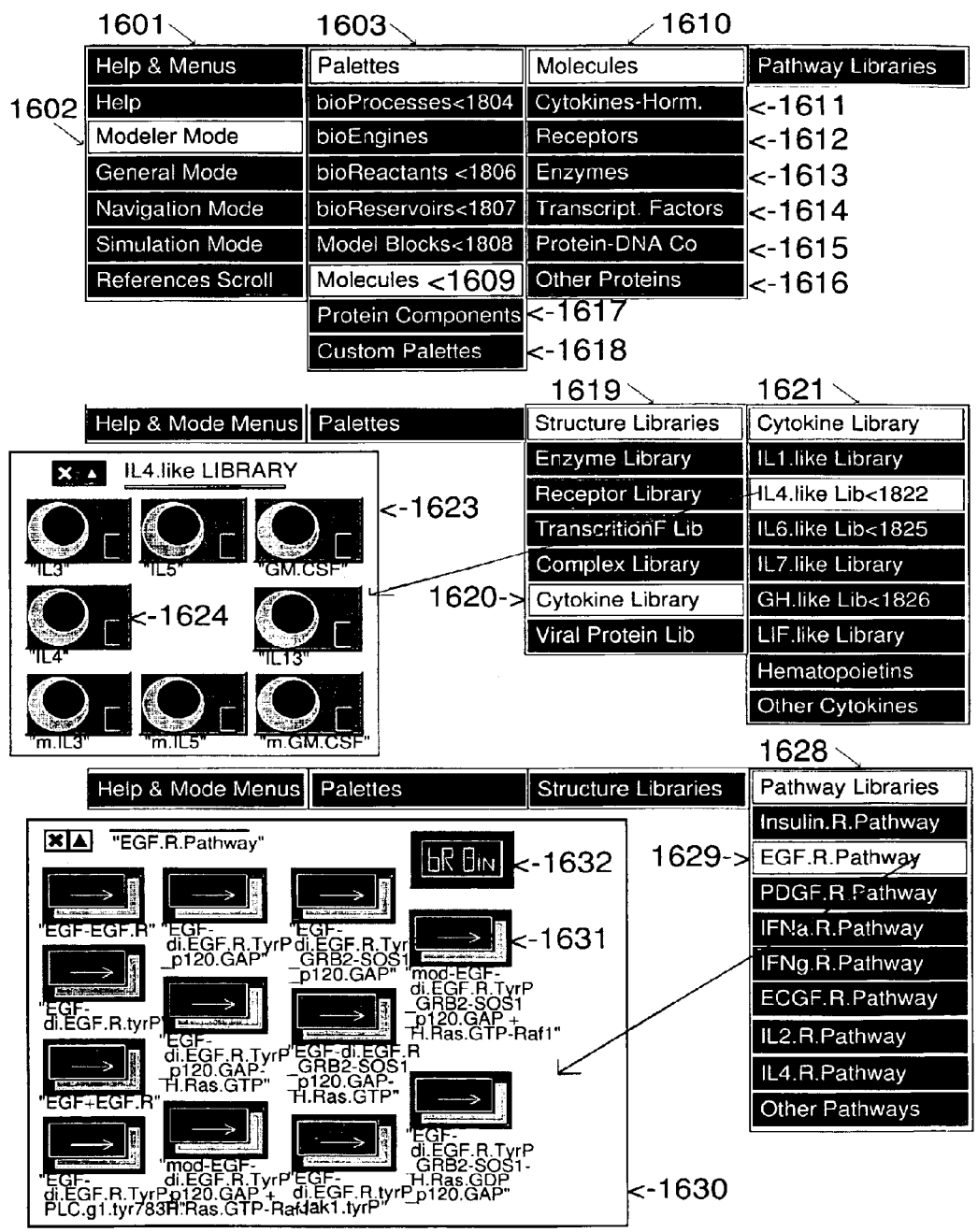
FIG. 16 shows domain menus of the modeler mode that allow modelers to access the different palettes of prebuilt building blocks.
Figure 17:
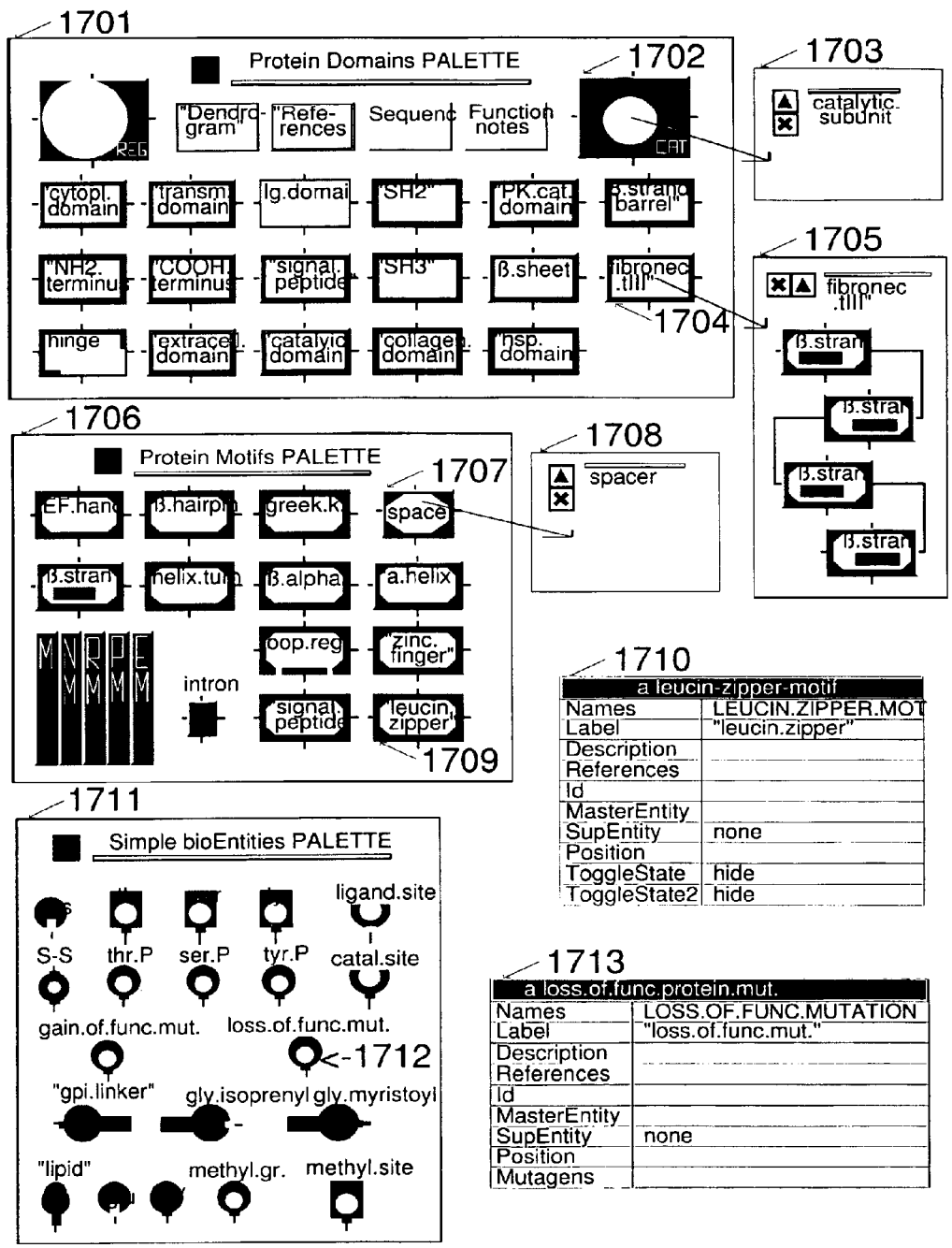
FIG. 17 shows examples of different palettes of prebuilt molecular components.

FIG. 16 shows the domain-menus associated with this mode, shown here pulled-down for demonstration purposes. Selecting the "Help & Mode Menus" option (1601) allows access to the available user modes, which upon selection causes a change to that mode of operation and displays the specific domain-menus associated with that user mode, only for the window from which it is selected. Selecting Modeler Mode (1602) displays the top layer of menu heads, which additionally comprise the options "Palettes" (1603), "Structure Libraries" (1619), and "Pathway Libraries" (1628), allowing to access parts of the Virtual Models by selecting the desired options from the menu, which usually requires navigating through a hierarchy of walking menus. The following discussion of this menu system also serves the purpose of discussing how the building blocks are organized in Palettes and how the iconic models build by the modeler are organized and stored in Libraries. Palettes contain domain-specific and generic building blocks built by the developer and to be used by the modeler, while Libraries contain application-specific models built by the modeler and to be used by different types of users. Palettes are provided to allow the modeler to quickly create new instances from prebuilt generic bioEntities, bioReservoirs or bioProcesses, or any of their components, which comes with their corresponding default or no values, to be then configured by editing their tables of attributes. A facility is provided, the Modeler-Palettes-Bin, to automatically create new empty Palettes to be populated by modelers, to allow them to expand and complement the built-in library of building blocks to satisfy their more specific needs. The Palettes provide a large number of characteristic types of bioObjects, grouped by subclasses and organized in special subworkspaces of named go-to-sw buttons organized in the subworkspace of a "Palettes-Bin". Palettes are accessible through the domain-menus, and because of their defined user-restrictions, selection of any bioObject upon a Palette in Modeler Mode implies clone, which automatically results in a clone of such bioObject (including its subworkspace and all structures upon it, and all the further levels of encapsulation) to be attached to the mouse-pointer and ready for the modeler to transfer it to the desired subworkspace. Selecting "Palettes" (1603) pulls down its options, which may point directly to the palettes of important classes of bioObjects and model-blocks, such as 1604>2001 and 1608>1901, and 1616 points to 2301. In the case of classes with large number of building blocks, those may be grouped further in a number of palettes that can be accessed through walking menus, such as when selecting "Molecules" (1609) displays a pull-down menu headed by "Molecules" (1610), which options may now point directly to Palettes. Examples are shown in FIG. 17, such as when selecting "Protein Components" (1617), the options of the walking menu generated lead, among others, to "Protein Domains" (1701), "Protein Motifs" (1706), and "Simple bioEntities" (1711).

Libraries Comprise among Others Two Types:

Structure Libraries, are hierarchically organized workspaces (1623) containing models of specific complex-bioEntities (1624) that model the functional structure of molecules or molecular-complexes at various levels of complexity, and which can be accessed by selecting the options of the menu head "Structure Libraries" (1618). For example, Selecting "Cytokine Library" (1620) displays the menu (1621), which options refer to libraries of different families of cytokines., and further selecting one, such as "IL4.like Library" (1622), displays the library (1623) of the IL4 family, which contain several cytokines with similar structures, which prototype is IL4 (1624), which subworkspace contains several domains, motifs and groups. Those icons may be used to: a) be cloned and modify to build different but related structures; b) be placed in the subworkspace of protein-complexes, as shown in FIG. 18; or c) they may be preferentially named and copied, as described below, and the dummy copies that refer to the original are used for several of the more complex structures.

Pathway Libraries, are hierarchically organized workspaces (1630) containing sets of related bioProcesses, such as those contained in the subworkspace of a submodel, and a bioReservoir-Bin with the bioReservoirs connected to those bioProcesses, where those bioProcesses and bioReservoirs are connected forming the nodes of a pathway that may be or not multidimensionally branched. The pathways included in the libraries are those that are common to several systems, although they may require some modifications, and they can be cloned instead of being built from scratch. Alternatively, the "Pathway Libraries" (1628) menu may be used to hierarchically access any submodel of the Virtual Model, as an alternative to interactively navigate through all the layers of subworkspaces involved. The options of the menu head "Pathway Libraries" (1628) point directly to submodels, which subworkspaces are displayed. For example, selecting "EGF.R.Pathway" (1629) displays the components of the initial specific steps of such pathway (1630) containing bioProcesses (1631) and a bioReservoir-Bin (1632). To conveniently handle large and complex pathways, the components can be partitioned into more submodels, by simply transferring related sets of bioProcesses and their corresponding bioReservoirs to the subworkspace of another submodel, without affecting the connectivity of the pathways in any way. When the application grows larger and the number of submodel increase, those direct domain-menus options are replaced by other options that lead instead to walking menus offering as many hierarchical levels as necessary. Modelers can also clone submodels, in which all the bioProcesses organized in its workspace, together with the contained bioReservoir-Bin and all the bioReservoir organized in its workspace, are also cloned preserving the labels and any other attributes, but with no names, since names are unique. All new bioReservoirs and bioProcesses have to be named (with the same basic name and different tags), and the connections have to be reestablished by naming the bioPosts and setting the ref-attributes, as discussed elsewhere for new sets.

Creating New Composite Objects

There are several alternatives for building new generic types of composite bioObject. One method comprises the following steps: a) an instance of the desired class, such as bioProcess, is created by selecting from the menu of the object-definition of that class the "create-instance" option and transferred to a workspace; b) the subworkspace of such instance is created by selecting from its menu the "create-subworkspace" option; c) the desired set of instances of characteristic classes of visualObjects are created or cloned and transferred to such subworkspace; and d) the newly created instances are positioned and connected in specific ways, to conform to the designs specified in this invention. A preferred alternative way is to "clone" an existing composite bioObject that is similar to the desired one, and delete and/or add components, as desired. The additional generic building blocks are added to palettes accessible through the domain-menus, and are used to create new instances of the same type by cloning such generic structures. Cloning an object in this invention means cloning also its subworkspace, and all objects upon its subworkspace, and any objects upon the sub-workspace of each of those objects, and so on. The modeler can then further individualized each newly cloned instance by configuring the attribute tables of the superior object, or by configuring the attribute tables of the objects encapsulated within that superior object, either as attribute objects or as objects upon successive subworkspaces.

Furthermore, it is possible to create transient objects at run time in two ways: a) by using the "create a <class-name>" and "transfer" actions; or b) by using the "create a <class-name>by cloning <instance-name>" and "transfer" actions, which is the equivalent to the clone option described above, and is the preferred way for composite objects. Transient objects can be made permanent by using in addition the "make <instance>permanent" action after the instance has been transferred to a workspace. This invention makes extensive use of dynamically creating objects at runtime by cloning, such as when creating dynamic pathways, dynamic query-panels, dynamic query-output-panels, dynamic entry-panels, dynamic graphs, dynamic lists, and so on. A set of partially prebuilt complex sets of structures, such as those required for the different types of panels, are organized and stored in the subworkspaces of objects called bins, and used as master structures to be cloned and completed with additional context-dependent structures at runtime, as will be described under the General Mode and Simulation Mode headings below.

Modeling bioEntities

The modular functional representations (FIG. 18) of structure that are novel teaching of this invention allow to represent the modular structural patterns frequently used by nature. The iconic structural representation is used to abstract the detailed structure of different molecules to highlight their similarities, and to show that even prototypes for different families present several similarities. Abstraction is obtained in part by selectively hiding some detail in the subworkspaces of other components focusing on components and the way they are arranged that relate to their function, to offer users visual models that facilitate their reasoning about structure-function relationships. The components of a molecule are used by the user to reason about its function, since the presence of given domains, motifs, or simple-bioEntities usually is associated with described function, therefore directing the scientist's attention to further focus on those functions. Each of those instances of bioEntities have their associated tables of attributes, where the modeler can include additional information, data, and references to access other sources of information about those models, which can provide to the user a wealth of knowledge in the form of an intuitive and interactive visual database. The knowledge extracted from those models can be integrated in this invention with other forms of knowledge, related to the function of those bioEntities, provided by the pathways related models. For example, the members of each family may be involved in similar mechanisms but result in very different and even opposing effects, due to the participation of their bioPools in different pathways. That knowledge integration is performed sometimes interactively by the user, and sometimes programmatically as a result of an interactive request by the user, depending on which of the many capabilities of this invention is used. Each superior bioEntity represents the structure of a biochemical physical entity in a particular state, such as different chemical modifications, different states of association with other entities, or the products of different mutations or artificial manipulation or quimeric constructions, which corresponds to the concept that different bioReservoirs hold molecules or complexes in different states. The structural and other types of information about the units that form a bioPool, as provided in the corresponding bioEntities, is supplemental and is not necessary for creation or navigation thought the pathways, or for simulation. This information is used independently of the pathways, or they may be used in combination, as in the complex queries.

FIG. 17 shows the Palettes with representative examples of master instances of some of the different subclasses of protein-domain (1701), protein-motif (1706), and simple-bioEntity (1711), are accessed through the walking menu of "Protein Components" (1616). Some of those building blocks are very generic or "empty" structures, such as the examples shown of the subworkspaces (1703 and 1708) of catalytic-subunit (1702) and spacer (1707), respectively, while others may contain more or less detailed prototypic structures, in which case they are named master-structures that may be referred to by the master-bioentity attribute of its copies, such as the example shown of the structure (1705) of a fibronectin.type.III-domain (1704. Each instance of these components have an associated menu (1805) from which options specific for each class can be selected to perform generic or specific tasks. Selecting the "table" option (1823) shows their tables of attributes, such as the examples shown for the tables (1710 and 1713) of a leucin-zipper-motif (1709) and a loss.of.function.protein.mutation (1712), respectively, providing options for the modeler to include additional information, which in this case is specific for each instance or copies. Clones of those instances can be combined in different ways to model, using the basic paradigm of "Clone, Connect, Configure and Initialize", at the desired level of detail, the structure of a bioEntity.

In addition to the standard Shell's "clone" capability, which applies to every object, there is a novel domain-dependent capability associated with the class complex-bioEntity and all its subclasses. Selecting the "create-local" option (1824), restricted to Modeler Mode and when the bioEntity has a name, starts the et-create-local-proc (Table 89) and allows the modeler to create local copies from any instance. The term clone means in this invention a complete reproduction of the original, with exception of the name, while the term copy means an incomplete reproduction that is usually stripped from the contents of the subworkspace of the original, but has a pointer to the original and is used in conjunction with it. The master-bioentity attribute of the copies is automatically set to refer to the named master-structure. The dummy copies refer to the original when the "master-details" is requested, which subworkspace with the prototypic structure is displayed. Local copies of any complex bioEntity (including bioEntity-components), may have private specific information in its table of attributes and in its subworkspace, shown by selecting the "local-details" option, while it can also display the subworkspace of its master bioEntity. Simple-bioEntities do not have a subworkspace and do not have master-bioentity attribute. This implementation is preferred to avoid redundancy, including saving storage resources, and allowing modification at only one site when the details of the structure have to be modified.

As shown in FIG. 18, the subworkspace (1807) shown for a specific multi-unit receptor-complex (1804) contains the icons of its various components, which may be copies, such as those referring to structures in the Libraries (1808, 1815, and 1817), or may be originals, such as for the simple components or some specific complex components (613, 619 and 621 are originals within the original master structures). Upon clicking on each of those components, their subworkspaces or the subworkspaces of their master structures are displayed on the screen, showing their structural composition. The level of detail is optional, and components at different levels in the hierarchy of subclasses can be connected to each other. For example, clicking upon a subunit of the receptor (1808, a copy) shows its structure (1809, from the master) composed of domains, other simple-bioEntities, and other optional auxiliary structures, such as those that may encapsulate: notes about its function (1810), sequence (1811), references (1812), or a GIF image of its three-dimensional structure. Any of those components may encapsulate more detailed information, such as that displayed when clicking in one of those domains (1813), which structure (1814) is composed of other domains, spacers and other simple-bioEntities. Back to the main structure, clicking on a kinase (1815, copy) that forms part of the complex, its structure (1816, from the master) may be represented by its two subunits, a regulatory-subunit and a catalytic-subunit, each containing or pointing to additional detail. Or the structure can be directly represented directly by it lower level components, such as when clicking on other associated kinase (1817), which structure (1818) is composed directly by several domains and other simple-bioEntities. Any of those molecular components may encapsulate in their subworkspace any type of other relevant information, when more detailed structure is not available or not desired. For example, clicking on one of the domains (1819) shows (1820) differences in the sequence of a functionally important homology region of that domain for different members of that family of molecules (which allows to represent all members of the family by just one structure, by describing additionally the differences between the different members), while clicking on another domain (1821) shows more information (1822) about conserved subdomains within that family. In general, simple-bioEntities may be linked to a motif, a domain or even to a subunit or a molecule. The structure may focus on only those parts of the structure that have functional relevance. If intermediary stretches within the structure are unknown or that detail is not desired, they may be represented by domains called spacers.

Modeling Pathways

The bioReservoirs Palette contains prebuilt default instances of:

BioReservoir-Bin (2306), used to store a set of related bioReservoirs upon its subworkspace and prebuilt with the standard set of navigation buttons used on most subworkspaces, a go-to-sup-obj-button and a hide-sup-ws-button, and a bioObject-title, which is standard for the subworkspaces of all bioModels as well as of all complex-bioEntities;

On-Hold-Bin (2003), used to store upon its subworkspace bioReservoirs and/or bioProcesses connected into pathways that the modeler may want to offer as alternatives, and which the user may include or exclude from a simulation or other uses at will, by using any of three alternatives: a) desired individual structures can be moved out of the On-Hold-Bin and transferred to the subworkspace of such submodel, or its bioReservoir-Bin if bioReservoirs; b) if all structures are desired for inclusion, the subworkspace of the On-Hold-Bin can be activated and deactivated at will; or c) two On-Hold-Bins can be used to transfer those structures between them at will, one to be permanently deactivated and the other be activated and to hold only those structures desired for inclusion. If any of those structures are substitutions for other bioReservoirs and/or bioProcesses contained in such submodel, then those structures they are replacing should be removed to a deactivated On-Hold-Bin. This subworkspace is prebuilt with an additional hide-and-deact-sup-ws-button, which upon clicking on it when the sub-workspace is activated, hides and deactivates such subworkspace; and A set of different prototypes of bioReservoirs, representing all the subclasses, which differ in the instance of the bioPool they encapsulate of the one corresponding subclasses of bioPool, and in the color of the type-color region of their icon. Each of those prototypic bioReservoirs comes with a minimal set of basic structures, and model-boxes and additional bioPosts are added interactively when needed. By cloning a bioReservoir from its Palette and transferring it to the subworkspace of a bioReservoir-Bin, it can then be connected to a bioProcess. Another alternative for adding bioReservoirs to the Virtual Model is to clone existing bioReservoirs with similar characteristics, by selecting the "clean-clone" option (1239) from their menu, and configure the new name and desired attributes. The "clean-clone" option starts the BR-clean-clone-proc, which creates a clone of such bioReservoir and sets the values of all the attributes of all structures involved, including the bioReservoir and its subworkspace and all structures upon it, to their default values. This capability is useful to create clean bioReservoirs of desired types that are available on the working submodel, without the need to open the Palette. The modeler can add, modify or remove connections to bioProcesses, by creating and naming the corresponding bioPosts. That established distant connectivity is independent of the location of bioProcesses and bioReservoirs throughout the Virtual Model or the workspace hierarchy, and no additional changes are required when moving those structures from one location to another. Various menus options and associated methods are offered to automate the task of establishing those connection, which will be described after the discussion of the creation of bioProcesses.

The modeler can also model inputs or outputs to a bioPool as mathematical models using model-blocks (1222) held in model-boxes (1218), as previously discussed (FIG. 12). A set of menu options, restricted to Modeler Mode, are defined for the class bioPool to automate the task of adding a scaled-input-model-box (1218), input-model (1236), or output-model-box (1237), when desired. The options labeled "add-scaled-input" (1325), "add-input" (1326), and "add-output" (1327), start their associated methods, create-scaled-input-model-box-proc (Table 90), create-input-model-box-proc, and create-output-model-box-proc, respectively, which result in the cloning of the corresponding prebuilt master model-boxes, and then transferring the new instance to its specified position in relation to the bioPool. The modeler has only to extend its stub to join it with the color-matched stub of the bioPool. Each of those named master structures is simply a generic model-box, each of the subclass referred to by its name, with a color-coded subworkspace containing a connection-post, which attribute Superior-connection has been set to refer to the only connection stub of the superior model-box. Any model-block connected to such connection-post of a model-box is connected also with any object to which the model-box is connected, resulting in the ability to establish a connection between an encapsulated model-block and a bioPool, by cloning the desired model-block from the Palette and connecting to the connection-post of a model-box connected to that bioPool. The generic formulas that provide the value for the Accumulation of each bioPool already integrates the output of any such connected model-block as either an absolute input, a scaled input or an output, depending on the class of the model-box that encapsulates the model-block.

As shown in FIG. 19, the Model-blocks Palette (1901) is provided to the modeler with a default instance of each of the subclasses of model-block. Model-blocks (Table 22) and the different generic simulation formulas (Table 87) to compute their value of their output-I attribute have been previously defined. Some examples of the attributes for some subclasses with their default values are shown through the tables of attributes of: constant.f (1902), exp.c.pdf (1903), exp.rn.pdf (1904), unif.c.pdf (1905), sigmoid .f (1906), and generic.model.block.f (1907). The latter is a very generic block that allows the modeler to create instances and configure as many attributes as required by defining their slots with any desired type of value, including instances of model-block-var, in which case their specific formula would also have to be defined. The output-I of this block is also a variable for which the modeler has to write its formula, to incorporate as arguments the newly configured attributes.

As shown in FIG. 20, the bioProcesses Palette (2001) provides the most representative types of generic BioProcesses, prebuilt and ready to be cloned and further configured. These preassembled and stored structures allow the repeated use of bioProcesses as building blocks of more complex pathways. Like in chemical systems, some bioProcesses are relatively simple and some may become more complex, but all are built with the basic building blocks (2504–2511). The modeler can, for example, clone a R2.L1, which subworkspace (2008) comprises one receptor-bioengine connected with two receptor.r (which may each be connected to different bioPools, if the active receptor is an homodimer of two equal molecules, or to the same bioPool, if an homodimer of two equal molecules), and one ligand.r at the top, and one bioProduct at the bottom. After transferring the clone to the desired workspace (2409), the bioProcess can now be configured, by clicking on its icon and selecting its "table" (1403) of attributes. Selecting "details" (1416) from its menu displays its subworkspace and provides access to all its components, which can now be configured by accessing their tables of attributes. BioProcesses have activatable-subworkspaces, which means that any object upon such subworkspaces is not recognized by the inference engine or the simulator unless the subworkspace is activated.

An alternative to the Palette is to clone another existing bioProcess with similar characteristics and labels directly from a submodel, and then transferring them to the desired submodel and the configuring its components. Two menu options are provided to facilitate that task, "labeled-clone" (1427) and "clean-clone" (1428), which start either BP-labeled-clone-proc or BP-clean-clone-proc, respectively. The first procedure creates a clone of the bioProcess, and then sets the values of all the attributes except the label of all structures involved, including those of the bioProcess and of all the structures upon its subworkspace, to their default values. The second procedure calls the first one, and also sets the values of the labels attribute of all structures involved to their default values.

Figure 21:
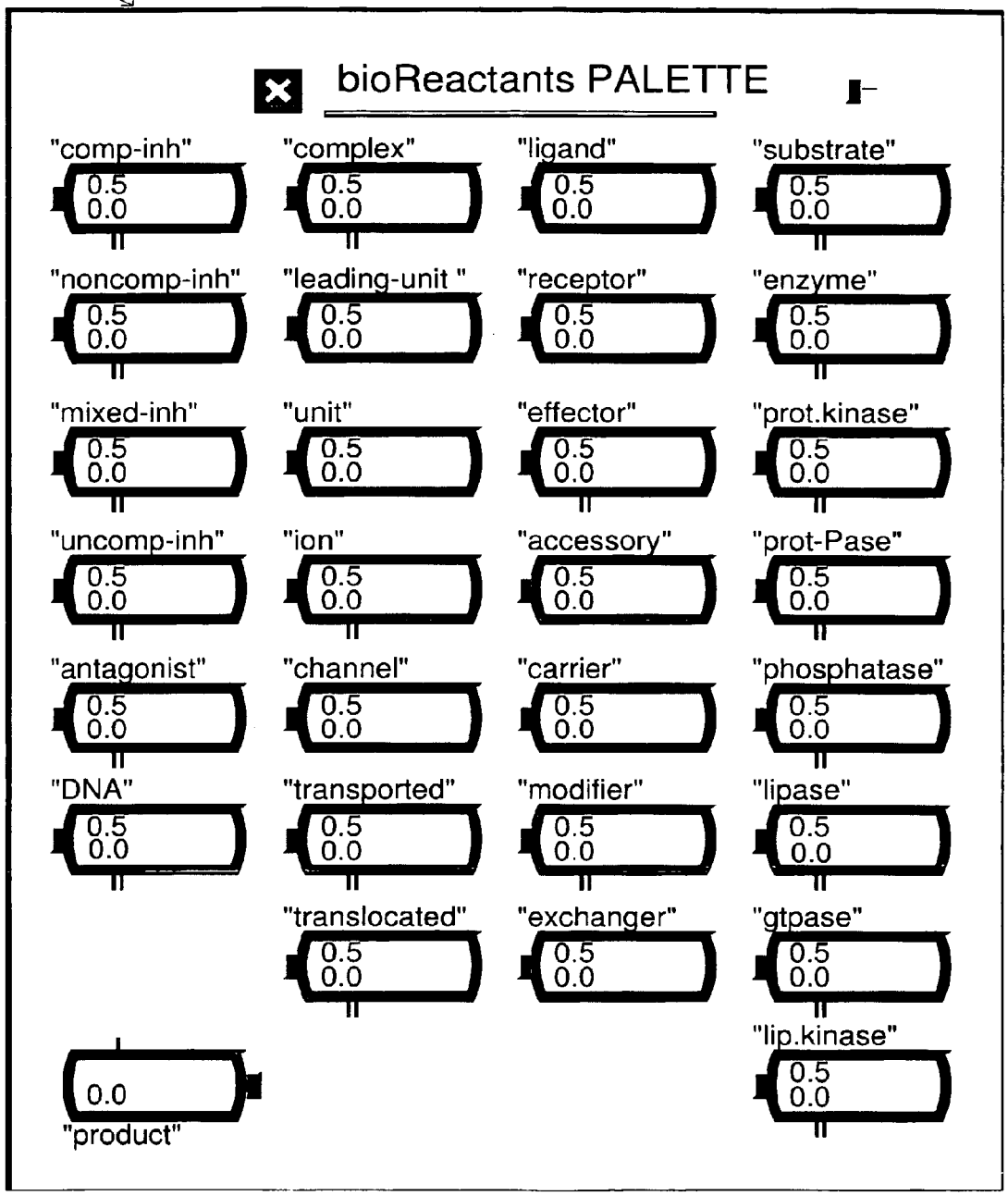
FIG. 21 shows a palette with examples of prebuilt reactants.

The bioEngines Palette and the bioReactants Palette shown in FIG. 21 are provided for the purpose of allowing the modeler to: a) modify individual instances of bioProcesses cloned from the Palette, to accommodate particular infrequent needs; and b) to design new prototypic bioProcesses, by starting from a clone of an existing bio-Process and adding or removing bioReactants or bioProducts, or by exchanging the bioEngine for another of compatible type. The modeler may want to modify the Velocity attribute of any bioEngine, and to provide specific formulas to represent their favorite equations to best describe the process being modeled, which have to refer to the specific set of bioReactants connected to that bioEngine. Such newly designed bioProcesses may be stored as building blocks in the appropriate Palette within the Modeler Palette Bin, as described.

In addition, the modeler may use a tabular-function (Table 74) as a look-up-table, from which the program is able to interpolate, to model a process by entering experimental pairs of values of the independent and the dependent variables in such table, such as a dose response. To facilitate that task, the option "create-sw" (1526, Table 91) is defined for the class bioEngine that starts the create-sw-for-bioengine-proc, which creates a subworkspace for the bioEngine by cloning the subworkspace of the bioengine-sw-master, which contains a tabular-function-of-1-argument and instructions for the modeler about how to use such a tabular-function.

As shown in FIG. 22, several steps are required to establish the connection between a bioReactant or a bio-Product and a bioPool. To facilitate this process and to reduce the sources of error while entering those values by the modeler, various methods are offered to automate the tasks of: creating and naming, or removing the names, of bioPool-posts, removing the names and the references of bioRole-posts, and to set the appropriate values for the ref-bioprocess of BioPool-posts and ref-bioreservoir of bioRole-posts, as following:

The first step is to select the bioProcess (2201) and bioReservoirs (2205, 2207, and 2209) to be connected, if already in existence, otherwise they are created by cloning from the Palettes and named. BioProcesses and bioReservoirs have to be named before their bioPosts can be named.

By selecting the "details" option (2203) from the menu (2202) of the bioProcess, and such of the bioReservoirs, their subworkspaces (2204, 2206, 2208, and 2210, respectively) are displayed. Selecting the menu (2214) option "add-top-post" (2215) of the bioPool (2213) starts the createbiopool-p-post-proc (Table 92), which first scans for the first free stub of those defined at an even-numbered port (p02 to p12) and a) if one is found, it creates an instance of biopool-p-post (2217) and aligns it opposite to such stub within the first layer, b) if none is found, it then scans for the first free stub of those defined at an uneven-numbered port (p01 to p11) and, if one is found, it creates an instance of biopool-p-post and aligns it opposite to such stub within a second layer (more distant from the bioPool) of such bioPool-posts, and if none is found, then: i) it moves the existing biopool-p-post connected at the first port (p01) to a more distant position, to start the next layer, ii) it creates an instance of biopool-p-post and transfers it to the next free predefined position within that layer; and c) it sends a message to the modeler with instructions for making the specific connection. Then it calls the pool-post-name-it-proc (Table 93) and returns. The "add-bottom-post" (2216) functions in a similar way, but it adds instead biopool-r-posts at the bottom of the bioPool.

To connect each of the bioRole-posts (2212, 2218, and 2225) to a complementary and not yet connected BioPool-post of the appropriate bioReservoir requires to create a new bioPool-post of the appropriate subclass and to establish the connection to the bioPool by extending its stub and joining it to the closest free stub on the bioPool, and then establish the distant connection to the bioReactant-post (2218). Here is shown how a distant connection is established between and already named and connected bioPool-p-post (2219) and the bioProduct-post (2225). Clicking on the bioPool-p-post (2219) in Modeler Mode displays its menu (2220), and selecting "table" (2221) shows its attributes (2222). The tables for a bioRole-post (2222) and a bioPool-post (2228) are shown with all the values already set. At this point in the connection process, the values for the Ref-bioprocess (2235) would be the default value none, while the values of the Names (2223) and the Label (2224) attributes will be already set, with the value of the Label set to be the same as its name in the case of all bioPosts to be used at run-time when using the alternative simulations procedures, as discussed under the Simulation Mode heading.

To give the bioRole-post (2225) the same name as the name of the bioPool-post (2219) to which is to be connected is accomplished by selecting either the "name" option (2227) or the Names attribute value slot (2232) of the bioRole-post (2225) and clicking on the name-display (2228) of the bioPool-post (2219), since name-display has text-insertion capabilities and automatically inserts its text. This completes the basic connection process that allows the inference engine and the simulator to reason about those connections. Once the bioRole-post (2225) and the bioPool-post (2219) are equally named, the Ref-bioreservoir attribute (2234) of the bioRole-post and the Ref-bioprocess attribute (2235) of the bioPool-post are automatically set to refer to each other's superior bioObjects by selecting the "set refs" option (2229) of the bioRole-post, which is only available when it has a name. These attributes are used by the program when the user selects the "show-br" option (2241) or the "show-bp" option (2242), which are available in the menus (2220 and 2229) of bioRole-posts and bioPool-posts, respectively, only when those attributes have a value.

A more detailed description of those methods, with references to their definitions follows:

the option "name-it" (2240, Table 93) upon its selection starts the pool-post-name-it-proc (Table 93). This procedure gives the "names" attribute of the bioPool-post a name composed of the base name of the superior bioReservoir (removing the ending BR tag) followed by the default value of the "label" (2224), which is a reference to the class and relative position of that bioPool-post, such as PP8 referring to bioPool-p-post connected at port p08, and also colors the face-color region of its icon.

the option "unname-it" (2236, Table 94) upon its selection starts the poolpost-remove-nameproc (Table 94), which changes the values of the names and the ref-bioprocess attributes of the bioPool-post to their default value none, removes the base-name from the value of the "label" (2224) restoring it to its default value, and resets the face-color of its icon to gray.

the option "set-refs" (2229, Table 96) upon its selection starts the rolepost-set-refs-proc (Table 96), which changes the values of the "ref-bioreservoir" (2234) of the bioRole-post and the "ref-bioprocess" (2235) of its connected bioPool-post to equal the names of the bioReservoir (2209) superior to such bioPool-post (2219) and the bioProcess (2201) superior to the bioRole-post (2225), respectively.

the option "unname-it" (2237, Table 95) upon its selection starts the rolepost-remove-name-proc (Table 95), which changes the values of the "names" (2232), "label" (2233), and "ref-bioreservoir" (2234) attributes of the bioRole-post, and the "ref-bioprocess" (2235) attribute of the bioPool-post, to none.

The metabolic and regulatory pathways of cells and organisms are composed of a large number of processes. To simplify the overall structure of the system, or when the intermediary detail is unknown, it is possible in the currently preferred embodiment of this invention to consider parts of such pathways as black-box-bioProcesses with inputs and outputs connected to other modeled pathways or to other black-box-bioProcesses, which are not modeled in detail. If and when it is desired to model disturbances at specific points in the pathway represented by a black-box-bioProcess, it can be split into the pathway before and the pathway after the regulated location, which is represented by a normal bioProcess, with the two new pathway segments now represented by two new black-box-bioProcesses, and the segment where the disturbance occurs to be defined and modeled.

In addition, it may be desirable to model a pathway as a single lumped bioProcess. Such may be the case for an enzymatic pathway for which: a) the details may be unknown or not desired, b) only the inputs and the outputs are relevant, and c) sufficient quantitative or qualitative information is available about the rate limiting enzymes and the inputs. Because of metabolic and energy/mass conservation constraints, only a few of their net conversion rates are independent variables, and the others are mutually dependent, various of those reactions can be combined and the pseudo-steady-state approximation of the combined process can be used instead. For these cases, the currently preferred embodiment of this invention provides enzyme-bioProcess subclasses with two or more enzyme-bioReactants, with their Velocity depending only the Concentrations of those enzymes, together with the substrates that are inputs to the pathway and the products are outputs of the pathway, ignoring the intermediaries and other participating enzymes. The following are examples of overall rates of synthesis resulting in the production of a cytokine, IL2, as a cellular response to its binding of another extracellularly provided cytokine, IFN-a, that could be represented by a set of bioReservoirs and bioProcesses, to represent each of the terms of the equation:

$rs(TF-IFN-a)=k1*[IFN-a]$ and $rs(mRNA-IL2)=k2*[TF-IFN-a]$; or $rs(mRNA-IL2)=1+ka[IFN-a]/1+ka[IFN-a]+ks$;

$rs(IL2)=k3*[mRNAIL2]$.

Biochemical Modeling Techniques

The metabolic and regulatory pathways of cells and organisms are composed of a large number of processes. To simplify the overall structure of the system, or when the intermediary detail is unknown, it is possible in the currently preferred embodiment of this invention to consider parts of such pathways as black-box-bioProcesses with inputs and outputs connected to other modeled pathways or to other black-box-bioProcesses, which are not modeled in detail. If and when it is desired to model disturbances at specific points in the pathway represented by a black-box-bioProcess, it can be split into the pathway before and the pathway after the regulated location, which is represented by a normal bioProcess, with the two new pathway segments now represented by two new black-box-bioProcesses, and the segment where the disturbance occurs to be defined and modeled.

In addition, it may be desirable to model a pathway as a single lumped bioProcess. Such may be the case for an enzymatic pathway for which: a) the details may be unknown or not desired, b) only the inputs and the outputs are relevant, and c) sufficient quantitative or qualitative information is available about the rate limiting enzymes and the inputs. Because of metabolic and energy/mass conservation constraints, only a few of their net conversion rates are independent variables, and the others are mutually dependent, various of those reactions can be combined and the pseudo-steady-state approximation of the combined process can be used instead. For these cases, the currently preferred embodiment provides enzyme-bioProcess subclasses with two or more enzyme-bioReactants, with their Velocity depending only the Concentrations of those enzymes, together with the substrates that are inputs to the pathway and the products are outputs of the pathway, ignoring the intermediaries and other participating enzymes. The following are examples of overall rates of synthesis resulting in the production of a cytokine, IL2, as a cellular response to its binding of another extracellularly provided cytokine, IFN-a, that could be represented by a set of bioReservoirs and bioProcesses, to represent each of the terms of the equation:

$rs(TF-IFN-a)=k1*[IFN-a]$ and $rs(mRNA-IL2)=k2*[TF-IFN-a]$; or $rs(mRNA-IL2)=1+ka[IFN-a]/1+ka[IFN-a]+ks$;

rs(IL2)=k3*[mRNAIL2]; For bioReservoirs that represent the input into the system of a synthetic agonist or antagonist, the Concentration has a normal default initial value of 0.0, it has no modeled inputs from bioProcesses, and it may be modeled by a model-block. However, quantities of that compound may be transferred to another regular bioReservoir in a different compartment.

It may not be desired in most occasions that the synthesis of macromolecules be visually modeled by bioProcesses, because of its complexity and the large number of steps or components involved. In these situations, the synthesis may be modeled by adding a model-block to one input-box connected to the bioPool, which is represented by the additional term already integrated in the Accumulation equation. The output of this model-block may define a global synthesis-rate that may be made dependent on the values of any other variable of the system multiplied by a synthesis-rate-constant ($k_{rs}$) parameter, a separate attribute of the model-block. The krs may also be dynamically increased or decreased (by multiplying by appropriate factors) as defined in rules or procedures, which are fired or called as a result of the activation or deactivation of other bioProcesses, which directly or indirectly regulate the processes of DNA-transcription into mRNA, mRNA-splicing, mRNA-translation into protein precursors, or the processing of the precursors into the active-form of the proteins (all or part of which may or may not be visually modeled).

When degradation or diffusion are important components of the model, they can be separately modeled by: a) using additional bioProcesses to model those processes, b) adding a model-block to the output-box connected to the bioPool, or c) using additionally defined degradation-rate or diffusion-rate parameters, respectively, and modifying the formula accordingly by adding the corresponding terms. The first two approaches are recommended because they are more flexible and modular.

Processes in which the binding step is the limiting factor (the catalytic or other actions are fast so that the ES complex is very short-lived), are usually modeled by a single bioProcess. If the complex stays around exposed to other interactions, two bioProcesses may be used: complex-formation and catalytic or other action, each with its respective constants. Inhibitors and antagonists should be modeled by separate bioProcesses.

In the system of this invention, the intermediary complexes that are formed in enzymatic reactions, and their concentrations such as [ES1] or [ES1S2], are preferably not explicitly represented, unless they are the specific targets of regulation or translocation to different compartments. Otherwise, they are implicitly represented within the model equation of the bioEngine.

Reaction systems with two or more substrates of the ordered or ping-pong types, may be represented by either one bioProcess with two substrate.r, in conjunction with the appropriate Velocity equation, or by two separated bioProcess in series. Preferable, these types of reactions are modeled by two bioProcesses in which the participants are represented as following: a) the enzyme and the first substrate are the enzyme.r and substrate1.R of the first bioProcess, b) the bioPool of the enzyme-substrate1 complex is represented by both a bioProduct of the first bioProcess and by the enzyme.r for the second bioProcess, c) the second substrate is the substrate.r of the second bioProcess, and d) one bioProduct of the second bioProcess may be represent the bioPool of the enzyme. To be more accurate, in the ping-pong case the bioProcess cannot be said to be first or second, since the enzyme oscillates between the "free" and the "complexed" states.

In reactions with cooperativity, such as allosteric reactions of an enzyme with n equivalent substrate binding sites, can be either modeled by: a) one bioProcess with a 1E.nS.1I.HMME bioEngine with each of the n substrate.r representing the same bioPool, each with a stoichiometric coefficient equal to 1, but each with a different effective Km corresponding to each additionally bound molecule, and a Velocity formula representing a Henry-Michaelis-Menten equation, as shown, or b) one bioProcess with a 1E.1S.1P.0I.HE bioEngine with one substrate.r with stoichiometric coefficient equal to n, and the Velocity formula representing a Hill equation. In that case, the overall affinity constant (K=j*K'^(n), where j=a*b*d* . . . x) is equivalent to the product of the K1' of the first bound site times the series of Ki' times the coefficients by which each molecule of ligand bound modifies the affinity of the other sites.

Allosteric reactions of an enzyme with binding sites for two or more different ligands, either substrates, inhibitors or modifiers, can be either modeled by: a) one bioProcess in which each ligand is represented in the formula for appropriate class of variable providing the Velocity, or b) two or more bioProcesses, in series or parallel or both, when the mechanism of the reaction is known and information is available. The latter case is preferred where separate bioProcess, one for each ligand, compete with each other for the common component(s), with an strength dependent on their respective affinities and Concentrations. In addition to the cases above, it is in general preferable to model several complex-form-process in the following cases, as described in more detail below:

all types of inhibitions in which an irreversible complex is formed, such as E+I->EI, or E+S+I->SEI, the effects of antagonists, such as R+Ant->R–Ant, and the feedback activation or inhibition by products, such as E+X+P->P+Y+Z, where P is the product of either this reaction or a downstream reaction. Different types of inhibitors may be modeled in a variety of ways to show different behaviors, usually involving a complex-form-process in which the resulting complex would have different characteristics:

A competitive inhibitor and the substrate are mutually exclusive, which means that EI does not bind S, but it may result in E+S+I<->ES+EI->P. This type of reversible competition is best modeled as one enzymeEngine comprising enzyme.r, substrate.r and inhibitor.r with its matching standard kinetic equation. The intermediary complexes may be modeled if desired by editing the value of the time-lag, to account for the time the E, S and I spend in the complex forms ES and EI, not explicitly modeled otherwise. The same approach can be applied to any other class or type of bioProcess, when appropriate.

An irreversible inhibition is equivalent to enzyme removal from the system, with the Vmax reduced, and it is therefore best represented by two parallel bioProcesses: an enzymeProcess for E+S->P, and b) a complex-form-process for E+I->EI. The production rate of P is influenced by the Concentration of S, directly, and I, indirectly, while the production rate of EI is indirectly influenced by the Concentration of S. It may also be represented by one enzyme-process encapsulating enzyme.r, substrate.r and inhibitor.r, and two bioProducts (E+S+1->P+EI), with its matching standard kinetic equation.

An uncompetitive inhibitor may bind reversibly to the ES complex yielding inactive ESI complex, but it does not bind to enzyme alone. This model needs some modifications of the regular bioProcesses, because it requires access to an intermediary complex that is not explicitly modeled in the system of this invention in a standard enzyme-process (E+S+I->P). This type of reaction may be represented by three bioProcesses, first in series and then in parallel: a) complex-form-process: E+S->ES; b) enzymeProcess: ES->E+P; and c) complex-form-process: ES+I->ESI. It may also be represented by one enzyme-process comprising enzyme.r, substrate.r and inhibitor.r, and one bioProduct (E+S+I->P), with its matching standard kinetic equation.

A noncompetitive inhibitor and the substrate do not affect each other's binding to the enzyme, however the trimeric complex SEI (ES+I->SEI or EI+S->SEI) may be inactive. The main effect is a sequestering of either enzyme or both enzyme and substrate, and the Vmax is reduced. This type of reversible competition is best modeled by three different bioProcesses: an enzyme-process E+S->P (a), and two complex-form-process: E+I->EI (b), and E+S+I->SEI (c), where (a) and c) have the same Ks and (b) and (c) have the same Ki. It may also be represented by one enzyme-process comprising enzyme.r, substrate.r and inhibitor.r, and three bioProducts (E+S+I->P+EI+SEI), with its matching standard kinetic equation.

A mixed-type inhibitor I is such that reversible binding of either I or S to E changes the Ks or Ki of the other by a factor a, yielding ES, EI and inactive ESI complexes. It may be best represented by three different bioProcesses: an enzyme-process E+S->P (a), and two complex-form-process: E+I->EI (b), and E+S+I->SEI (c), where (a) and (c) have different Ks and (b) and (c) have different Ki. The Ks' of (c) may equal the Ks of (a) multiplied by a, or similarly, the Ki' of c=a*Ki, where a is a cooperativity-coefficient that may be introduced as a factor in the formulas of the respective Ks or Ki.

Different types of feedback regulation by downstream products are represented by different sets of bioProcesses. As examples are given the following cases of feedback inhibition by more than one product:

Cooperative or synergistic inhibition is when mixtures of P1 and P2 at low concentrations are more inhibitory than the sum of inhibitions by each at those concentrations, and at saturating levels of either one of the products P1 and P2, the velocity of the reaction may be driven to zero. It means that both P1 and P12 can combine with E simultaneously to form EP1P2 complexes. This system may be represented by 4 BioProcesses: an enzyme-process: E+S->P (a), and three complex-form-processes: E+I1->EI1 (b), E+I2->EI2 (c) and E+I1+I2->EIII2 (d), where I1=P1, and I2=P2, and where (d) have different Ki1 and Ki2 than (b) and (c) (the K'i1 of (d)=a*Ki1, and the K'i2 of (d)=b*Ki2, where a and b are cooperativity-coefficients).

Cumulative or partial inhibition is when each end product is a partial inhibitor, and a saturating level of one alone cannot drive the velocity to zero. Each of I1 or I2 alone, either increases the Ks of S (partial competitive inhibition) or decrease kd of E (partial noncompetitive inhibition) or both (partial mixed-type inhibition). True cumulative inhibition results in the second case, where the total inhibition factor is iT=i1+i2*(1−i1). This type of reversible competition is best modeled by three different bioProcesses: an enzyme-process: E+S->P (a), and two complex-form-processes: E+I1+I2->EIII2 (b), and E+S+I1+I2->ESIII2 (c), where (a) and c) have the same Ks and (b) and (c) have the same Ki and Ki2. It may also be represented by one enzyme-process comprising enzyme.r, substrate.r, inhibitor1.r and inhibitor2.r, and three bioProducts (E+S+I1+I2->P+EIII2+ESIII2), with its matching standard kinetic equation.

Concerted or multivalent inhibition is when both end products have to be present to be inhibitory, and either alone has no effect on E. It means that either EIII2 does not bind S or ESIII2 is inactive. It may be represented in two alternative ways, either by: 1) two bioProcesses: one enzyme-process: E+S->P (a) and one complex-form-process E+I1+I2->EIII2 (b); or 2) one enzyme-process: E+S+I1+I2->ESIII2 (c). In both (b) and (c), the matching standard kinetic equations include a term to represent the concerted effect of I1 and I2, that is proportional to the Concentration of I1 multiplied by the Concentration of I2.

Additive inhibition implies the presence of two distinct enzymes or catalytic sites, each sensitive to only one of the feedback inhibitors. This type of reversible competition is best modeled by three enzyme-processes: a) E+S1+S2->P; b) E+S1+S2+I1->P; and c) E+S1+S2+I2->P. It may also be represented by one enzyme-process comprising enzyme.r, substrate1.r, substrate2.r, inhibitor1.r and inhibitor2.r, and one bioProduct (E+S1+S2+I1+I2->P+EIII2+ESIII2), with its matching standard kinetic equation.

Sequential inhibition is when downstream of E1 and S1, one product P1 inhibits enzyme E2 and another product P2 inhibits enzyme E3 of another pathway of utilization of S1. When both P1 and P2=are at high levels, S1 accumulates, and S1 may also inhibits E1. This type of feedback inhibition is best represented visually by a combination of the appropriate bioProcesses, as described above, in parallel and in sequence as required.

Lumped Enzymatic Pathways: In occasions, it may be desirable to model a pathway, such as an enzymatic pathway, for which: a) the details may be unknown or not desired, b) only the inputs and the outputs are relevant, and c) sufficient quantitative or qualitative information is available about the rate limiting enzymes and the inputs. Because of metabolic and energy/mass conservation constraints, only a few of their net conversion rates are independent variables, and the others are mutually dependent, various of those reactions can be combined and the pseudo-steady-state approximation of the combined process can be used instead. For these cases, the currently preferred embodiment of this invention provides enzyme-bioEngines classes with templates and stubs for two or more enzymes, and which formulas consider only those enzymes, together with the substrates that are inputs to the pathway and the products that are outputs of the pathway, ignoring the intermediaries and other participating enzymes.

Black-box-bioProcesses: The metabolic pathways of cells and organisms are composed of a large number of chemical reactions and compounds, that, assuming normal physiological conditions, maintain the steady-state of the system. To simplify the overall structure of the system, in the currently preferred embodiment of this invention many of such metabolic pathways are considered as a black box with inputs and outputs connected to other modeled pathways or two other black boxes, and are generally not modeled. The black boxes are considered, until better defined, as a collection of constitutive bioEntities interacting under steady-state conditions. If and when it is desired to model disturbances at specific points in the pathway, the black-box can be split into the pathway before and the pathway after (both of which remain like black boxes), and the segment where the disturbance occurs to be defined and modeled.

Handling Challenging Aspects of Modeling Complex Systems' Behavior

Modeling Internal Mechanisms of Cells

The transfer of molecules from compartment i to compartment j does not happen at once, but rather follows a Gaussian distribution, which may be modeled using the corresponding model-block from which the translocation-rate would be dependent. The bioEngines have also a "time-lag" (1510) attribute, defined as the time interval between the availability of the bioReactants to the bioProcess and the availability of the bioProducts to the next bioPool, which can be used for processes where translocations of molecules or cells are involved. The analytic equations for the distribution of bioEntities in consecutive pools are a function of the initial concentration of the first bioPool and the corresponding translocation-rate constant (k, 1507) and time-delays (d, 1510), respectively, of the successive bioEngines. For example, to model the series of translocations of proteins through the several compartments in which they are processed after their synthesis, with the system of this invention the modeler would clone from the Palettes a set of bioReservoirs and bioProcesses of the appropriate types o represent the different terms of the following equations, which are then transferred to the appropriate compartments, connected and configured, and desired values are given to the model parameters. Translocation rates between compartments could be expressed as translocation half-times, defined as: $t_{1/2,nu}$=In $(2/K_{nu})$, where $K_{nu}$ is the rate constant for processing in the nucleus or the rate constant for transport from the nucleus to the ER, or both lumped together. For steady-state balanced growth, where m=0 and rp(t) is the rate of transcription in the nucleus (molecules/hour/cell): $[RNA]_{nu,ss}(t)$=rp(t)/$K_{nu}$. The additional equations that follow are similar to those proposed for cell cycle-dependent protein accumulation by Bibila & Flickinger (1991) Biotechnology and Bioengineering 38: 767–780, and have to be adapted for use in the simulation formulas of the system of this invention, which takes a dynamic approach:

$[X_1]=\$X_1*[X_1]_o*e^{-k1*t}$ (this is ER)

$[X_2]=\$X_2/\$X_1*[X_1]_o*(e^{-k1*t'}-e^{-k2*t'})*k_1/(k_2-k_1)$, where $t'=t-d_1$ (this is Golgi)

$[X_3]=\$X_2/\$X_1*[X]_o*(-(e^{-k1*t''})/k_1+(e^{-k2*t''}-1)/k_1)/(k_2-k_1)$, where $t''=t-d_1-d_2$ (this is extracell. comp. for secreted proteins)

On many occasions, the newly generated molecules are secreted, while on other occasions, the newly generated molecules are retained in the cell, either to maintain housekeeping functions, which are usually included in the steady-state and no implicitly modeled, or they result in new cellular functions in which case its mechanisms are graphically modeled. If this response results only in proliferation, the inference engine may monitor the simulation of the cell mechanisms (FIG. 28), and based on the values of certain variable or sets of variable, may cyclically activate (2802) the next phase-compartment in the cycle. However, if the response results in cellular differentiation, the inference engine activates (2805) a different cell-bioModel, if such exits, that represents the new stage of differentiation, or will send a message to the user otherwise.

The different bioProcesses in a cellular bioModel may be activated for different periods of time, if placed within sequential time compartments (2421), but they will be overlapping with many other bioProcesses encapsulated in the G0-phase-compartment (2404), which are not deactivated during a simulation. BioReservoirs that may be participate in two different sequential time compartments are preferably located and contained within the G0-phase-compartment, to maintain the continuity and to carry over the values of its concentration/density/scaled-amount from one sequential discrete time compartment to the next. These temporal compartments represent somewhat defined cellular phases with different activities.

Mechanisms that are well studied in one animal species can be interpolated in the pathways of other species where the pathway may be less understood, such as in humans, by cloning the submodel (2408) encapsulating the bioReservoirs (2413) and bioProcesses (2409) from the first species and transferring to the appropriate compartment of the second, and then renaming and reestablishing the appropriate connections. For instance, the genes that participate in programmed cell death or apoptosis in the nematode *C. elegans* have been identified, and it appears that ced-9 acts by inhibiting ced-3 or ced-4 activity. Since the human bcl-2 is also active when inserted into *C. elegans* (Vaux et al., Science 258: 1955) and it is also believed to be the homologue of ced-9, a model equivalent for that for the interactions of ced-9 with ced-4 or ced-4 can be also constructed for bcl-2 with ced-3-like or ced-4-like.

BioPools that represent points of entry for non-physiological substances, such as drugs or synthetic agonists, antagonists or inhibitors that are not produced within the cells, at the compartment where it is first introduced have the following characteristics: a) they receive their values only from external sources, such as a simulation-panel, initially, the concentration equals the external input, and therefore Σ inputs=entry Value; b) they have a basal-Concentration value of 0, c) they have no schematically modeled inputs, d) e) they may have several schematically modeled outputs, through modification- and translocation-bioProcesses, in addition to the decay term that represents diffusion, degradation and dilution, and e) the quantity variables of those bioPools cannot obtain values higher than those inputted by the user, but may get smaller over time due to the outputs and the decay factor ([As]* (m+Σ outputs)≦[entry]). When that compound is modified or translocated to another compartment, the latter's is a regular bioPool, but still constrained.

Modeling Cell Population Dynamics

There is a number of ways of modeling and simulating cell population dynamics, using this invention. A number of attributes defined for the classes cellReservoir (Table 48), cellPool (Table 51), cell-bioModel (Table 68), and other bioObjects can be used to hold parameters and variables to be used for that purposes. Following the teachings of this invention, other attributes can be similarly defined and used to better meet any particular biological system to be modeled, or hypothesis that a user may want to test, or to meet the needs for any monitoring or control system that use those biological models. Some examples are presented below.

The state transitions are represented in the system of this invention by translocation bioProcesses (405, 407, 414, 417) between two bioPools of entities in the former and in the latter states, at a rate that is determined with one of three approaches: a) mechanistic approach; b) probabilistic approach; or c) deterministic approach.

In the mechanistic approach, the rate of the translocation process will be dependent on the dynamically changing values of certain variable or combination of variables, implicitly modeled inside an indicated cell-bioModel (FIG. 24), reaching some threshold value(s). With this approach, the high-level models may be integrated with the mechanistic models, representing both the spatio-temporal integration in a single cell-bioModel and the quantitative data about populations of such cell modeled. This mechanistic approach is currently difficult to implement for the particular domain selected for this invention, since there is not sufficient information available. This approach can be implemented with better known systems in other domains.

For some simplified in vitro biological systems, such as oocyte extracts, a mechanistic approach is used to model a transition for which a mechanism is known or expected, such as the role of the interplay between cyclin-B2 and the phosphorylated and dephosphorylated forms of the cdc2-kinase in the transition from the G2 to the mitosis phases of the cell cycle. The rate of increase in the number of cells with a cdc2**cyclin (cc) level greater that ø in a given cell cycle phase=fraction of cells in that phase $(G_1)$*{the rate at which cells within that phase reach a cdc2cyclin level ($[cc]^{G1}$) greater that ø–the rate at which cells with cdc2cyclin level greater that ø leaves that phase}:

The following is an example of how a simplified mechanistic approach can be implemented. The rates of growth in eukaryotes and the rates of translocation from one cell-state-pool to the next can be represented as linear or non-linear functions of the concentrations of specific molecules, such as external regulatory factors, regulatory enzymes, and total and specific mRNAs. For example, if a limiting protein L determines the transition from one time-compartment to another, then the expression of the mRNA for L could regulate that transition. Furthermore, the growth-rate m can be represented as a linear function of the concentration of a given specific mRNA, and the rate of mRNA transcription can be represented as a non-linear function of the concentrations of two or more growth factors (or other regulators), or it can be assumed to be a combination of growth associated and stimulus-dependent kinetics. In turn, the steady state values of all enzyme synthesis rates and the total specific RNA level are a function (linear for RNA) of the steady-state specific growth-rate m. The total RNA can be used as a measure of the growth resources of the cells, since the ability to increase a stimulus-induced specific sRNA is limited by the amount of synthesis proteins, which is limited by the amount of total RNA. Because the relatively high rate of RNA turnover and the dilution effect of cell growth, the [sRNA] responds immediately to a removal of the stimulus-effector. With an increase of the stimulus-effector, the rate of increase of [sRNA] is controlled by a time constant, which is inversely proportional to the total RNA of the cell (Copella &Dhurjati 1990. Biotech. Bioeng. 35: 356–374). The modeler would clone from the Palettes set of bioReservoirs and bioProcesses of the appropriate types o represent the different terms of the following equations, which are then transferred to the appropriate compartments, connected and configured, and desired values are given to the model parameters. The following equations have to be adapted for use in the simulation formulas of the system of this invention. $(m=k_x*([mRNA]-[mRNA]o)->(1/h)=(gX/gRNA)*(gRNA/gX/h); t=k_x/(m+k_x[mRNA]o/[X])$, where $k_x$ is the rate constant for mRNA transcription (gRNA/gX), t is the time constant (gX/gRNA), and [mRNA]o/[X] is the specific [mRNA] at m=0. The growth rate can also be viewed as the sum of all rates in one simple anabolic pathway divided by the total mass (growth from glucose in bacteria): $m=(\Sigma r_i)/[X]$. The number of generations: F=log(2)((X−Xo)/Xo)); $m*G_1*e^{mt}*\int_{526}^{\infty} 1^{G1}(x)dx = G_1*e^{mt}*([cc]^{G1}(ø)*1^{G1}(ø)-r(G_1->S)*\int_{ø}^{\infty} q(x)dx)$, where $1^{G1}(x)$ and q(x) are the frequency functions describing the cc content distribution for cells in $G_1$ and $G_1->S$ transition, respectively, and $r(G_1->S)$ is the rate constant that describe that transition; $r(G_1->S)=m/G_1*(N_0+G_2+S)$; $r(S->G_2)=m/S*(N_0+G_2)$; $r(G_2->G_1)=m/G_2*N_0$.

The following equations are examples of how overall rates of synthesis can be used to implement black-boxes, where each of those equations provide the value for the Velocity of the black-boxes to be represented by the corresponding type of bioProcesses: for IFN-a->IL2: rs(TF−IFN-a)=k1*[IFN-a] and rs(mRNA−IL2)=k2*[TF−IFN-a] (or rs(mRNA−IL2)=1+ka[IFN-a]/1+ka[IFN-a]+ks); rs(IL2)=k3*[mRNAIL2].

By using the concentrations variables of sol-mol-pools, expressed as moles per volume units rather that per cell, it would not be necessary to adjust the steady-state concentration with growth for constitutive enzymes, since it is assumed that both increase at the same rate, while for regulated enzymes, the dilution effect is more apparent, since it is not paralleled by synthesis. In the current implementation focusing on regulatory processes, since most of them take place in the form of large molecular complexes, highly localized in some parts of the cell, it would be more meaningful to use the defined density variables (molecules per cell). To synchronize the simulation from the intracellular to the cellPool level, the quantities of all the bioPools of extracellular molecules are halved at each cell division transition. In addition, specific rates are rates per cell, and total rates are specific rates multiplied by the cell density. Specific cell components may increase throughout the cell cycle: a) continuously at a constant rate, b) at a rate that doubles when the DNA is replicated, c) at a progressively increasing rate that follows fist-order kinetics, or d) discontinuously, according to a sequence of events that changes the rates in a complex pattern.

When the mechanisms are unknown, a deterministic approach may be taken with the transitions modeled as time-dependent events. As shown in FIG. 3, the cell-phase compartments, which are holders of mechanistic models, also have an attribute Interval (317) to hold information about the experimentally observed duration of that phase of the cycle, which can be used during a simulation-run to deterministically deactivate such subworkspace when that period of time has elapsed since the subworkspace was activated, or whenever any type of known constraints are met (FIG. 28). In the deterministic approach, the rate of the translocation process is defined by a rate constant, which may have a constant predefined value, or its value may be variable and set at run-time by a simulation formula, an expert rule, or procedure, such as one that reads the phase's "interval" just described, or it can be modeled by a model-block. The transfer of cells from cellPool i to cellPool j does not happen at once, but rather follows a Gaussian distribution, which may be modeled using the corresponding model-block.

Following is an example of a high-level representation of the effect of some drug on cell growth, when there is partial mechanistic knowledge available, but where most of the many other steps in the pathways leading from the external drug to the regulation of cell growth are unknown. In a system where enzyme X1 produces a soluble substance c that is used in the formation of active enzyme X2. If X1 and X2 represent the total amounts of X1 and X2 contained in n cells, and if X2 is the component that, upon reaching a threshold, determines the occurrence of cell division, so that n=bX2, where b is a constant, then, assuming steady-state, when c remains at a steady concentration and therefore the formation of X2 is proportional to [X1]), follows that: d[c]/dt=A (X1/n)−B (X2/n)[c]−C[c]=0, (1) where A, B, and C are constants. From (1) it can be said that c=b X1/X2, and following a set of derivations it results that the growth rate is: k=d (ln n)/dt=d(ln X2)/dt. If now c decreases from the action of some drug, then X2, which is proportional to [c], decreases. The cell growth rate dn/dt=b dX2/dt will also decrease. The effect of the drop in c is an increase in X1 relative to X2, until a new level of X1 is reached that restores the cell growth rate to its initial value. In the representation used in this invention:

the 1st term is represented by an enzyme-bioProcess corresponding to the formation of c by X1, where the enzyme-bioReactant would be connected to the bioPool of X1, the substrate-bioReactant would be connected to the bioPool of the precursor of c, and the bioProduct would be connected to the bioPool of c;

the 2nd term is represented by an complex-formation-bioProcess corresponding to the consumption of c in the formation of X2 from c and other subunit(s), connected to the appropriate bioReservoirs; and the 3rd term could be represented, depending on the specific biologic mechanism to be modeled, by: a) a complex-formation-bioProcess corresponding to the consumption of c in the formation of a complex leading to the loss of c by degradation by a ubiquitin-dependent mechanism, connected to the appropriate bioReservoirs; or b) a translocation-bioProcess, representing other mechanisms of loss of c, such as by diffusion, connected to the appropriate bioReservoirs; or c) implicitly represented by the degradation-coeff within the formula that determines the current amount of c, which includes a term with default degradation;

in this system, the scaled-amount set of variables is used, because what is relevant for the behavior of the system are the relative value of X2 in relation to its threshold, which determines cell division, and the ratio between X1/X2, which regulates the rate of production of X2, and not their absolute amounts;

the value of the number-of-cells attribute of the cell-bioModel that encapsulate those bioProcesses and their corresponding bioReservoirs, is doubled when the scaled-amount of the bioPool of X2 reaches the threshold, and at the same time, X1, X2 are halved while [c] remains constant.

The above example is an oversimplification, and in fact much more is currently known about the mechanisms that determine the initiation of mitosis, in which complex inter-dependencies are involved, such as the equivalent of X2, a complex, regulating not only the rapid increase in its production by a positive feedback loop upon the equivalent of X1, but also X2 regulating its destruction by activating an enzyme in the ubiquitin-dependent mechanism, and X2 regulating its inactivation by activating another enzyme that converts X1 back to c. In general, in the absence of diffusion, the simple case that might produce organization in time is that of two concentration variables. X1 and X1, where the value of each is dependent on the value of both, such as when: d[X1]/dt=v1(X1,X2); and d[X2]/dt=v2 (X1,X2) .Other high-level physiological events can be modeled in a similar manner, such as considering different cells subsets (i.e. neutrophils) changing compartments (intravascular->interstitial space during inflammation) as induced by cytokines (i.e. TNF-a: which is produced upon activation by macrophages, neutrophils, T-lymphocytes, natural killer cells and mast cells) in chemotactic-bioProcesses. The time-period that a cell subset stays in such a compartment depends in part on the expression of adhesion proteins (such as E-selectin (ELAM-1) or ICAM-1 by endothelial cells, which expression is induced by TNF-a), which will be components of cell-interaction-BioProcesses.

Modeling Progression through Different Cell States: the Cell Cycle and Cell Differentiation Each cell-phase (Table 69) and cell-bioModel (Table 68) has two attributes called the Generation-number (318, F) and the Number-of-cells (319, N, per volume unit). At each cell division at the mechanistic level, that is, when the subworkspace of the M-compartment is deactivated and optionally the subworkspace of the G1-compartment is activated, predefined expert rules (Table 78) set F=F+1 and N=2n for each cell-phase of that cell-bioModel. Another attribute called Mass-per-cell (X), can optionally be given a value and used to calculate specific values as a function of cell mass, in which case predefined expert rules (Table 78) set X=X/2 for the G0-phase, and the G1-phase if applicable, of that cell-bioModel, and then the value of that attribute would be modeled as dependent on time or as dependent on any other variable(s), such as the concentration of some specific mRNA(s) or protein(s), until reaching again a value of X or close to X. In turn, the value of X can be used to adjust other quantities or to control the activation and deactivation of the subworkspaces of each successive cell-phase of that cell-bioModel, making it dependent on cell-size. The equivalent at the population level at mitosis is that n cells from the M-phase bioPool are translocated to the G0-phase (or the G1-phase depending on the situation) bioPool while multiplied by 2, so that the G0(G1)-phase bioPool receives 2n cells.

FIG. 28 is a representation of the mechanistic approach, and attempts to represent on paper what can be achieved dynamically at run-time applying the innovations of this invention. If we assume that a cell is in Go-phase state and focus on that state's sub-workspace (2801), and there we assume that variables represented as Z and W have received the values z and w, respectively, then following the implementation described in this invention, a rule will be invoked (2802) that will activate the subworkspace of the G1.1-phase (2803) compartment. Activation of G1-phase.sw implies that all the variables and parameters encapsulated within the bioObjects contained upon that subworkspace will be available to the simulator, and the data flow can now continue through any branch of the pathways represented there. Therefore, upon required events being satisfied, such as Z and W reaching certain thresholds—which could be an effect of binding one or more growth factors to their receptors on the cell membrane—, the cell makes a transition from the G0 to the G1.1 phase. The subworkspace of the G0-phase remains activated during the whole simulation run because it encapsulates all those bioProcesses that are not cell cycle specific. Focusing now on the simulation of the G1.1-phase (2803), two expert rules could be invoked, saying that "Whenever variable A receives a value a>ø1 then activate G1.2-phase.sw" (2804), or "If X and Y receive values x>ø2 and y>ø3 then activate Differentiated-Cell.sw" (2805) and depending on which one is invoked first, either the subworkspace of the G1.2-phase (2806) compartment or the subworkspace of the Differentiated-Cell.sw (2807) compartment will be activated, since the subworkspace of the G1.1-phase (2804) compartment will be deactivated by another two expert rules that state that "Whenever the subworkspace of the G1.2-phase (or Differentiated-Cell) is activated then deactivate the subworkspace of the G1.1-phase". This way of reasoning applies to the other cell-phases as well, with the difference that the options vary for each cell-phase. For example, the G1.2-phase (2806) and S-phase (2808) may be committed to only one option, with the time for progression to the next phase being determined by one rule, as shown, while the G2-phase (2809) and M-phase (2810) have two options, and which one will be activated is controlled by two rules, as described above. One of the options, Apoptosis (2811) is a dead-end stage, representing regulated cell death. While in M-phase (2810), a live cell's program tells it, before or during cell division, to continue proliferating, in which case one or both the daughter cells entering again the G6.1-phase, by activating the subworkspace of the G1.1-phase, or to exit the cell-cycle, in which case the simulation continues with only the Go-phase. Note that the options for each one of the cell-phases have been predefined by the characteristic number of stubs for each subclass.

The dynamics system diagram (2812) in that figure is used to represent that the defined attributes of the subclasses of cell-phase contain a variable that allows to keep track of the proportion of the cells, from the original number on Go-phase, are progressing through the phases of the cycle, as an alternative to build a model with a set of bioReservoirs and bioProcesses. This variable can be modeled using a probabilistic or mechanistic approach. In a probabilistic approach for representing cell-phase distributions, a balanced growth type of cell population is characterized by such distributions, which is a time invariant property even if their total number increase exponentially with a constant specific growth rate m. Each of the subsets of that population, which represent different cell-phases, and which can also be represented as separate cellPools in the system of this invention, increase in number at the same specific rate and are also characterized by time invariant property distributions, which is represented by the Typical-fraction (320, Table 69) attribute of each of the cell-phases. At some steps during a simulation, the alternative cell-phase compartments that could follow may exclude each other at the single cell level, but not at the cell population level, so that different subsets of a population may follow different paths, with the distribution depending on the strength of signaling events generated within the simulation itself. Therefore, the simulation of the value of this variable could be modeled to represent the probabilistic distributions, independently of which subworkspaces are activated first following the mechanistic approach. Kromenaker & Srienc (1991). Biotechnology and Bioengineering 38: 665–67.

As shown in FIG. 29, If a cellular response results only in proliferation, the simulation of the population cell dynamics involving bioPools of cells in different states, results in cells that keep translocating from bioPool to bioPool, each representing a different one from a discrete number of states, resulting in cycles through a closed-loop set of cell-state bioPools, one of those. However, if the response results in cellular differentiation, it generates branching to a new closed-loop set of cell-state-pools.

FIG. 29 also shows how a cell populations approach bioModel can be build to model the translocation of cells between the major states considered, as mechanistically represented by the defined subclasses of cell-phase, by creating and connecting a set of bioReservoirs and bioProcesses, as the example detailed in the figure shows. Although the cell cycle is a continuous one, it can be compartmentalized into functional cycle intervals whenever it is deemed useful to better represent the dynamic simulation of the system. The initial state is the resting state, represented by the cellPool Cell-X1-Go (2901) of cells of type X1 (or in differentiation stage X1) in the Go-phase. That cellPool may receive inputs (2902) from various sources, represented by bioProcesses in which cells are added to the resting pool after having been activated or cycling as the result of a variety of factors, and its outputs (2903) may contribute also to a variety of such bioProcesses, such as the one that will be here described. While at Go-phase, if the cell is activated (2904) by a growth factor (2905), antigen or any other activating stimulus, the cell enters the activated state or G1.1-phase (2906) and it is added to the corresponding bioPool (2911). From that bioPool (2911), all the cells may follow one of the two different options, or different cells may follow different options for the next cell-phase, depending on the type and strength of the signals received, either: a) following the cell cycle (2908) if certain growth factor(s) (2909) are sufficiently present, resulting in cells X1 in G1.2-phase pathway (2910) and added to their corresponding bioPool, or b) following the cell differentiation pathway (2912) if certain differentiation factor(s) (2913) are sufficiently present, resulting in cells X2 in G1.1-phase (2914) and added to their corresponding. Each of the cell types will be then running in parallel, with their own set of bioReservoirs and bioProcesses. The same reasoning applies to the rest of the system, as detailed in the figure, which will not be further explained, only to say that at the end of the cell cycle, in the cellEngine (2916) that returns cells from M-phase (2917) to Go-phase (2918), has not only a translocation function, but in addition, given that the Stoichiometric-coeff of cell-X1-Go is 2 while the Stoichiometric-coeff of cell-X1-M is 1, it doubles the number of cells to be added to the cell-X1-Go-pool.

In fast growing organisms, the dilution factor resulting from cell growth is represented by m, while in slow growing cells direct enzyme degradation is more important, since the levels of many enzymes in animal cells is controlled by the balance between enzyme synthesis and degradation, called turnover. The synthesis of an enzyme is a zero-order process, while the degradation usually has a first-order kinetics (proportional to the concentration of enzymes). It is very difficult to measure directly the rates of change of different cellular components at the single cell level. A modeling framework requires at least data from measurements about the distributions of single-cell components in growing cell populations, and at the time of cell division and birth, which in some cases can be obtained by multiparameter flow cytometry.

Growth Rate in Terms of Net Rate of Protein Accumulation in Single Cells in each Phase of the Cell Cycle:

The growth rate in terms of net rate of protein accumulation in single cells in each phase of the cell cycle can be calculated, for balanced growth cell-populations, based on the measured distributions of single-cell protein content in the total cell population. Similarly, net rates of accumulation of any specific protein as well as any other compound or property can be calculated whenever the properties and their distributions can be measured on a single cell basis, such as with multiparameter flow cytometry with gating features, that permit direct correlation with the cell-cycle phase. Kromenaker and Srienc (1991) defined balanced growth-cell populations as those characterized by: a) the total cell number increasing exponentially with time according to a specific constant mean growth rate, and b) the total cell population and any of its sub-populations having a time invariant single-cell property distributions. They developed equations to represent the dynamics of a given protein content range in an individual cell cycle, and after deriving restrictions that apply to the rate constants and substituting those in the original equations, the obtained expressions for the growth rates for each individual cell cycle. The transformation of this model into the graphic language proposed in this invention, and the incorporation of those equations, is an example of a currently preferred embodiment of this invention, which is explained in more detail in Exhibit M1.

The transition between different time-compartments may also be made a function of cell size, or its equivalent total-protein content, both of which are attributes of cell-bioModel. At the population level, the transfer of cell-units from the bioPool of cells in G1.1-phase to the bioPool of cells in G1.2-phase is also based on the value of such attributes. For example: the rate of increase in the number of cells with a protein content greater than a given value p in G1, which may be established to delimit the G1.1-phase from the G1.2-phase compartments, equals the rate at which cells with a protein content greater than p enter G1-phase+ the rate at which cells within G1-phase grow into the class of cells with a protein content greater than p—the rate at which cells with a protein content greater than p exit the G1-phase.

Additional sub-phases can be analyzed whenever appropriate landmarks can be observed to define additional transitions. To represent a specific form of cell death, which is highly regulated and known as programmed cell death or apoptosis, a separate time-compartment (2430) is defined in this system, which is equivalent to a cell-cycle phase compartment but with the difference that has a dead end and does lead to a next compartment, but rather eliminates cells that have passed through certain specific combination of events. In addition, an additional term representing the rate of exit from each cell-cycle compartment via other types of cell death may be introduced into each of the population balance equations.

In this system, in general it is assumed that cell division is symmetric, and that total protein is conserved at cell division. The G1-phase is bounded by cell birth and initiation of DNA replication; S-phase is bounded by the initiation and completion of DNA; G2-phase is bounded by the completion of DNA synthesis and the initiation of mitosis; and the M-phase is bounded by the initiation of mitosis and cell division. At balanced growth, each subset of cells in each cell cycle phase increase in numbers at the same specific growth rate as the overall population. The rate of entry into the G1 phase is twice the rate of exit from the M phase. Additional phase compartments can be added whenever other transition landmarks can be measured, as well as the cell distribution at each side of the transition. The following can be used as the equations to model the rates: $rG2G1=k*No/G20, rG1S=k*(No+G20+S0)/G10, rSG2=k*(No+G20)/S0$, where No is the number of cell in the total population at some reference time, and $No=G10+G20+S0$ at this time. Kromenaker & Srienc 1991, Biotechn. Bioeng. 38:665–677.

The currently preferred embodiment of this invention deals with different stages of cell differentiation, each representative of a characteristic set of behaviors, as separate pools of cells. All the cells in a pool have identical behavior and, again, in the system of this invention when one refers to an instance of a cell with a particular phenotype it does not mean an individual cell but rather a pool of equal cells that is characterized by its behavior and also by a cell-number and a cell-density. We have also considered previously cases where individual cells grow and differentiate in response to specific signals provided when environmental factors activate specific receptors that initiate a signal transduction pathway within the cell. However, different cells respond by following diverse pathways in response to an identical signal, and this specific response depends on the history of that cell. For example, erythroid cells could be allotted to three pools with phenotypes characterized by the presence of two cell differentiation surface markers CD34 (a glycoprotein) and CD71 (the transferrin receptor): a) $CD34^+$ include most immature erythroid progenitor cells; b) $CD71^{low}$ includes intermediate stages; and c) $CD34^- CD71^{high}$ includes most mature erythroid progenitors. Each of this populations have different predominant form of the erytropoietin receptor, and respond in different ways to erytropoietin: $CD34^+$ express a truncated form of the receptor and respond by proliferation, while $CD34^- CD71^{high}$ respond by differentiation and are protected from apoptosis or programmed cell death (Nakamura et al., Science 257, 1138–1141, 1992). In the currently preferred embodiment of this invention, the particular history of each cell pool is reflected in the specific bioModels as determined by the particular procedures to be followed, which are encoded in the corresponding attributes of the bioObjects that are components of that cell's specific bioModels.

Navigation and General Modes: Exploring and Queering the Virtual Models

Menus and Panels

The domain-menus associated with the Navigation Mode and the General Mode, the default user mode for users with no modeler or developer rights, comprise the headings: "Help & Mode Menus" (1601), "Structure Libraries" (1619), "Pathway Libraries" (1628), previously discussed, and "Panels", which options include panels of various types used to access tasks that are not initiated from one single bioReservoir or bioProcess, or their components, but which are either application-wide or including more that one starting points.

The Initialization Panel is used to request the initialization tasks associated with each of the buttons. Here we will discuss the methods associated with each of those buttons. An initially rule (Table 97) causes this panel to be automatically displayed when the program is started. Selecting the "Menu" button calls the basis-menu-head-callback (Table 98), which causes the creation of the specific domain-menus, by calling other procedures defined within the Shell and, depending on the current value of the user-mode of the window from which the request has been made, it passes as argument the name the menu-structures specific for that mode.

Selecting "References Scroll" displays the subworkspace of the References Panel, discussed below. Selecting "Structure Queries" creates a clone of Master-General-Structure-Query-Panel and displays its subworkspace discussed in more detail below in relation to FIG. 30. Selecting any of the "Experiment Setup #" displays the subworkspace of the corresponding "Experiment Setup Panel", which are variously modified clones of the Master-Experiment-Setup-Panel, one of which will be discussed in more detail under the Simulation Mode heading in relation to FIG. 35, since part of the capabilities provided within this type of panels can be used under the General Mode, and all the capabilities can be used in Simulation Mode.

Initialization

Selecting the "Navig Init" button calls the navig-init-callback, which calls the navig-init-proc (Table 99) resulting in the activation of the subworkspaces of all bioProcesses and bioReservoirs and then successively calling the following procedures:

the br-initialization-proc (Table 100) sets the appropriate values of the Master-bioReservoir (1208) attribute of all bioReservoirs, highlights the flag-color region of the icon of those bioReservoirs that have Warnings, sets the appropriate values of the Ref-bioprocess (2235) attribute of all bioPool-posts of all bioReservoirs, and establishes all the appropriate "a-down-bioProcess-of" and "an-up-bioProcess-of" relations (Table 75) between bioProcesses and bioReservoirs, making then those changes permanent (note that relations are transient in this Shell, and therefore they are lost when the application is restarted);

the bp-initialization-proc (Table 101) changes the color of the type-color region of the icon of each bioProcess to equal that of the bioEngine it encapsulates, sets the appropriate values of the Master-bioprocess (1405) attribute of each bioProcess, highlights the flag-color region of the icon of those bioProcesses that have Warnings, sets the appropriate values of the Ref-bioreservoir (2234) attribute of all bioRole-posts of each bioProcess, establishes "an-upstream-bioReservoir-of" and "a-downstream-bioReservoir-of" relations (Table 75) between certain pairs of bioReservoirs that are separated only by one bioProcess, and establishes "an-upstream-bioProcess-of" and "a-downstream-bioProcess-of" relations (Table 75) between certain pairs of bioProcesses that are separated only by one bioReservoir;

the downstream-chaining-proc (Table 102) completes the downstream chaining process by extending those relations to distant bioReservoirs and bioProcesses, by establishing the appropriate "a-downstream-bioReservoir-of" relations (Table 75) between any bioReservoir A and each other bioReservoir that is positioned downstream of A in any pathway, and establishes all the appropriate "a-downstream-bioProcess-of" relations between any bioProcesses B and each bioProcess that is positioned downstream of B in any pathway;

the upstream-chaining-proc (Table 103) completes the upstream chaining process by extending those relations to distant bioReservoirs and bioProcesses, by establishing the appropriate "an-upstream-bioReservoir-of" relations (Table 75) between any bioReservoir A and each other bioReservoir that is positioned upstream of A in any pathway, and establishes all the appropriate "an-upstream-bioProcess-of" relations (Table 75) between any bioProcesses B and each bioProcess that is positioned upstream of B in any pathway;

the biomodel-initialization-proc (Table 104) scans each bioModel for other encapsulated bioModels, bioProcesses and bioReservoirs, going down the subworkspace hierarchy, and establishes the following relations between any combination of them: bm-contained-in between a bioModel and a bioModel, bp-contained-in between a bioProcess and a bioModel, and br-contained-in between a bioReservoir and a bioModel (Table 47). Those relations are important for all further processing, and are used by the newly defined query procedures, navigation procedures, and simulation procedures described below.

A rule (Table 119) monitors the application at run time, and whenever the user moves a bioModel the rule starts the biomodel-ws-check-proc, which checks whether the bioModel has been moved to a different workspace, in which case it calls the remove-biomodel-containing-proc (Table 119), to brake the old relations that no longer apply, and calls this biomodel-initialization-proc (Table 104) to establish the new relations. The upstream and downstream relations are also created and broken at run-time by a set of rules (Table 76) and a parallel set for bioReservoirs, not shown) that monitor whenever any such chaining relation is newly established or broken, and in response to such events they establish or brake other relations, according to similar criteria, which trigger the same rules for a chain of other bioReservoirs or bioProcesses. The use of those rules makes sure that if a modeler or user deletes a bioReservoir or bioProcess that is part of one such chain of relations, then the chain is broken between the elements of both sides on the breaking point. Such sets of rules are used for establishing relations whenever new connections between bioReservoirs and bioProcesses are made by the modeler.

The "Add Query" button is to be selected only after the "Navig Init" was been successfully concluded. If changes to the database have been made by the modeler since the "Navig Init" was last concluded, or if the application has been restarted, then the "Query Init" button should be selected. The common purpose of both buttons is to organize knowledge about the structure of all the bioEntities in the application, and to create a set of structures to hold that knowledge, to be used any time that the user request a predefined query that involves that kind of knowledge. Selecting the "Add Query" button calls the add-query-callback (Table 105), which calls the two procedures that follow. Selecting the "Query Init" button calls the query-init-callback (Table 106), which calls the navig-init-proc (Table 99) and the two procedures that follow:

the et-initialization-proc (Table 107) scans the loaded application for every copy of each named complex-bioEntity, and then assigns a value to the Id attribute of each such copy that is equal to the name of such bioEntity complex-bioEntity ended by the copy number. Copies are numbered consecutively, in the order found, with the original being –0:

the init-query-tables-proc (Table 108) activates the subworkspace of the Query-Arrays-Bin and deletes any old array upon it, and also deletes any old list upon the Query-Lists-Bin, and then calls the following procedures:

the find-bioentity-definitions-proc (Table 109) scans the Bioentities-Defs-Bin, which contains all the object definitions of all the subclasses of the class bioEntity, and for each of those subclasses it calls the create-query-array-proc (Table 110), which creates a query-array, sets its Major-class attribute equal to the name of the superior-class of such subclass, sets its Ref-component-class attribute equal to the name of such subclass, and sets its Name attribute equal to the name of such subclass followed by the ending-query-array, and transfers such query-array to the Query-Arrays-Bin at a location specific for each superior-class:

the create-query-lists-proc (Table 111) creates a query-list to correspond to each query-array in the Query-Arrays-Bin, and transfers the list to the corresponding location upon the Query-Lists-Bin, sets its Ref-array attribute equal to the name of such array, and sets its Ref-component-class attribute equal to the Ref-component-class attribute of such array; then, for each of those lists and for each bioEntity of the subclass named by the Ref-component-class of such list, it calls the find-named-bioentities-with-component-proc (Table 112), which in turn, if such bioEntity has a name it directly calls for such bioEntity the procedure that follows, otherwise it calls first the find-named-bioentity-proc (Table 113) to scan the hierarchy of bioEntities superior to such bioEntity, until one is found with a name, in which case, it now calls for the named bioEntity the procedure that follows:

the seek-bioentity-copies-proc (Table 114), inserts the argument bioEntity in such list, and then scans the application for any copy of such bioEntity, and if any is found then it loops back for such bioEntity by calling the find-named-bioentities-with-component-proc (Table 112) mentioned above, which will repeat the cycle back to this procedure, as described, until the various loops for each bioEntity of every list are completed.

When this process is completed, the list for each bioEntity subclass contains, with no duplicated elements, all the named bioEntities that encapsulate one such bioEntity, either directly or by reference. To give an example, that means that if a named protein instance-A encapsulates a protein-motif instance-B, then every named protein complex-instance-C that encapsulates an unnamed copy of instance-A (which does not itself encapsulate a copy of instance-B, but rather points to its master-bioEntity, instance-A, which encapsulates instance-B) will also be included in the list of all bioEntities that encapsulate a protein-motif. After all such lists are completed, it calls the following procedures:

the complete-query-table-proc (Table 115) simply transfer the values of the elements from each of those lists to their corresponding arrays, by fist setting the length of the array to match the length of the list, and then setting the text of the initial-values attribute of each array to equal a text string that mentions all elements of the list separated by commas, as illustrated in the example listed in Table 116, which shows a pair of corresponding instances of a query-list and a query-array of the subclass sup-et-array, which list named instances of bioEntities that contain an a-helix-motif, which in this small demo application consists only of a few master-structures from the library. In the table of attributes listed, the initial-values attributes is displayed, and the list of elements of either the list or the array can be displayed by selecting the "describe" option of their menus;

the create-auxiliary-query-arrays-proc (Table 117) adds a few empty arrays corresponding to the no-selection options of each query panel, which are simply programming aids, and to conclude it deactivates and activates again the subworkspace of the Query-Arrays-Bin for the purpose of initializing the query-arrays upon activation, which means that the elements of the array take the values given by the set initial values.

The "Icons Init" button calls the init-icons-callback (Table 118), which function is not essential for the functioning of this system, but which provides a very useful cosmetic function, by realigning the tracers in the subworkspaces of bioReservoirs and bioProcesses and making their connections invisible. Selection of this button is not necessary every time the application is started, and it can be selected any time thereafter, when problems are detected, in any mode other than Simulation Mode (where those subworkspaces may be deactivated). The same effect is achieved for individual bioReservoirs or bioProcesses by slightly moving and repositioning their bioPool or bioEngine, respectively, which triggers their respective icon-movement rules, as defined in Table 79, which also apply to repositioning the bioRole-posts any time a bioReactant or bioProduct is moved.

Selecting the "Init All" button calls all-init-callback (Table 118b), which calls all the initialization procedures mentioned above, and selecting the "Hide" button calls the hide-workspace-callback, which hides this Panel.

Navigation

In this invention, navigation refers to the domain-specific tasks of displaying and hiding either related bioObjects or their subworkspaces. The concept of related object include various types of associations, including some that are permanently stored in the knowledge-base, as defined by either graphic or distant connections, or containment in subworkspaces at any level in the hierarchy, and some that are transient such as relations, which are established and may be broken at run-time (note that in the system of this invention it is also possible to store run-time versions or snap-shots of the application, which also include transient objects, such as relations). Navigation tasks may be performed in any mode, but Navigation Mode has that name because the behavior of certain object classes, including the classes bioReservoir, bioProcess, bioModel, and complex-bioEntity, is restricted to do just that. This means that a navigation task is automatically performed upon clicking on the instances of any such classes, instead of displaying a menu with various other options as well, and therefore all those other tasks offered by the other options are not available in this mode. Navigation tasks are usually simplified in this filing by expressions like "selection of A starts proc-B, which displays C", but in reality these processes do more than that in this invention: selection of A invokes proc-B, which takes as arguments A (the item) and the current window, and causes C to be either displayed or hidden on the current window, depending on the value of the Toggle-state attribute of A, and in addition, the icon appearance of A is configured, switching between its pressed or depressed configuration, respectively, and the value of the Toggle-state attribute of A is alternated between on and off. In such cases, A may be either a button or any of the bioObjects that has a subworkspace, which in this regard behave similarly.

FIG. 24 will be described to summarize some of those navigation tasks when in Navigation Mode, while also referring to the definitions of the methods involved listed in the Tables. Any navigation task that is directly performed in this mode may be performed in any other mode when selected from the menu. Selecting any bioProcess (2410) in Navigation Mode implies selecting its "details" option that starts the details-bp-proc (Table 120), which displays its subworkspace (2411), in the same way that selecting any bioReservoir (2414) implies selecting its "details" option that starts the details-br-proc (Table 121), resulting in its sub-workspace (2415) being displayed or hidden, depending on whether the value of the Toggle-state is hide or show, respectively.

When selecting the "details" option of any bioProcess that has a master-bioprocess but has no subworkspace, conditions that when combined are characteristic of a copy bioProcess used in the creation of Pathways, causes such first procedure to call the bp-master-details-proc (Table 120), which in this case displays or hides the subworkspace of the original (master) bioProcess, in addition to configuring the icons of both the original and the copy bioProcess to their pressed or depressed appearance, respectively. In a similar way, when selecting the "details" option of any bioReservoir that has a master-bioReservoir but has no subworkspace, characteristic of a copy bioReservoir, causes the first procedure to call the br-master-details-proc (Table 121), which in this case displays or hides the subworkspace of the original bioReservoir, in addition to configuring the icons of both the original and the copy bioReservoirs to their pressed or depressed appearance, respectively.

BioEngines do not have subworkspaces by default, but the modeler can create one to store tabular functions. In such cases, a "show-sw" option is available, and selecting such bioEngines in Navigation Mode implies "show-sw", which starts the show-bioengine-sw-proc, which displays or hides its subworkspace and toggles the configuration of its icon.

The behavior of complex-bioEntities in Navigation Mode is similar, as shown in FIG. 18, where selecting any bioEntity (1808, 1813, 1815, 1817, 1819, or 1821) implies selecting the "details" option, which starts the et-details-proc (Table 122), which displays or hides its sub-workspace (1809, 1810, 1816, 1818, 1820, or 1822, respectively) and toggles the configuration of its icon. The combination of this option with the go-to-sup-obj-button (1826) upon each subworkspace allows to navigate up and down in their workspace hierarchies.

Selecting any bioProduct-post (711) or any bioReactant-post (703, 707), in General, Navigation, or Simulation Modes, implies selecting its "show-br" option, which starts the rolepost-show-br-proc, (Table 123), which displays the subworkspace (714 or 705) of the bioReservoir named by their Ref-bioreservoir attribute. Similarly, selecting any bioPool-r-post (704) or any bioPool-p-post (712) implies its "show-bp" option that starts the poolpost-show-bp-proc (Table 124), which displays the subworkspace (702) of the bioProcess named by its Ref-bioprocess attribute. This option is only available in the menu when the bioPool-post has a name. Selecting the go-to-sup-obj-button (1825) on the subworkspaces of each bioObject displays its superior object, while selecting the hide-sup-ws-button (x) hides its workspace. The combination of those capabilities allows to follow all the distant connections through the pathways of bioReservoirs and bioProcesses, and also up and down in their workspace hierarchies.

Selecting any model-box (1218, 1236, or 1237) in General, Navigation, and Simulation Modes, implies selecting its "show-sw" option, which starts the show-model-box-sw-proc, which displays or hides its subworkspace (1221) and toggles the configuration of its icon. This option is used to access the model-block (1222) upon that sub-workspace.

The "bioentity" option (Table 125) appears in the menus of bioReservoirs (1803), bioReactants and bioProducts (1525) only when the Ref-bioentity attribute of the bioReservoir has a value different from the default value of none, and upon selection shows or hides the subworkspace of the bioEntity named. The Ref-bioentity attribute is defined only for the class bioReservoir and the menu options of bioReactants and bioProducts refer to that attribute when connected. However, this attribute can be defined for those other classes as well, allowing access to a bioEntity independently of a bioReservoir.

Structure Related Queries

There are two major groups of Queries: a General-Query is based only on structure and is application wide, while a BR-Query is in reference to the bioReservoir from which it was initiated. The Query Panels are built hierarchically, with each radio-button from the first Selection Panel leading to another more specific Query Panel, where now the user can compose a selection and then initiate the Query. The word Panel is frequently used in a more general sense to refer to the subworkspace of an instance of the class query-panel.

A General-Query may be requested by selecting from the "Panels" menu head the "Structure Queries" option, which calls the create-general-structure-selection-panel-callback (Table 127), which clones the Master-General-Structure-Query-Panel, stores the clone in the Temporary-Panel-Bin, configures its radio-box with the aid of the set-radio-box-id-proc (Table 128) and displays its subworkspace. The user may now use such Panel to select any radio-button from its radio-box, which calls the select-general-structure-selection-panel-callback (Table 129) with such button as one of its arguments, which in turn: a) gets the value of the radio-button selected, and depending on the value of the On-value attribute of such button, clones the corresponding master-panel, then calls the create-general-query-panel-proc (Table 130) with such value and the new panel among its arguments, which completes such panel by scanning the panel for the presence of specifically labeled radio-boxes (related sets of radio-buttons) and configuring the radio-boxes with the set-radio-box-id-proc (Table 128), and b) displays the subworkspace of the new panel.

The user may now use that Query Panel to select any combination of one radio-button per radio-box and then selecting the "Query" button calls the query-general-structure-callback (Table 131), which calls first the query-general-structure-proc (Table 132), which scans such panel for the presence of specifically labeled radio-boxes and then calls find-specific-array-proc (Table 133), with such label as one of its arguments, to find the value of the selected radio-button and the matching array within the Query-Arrays-Bin (those arrays are created during the Query Initialization process, as described in the Initialization section above). An auxiliary scroll-text-list is created and, if only one radio-box is present in the Query Panel, then the elements of the corresponding array are transferred to such list. If two radio-boxes are present in the Query Panel, then two such arrays should be found, in which case the merge-two-structure-lists-proc (Table 134) is called, which scans those arrays to find the common elements, which are transferred to such scroll-text-list. A specific text-string is developed to include references to the selected options and to the outcome of the search, which is then given as a value to a free-text structure, which is displayed as a heading for the results of the search. The callback calls then the create-general-query-output-panel-proc (Table 135) with such scroll-text-list and free-text among its arguments, which creates an output panel by cloning the Master-Molecular-Query-Output-Panel, then creates a scroll-area to display the elements of such scroll-text-list, and transfers to the subworkspace of such output panel both the free-text and the scroll-area listing the results of the search, which is them displayed. The user can now use such scroll-area to interactively display or hide the structure of any number of bioEntities named by the options listed, as described below.

Pathway Related Queries

FIG. 30 illustrates an example of one of the several types of predefined Pathway Related Queries that the user can perform by just selecting the desired buttons from the options offered in the panels (3004, 3006). All the searches generated from this type of panels include bioReservoirs located anywhere within the pathways that are either upstream or downstream, depending on the selection, of such initial bioReservoir (3001), and also the bioEntities referred to by any of those bioReservoirs. Those upstream or downstream queries can be further restricted by the type of roles that those bioReservoirs play in different bioProcesses, as defined by the major classes of bioReactants to which their bioPools are distantly connected, which is referred here as function-related search. In complex queries of mixed type, such bioEntities can be further restricted to those encapsulating any particular component, similar to the Structure Related Queries described above. In such cases, the methods pertinent to the pathway search are applied first to generate the pathway-related set, followed by the function search, which is applied only to the pathway-related set and generates the function-related set, and finally the structure search, which is applied only to the function-related set, or to the pathway-related set if no function search has been selected, and generates the structure-related set. The structure search applies only to the bioEntities for the purpose of displaying the results, in the sense that all bioReservoirs that meet the selected pathway, and optionally function, requirements are listed in the scroll-area listing the bioReservoirs, regardless of whether they meet any of the bioEntity related criteria. This implementation is currently preferred because the Ref-bioentity of a bioReservoir is an optional attribute, and it is expected that many of the bioReservoirs will not have a corresponding defined bioEntity. This alternative provides a more complete search in terms of relative position and function of bioReservoirs, without being influenced by the implementation of an option.

These types of Query may be requested in two different ways: a) from a bioReservoir (3001) by selecting from its menu (3002) the "query panels" option (3003); or b) from the sub-workspace a bioReservoir by selecting the query-tracer (Q) connected to the bioPool. A query-tracer is a subclass of list-tracer (Table 30), which selection implies selecting the tracer's "show" option. Each of those options starts the create-br-related-selection-panel-callback (Table 138), which creates a clone of Master-BR-Molecular-Query-Panel, configures it, and displays its subworkspace (3004), the Pathway Query Selection Panel. Configuring this panel and any other panel that follows during the processing of br-related queries always includes setting the value of the Related-item attribute of the panel equal to the name of the bioReservoir from which the query was initiated, and this name is passed along when a new panel is originated from such panel. That is, any callback invoked from a button of a panel, takes the name of the bioReservoir from the Related-item of the panel upon which subworkspace it is located, and passes that name as an argument when calling other procedures.

The user may now use that Pathway Query Selection Panel to select any radio-button (3005) from its radio-box, which calls the select-br-related-query-panel-callback (Table 139) with such button as one of its arguments, which in turn: a) gets the value of the radio-button selected, and depending on the value of the On-value attribute of such button, clones the corresponding master-panel, then calls the set-br-related-query-panel-proc (Table 140) with such value and the new panel among its arguments, which configures and completes such panel with the set-radio-box-id-proc (Table 128), and displays the subworkspace (3006) of the new panel, a Pathway Query Panel. This panel is composed of: a) the title (3022), which specifies the type of search being made from that panel and names the bioReservoir (3023) that is the point of reference for the search; b) the set of radio-buttons (3024) of the radio-box labeled "direction", defining the two possible alternatives; c) the set of radio-buttons (3025) of the radio-box labeled "function", which defines the possible alternatives available for function, which in this case we only show a small but important subset that is of high relevance to scientists; d) the set of radio-buttons (3026) of the radio-box labeled "motifs", which defines the possible alternatives available for subclasses of protein-motif. Many other possible sets of radio-buttons, such as those of the radio-box labeled "location", which defines the possible alternatives available for subcellular compartments, are not shown.

The user may now use that Pathway Query Panel to select any combination of one radio-button per radio-box. Selecting the "Upstream" option (3007) calls the upstream-query-lists-callback, which calls the upstream-function-query-lists-proc. Selecting the "Downstream" option calls the downstream-query-lists-callback (Table 141) and then the downstream-function-query-lists-proc, (Table 142), which do the following: a) it first calls repeatedly the create-br-query-list-proc (Table 143) to create a set of two lists per each predefined type of function, one to contain names of bioReservoirs and the other the names of bioEntities; b) then, it loops over all bioReservoirs that are upstream (or downstream) and scans for their connections to certain classes of bioReactants, which define their function, and enters their name in the corresponding one of those bioReservoirs lists, for example, if the bioPool of a bioReservoir is connected to both a kinase.r and a transcription-factor.r, then the name of such bioReservoir will be added to each of the two corresponding lists, so that a bioReservoir may be named in more than one function list, but is not duplicated within one single list; and c) for each pair of one of those bioReservoirs lists and its corresponding bioEntities list, it calls the fill-br.et-list-proc (Table 144), which scans all the bioReservoirs in the fist list for the value of their Ref-bioentity attribute, which if available is added to the second list. All those lists, to be used by the procedures described below, are associated by a relation to the panel from which they are created, are valid only for the bioReservoir giving the related-item of that panel, and are deleted when the panel is deleted.

The user can now select any combination of one radio-button per radio-box, such as receptors (3008) and β-strand-motif (3009), and then select the "Query" button (3010) to complete the processing and display the results of the query (Table 145), which first obtains the values of the selected radio-buttons of the "direction" (3024) and "function" (3025) radio-boxes, and then calls the get-br-function-list-proc (Table 146) with those values among its arguments, which are used to obtain and return the corresponding set of two lists from the bioReservoirs lists and bioEntities lists created and filled in the previous processing. Such bioReservoirs list is used to directly pass its values to the bioReservoirs scroll-area (3013) for final display, while such bioEntities list is used as the basis for the complex further processing that follows.

The callback scans now the Panel to find whether there are structure related radio-boxes, such as the "motifs" radio-box in this example, in which case it calls the query-br-structure-lists-proc (Table 147) with those previous values and the bioEntities list among its arguments, which does a complex processing as following: a) it finds the label of such structure related radio-box(es) and calls find-specific-array-proc (Table 133) to find the value of the selected radio-button for such box(es), such as B-strand-motif (3009), and its matching array(s) in the Query-Arrays-Bin (as described for Structure Related Queries); b) if there is only one structure related radio-box, like in FIG. 30, then it calls merge-br-function-structure-proc (Table 148), or if there are two structure related radio-boxes it calls merge-br-function-structure-structure-proc (Table 149), passing among its arguments the values of all selected radio-buttons, as well as the corresponding bioEntities list filled earlier, and the array(s) now found. These procedures create a new list, the bioEntities scroll-text-list, and then, taking into consideration the type and value of the arguments: a) they select a text specific for each situation, to be displayed as a title for the results, b) they call the br-fill-etl-list-proc (Table 150) or the br-fill-double-etl-list-proc (Table 151), which enter the common elements of both the bioEntities list and the array(s) in the scroll-text-list, and c) they return the text and the scroll-text-list to the previous procedure from which they where invoked, which returns them to the callback.

The callback passes such text to a free-text structure, and finally calls the create-double-query-output-panel-proc (Table 152) with the bioReservoirs list mentioned, the bioEntities scroll-text-list, and their two corresponding free-texts among its arguments, which creates an output panel by cloning the Master-Molecular-Query-Output-Panel and stores it in the Temporary-Panel-Bin, then transfers the two free-texts to it, creates two scroll-areas to display the elements of each of those lists in a scrollable and interactive format, and calls the complete-be-panel-proc and complete-br-panel-proc (Table 152), which configure those scroll-areas (3013, 3017) and transfers them to the subworkspace, which is them displayed (3011).

The user can now use the Pathway Query Output Panel (3011) so created to scroll through the lists of bioReservoirs (3013) and bioentities (3017) that are the output of the query. Selecting and unselecting any option of such scroll-areas allows to interactively display or hide the subworkspace of the named structure by calling the query-message-selection-proc or the query-message-unselection-proc (Table 136). Each of the titles (3012) are directly related to the scroll-area below them and vary with the results of each part of the search, and they may omit naming those groups of buttons where not selection was made, or indicate that some search or part of the search was empty. The scroll-area (3013) on the top shows the bioReservoirs that meet the direction and function requirements, which are those named by the options listed, and selecting any of its options (3014) displays the subworkspace (3015) of the named bioReservoir. The scroll-area (3017) on the bottom shows the bioentities that meet the combination of direction, function and structure requirements, as selected, which are those named by the options listed, and selecting any option (3018) displays the subworkspace (3019) of the named bioEntity. Those structures displayed can be used to navigate in any way previously described, including up and down the pathways from bioReservoirs (3015) to bioProcesses (3016) and so on, from bioReservoirs or bioReactants or bioProducts to their bioEntities as shown in FIG. 18, or up and down the workspace hierarchies, by combining the variety of tools and methods previously described. As before, all the Pathway Query Selection Panels, Pathway Query Panels, and Pathway Query Output Panels are dynamically created and transient, and when the search is completed they are no longer needed and they are deleted, as well as their associated lists, by selecting the "Delete" button (3027), which calls the delete-query-panel-callback.

More complex queries can be performed with an additional Master-BR-Molecular-Query-Panel with four additional options, to include queries previously described in combination with an additional constraint criteria, the location of the bioReservoirs selected by the previous criteria within the different cell compartments. Selection of any of those new options displays the corresponding Query Panel, and in this new set of Panels, the "Downstream" and "Upstream" radio buttons are associated instead with the downstream-function-location-callback (Table 153) and upstream-function-location-callback, respectively, which call the downstream-location-query-lists-proc (Table 154) or its upstream equivalent. Those procedures call some of the procedures previously described and also call the find-compartment-proc (Table 155). The user may additionally select any combination of one radio-button each from the radio-boxes offered in each particular panel, and then selecting the "Query" button now calls the query-br-related-location-callback (Table 156), which depending on the boxes available on the particular Panel, calls one of an alternative set of procedures, which call other procedures, as specified. The reader is further referred to the listings in Tables 157 through 169 for the details of such complex processing that is difficult to describe, and which uses a similar approach and methods as those previous described to create a new set of lists and to merge lists with bioReservoirs meeting the different criteria.

The underlying shell loads the desired application modules on memory for run time operations, but it is able to merge and remove modules while the system is running. Since the inference engine's reasoning and search space is limited to those modules that are loaded, it is necessary to create a mechanism to allow for searches in modules that are not yet loaded on memory. This is accomplished by maintaining in the repository module an object, called the query-arrays-bin, which holds in its subworkspace a set of item-arrays for intelligent dynamic merging and removal of the modules required at particular times, particularly when searching through the bioEntity-module and in order to allow for searches in a modularized application. Those contained-in-module arrays are built following similar methods as those described here for bioModels. The difference is that a new set of relation is defined, of the series-contained-in-module, and an initialization procedure that loops over all the workspaces of each loaded module, finding out the value of their assigned-module, and then looping over all the bioModel Libraries upon each workspace, and over all the bioModels upon each bioModel Library, and the continuing with the methods described in the previous section.

Interactive Lists and Pathways

In addition to the various query methods previously described, this invention provides several other tools and methods to enable the user to extract the knowledge build entered into the system by the modeler, in addition to the new knowledge created by applying the methods of this invention to analyze and integrate the knowledge provided by the modeler.

One of those capabilities is provided by the "list copies" menu option (I 825) defined for the class complex-bioEntity, which upon selection calls the et-list-copies-callback (Table 170), which creates a scroll-text-list and then calls the list-local-bioentities-copies-proc (Table 171), which scans all the bioEntities of the same major subclass as the one bioEntity from which the request originated to find if the master-bioentity of any of then matches the name of such bioEntity, in which case the value of the Id attribute of each of those copies is added to the list. If there is any element in that list, then the callback creates an Output Panel by cloning the Master-Local-Bioentity-Copy-Panel, creates a specific title and a scroll-area, which are then added to the Panel and configured, and finally the Panel is displayed. This Panel looks like the Query Output Panel (3017) discussed above, with a different title. Selecting and unselecting any option of such scroll-area call et-copies-message-selection-proc or the et-copies-message-unselection-proc (Table 172), which interactively displays or hides the subworkspace of the structures referred to by their Id, rather than by name. This also provides an example of how, in general, instances of bioEntities as well as bioReservoirs, bioProcesses and bioModels, or any other structure, can be referred to by the value of any attribute, rather than by their names, which have to be unique and sometimes inconvenient, but they can be avoided. Referring to attributes, defined for such or any other purpose, also allows to refer to groups of instances within a class, without having to refer to each individual member of the group.

Another novel teaching of this invention is the capability of creating lists (3107) of downstream and upstream bioReservoirs and bioProcesses. By selecting the icon (3208) of any of those lists, the user can display on a workspace (3209) the elements (3221) of that list, which are pointers to all the bioReservoirs (3210) or bioProcesses that meet the criteria set for each specific list, and each pointer further allows to either display the table of attributes of such object, or displays the object itself upon its workspace (3210), as described in more detail later (FIG. 32). Navigation can be now initiated from those objects as well as any other tasks described in this invention. This capability is accessible through the "show lists" options from the menus of bioReservoirs (3220) and bioProcesses (3103), which appear in the menus only when they are named, as well as from the list-tracers in their subworkspaces.

Figure 31A:
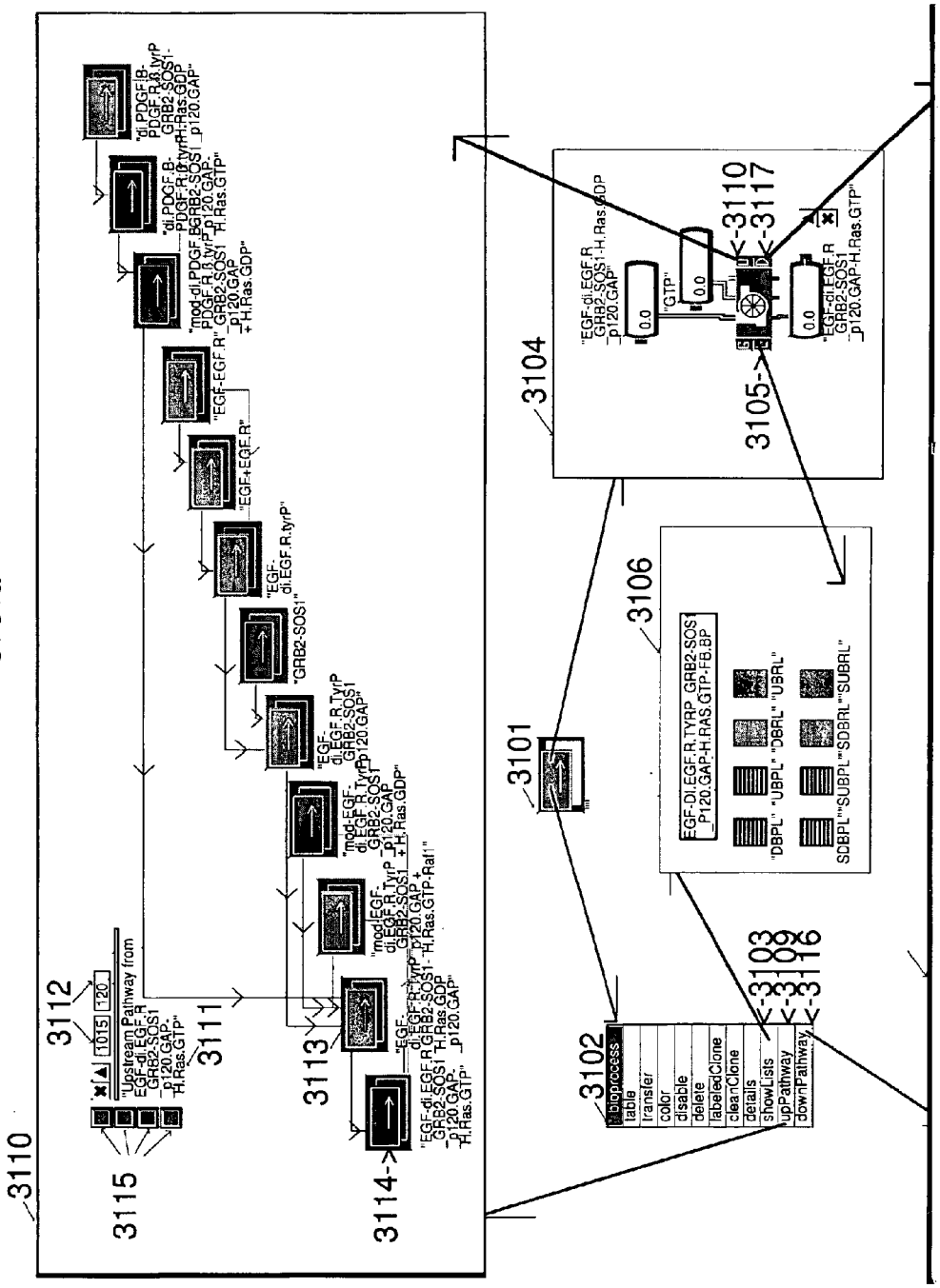
FIG. 31a and FIG. 31b describe how a user can request from any process within the Virtual Model the dynamic generation of the pathways of all the processes that are either upstream or downstream from that process.
Figure 31B:
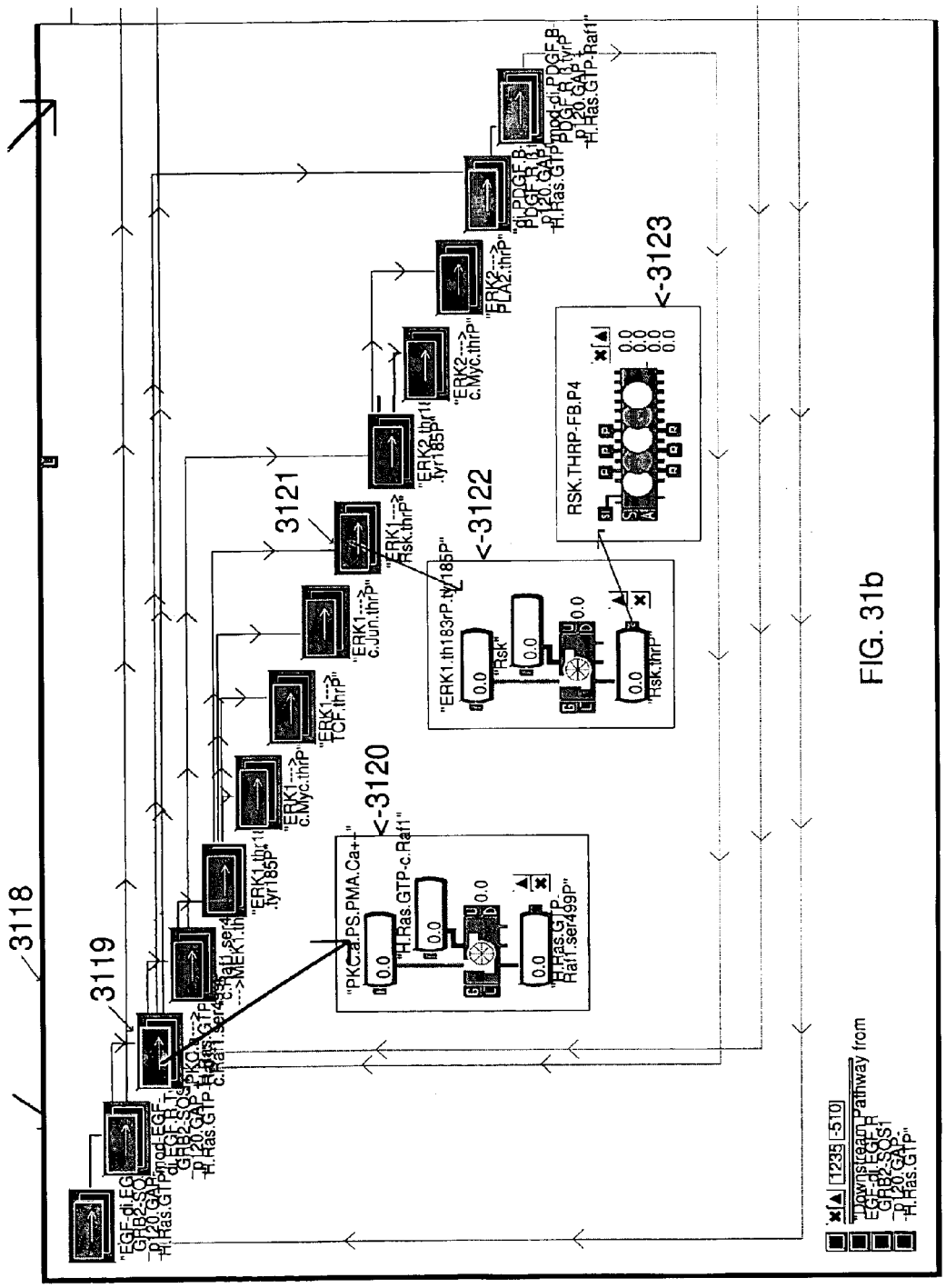

As illustrated in FIGS. 31*a* and 31*b*, chaining-tracers (Table 30) are iconic programmed objects connected to a bioPool (L) or to a bioEngine (L, 3105), where they are used to control the dynamic creation and display at run-time of a set of such lists of either bioReservoirs or bioProcesses that are either upstream or downstream of the bioReservoir upon which subworkspace such list-tracer is located. The "show" option (Table 31) is defined for the class list-tracer and is inherited by all its subclasses, including BR-chaining-tracer and BP-chaining-tracer. Selecting any such list-tracer by the user implies "show", which starts the list-tracer-handler-proc (Table 31), which configures the buttons and depending on the subclass of list-tracer, calls either the BR-chaining-proc (Table 173, also started upon selection of the "show lists" (3220) option of the bioReservoir), or the BP-chaining-proc (Table 174, also started upon selection of the "show lists" (3103) option of the bioProcess). The major actions performed by both of these procedures comprise: a) if the list-tracer already has a subworkspace, then it is displayed with its contents, otherwise a subworkspace for the BR-chaining-tracer or BP-chaining-tracer, respectively, is created by cloning the subworkspace of the prebuilt master structures BR-Chaining-Lists or BP-Chaining-Lists, respectively, which in both cases contain two sets of four predefined lists each, one set (3107) is meant to be used in any user mode, while the second set (3108) is to be used in simulation mode and contain elements from the first set that have been activated as a result of their inclusion in a simulation model (to be described below), and then such lists are displayed; and b) those lists are populated having as point of reference the bioReservoir (3201) or bioProcess (3101) from which they were requested, by using for each list of the set the following criteria: the elements of DBPL and SDBPL are downstream bioProcesses, the elements of UBPL and SUBPL are upstream bioProcesses, the elements of DBRL and SDBRL are downstream bioReservoirs, and the elements of UBRL and UDBRL are upstream bioReservoirs.

A further novel teaching of this invention is the capability to dynamically generate displays of interactive pathways, where these pathways comprise a chain of downstream, or upstream, bioReservoirs or bioProcesses, or both, orderly arranged in a graphic format with connections drawn between them to indicate those that are adjacent. By visually following those connections, the user can follow the pathways that indicate a dependency relationship between those bioReservoirs or bioProcesses or both. The capability to display interactive downstream pathways is accessible from several different types of structures: a) from an individual bioProcess (3116), in which case such bioProcess is the point of reference; b) from a Navigation Panel (to be discussed in conjunction with FIG. 32), in which case a bioReservoir is the point of reference; and c) from an Experiment Panel (to be discussed in conjunction with FIG. 35), in which case one or more bioReservoirs are the points of reference.

As illustrated in FIG. 31*a*, now we will refer to accessing such capability from an individual bioProcess, or from icons in its subworkspace that have such specific functions, to display either upstream or downstream pathways, and in either case the bioProcess is the point of reference. Up-path-tracer (3124) and down-path-tracer (3117) are iconic objects (Table 28) located upon the subworkspace (3104) of a bioProcess (3101) used to control the dynamic creation at runtime of a graphic display of such interactive upstream (3110) or downstream (3118) pathway, respectively, from the bioProcess from which it was requested. The "show" option starts the path-tracer-handler-proc (Table 29), which depending on the subclass of path-tracer calls either the draw-up-pathway-proc (Table 175, also started from the "up pathway" option 3109 from the bioProcess) or the draw-down-pathway-proc (similar to the one above but downwards, also started from the "down pathway" option (3116) of the bioProcess. The major actions performed by each of these procedures comprise:

a) it creates a subworkspace here called Upstream Pathway Display (3110) for the up-path-tracer (3124) by cloning the subworkspace of Master-Up-Pathway, which contains a set of prebuilt auxiliary structures. The text of the title (3111) is changed to refer to such bioProcess. The x-pos and y-pos (3112) are two integer-parameters (Table 3) used to keep track of the most distant bioProcess added to the Display and which: i) are used by the program to compute the position of the next bioProcess to be added, after which their values are updated, ii) are used by the program to be compared to defined threshold values that, when reached as the display dynamically grows, trigger a reduction in the size of the display, and iii) may be used also by the user to read the size of the Display, which may in occasion get very large, by observing their value as displayed in digital form. The set of resize buttons (3113) allow the user to resize the Display at will;

b) it creates a copy of such bioProcess, by cloning it and deleting its workspace, and then transfers the copy to the Pathway Display at a specified position (3114), and displays the Pathway Display on the window from which it was invoked; and c) it calls the create-local-up-bp-proc (Table 176) with such original bioProcess and its copy among its arguments, which for each bioReservoir that is an-up-bioReservoir-of the original bioProcess finds each up bioProcess that is an-up-bioProcess-of such bioReservoir and then for each such up bioProcess: i) if a copy of such up bioProcess already exists upon the Display then it proceeds to iv, otherwise it creates a copy of such up (or down) bioProcess, by cloning it and deleting its workspace, ii) it computes a new value for x-pos and y-pos, iii) it transfers the copy to the Pathway Display at the new specified position (3115), iv) it creates a connection between random locations at the icon of such new (or existing) copy and the icon of the copy that is an argument of this invocation of the procedure, and v) it calls itself (Table 176), but now with such up bioProcess and its copy among its arguments. Each of these procedures keeps looping and calling itself until all upstream bioProcesses have been processed, and their copies added to the Display and connected. The an-up-bioReservoir-of and a-down-bioProcess-of, as well as the a-down-bioReservoir-of and an-up-bioProcess-of, are inverse relations, as previously defined (Table 75), which were established during initialization (Table 100) between appropriate pairs of a bioReservoir and a bioProcess each. A similar set of procedures is used to display the downstream pathways from the down-path-tracer.

FIG. 31 illustrates short examples of Upstream Pathway Display (3110) and Downstream Pathway Display (3118). The connections are directional, with the directions of the connections above the bioProcesses indicating the direction of material flows, which is from the one that is upstream to the one that is downstream in relation to each other. The directions of the connections below the bioProcesses always show the right to left direction as a result of the next copy being one that already existed in the display, such as those connections that revert to 3119 from other posterior copies. Those pathways are interactive, and selecting the "details" option (Tables 120 and 121) of any of the icons, or changing to Navigation Mode and selecting the icons (3119, 3121), displays the subworkspaces (3120, 3122) of the originals of those copies, which allow further access to any of the navigation (3123) and all other capabilities associated with their iconic components, and allowing further access to possibly distant parts of the application.

Pathways with only BioReservoirs or pathways with alternating bioReservoirs and BioProcesses can be created with similar methods, using only minor modifications. In this invention the pathways with bioProcesses are preferred because they provide the most information about the interactions within the space constrains, while the connected bioReservoirs can be accessed by just clicking on two icons. Mixed pathways may become very large.

Navigation Panel

An interface and methods are provided to constraint all the capabilities provided in regard to navigation and display of pathways, to limit the scope of the search to a space selected by the user based on the different levels of compartmentalization. This feature can be accessed through: a) a Navigation Panel, which can be requested from each bioReservoir and is dynamically created with the bioReservoir as the reference point; or b) an Experiment Panel. The Navigation Panel is to be used in General Mode, and is not available in Simulation Mode, since the methods do not activate the subworkspaces of the selected structures, as do those associated with the Simulation Mode, described below.

As shown in FIG. 32, selecting the "navig-panel" option (3203) from a bioReservoir (3201) calls the create-direction-panel-callback (Table 177), which displays a Selection Panel (3204). Selecting now the Upstream radio button calls the select-direction-callback (Table 178), which in this case further calls the create-upstream-navig-panel-callback (similar to Table 179), which calls the navig-create-upstream-lists-proc (similar to Table 180), which creates two lists with all of its upstream bioReservoirs and bioProcesses, and the complete navig-panel-callback (Table 186), which creates a Navigation Panel (3205) containing a scroll-area (3206) already configured to list all the possible levels of bioModels, the compartments within the Virtual Model, in which such bioReservoir or all of its upstream bioProcesses are encapsulated. The user now has to select the desired scope of the search space by selecting one of those bioModels. By selecting for example in this case the cytosol of the G0 phase of a fibroblast (3211) and then selecting the LIST button (3207) calls the list-navigation-UBP-callback (similar to Table 181), which creates new lists and calls the navig-read-up-scroll-proc (similar to Table 182) to populate the new lists, displayed on the Panel (3208), with the members of the previous upstream lists that are encapsulated in such bioModel and all its encapsulated compartments. Those lists display the number of elements it contains, alerting the user about the potential size of the resulting pathway, and if too large or too small the operation can be reset and a different bioModel, lower or higher in the hierarchy, can be selected. Selecting any of those lists (3208) displays (3209) its members, and selecting any of those members (3221) allows direct access to the named bioObject (3210) on its original bioModel (3211), and displaying its details (3212) allows to further interactively navigate through the upstream or downstream pathways of such particular bioObject.

The user can now select the PATHWAY button (3213), which calls the navig-draw-UBP-callback (similar to Table 183), which calls the create-navig-path-tracer-proc (Table 185) and navig-create-local-UBP-proc (similar to Table 184) to create a navig-path-tracer (3214), by cloning a master structure, which subworkspace is partially built, and which is transferred to the Panel (3205) and its subworkspace (3215) is displayed and further configured by calling the navig-create-local-UBP-callback (similar to Table 184), which actions are similar to those previously discussed in reference to FIG. 31, resulting in the display of the selected pathway. Selecting any of those bioProcesses (3216) and displaying its details (3217) allows to further interactively navigate through the upstream or downstream pathways of such particular bioProcess. Selecting the RESET button (3218) calls the reset-navigation-callback (Table 187), which destroys the lists and the navig-path-tracer upon the Panel, enabling the selection of a different bioModel and repeats the process, and selecting the DELETE button (3219) deletes or recycles the Panel.

4. Simulation Mode: Simulating the Virtual Models

Initialization

The domain-menu comprises the heads "Pathway Libraries" and "Panels", and allows also changing between user modes. Before a simulation can be run, the application must be appropriately initialized for such purpose. This is accomplished by accessing the "Panels" menu and selecting the "Initialization Panel" option, which displays the Initialization Panel.

Initialization is necessary only if the application has been started or reset, or if additions or changes have been made in the part of the application to be simulated since the last Initialization. The "Add Simul" button is to be selected only after the "Navig Init" has been" successfully concluded. If changes to the database have been made by the modeler since the "Navig Init" was last concluded, or if the application has been restarted, then the "Simul Init" button should be selected, since it comprises the methods of the other two. The common purpose of both buttons is to scan the application for the availability of certain values of the bioReservoirs that define the initial conditions required by the simulation, and if those values have not been provided by the modeler, to infer those values from other values provided by the modeler, and if none of the alternative source of values are available, either default values will be used, including symbolic approximations, or, depending on the attribute which value is missing, to send messages to the user to provide any of the alternative values and also to provide messages any time that the user requests a predefined query that involves that kind of knowledge.

Selecting the "Add Simul" button calls the add-simul-callback, which calls the simul-init-proc (Table 188), while selecting the "Simul Init" button calls the simul-init-callback (Table 188), which differs in that it first calls the navig-init-proc (Table 99), before calling the simul-init-proc (Table 188), which does the following:

a) it calls the send-no-input-messages-proc (Table 188), which scans the loaded application for every bioReservoir that has a name but that has no inputs, either in the form of bioProcesses connected to its biopool-p-posts, or as input model-blocks connected to its bioPool, and it sends a message to the user for each of those bioReservoirs found with no inputs, as a warning for the user to take appropriated measures if those bioReservoirs are to be involved in a simulation. The simulation proceeds also without those values, since inputs can also be provided through the Simulation Panel as user inputs, or otherwise the quantity of such bioPool will initially be whatever value the modeler has set or the program will set for the basal-quantity parameter used, or its default value, and it may or may not be exhausted during the simulation run; and b) it creates a set of four lists, which are transferred to the Initialization Panel, provided to inform the user about the source of the values for the Scaling-Density 1307) attribute of each bioPool, by adding the name of each bioReservoir to one of those lists that meet the following criteria: i) the list labeled UNList contains all bioReservoirs for which the initial-value of their Scaling-Density was provided by the modeler; ii) the list labeled ANList contains all bioReservoirs for which the initial-value of their Scaling-Density was set by the program to equal the value, provided by the modeler, of the if-scaling-amount of that bioReservoir; iii) the list labeled RNList contains all bioReservoirs for which the initial-value of their Scaling-Density was set by the program to equal the value of the if-scaling-amount (1210) of the bioReservoir which name was entered by the modeler in the If-scaling-bioReservoir (1211) attribute of the original bioReservoir; and iv) the list labeled DNList contains all bioReservoirs for which the initial-value of their Scaling-Density was set by the program to equal the default value of 100.0. To do so, for each bioReservoir the proc scans the value of its Scaling-Density and if it has a non-default value it enters the name of such bioReservoir to the first of those lists, otherwise it calls the set-scaling-density-proc (Table 188), which sorts and adds the bioReservoir to one of the other three lists, following the criteria mentioned above, after setting the value of the Scaling-Density of its bioPool accordingly.

The set-scaling-density-proc (Table 190) discussed above is the method used in the current implementation of this invention in conjunction with the scaled reasoning used as default. An alternative method for setting the values of the scaling-density attribute, to be used when more quantitative information is available for the system to be modeled if the modeler prefer the mixed absolute/scaled type of reasoning, is the long-set-scaling-density-proc (Table 189), which is much more complex but also more specific, and involves the known values of the kinetic-parameters of the participating bioReactants for each process. A mixed approach can also be developed where if those kinetic-parameters are known then the reasoning of this procedure is applied, and if they are not available, then the previous more generic procedure is called.

The "Icons Init" button calls the init-icons-callback (Table 118), which function is not essential for the functioning of this system, but which provides a very useful cosmetic function, by realigning the tracers in the subworkspaces of bioReservoirs and bioProcesses and making their connections invisible. The same effect is achieved for individual bioReservoirs or bioProcesses by slightly moving and repositioning their bioPool or bioEngine, respectively, which triggers their respective icon-movement rules, as defined in Table 81, which also apply to repositioning the bioRole-posts any time a bioReactant or bioProduct is moved.

Selecting the "Init All" button calls all-init-callback (Table 119), which calls the all the initialization procedures mentioned above.

With the one alternative way of simulation where the original bioObjects are used, when selecting Simulation Mode from another mode starts the version of the change-mode-proc shown in Table 27, which causes the subworkspaces of all bioReservoirs and all bioProcesses to be deactivated, and during the processing involved in activating a submodel for simulation, the subworkspaces of only the bioReservoirs and bioProcesses selected to participate in such simulation will be activated; while when leaving Simulation Mode to another mode causes the subworkspaces of all bioReservoirs and all bioProcesses to be activated again. The version of the change-mode-proc used with the other simulation alternative, where clones of only those bioObjects to be used are created, does nor contain the lines refering to activation or deactivation of subworkspaces.

Simulation Panel and Procedures

Because the applications build with this system can become very large, it is important to have control over which parts of the Virtual Model are included in a given simulation. To control performance, two implementations are provided with this system, each having advantages over the other depending on the hardware facilities available:

In the first implementation, the constraining of the simulation space is achieved by using activatable subworkspaces for composite bioObjects, such as bioReservoirs, bioProcesses, and certain time-compartments, and by having all those structures initialized to a deactivated state. When the subworkspace of an object is deactivated, any structure upon that subworkspace is not seen by the inference engine or the simulator. Only the subworkspaces of the desired structures at any given time are activated, and only their contents are therefore participating in a given simulation and associated inferences. Methods associated with buttons on the entry-panels used for simulations and experiments, activate the subworkspaces of bioObjects connected along the desired pathways and encapsulated in the selected bioModel or compartment, and this activation is necessary for propagating values along the pathways. Inactivation of those subworkspaces occur upon resetting the selection within those panels. This mechanism is also very utile in activating or deactivating entire branches of a simulation model at run-time. The efficiency of large scale simulation applications is further improved by having the initiation of the simulation of different subcomponents of the high-level bioModel be driven by events, when appropriate, or by time intervals. This implementation allows only a single user to run simulations concurrently, since the attribute values of the bioObjects change during the simulation, as well as the activation state of such subworkspaces. For multiple users, multiple processes of the program have to be started.

A second implementation is based in dynamically cloning those bioReservoirs and bioProcesses, or certain time-compartments, required by the simulation, and to use those clones to hold the changing attribute values, rather than the originals. In this implementation, the subworkspaces of bioReservoirs and bioProcesses are not activatable, remaining always activated. On the other hand, the subworkspaces of certain time-compartments are still activatable, are deactivated when created, and their activation is controlled during the simulation, operating as in the first implementation. This implementation allows multiple users to run simulations concurrently, each on a different window, but increases the burden on the system by increasing the required RAM to hold the additional transient copies and to run more than one simulation concurrently. Since the system of the current invention is modularized, and the modules can be dynamically up-loaded and down-loaded, part of this problem can be solved by up-loading the module(s) that contain the originals, creating the copies for the various simulations on the top module, and removing the modules that are no longer required from the memory, before the simulation is started. A simulation can be initiated from any named and connected bioReservoir in the Virtual Model, from the bioPool of such bioReservoirs, or from the bioReactants and bioProducts connected to such bioPools. As shown in FIG. 33, selecting the "simul panel" option (3303) from the desired bioReservoir (3301), which is only available when in Simulation Mode, calls the create-input-type-proc (Table 190), which creates one of two types of entry-panel by cloning one of the prebuilt master structures and displays the subworkspace (3304), called a Simulation Selection Panel, depending on whether the subclass of bioPool involved represents soluble or bound bioEntities (Concentrations or Density inputs, respectively). Either Panel (3304) prompts the user to select the type of input, and the choices offered are combinations of absolute or scaled values with one-time or periodic inputs. Selection of one of the radio-buttons calls the select-input-panel-callback (Table 191), which: a) according to the user's selection it calls one of a set of specific procedures, including such called in this example, the create-periodic-relative-input-panel-proc (Table 193), which creates and partially configures one entry-panel of the specified type by cloning one of the several prebuilt masters; b) it creates two lists and then calls the fill-br-downstream-lists-proc (Table 194) to search the application for all bioReservoirs that are downstream of such reference bioReservoir, as defined by the relations established during the initial initialization, and fills the DBR list with those bioReservoirs, and then do the same for the downstream bioProcesses to be added to the DBP list, and uses those values to configure the scroll-area, and c) it calls complete-input-panel-proc (Table 192) to complete that panel and display its subworkspace (3305), called here a Simulation Panel. Each of the entry-panels is related to the bioReservoir (3301), or the bioReservoir referred by the bioReactant, from which the request was originated, that is, the Related-item attribute of the entry-panel newly created is a pointer to such bioReservoir. The difference between the one-time or periodic inputs types of Simulation Panel is that the latter has two additional entry-boxes to allow the user to enter the time interval for subsequent entries (3309) and the number of subsequent entries (3308) at such intervals of the amount indicated by the entry value (3306) and starting at the indicated time (3307). The difference between the absolute or scaled inputs types of Simulation Panel is that the entry value in the former is given in some units standardized throughout the application while the latter is a dimensionless value. The prebuilt panels contain the overall layout with the common components, while other structures specific for each bioReservoir are added dynamically at run time.

The Simulation Panel (3305) can now be used to interactively set-up and start simulations comprising a desired bioModel by selecting one from the scroll-area (3312), as described in relation to FIG. 32, to allow selection of an adequate size of the model to be simulated. The parameters and optional capabilities used for the simulation at run-time are configured by using an structure upon the Simulation Panel specific for that purpose, the Shell's model-definition (3318). Its table of attributes (3319) allows the configuration of any desired attributes. The Items-belonging-to-this-model (3320) is set by the program to name the bioModel selected by the user, and the variables and parameters that form part of the simulation model are all those encapsulated in any of the bioReservoirs and bioProcesses in the pathway contained in the workspace named by such attribute. This is important when dealing with very large systems, allowing to focus the computer resources on the subsystems of interest. Further attributes are used to set the time interval (3411) between simulation cycles, the type of integration algorithm (3412) desired for the state variables; the configuration for any external simulator (3413) that can also be used to receive or provide values of the variables in this model; the name of any main procedure (3414) that is invoked once every simulation cycle, which may start or call any other procedure, and which in this case calls the model-simulation-proc (Table 204); a choice to send all the values to external databases or simulators (3415) at the beginning of each cycle; an indicator (3416) of whether the simulation is not-running, running or paused, or whether is nothing to simulate or is a simulation error; and the configuration of the simulator clock (3417) to run either synchronously or as fast as possible, which is more appropriate for simulating models where actions take place over long time periods.

This Panel permits the user to enter the input value (3306) to be added to the Accumulation of such bioReservoir and the time (3307) of such input. Help buttons in each section of the Simulation Panel provides instructions for the user in how to proceed, such as the one (3310), which subworkspace is shown (3311). Following those instructions, selecting the LIST button (3313) calls the list-simul-callback (Table 195), which finds the previous lists and then calls the read-scroll-proc (Table 196) to search for the members of those lists that are encapsulated in the bioModel selected by the user, as previously discussed, and fill the lists labeled DBRL (3314) with downstream bioReservoirs, the SDBPL list (3315) with downstream bioProcesses, and the UBRL list with bioReservoirs that provide the inputs for such bioProcesses but which are not included in the first list.

As shown in FIG. 34, selecting one of the bioReservoir lists (3314) displays a workspace (3401) with pointers (3402) to each of the elements of that list, which allows to examine the bioReservoir that are to be included in the simulation. Selecting any of those pointers (3402) allows the user to either display the table of attributes (not shown) of that bioReservoir or to directly display the bioReservoir, and its subworkspace (3419), upon its bioReservoirs Bin. In a similar way, selecting the SDBPL list (3315) displays the pointers (3405) to the bioProcesses that are to be included in the simulation, which upon selection (3406) directly displays the bioProcess and its subworkspace (3425). The user can examine those lists to decide whether the selection made is appropriate before proceeding. If not satisfy the user can reset the panel, and transfer to the panel additional or different submodels, and press the "List" button again.

When a Simulation Panel is created, the ACTIVATE (3316) and START (3322) buttons are disabled to prevent the user of taking such steps prematurely. When the processing associated with the LIST (3313) button is completed, the ACTIVATE button (3316) is enabled, and when selected it calls its associated procedure, which is one of three listed (Table 197) and specific for each type of Simulation Panel. Such procedures check that a value has been entered by the user and then call activate-simulation-proc (Table 198), which in turn: a) looks on the Panel for the three lists created above and calls the activate-model-proc (Table 199) with those lists as arguments. Upon entering the Simulation Mode the subworkspace of all bioReservoirs and bioProcesses are deactivated, so that their variables become inaccessible to the simulator. The function of this procedure is now to scan the DBRL (3314), DBPL (3315), and UBRL lists and activate the subworkspaces of each of their elements, which are the ones that will be now included in the simulation, after which returns back to the previous procedure, which scans for the Basal-Density attribute of the now accessible bioPool of each of the bioReservoirs on those DBRL and UBRL lists and if its value has been modified by the user then it adds the name of the bioReservoir to the User-BC list of the set described below, and if its value has a default value then it calls the basal-density-proc (Table 200) for such bioReservoir.

A simulation starts with the baseline model, after being initialized by setting the initial values of the initial amounts of the bioPools (concentrations, densities, scaled-amounts, or other quantities, depending on how the bioPools involved where defined) to be equal to the values of the corresponding basal amounts. In order to activate the system, a disturbance may be introduced by entering one or more input values through the entry-panel of the desired bioReservoir, or through the desired experiment-selections of the Experiment Panel (below). By entering different values for those variables, or by changing the values of the constant parameters, what-if analysis can be performed on the system. Montecarlo simulations can be performed using a montecarlo-model-block as an input to each of the bioPools desired as test inputs, as explained in other section, and the simulation can then be started from either the entry-panel of a desired bioReservoir, or through the desired experiment-selections of the experiment-panel, without entering entry-values. The history of values for each of the variables of interest can be stored in the form of a matrix-like structure that is an array of arrays of values for each variable or parameter. The values of those arrays are transient values that can be used for statistical and sensitivity analysis within this system, or can be archived to a text file external to the system of this invention, or the values can be transferred to an external statistical package for further analysis. In addition, if the values of those arrays are desired in a permanent form within this system, this is accomplished by using the procedure provided to make the initial values of an array equal to the list of its current values, separated by commas.

The basal-density-proc (Table 200) has an important inference role since the value of the Basal-Density (or the Basal-Concentration) is used when the simulation is started as the initial value for the state variable of the bioPool, the Accumulation. The task of this procedure is to obtain a value for that attribute, if the user has not specifically entered one, from other data and information contained in other attributes of that bioReservoir or its bioPool. It also uses a set of lists encapsulated in the structure labeled BA (3317) upon the Simulation Panel to sort and list all the bioReservoirs to be included in the simulation, to indicate the source of those values used for the Basal-Density. The user can examine the results of that inference after the processing associated with the ACTIVATE button is completed, when the button becomes disabled and its appearance changes.

Selecting the BA button (3317) displays its subworkspace (3523) with a set of lists filled by the program following the criteria discussed below. Those lists can now be examined, by selecting their icons to find out which of the bioReservoirs got the value from each of the alternative more or less precise sources.

Various alternative versions of this procedure are made available, which are disabled and the one preferred is enabled by the modeler to better match the particular application. Alternatively, each of the alternative versions could be made specific for particular subclasses or groups of bioReservoirs. This procedure initially scans the normal-basal-density value of the bioReservoir and if that value is different from the default value of 9.99e–99 then the Basal-Density is set equal to its value, and the name of the bioReservoir is added to the NBD-BC list. If the subclass of bioReservoir is sol-mol-reservoir then the Basal-Concentration would be set equal to the value of the normal-basal-concentration if different from the default value. In the alternative implementation shown here, if the subclass of bioReservoir is sol-mol-reservoir this procedure scans the normal-basal-concentration value of the bioReservoir, if that value is different from the default value, 9.99e–99, then the Basal-Density is set equal to its value multiplied by the Avogadro's number, which states that each mol has 6.023e23 molecules, and the name of the bioReservoir is added to the NBC-BC list. The conversion is made when modeling complex mixtures of bound and soluble molecules. For example, for many biochemical systems where the molecules form large localized active complexes molecules are not homogeneously distributed, and therefore it is more meaningful to integrate in a bioProcess the quantities of both types of bioPools representing bound and soluble molecules using the number of molecules rather that their concentrations. If the normal-basal-density (or normal-basal-concentration) has the default value, then this procedure scans for the Scaling-Density attribute of the bioPool and if it has the default value then the bioReservoir is added to the "NO BC" list. Otherwise, this procedure scans for the Scaled-Basal-Amount of the bioPool, and if its value is not the default value, then the Basal-Density is set equal to the value resulting from multiplying the Scaling-Density by the Scaled-Basal-Amount values, and the name of the bioReservoir is added to the SBA-BC list. Otherwise the Basal-Density is set equal to the value resulting from multiplying the Scaling-Density by a factor associated according to the symbolic value of the Abundance attribute of the bioReservoir, which value is set by the modeler or otherwise the default value is used, and the name of the bioReservoir is added to the PAB-BC list. The inference engine may proceeds the search for other sources of values, such as in an alternative method, where this procedure sets the value of the Basal-Density equal to a value proportional to the physiol-max-density (or physiol-max-concentration) of the bioReservoir if this value is different from default. If the user has not entered any of those values, then the program sets the value of the Basal-Density equal to the average of any known thresholding parameters of any bioReactant connected as an output of this bioReservoir, such as the Km, Ks, Ki or 1/(2*Kp). This alternative method emulates the following reasoning: the value of Basal-Density represents physiological conditions and it is assumed that physiological concentrations approach the midrange functional concentrations in the most relevant bioEngine in which the bioReservoir participates, as represented by constants such as the Km for a substrate, the Ki for an inhibitor or the Ks for a ligand or complex-subunit. If those values are not known, a message is displayed requesting the user to assumed some values, based on comparisons with similar systems. Under normal in vitro assay conditions, an enzyme is generally present in limiting or catalytic amounts, in a range between 10e−3 nM and 10e2 nM, while a substrate is generally in the range of 10e3 nM to 10e7 nM. This value can be adjusted at a later time as more is learned about the system. If none of the alternative means are provided the system's default values are set.

Once the participants in the model have been activated and configured, the input values have been entered, and the model-definition has been configured, the simulation is started by selecting the START button (3322), which depending on the type of Simulation Panel will call one of the six procedures specific for each of the one-time Panels (Table 201) or for each of the periodic Panels (Table 202), which read the input values entered by the user and perform different types of processing depending on the types of variables involved. The concentration-entry-panel is used to input the absolute concentration value entered by the user in the input-value edit-box, in units such as molar, which is added as a concentration or is converted and added as a density (depending of the alternative options available in this implementation). In a similar way the density-entry-panel is used to input an absolute density value, such as units/compartment, while the relative-entry-panel is used to input the scaled dimensionless value. Those input values are used the values of the corresponding attributes in each type of BioPool, such as the density-entry or the scaled entry at the time of entry value entered by the user, where these values are then integrated by the formula of the Accumulation of such bioPool at the next simulation cycle, and the values of such attributes are reset to 0.0 after one simulation period has elapsed since the time the input values were set. The set of periodic type of Panel follow initially the same type of processing, but the setting of the values of the density-entry or the scaled entry attributes of the bioPool occurs then repeatedly as many times as entered by the user in the entry frequency edit-box at times intervals as entered by the user in the time-interval edit-box, beginning at the simulation time entered by the user in the input-time edit-box. Each of those procedures then call start-simulation-proc (Table 203), which requests the simulator to run the model as previously defined in the model-definition.

During the simulation run the model-simulation-proc (Table 204) is called once every simulation cycle, which sets the values of the attributes current-simulation-time and current-simulation-time-increment of the entry-panel. The user can select the "T" button (3325) to display its subworkspace (3418), which contains a digital display of those values as well as the values of other performance parameters. This procedure also calls the compute-graph-transform-proc (Table 205) described below.

By selecting the PAUSE button (3323) or the RESUME button (3324), which call their associated procedures (Table 206), the user can pause and resume the simulation at will. By selecting the RESET button (3326) the reset-simulation-callback (Table 210) resets all the buttons on the Panel and calls the reset-proc (Table 207), which: a) first it scans the DBRL, UBRL, and DBPL lists and resets each of the bioReservoirs and bioProducts listed, including their status attributes, their icons and deactivating their subworkspaces; and b) then delete those lists. The DELETE button (3327) is disabled when the LISTS button is selected and it is not enabled until the reset is completed, preventing the user from deleting the panel before all the participants in the simulation that may have been modified are reset.

The procedures that are modified for the alternative implementation of the simulation, when copies are used instead of the original bioProcesses and bioReservoirs so that the values of the originals are not modified, are listed in Tables 211 through 221).

Digital and Graphic Displays of Dynamic Values

This system's graphic interface allows simulations to be followed in different ways, including:

a) creating pathways on a workspace where dummy copies of the bioProcesses involved, or full copies of both the bioReservoirs and bioProcesses involved (depending on the alternative method of simulation used) of all the participating), are located in sequence and the corresponding connections between them are drawn. These structures allow to further interactively navigate through the system as usual, including back to the originals from which the copies were made;

b) animation by color changes of the activated components;

c) display of the current values of desired variables in digital form;

d) dynamically created graphs of a set of time series of the values of desired variables; and e) dynamic charts of the values of a variable versus another variable.

Selecting the "details" option of any of the bioReservoirs or bioProcesses that take part in the simulation allows to follow up the quantitative simulation by providing access to the different structures in their subworkspaces. Only the icons upon subworkspaces that are activated are active. The current values of the variables of each bioReservoir or bioProcess are by default displayed in digital form (3403 and 3404). To dynamically display the time course of the values those variables for the time frame selected during a simulation graph-tracers are used, which subworkspaces with a graph and associated structures are not stored, but are rather created or deleted when the user selects one of such tracers.

A graph-tracer is an object (Table 32) connected either to a bioPool (3420 and 3421) or a bioEngine (3426), used to control the dynamic creation and display at run-time of a graph which plots the values over time of key variables or parameters of the bioObject where they are contained, scaled or absolute versions for bioReservoirs. Selecting the "show-plot" option calls the graph-tracer-handler-proc (Table 33), which depending on the class of the graph-tracer from which it was invoked calls either the scaled-BR-graph-proc (Table 207), the absolute-BR-graph-proc, or the scaled-BP-graph-proc, which first create a subworkspace (3422 or 3427) for that tracer (3421 or 3426) with all its contents by cloning the subworkspace of the corresponding prebuilt master structure, and then configure the labels of the graphs (3423 and 3428) and the ref-bioreservoir or ref-bioprocess attribute of each of the graph-tranf-vars (3424 or 3429) upon such new subworkspace to refer specifically to that bioReservoir (3419) or bioProcess (3425), respectively.

The design of graphs and associated structures deal with plotting multiple variables, which values differ by orders of magnitude on graph structures that do not provide multiple axis scales. In the current implementation, the system automatically adjusts the scale to the current values of the time-series to be plotted, using a system of intermediary variables to dynamically transform those disparate values into others that fit a common scale. This set of new variables are instances of subclasses of the class transf-factor-var (Table 15), a float-variable. A representative example of the attribute table of a default instance of one of those subclasses, a velocity-transf-factor, is shown (Table 208). Among the attributes of transf-factor-var are: "transform", which value is given by an instance of the class graph-transf-var (Table 14); and Ref-variable, which makes reference to the particular attribute of a bioObject that provides the input value. The Label and the Transform value are displayed. The role of the graph-transf-var is to hold a transformed value of the current value of the parameter or variable referred to by its Ref-variable. The transformed value is suitable for plotting within the scale of the related graph. The role of the transf-factor-var is to hold the value of the factor necessary to obtain the desired transformation, as inferred by the compute-graph-transforms-proc (Table 205) only when a simulation-model is running. Each subclass of the class transf-factor-var corresponds to one of the bioObject's attributes to be transformed, which matches the value defined for the Label attribute of each subclass. The transf-factor-var *provides* by itself the order of magnitude of the variable it transforms.

Selecting the "hide-s.graph" option (Table 209) of the bioReservoir, which appears only when the graph upon the subworkspace of the scaled-BR-graph-tracer exists, or deselecting the graph-tracer, or selecting the delete option directly from the subworkspace of the tracer deletes that subworkspace with its contents. The same applies for the other classes of graph tracers.

Scaled Computation Approach for the Variables of bioReservoirs and bioProcesses

The formulas of the parameters and variables that dynamically characterize a bioPool, depend on other numeric variables or parameters that are either attributes of the bioPool (FIG. 13) or its bioReservoir (FIG. 12), or that are attributes of the bioReactants (FIG. 14) and bioProducts (FIG. 15) that represent such bioReservoir in different bioProcesses. Table 83 lists a representative set of formulas, as examples of generic simulation formulas comprised in this invention to simulate a set of scaled-valued variables and Table 84 lists a set of generic simulation formulas specific for the Contribution of different subclasses of bioReactants that incorporate the values of scaled-valued variables or parameters. Table 86 lists a set of generic simulation formulas that are alternatives to the formulas in the set shown in Table 84, and which can be used in this invention to incorporate the values of absolute-valued variables or parameters into the Contribution of each bioReactant. These formulas for the Contribution do scale those absolute values using either a linear or sigmoid approach, depending the role in a bioProcess represented by each class of bioReactant. Therefore, since the output of the Contribution is dimensionless, whether the inputs are scaled (as in the case of using the formulas in Table 84) or absolute (as in the case of using the formulas in Table 86), it is now possible to integrate in a single bioProcess a mixture of bioReservoirs, where some of those bioReservoirs use only the scaled-valued variables while other bioReservoirs, called of mixed-type, use a mix of the scaled-valued variables, such as the Scaled-Amount, and absolute-valued variables, such as the Density. Those two values are interconvertible by using the value of the Scaling-Density, as computed by the formula for the Density in Table 86, so the user may be able to display the output of a simulation also as converted back into Density units in this case. The Contribution can be used in conjunction with either absolute-valued or scaled-valued variables, and therefore allows to integrate parts of the simulation where the absolute values of parameters and initial conditions are known, where other parts of the simulation where those values are unknown an have to be approximated, which is best done when using dimensionless values.

The Quantity of the bioPool is the only quantitative output value propagated from any component of a bioReservoir to any component of a bioProcess. That output quantity value of the bioPool is used to compute either: a) the value of the Velocity of each bioEngine connected to each bioReactant connected to such bioPool, which is the method normally used when using the absolute computation approach, to be discussed below; and b) the value of the Contribution of each bioReactant connected to such bioPool, which is an intermediary variable that is used to compute the value of the Velocity of the bioEngine to which that bioReactant is connected, in combination with the Contributions of all bioReactants connected to such bioEngine, this being the preferred method used when the scaled reasoning mode of simulation is preferred by the modeler or user. The formulas for the variables that give the value for the Contribution are specific for different classes of bioReactants, as more specifically defined in Tables 83 and 84. The formulas for the classes that represent reactants that bind to specific sites other reactants, such as substrate.r, ligand.r, inhibitor.r or ion.r, are designed as to provide a sigmoid scaling around their characteristic kinetic parameters, which implicitly provides a smoothed thresholding of the Quantity of the bioPool for that particular bioProcess, as represented by the bioReactant. When using the scaled-valued set of variables, the Scaled-Amount is used in conjunction with the corresponding scaled kinetic parameter, as the examples given in Table 86 show. The formulas for the Contribution for other classes of bioReactant, such as receptor.r or enzyme.r, are designed as to provide a linear scaling from none to their maximum observed value, represented as 100 if such absolute value is unknown. In contrast with the absolute mode of computation, where there may be great variability in the formulas needed to provide the value for the Velocity, depending on the class of bioEngine involved, in the scaled mode of computation the variability is introduced, to a much lesser extent in the simulation formulas that provide the value for the Contribution, while only one very generic simulation formula is required for the Velocity of all classes of bioEngines. As listed in Table 83, the very generic simulation formula for the Velocity included in the current implementation of this invention integrates various coefficients and a rate-constant to give the modeler or user the flexibility of by changing the values of those attributes of the bioEngine to modify the behavior of the system in different ways, without the need to write specific formulas for each situation, while the default values of those attributes do not affect the system.

The Velocity of each bioEngine is used to compute: a) the Production-Rate any bioProduct connected to such bioEngine; and b) the Consumption-Rate any bioReactant connected to such bioEngine, which may be 0.0 if such bioReactant represents a reactant that is not consumed in such process, or may have a value that may be withdrawn from a bioPool as an output (like any standard Consumption-Rate), but then retained for a period of time and then returned back to the bioPool as an input (like any standard Production-Rate will do), as specified by methods specific for the variables of such particular pair of bioReactant and bioPool, or for a group of such pairs that are identifiable by some specific common attribute, or that are defined as separate subclasses of their respective classes.

Several bioProcesses may contribute through their outputs to the Input-Rate of that bioPool, which values are then integrated when computing the value of the Accumulation of that bioPool. Users can also add (or remove) an absolute or scaled amount during a simulation to the selected bioPool, by having specific procedures setting the values of specific attributes of the bioPool, as discussed above, which are then integrated into the Accumulation by its simulation formula. The Basal-Quantity (which may be either a Basal-Concentration, a Basal-Density, or a Scaled-Basal-Amount) represents the initial conditions, and provides the initial-value for the integration of Accumulation, which is a state variable that integrates all other dependent variables. When using the scaled-valued set of variables, the value of the Scaled-Amount is the value of the Accumulation constrained to a range within 0.0 and 1.0. The values of the Concentration or Density are constrained to not be less that 0.0.

In this invention, when the user selects simulation mode, the subworkspaces of all bioReservoirs and bioProcesses are deactivated, and only those that are to participate in a simulation run are activated. This is a mechanism to improve performance of what may become an extremely large system of parameters and variables. In the current implementation of this invention, each of the values is computed once each simulation cycle using the equations defined by simulation formulas.

The implementation of the intermediary variable, the Contribution, is a novel and very important teaching of this invention, particularly in applications when the knowledge of the quantitative parameters and initial conditions of the system are incomplete, or when a more abstract and generic system is desired, such as when providing a Shell to be used in different and unpredicted ways. This implementation is relevant in several different ways. It allows to treat each of the bioReactant of a bioProcess as a generic self-contained unit, which allows to model also participants in a bioProcess that are known to interact but which exact roles in such process are unknown, where the velocity is generically computed by simply multiplying the contributions of any participant that the modeler may want to model. These generic units become even more generic when used in combination with the set of scaled-valued variables, which allow the user to enter values based on expert knowledge, or quickly perform what-if analysis. Another important result of using the Contribution is that it allows to perform quantitative simulations that integrate into the Velocity of any bioProcess values originated from bioReservoirs with both types of absolute-valued and scaled-valued variables. This means that those parts of the complex model where the absolute values of their kinetic parameters and initial conditions are known can be integrated with other parts of the complex model where relative values are used because the absolute values may be unknown.

The abstraction provided by the Contribution also facilitates the use of bioProcesses as black-boxes, which are also be implemented in the current invention without using the Contribution. Black-boxes are used to represent any type of participant that is known to cause something to change somewhere down the line, even if it is known that other intermediaries are involved, but where the details or identity or even the existence of those intermediaries is unknown. The bioReactants in a black-box represent the entities (of bioPool(s)) that cause some effect on some other distant entities or bioProducts (the input to other bioPool(s)), and like in other generic bioProcesses, either the kinetic-coefficient (scaled or absolute) that modifies each bioReactant, or the rate-constant that modifies the overall process, representing the proportionality factor between the quantity of cause(s) and the quantity of effects, can be used.

Absolute Computation Approach for the Variables of bioReservoirs and bioProcesses More standard ways of quantitative simulations using the known absolute values of the system parameters and initial conditions, can be performed by using only the set of absolute-valued variables or parameters, and by using a different set of generic simulation formulas, such as those shown in Table 85. From those variables, the one that offers more variability in the formulas needed for each class of bioEngine is the Velocity, which is in contrast with the scaled mode of computation where only one very generic simulation formula is required for the Velocity of all classes of bioEngines. It is also possible to write very complex simulation formulas to encompass a variety of different situations, such as that in Table 82 to be described below. The value of the Velocity of a bioEngine in this approach depends directly on the Quantities of the bioPools connected to each bioReactant connected to such bioEngine, which is the method normally used when the formulas that give the value of the Velocity are those that represent the equations that a biochemist will normally use to compute the velocity of a reaction, based on the quantities of the reactants and on some known kinetic parameters, such as the Michaelis constant (Km), inhibition constant (Ki) or the equilibrium dissociation constant, and which the preferred method used when the absolute reasoning mode of simulation is preferred by the modeler or user. The simulations formulas for the Velocity of absolute-valued enzymes, such as that listed in Table 85 (which is equivalent to the Briggs and Haldane approach where $V=n*kp[E]*[S]/([S]+Km*X)$, where $X=1$ if no inhibitor.r is connected to the bioEngine, or $X=(1+[I]/Ki)$ if an inhibitor.r is also connected to the bioEngine), assume the instantaneous or initial velocity approach, since increases or decreases in the Concentration of the substrate are updated at small time intervals in this invention.

Following are some examples of how the common knowledge of biochemists is implemented in the current invention.

For receptor-bioEngines or enzyme-bioEngines with multiple equal binding sites, the velocities can represent reactions of two major types: a) the generic simulation formula for non-cooperative-binding is equivalent to $V=n*Kp*[E]*[S]/(Ks+[S])$, and represents the situation where binding at one site has no effect on the intrinsic dissociation constants of the vacant sites, yielding hyperbolic velocity curves, and being impossible to tell from the kinetics whether there is 1 pmole with n identical sites or n pmoles of 1 site; and b) the generic simulation formula for cooperative-binding represents the simple sequential interaction model of an allosteric enzyme with 2 cooperative substrate sites. It is modeled as two substrate.r connected to the same bioPool, but each of those bioReactants have different dissociation constants, and the simulation formula is equivalent to $V=n*kp*[E]*([S]/Ks1+[S]^2/Ks2^{\wedge 2})/(1+2*[S]/Ks1+[S]^{\wedge 2}/Ks2^{\wedge}2)$. Here, the binding of one substrate molecule increases the affinities of the vacant sites for the next substrate molecules, yielding sigmoid velocity curves. Thus, the sigmoid response acts as a smooth "on-off" switch", and at intermediate specific velocities, this provides a much more sensitive control of the reaction rate by variations in the substrate Concentration. Allosteric enzymes generally result in sigmoid velocity curves due to cooperative binding, either positive or negative (binding one molecule facilitates binding of the next). The Hill Equation is used for an enzyme with n equivalent S binding sites, if the cooperativity is very marked, in which case the Km of the single substrate.r has to be set, not equal to the real Km but rather equal apparent Km to the n power. Under these conditions, dominated by $[S]^n$, the equation can be simplified to $V=kp*[E]*[S]^n/(Km'+[S]^n)$. For enzyme-bioEngines, the application in this invention focus on regulatory pathways, which are controlled by enzymes that active form is only present in catalytic amounts and a steady-state is assumed. For receptor-bioEngines, which include processes for other specific binding proteins, the generic formula for the velocity represents the system at equilibrium, and is equivalent to $v \approx [RL]=n[R]t/(1+(Ks/[L]))$.

Inhibition can be modeled in different ways, and the modeler has to decide what best represents each situation. Table 82 lists a very generic formula that allows the modeler to connect to the bioEngine one inhibitor-reactant that can be of any one of the four common types represented by the four defined subclasses of inhibitor-reactant. This formula is capable of first detecting which subclass of inhibitor-reactant is connected to the bioEngine, and then applying the equation with one of the alternative modifiers included that apply to that particular type of inhibitor. However, some of those types of inhibitors may be better represented in the system of this invention as competing with the substrate from a separate bioProcess, which allows for a more intuitive representation and understanding of such competition and a higher level of manipulation by the user, which are in fact some of the advantages offered by the system of this invention when compared with other more global modeling approaches. Competitive inhibition may be modeled within the corresponding bioEngine, with the generic formula such as that in Table 85. Noncompetitive inhibition is best modeled as a separate complex-formation-process between the enzyme and the inhibitor that competes for the enzyme by being connected to the same bioPool. Feedback inhibition should always be modeled by a separate bioProcess. Any further velocity equations can be derived in the same manner, by using well established equations in the field of biochemical kinetics, and the reader is referred to standard references, such as Segel, I. H., 1976, Biochemical Calculations 2nd Edition, John Wiley & Sons, New York.

Experiment Panel and Procedures

Figure 35A:
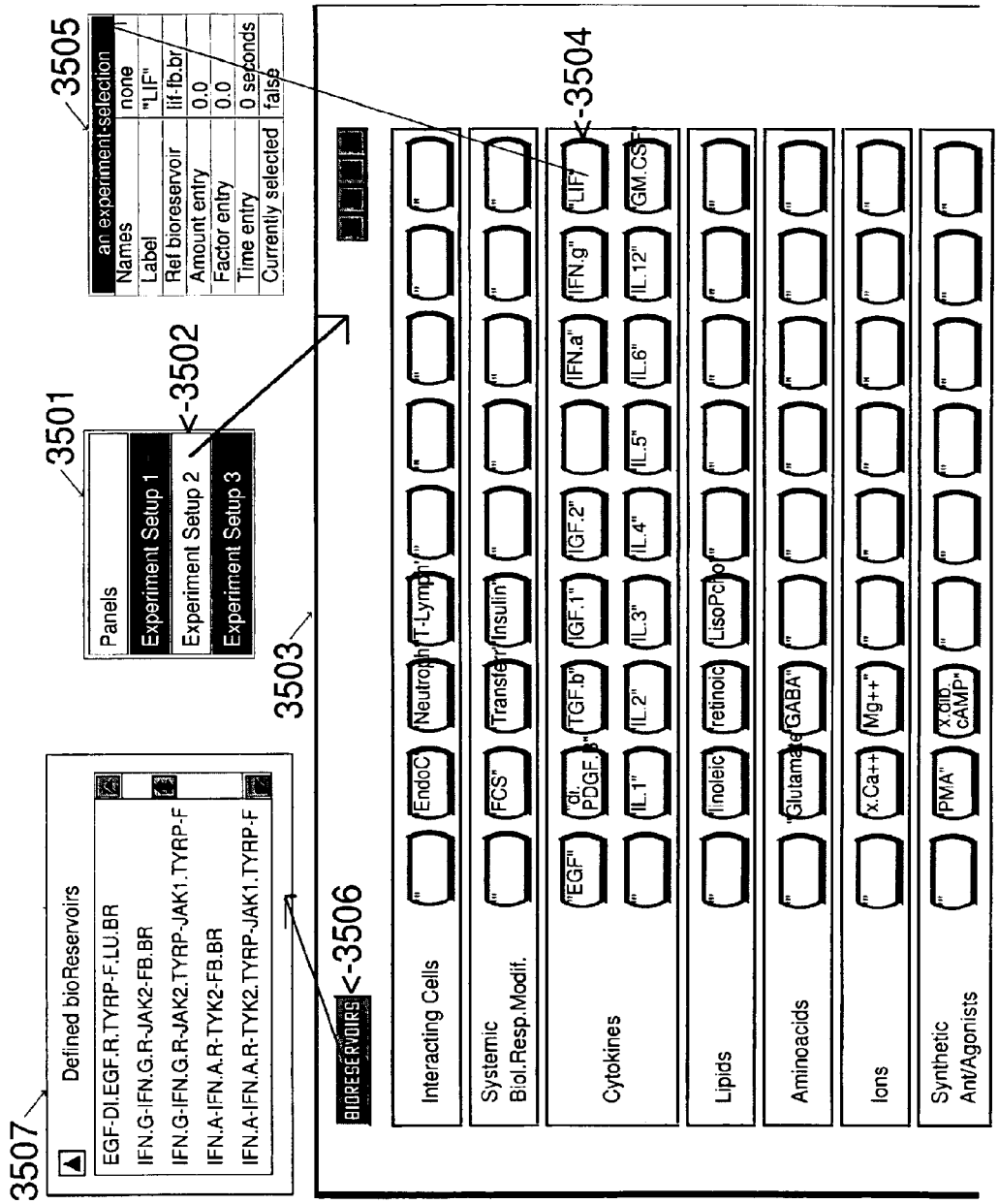
FIGS. 35a and b describe an example of the predefined Experiment Panels that the user can select from the domain menus to request the dynamic generation of constrained pathways from multiple initial points and for the control of the dynamic simulation of the kinetics of those pathways.
Figure 35B:
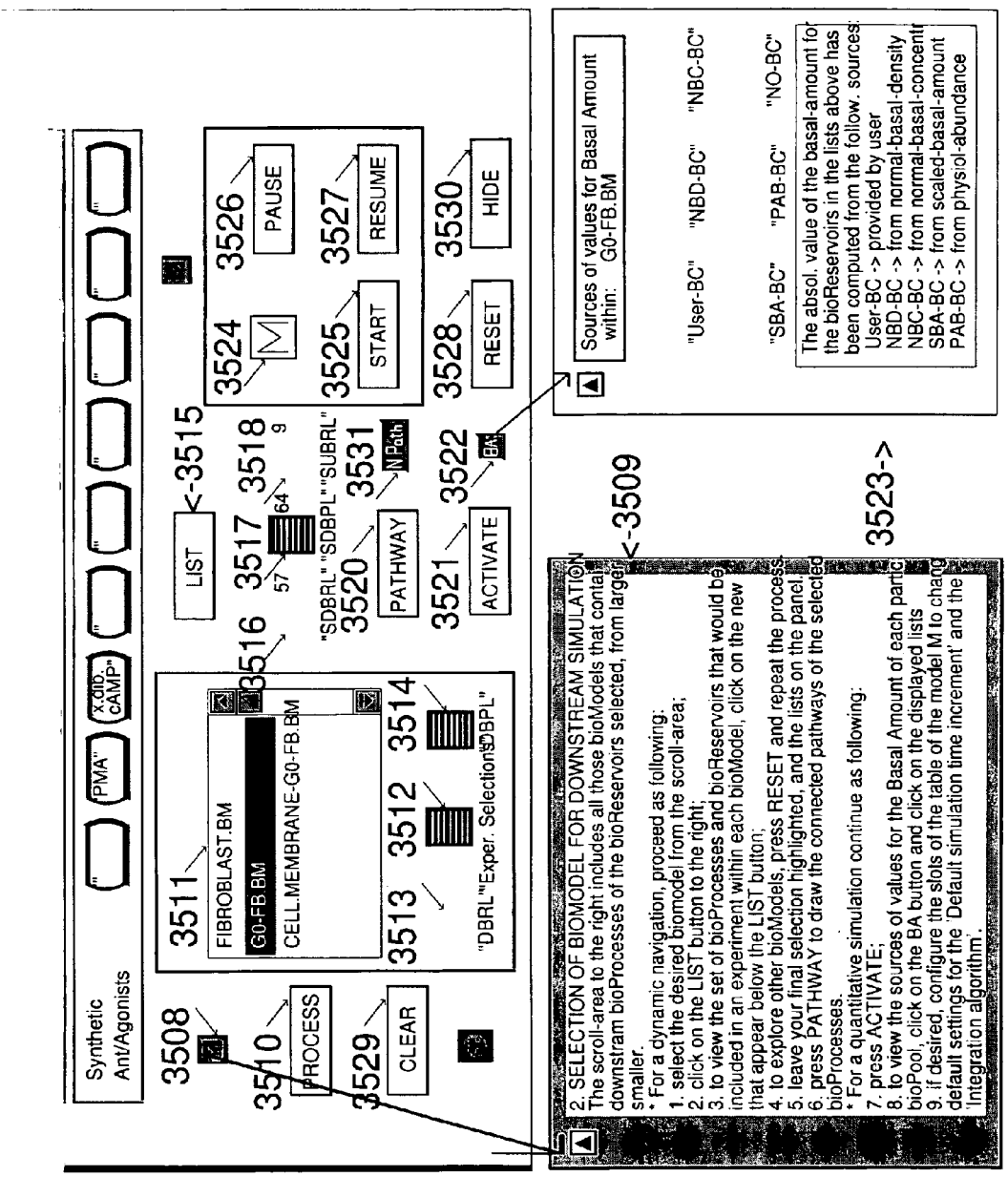

An Experiment Panel (3503) is a facility that allows to perform many of the tasks previously discussed, but with the additional capability of using multiple points of reference for the generation of lists, creation of pathways, or as the recipients of quantitative inputs for simulations. In contrast to the Simulation Panels, which are dynamically created and deleted when requested from the bioReservoir that serves as point of reference, a Library of Experiment Panels are created as permanent generic structures with different designs, accessible through the "Panels" head (3501) of the domain-menus associated with the General Mode and with the Simulation Mode previously discussed. Each Experiment Panel is the subworkspace of an instance of entry-panel created by cloning the Master-Experiment-Setup-Panel. As shown in FIG. 35, selecting one of those options (3502) from the domain-menu (3501) displays the subworkspace (3503) of the named entry-panel, which corresponds to one of those predesigned Experiment Panels. The new components of such Panel are the structures (3504) organized in columns and rows, which are instances of class experiment-selection (Table 222). New designs are created by deleting of adding any number of such auxiliary structures, used to select the combination of bioReservoirs that are to serve as the points of reference in such experiments, and also to allow the user to enter the input values for quantitative simulations of such experiments.

Selecting one of the experiment-selections (3504) displays its table of attributes (3505), which allows to: a) enter a short name in its Label attribute displayed on top of the icon, b) select a bioReservoir, as entered in its Ref-bioreservoir slot, and c) enter whether Currently selected is true or false. The values of those attributes are sufficient to perform any of the qualitative tasks associated with this panel. If a quantitative simulation is desired, any of the values for the other optional attributes may be entered, such as those for an absolute-valued input or an scaled-valued input, time of input, time interval for periodic entries, and entry frequency, which have the same use as those previously discussed in relation to FIG. 33. The configurations of any or all those experiment-selections can be stored for later use, and the combinations of different experiment-selections to be included in a particular experiment may be quickly changed at will by changing the value of the Currently selected, since only those with such value set to true, which get also highlighted with a different color, are included in the processing when any of the tasks is requested. This allows the user to have a set of experiment designs for those types of experiments most frequently used. The BIORESERVOIRS button (3506) provides a graphic tool to facilitate the task of the user in selecting the appropriate name to enter in the Ref-bioreservoir attribute of those experiment-selections, to be selected from among the large number of bioReservoirs in the Virtual Model. Selecting this button displays its sub-workspace (3507) if one exists, or calls the BR-scroll-callback (Table 223) that creates one, containing an scroll-area listing in alphabetical order all the named bioReservoirs loaded on memory, and which in addition to providing the specific nomenclature used for desired bioReservoirs, it allows to directly access and verify the details of a selected bioReservoir.

Upon entering the choices of Ref-bioreservoir and setting the value true for the desired combination of experiment-selections, the user can proceed by selecting the PROCESSS button (3510), which calls the process-exper-callback (Table 224), which creates a set of lists and then scans the Panel to find all experiment-selections for which Currently-selected is true and the Ref-bioreservoir has a value, which are inserted in the "Exper. Selections" list (3512), and for each such experiment-selection found, it calls the same fill-br-downstream-lists-proc (Table 194) called from the Simulation Panel to fill the other two lists, one (3513) listing all downstream bioReservoirs of all those bioReservoirs named by the experiment-selections in the previous list, and the other (3514) listing all downstream bioProcesses of all those bioReservoirs named by the experiment-selections in the first list; and then finds all the bioModels that include all of those bioReservoirs and bioProcesses listed in those lists, and creates an scroll-area displaying those bioModels, to allow the user to select the desired scope of inclusion. Selecting the CLEAR button (3529) calls clear-exper-callback (Table 225), which deletes those lists and the scroll-area, to allow making different selections and repeating the PROCESS. The other buttons and structures on the Panel (3515, 3521–3530) have similar or equal functions as those described for the Simulation Panel, and therefore here only the differences will be briefly highlighted. The reader is referred to the Tables 225 through 233 for a more detailed description of the processing involved. Selecting the LIST button (3515) calls the list-exper-callback (Table 226), which creates a new set of lists: SDBRL (3516), SDBPL (3517), and UBRL (3518) lists, and finds the members of the previous sets of lists that are encapsulated in the selected bioModel.

Selecting the PATHWAY button (3520) calls the draw-exper-pathway-callback (Table 227), which creates a navig-path-tracer (3531) together with its subworkspace by cloning the Master-Navig-Pathway and transfers it to the Panel, and then it scans the "Exper.Selections" list (3512) and for each bioReservoir listed calls the create-local-exper-BP-proc (Table 228), while setting the value of the x-pos to a value close to the initial position when changing from one bioReservoir to the next, which performs a processing very similar to that described earlier for the create-local-UBP-proc (Table 176) for the upstream direction. Now, instead of once as before, that procedure is called as many times as bioReservoirs are in the "Exper.Selections" list.

Figure 36A:
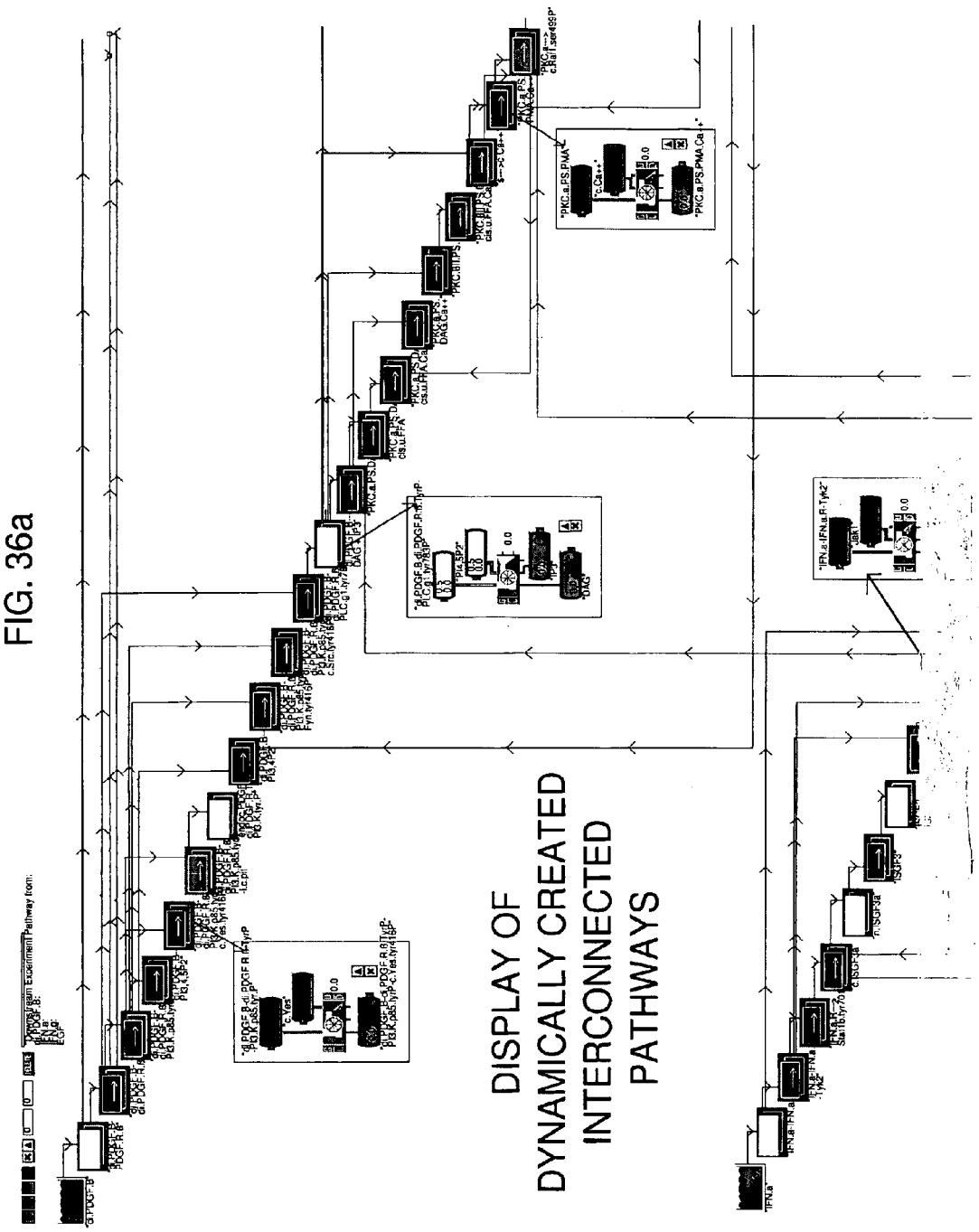
FIGS. 36a and b describe an example of such set of pathways from multiple initial points.
Figure 36B:
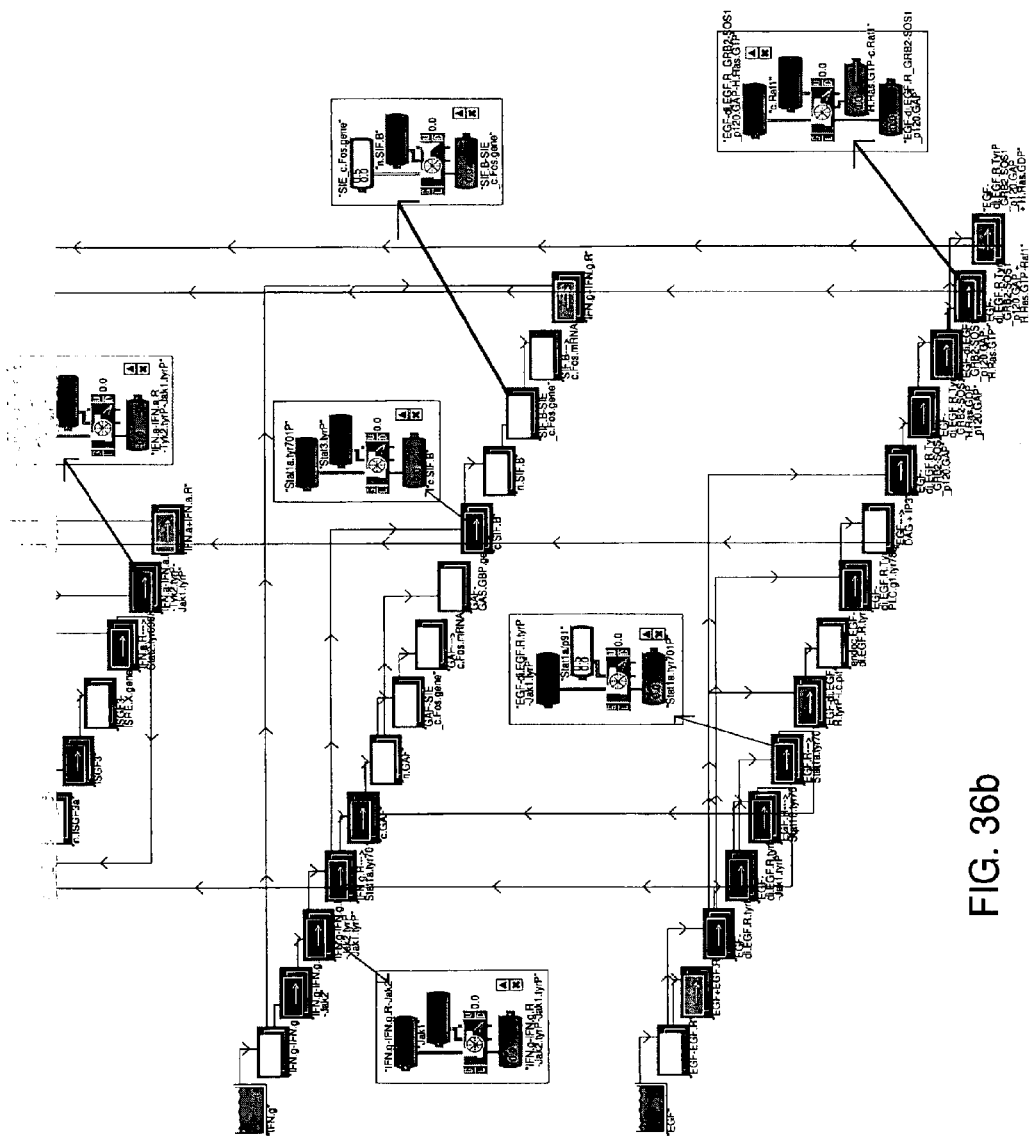

One example of the display of one of those multi-origin pathways is shown in FIG. 36, which are more complex. The pathways start from multiple initial bioReservoirs, and the pathways from latter initial points are connected, whenever the possibility arises, to the pathways from former initial points already on the Experiment Pathway Display. Alternative implementations of any of the types of pathways are to include in the drawing of the pathways not only the bioProcesses, but also the bioReservoirs that are intermediaries between those process in the chaining process.

The procedures for those alternative implementations (not shown) apply the same methods and need only minor modifications to create, transfer and connect the intermediary bioReservoirs.

This Experiment Panel can be used either for the only purpose of generating those complex pathways, or they can be further used to perform quantitative simulations that apply to the variables and parameter of the components of those pathways. For that purpose, the remaining buttons and structures to be used in the subsequent steps have been described before, and the procedures called upon selection of the such buttons (Tables 229 through 233) are only minor modifications of those described for the corresponding buttons of the Simulation Panel, to incorporate the fact that now there is not just one bioReservoir but the various bioReservoirs in the "Exper. Selections" list to consider.

Simulating Complex Models

To deal with complex systems where some parts of the system may be more precisely defined than others, the system of this invention integrates a variety of methods to allow modeling and simulations while accommodating the uneven types of knowledge available. The following describes how the heterogeneous forms of knowledge are integrated in the system of this invention:

In some cases, sufficient information has allowed scientists to develop mathematical models to represent a particular behavior of a system, and some of those models may be suitable for adaptation to be included in the knowledge-base, giving the user the option to integrate them in their simulations. This type of knowledge is usually included in the form of the parameters characteristic of the system and the initial conditions once the underlying architecture of the network is matched, or it can be implemented directly by modeling particular inputs or outputs as model-blocks.

Intermediate levels of information about a sequence of events, or effects following a cause or combination of causes, allows the construction of semi-quantitative behavioral networks that are constrained by the data available, such as time intervals, context and compartments in which behaviors occurred, concentration levels at which different behaviors were observed, and so on . . . . This type of information is used to design the compartmentalized architecture of the network, and to provide semi-quantitative values to the scaled parameters and initial conditions.

Heuristic and shallow knowledge can be integrated in the form of either rules or formulas for inferred variables that connect a cause with a distant effect, without detailed description of the unknown underlying mechanism.

Depending on the amount and type of information and data available about the system to be modeled, and the nature and size of the bioModels to be developed, the system of this invention's may operate in either quantitative or semi-quantitative simulation mode. With well known metabolic pathways, the simulation may be run in quantitative mode, but since in most biological systems both qualitative and quantitative information is incomplete, it may be difficult to simulate with accuracy such biological systems. However, the semi-quantitative methods integrated in the system of this invention allows to gain insight about the degree and direction of change in the model variables, and their quantity levels at different points in time.

Of major importance in simulating the behavior of biological systems is the need to model the different states in which complex biological entities, such as cells, can be found at different points in time, and also to model the events that cause the transitions from one state to another. There are several major types of states and transitions to be considered, depending of whether the biological entity to be considered is a biological system, organ, cell, cellular compartment, molecule or any other entity. We are providing here with just a few examples among the many considered in the currently preferred embodiment of this invention.

The modeler is provided with several methods to fine tune any specific parts of the complex model, including in the ability to write formulas specific for the individual instances of variables that are attributes of the bioReservoirs or bioProducts that model any such specific part of the complex model. Within those formulas, temporal reasoning is further achieved in the system of this invention in several ways, such as by specifying times or time intervals, using quantitative time constraints such as the expressions: during the last 30 seconds, as of 5 minutes ago, or between 3 hours ago and 4 hours ago. Fuzzy time intervals and time constraints may be specified if so desired to handle the uncertainty encountered in biochemical systems. The simulation can be synchronous or asynchronous, by setting different simulation time intervals for sets of variables of bioProcesses and bioReservoirs that represent different parts of the complex model.

The simulation can be continuous or time-constrained, and either way may be differentially applied to different parts of the complex model. To accomplish that, the simulation formulas can be complemented with rules that monitor those simulated variables to either set other values, particularly those that are further integrated into an state variable, or by controlling parts of the model. For example, a bioProcess or a bioReservoir can be programmed to be active only for certain time intervals during a simulation run, by means of rules or procedures that control the activation and deactivation of its subworkspace. Those time intervals may be either directly specified or dependent on the values of other parameters or variables or any of their combinations. Rules may be defined to monitor the simulated values of specific variables, such as the Quantity of a given bioPool or the Velocity of a given bioEngine, to be compared with a specified threshold, that when reached causes that rule to trigger some actions, such as setting the values of other parameters or variables, or activating and deactivating the subworkspace of one or more bioProcesses or bioReservoirs, or starting one or more procedures. Such rules may be: a) if-type rules with their Scan-interval attributes set to a specified time interval that preferably matches the time-interval used for the simulated variables, which means that such rules are invoked once every such interval; or b) whenever-type rules that are invoked whenever the specified variable receives a value and which trigger specified actions when such value fulfills any specified constraints; or c) initially-type rules, that may for example be hidden in the subworkspace of a bioEngine or bioPool, and which will be invoked once every time the subworkspace of their superior bioProcess or bioReservoir is activated, and which may trigger any of the actions described above which may apply to any bioProcess or bioReservoir in the complex model.

One of the several applications of this invention is that of a system for signal processing and signal integration. In such system, simulations can have three levels of control through: a) the interactions explicitly modeled in the architecture of the graphic design of this invention, namely the network of connected bioReservoirs and bioProcesses, which represent and determines the specific interactions of the different components of the complex model; b) the propagation through such network of the dynamic changes in the values of the variables of such components; c) through the signals transmitted by the smoothed thresholding implicit in the design of the Contribution variables of the bioReactants that determine the output values of the Velocity of the bioEngines, and d) through the rates of consumption of the bioReactants and the rates of production of the bioProducts, that determine new changes in the values of the Concentrations, now amplified to a larger number of bioPools, which initiate new waves of value propagations.

The simulation starts after a perturbation, such as a Concentration-Entry, Density-Entry or Scaled-Entry, has been introduced and integrated in the overall system's equation: $d[E](t)/dt=[E](t)+entry+\Sigma \ inputs(t)-m*[E](t)-\Sigma \ outputs(t)$. In this system, the bioReservoirs and bioProcesses placed in a biological compartment-layer are activated successively in time and space, as the activation signal is propagating forwards based on various chaining relationships between those structures established during the initialization process according to the downstream or upstream positions of each of those structures respect to the others.

When starting the knowledge-base, the G2-s finds the initial values for all variables that receive values from simulation formulas, and then executes the main simulation procedure. For each simulation cycle, the G2-simulator evaluates in order: 1) simulated state variables and parameters, 2) dependent variables and parameters, and 3) the main simulation procedure. The G2-simulator only evaluates one, the most specific simulation formula for each variable.

BioReservoirs which variables have scaled values can be mixed in a simulation with BioReservoirs which variables have quantitative values, since both types of outputs are integrated at the bioProcess level only after being transformed to a scaled value. However, the output values of the variables of BioReservoirs and of the thresholding parameters, such as Km, Kd, Ki or kp, have to be of the same type, either quantitative or scaled. The choice of scaled values between 0.0 and 100.0 for basal-Concentration, based on the knowledge of the domain expert, can also be entered manually within the table of attributes of the bioReservoir.

Tabular functions of one argument allow to deal with situations when the algebraic relationship between two bioVariables is not known but experimental data is available, which allows to build a table that relates a set of values that represents the magnitude of a cause with the set of values that represents the magnitude of the corresponding mechanistic effects or cellular responses, and straight-line interpolation is optional. These are important tools to biologist who frequently measure complex cellular responses to external factors.

5. Alternative Implementations and Variations

An equivalent system can be build with a less graphic interface by substituting each of the components represented in the current implementation as iconic bioObjects upon of the subworkspace of bioReservoirs and bioProcesses, and representing them instead as attributes of the bioReservoirs and bioProcesses, respectively. The corresponding methods would need only minor modifications, such as for example, by substituting the current expression "the bioPool upon the subworkspace of bioReservoir X" with "the bioPool that is an attribute of bioReservoir X"; or substituting the current expression "the bioReactant-1 connected at port-1 of the bioEngine upon the subworkspace of bioProcess X" with "bioReactant-1 of bioReservoir X", where each of the specific bioReactants connected to each of the specific stubs of a specific type of bioEngine are now converted into specific attributes of the specific type of bioProcess, and where those attributes are not values but objects, and where those objects may have as attributes other objects. For example, the bioPosts now connected with each bioReactant and bioProduct can also be implemented as and attribute of such bioReactant or bioProduct, while the two sets of bioPosts connected to a bioPool can now become two sets of attributes objects of the bioReservoir, such as Input-1 or Output-3. By defining a specific attribute, such as Post for these new classes of objects, the specific distant connections can now be established by giving the same unique value to the Post attributes of one of the bioReactant attributes of a bioProcess and one of the Output attributes of a bioReservoir, or by giving the same unique value to the Post attributes of one of the bioProduct attributes of a bioProcess and one of the Input attributes of a bioReservoir. The result of this alternative implementation is that the different levels of encapsulation currently provided through the workspace hierarchy would then be provided by an attribute hierarchy, and the current representation of those components by their icons would be then limited to their representation by their tables of attributes, which are also part of the current implementation. Many of the tasks associated with the menus of the icons of those components or other auxiliary icons can be associated in the alternative implementation as menu options of the superior bioReservoirs and bioProcesses, as many of those are already currently implemented. The advantage of using the approach described in the currently preferred embodiment of this invention is that the more graphic interface is more intuitive for the user, and easier to use. The disadvantage is the additional memory required to store the additional graphical structures.

Another alternative is to replace the complex knowledge-structures bioReservoir and bioProcess by the components encapsulated in their respective subworkspaces, after some modifications. One of the several possible alternatives is to bypass the bioReservoir and the bioProcess structures altogether, and to encode the pertinent information here defined within the bioReservoir's table of attributes in the bioPool's table of attributes, and to encode the pertinent information here defined within the bioProcess's table of attributes in the bioEngine's table of attributes, and to construct the iconic components now contained in the subworkspaces of the bioReservoirs and bioProcesses directly on the desired workspace. The advantage of using the approach described in the currently preferred embodiment of this invention is that the bioReservoir and bioProcess structures encapsulate the details and simplifies the schematics, and makes easy the cloning and transfer of the pre-constructed structures from one location to another, making the task of developing new models or modifying existing time much faster and keeping complex schematics simpler. The disadvantage is the additional memory required to store the additional graphical structures.

An alternative more compact implementation that would still allow developing multidimensional pathways, bypassing the need for bioReservoirs, is to directly connect all the bioReactant-post and bioproduct-post that in the current implementation are connected to the same bioPool, by giving them all the same name. In such implementation, the Ref-bioentity attribute, as currently defined for the class bioReservoir could instead be defined for the classes bioReactant and bioProduct, allowing in that way access to the bioEntity corresponding to an instance of bioReactant or bioProduct that would provide the physical description of such bioReactant or bioProduct, allowing integrating the description of structure with function. In another related implementation, the variables and parameters, inputs and outputs, as well as other attributes, as currently implemented as attributes of the bioReservoir or its bioPool, or as separate icons within the bioReservoir, could be implemented as attributes of the currently corresponding bioEngine.

Other of the many alternatives includes storing the bioReservoir or equivalent structure within the subworkspace of the bioEntity; or storing the bioEntity within the subworkspace of the bioReservoir. However, in the current implementation, the bioEntities are stored independently of the bioReservoirs because in many cases, and particularly dealing with very large applications, it may not be necessary to store one bioEntity for each bioReservoir, and instead prototypic bioEntities can be used that are shared by many bioReservoirs. In such cases, another alternative is storing all the bioReservoirs that in the current implementation would refer to the same bioEntity in the subworkspace of such bioEntity.

The concepts and methods subject of this invention can be applied with each of the object-oriented expert system shells from various vendors, after those capabilities not provided by that particular shell are additionally encoded. An equivalent of those capabilities of the selected shell that are required to apply the concepts and methods of this invention may also be custom built from scratch or by combining a set of off-the-shelf components.

There are many sophisticated capabilities that can be further developed with this system, which a knowledgeable expert can derive from the teachings of this invention. Here, only a few important ones of which will be described in detail:

As an alternative, the methods here represented could in part be compiled using this Shell or other shells of the compiled type, including but not limited to RTworks and Activation Framework. The compilation may improve performance at runtime by eliminating graphical interpretation of the iconic components. However, compilation does not facilitate frequent modifications of the design and information encapsulated in the iconic components, a feature that is of great importance when modeling biochemical systems, the knowledge of which is being continually updated and improved.

The same concepts described in this invention can be slightly modified by a person skilled in the art, to incorporate multiple inheritance capabilities, allowing the bioObjects to inherit attributes from two or more superior classes. Additional controls and code may be required in that case to resolve conflicts that may appear when more than one superior class have the same attributes but receiving values from different sources, or through different methods.

Many of the symbolic variables or parameters could be also represented as logical variables or parameters, with or without fuzzy-beliefs, by simply changing the language of the attribute name and its values. For instance, an attribute called status could have values: available, unknown and unavailable; or it could alternatively be called is-available and have values true, unknown or false, the unknown associated with fuzzy-beliefs, such as the range 0.2–0.8.

To further control the behavior of any component of a simulation, different types of filters could be applied to, for example, the Density (or Concentration) of bioPools or to the Velocity of bioEngines. These filters can be of any of the types of filters used in signal processing control systems, such as low-pass or ideal high-pass filters (such as $H(jw)=e^{-jwto}$ for $|w|>w_c$, else $H(jw)=0$), or Gaussian filters ($H(w)=e^{-a(w)^2}*e^{-jwto}$ and others). Such filters could be executed in either formulas or procedures, that could be generic for a whole class of variables, or more specific for certain instances or group of instances. The specific filters are more useful if fine control is required.

The Density (or Concentration) of a bioPool is the result of multiple interactions and is represented as a differential equation in the present embodiment. Alternatively, it could be represented as a discrete-time linear system or a continuous-time linear system of equations, or whenever the Shell is able to handle vectors, as their equivalent matrix system. Difference or differential equations can be converted to state form, and the state variables of the system are them described as a state vector, the coefficients of the variables are described as a system matrix and the forcing terms are described as the forcing vector, following standard procedures.

What is claimed is:

1. A computer readable medium or media comprising a virtual model of a complex system implementable in a computer system, comprising a plurality of model elements and program instructions, wherein: i) the model elements include first elements representing pools of any number of entities of a given type, state and/or compartment, and a plurality of second elements representing processes of different types in which the pools of entities participate; ii) there are a plurality of input, regulator and output references or links between a plurality of said first and second elements; and iii) the program instructions comprise functions to integrate in the computer system said first and second elements according to said references or links, resulting in a network of one or more pathways, at least one of said first or second elements acting as junctions where different pathways merge or different pathways branch, or both, the network representing the topology of the interactions detected between the components of the complex system.

2. The computer readable medium or media of claim 1, the program instructions further comprising functions to generate visual representations of said network of pathways on the display means of said computer system.

3. The computer readable medium or media of claim 1, wherein said program instructions further comprise functions to generate on-the-fly visual representations of subsets of networks of pathways which meet user-defined criteria, including the selection of at least one of said first or second elements as starting nodes or a direction upstream or downstream from said starting nodes, or any combination thereof.

4. The computer readable medium or media of claim 1, wherein said program instructions further comprise functions to display visual representations of said elements on the display means of said computer system, and navigation functions associated with said visual representations, enabling interactive navigation between related elements.

5. The computer readable medium or media of claim 1, wherein at least one of said regulator references or links represents an activator, inhibitor, catalyst, ligand, agonist, antagonist, repressor, or promoter.

6. The computer readable medium or media of claim 1, wherein a plurality of said elements are classified according to a semantically meaningful hierarchy.

7. The computer readable medium or media of claim 1, further comprising an inference engine capable of data type reasoning over instances of said elements or over the values of properties or attributes of said instances.

8. The computer readable medium or media of claim 1 wherein said program instructions comprise chaining functions to establish downstream or upstream relationships between chains of first or second elements, or any combination thereof, identified based on the sequential order of said first and second elements as defined by said references or links.

9. The computer readable medium or media of claim 1 wherein said program instructions further comprise query functions in reference to one or more of said first or second elements, or any combination thereof, including criteria based on the upstream or downstream position within said network, or both, of any first or second element in relation to said one or more reference elements.

10. The computer readable medium or media of claim 1, wherein said program instructions further comprise query functions to identify a downstream set of any number of said first or second elements, or any combination thereof, of said virtual model which represents a set of pools of entities or processes, or any combination thereof, of said complex system which are putatively affected by manipulating at least one other of said entities or processes represented by a reference query set of at least one of said first or second elements.

11. The computer readable medium or media of claim 1, wherein said program instructions further comprise query functions to identify an upstream set of any number of said first or second elements, or any combination thereof, of said virtual model which represents a set of pools of entities or processes of said complex system which are putative targets for manipulation to achieve any desired outcome, including affecting entities or processes represented by a reference query set of at least one of said first or second elements.

12. The computer readable medium or media of claim 1, the model elements further comprising a plurality of entity elements, each comprising descriptions of the common structure, composition or state, or any combination thereof, of the entities represented by one or more of said pools of entities.

13. The computer readable medium or media of claim 12, wherein said program instructions comprise query functions including criteria based on the structure, composition or state described in the entity elements.

14. The computer readable medium or media of claim 1, the model elements further comprising a plurality of organizing elements representing compartments, including space, time-interval, or function compartments, or any combination thereof, organized in one or more levels of a hierarchy, each level representing a respective level of complexity, wherein said first and second elements have relationships with their corresponding organizing elements in the hierarchy.

15. The computer readable medium or media of claim 14 wherein said program instructions further comprise query functions in reference to one or more of said first and second elements selected as reference elements, including criteria based on the upstream or downstream position within said network of any first or second element, the types of its references or links, its relationship with any organizing element, or any combination thereof.

16. The computer readable medium or media of claim 14, wherein said complex system is a biological system, and said organizing elements comprise elements to represent compartments of biological organization.

17. The computer readable medium or media of claim 16, wherein the biological organization represented by said organizing elements comprise organization at the molecular assembly, reaction cascade, subcellular, cellular or multicellular levels, or any combination thereof, in one or more levels of a hierarchy.

18. The computer readable medium or media of claim 16, wherein said organizing elements comprise one or more elements to represent different stages during cell activation, cell cycle, apoptosis, differentiation, disease or life cycle, or any combination thereof, organized in one or more levels of a hierarchy.

19. The computer readable medium or media of claim 1, wherein said virtual model represents a biological cellular system applicable to model the transduction of signals provided by ligands in their external environment to the interior of the cell, resulting in the execution of specific functions.

20. A method for predicting pathways affected by a perturbation comprising applying the virtual model and program instructions of the computer readable medium or media of claim to identifying the signal cascades which occur through the pathways when stimuli are introduced to the complex system and dynamically generating results during execution of said model in a computer system.

21. The computer readable medium or media of claim 1, wherein at least one of said elements implements a lumped parameter system, black-box system, encapsulation or aggregation.

22. The computer readable medium or media of claim 1 wherein a plurality of said second elements comprise stoichiometric coefficients relating said inputs and outputs.

23. The computer readable medium or media of claim 1 wherein: a) a plurality of said second elements comprise rate variables representing quantitative or semi-quantitative rates of conversion of inputs into outputs; and b) said program instructions comprise simulation functions to infer or compute, or any combination thereof, the value of said rate variables when simulating the behavior of said complex system.

24. The computer readable medium or media of claim 23 wherein: a) said rate variables are of a plurality of different types, representing different types of processes; and b) said simulation functions comprise a plurality of different types of functions to infer or compute, or any combination thereof, the value of the corresponding different types of rate variables.

25. The computer readable medium or media of claim 1, wherein said complex system is a biological system and a plurality of the entities represented are of at least one of the following types: cell, gene, mRNA, protein or any assembly, complex or combination thereof.

26. The computer readable medium or media of claim 25, wherein a plurality of said elements further comprise links to a plurality of databases, the model providing a mechanism for integration of data in said databases.

27. The computer readable medium or media of claim 25, wherein said program instructions further comprise query functions in reference to a set of one or more of said first or second elements, or any combination thereof, selected as reference, including criteria based on the upstream or downstream position within said network, or both, of any first or second element, or the types of its references or links, or any combination thereof, the result set representing any number of pools of entities or processes which are putative targets for or affected by manipulation of said biological system.

28. The computer readable medium or media of claim 27, wherein said query functions identify an upstream set of any number of said first or second elements, or any combination thereof, representing pools of entities or processes of said biological system which are putative targets for manipulation to achieve any desired outcome, including affecting the expression of any gene(s) or receptor(s), or the secretion of any substance(s), or any combination thereof, wherein the one or more pools of entities or processes which are biomarkers for the outcome are represented by the reference query set.

29. A method for identifying desirable targets for screening agents or combination of agents to be further tested for the prevention or treatment of adverse conditions on a human or any other living organism, or any part thereof, comprising applying the virtual model and program instructions of the computer readable medium or media of claim 28 in a computer system to identify pools of entities or processes, represented by said upstream set, which are putative targets for manipulation in said human or other living organism, or any part thereof, to achieve any desired outcome known to affect the prevention or treatment of said adverse conditions, wherein said reference query set represents the one or more pools of entities or processes which are biomarkers for the desired outcome.

30. A method for designing strategies for controlling the expansion or further differentiation of progenitor or other precursor living cells in a cell culture or reactor to produce outcome cells of one or more types having characteristic phenotypes, comprising: i) applying the virtual model and program instructions of the computer readable medium or media of claim 28 in a computer system to identify the upstream set of pools of entities or processes which are putative targets for putative inducing agents, the reference query set representing the pools of entities or processes which are biomarkers for the one or more phenotypes of the desired outcome cells; and ii) applying the one or more of said identified targets for designing a strategy for controlling the expansion or further differentiation of said precursor cells in said cell culture medium.

31. A computerized storage and retrieval system of biological information comprising the virtual model and instructions of the computer readable medium or media of claim 27.

32. A method for identifying or characterizing candidates for agent development, including drugs or any other preventive, diagnostic, prognostic or therapeutic agents or procedures, or any combination thereof, comprising applying the virtual model and program instructions of the computer readable medium or media of claim 27 in a computer system to determine the pools of entities or processes in said biological system which are putatively affected by applying said at least one candidate agent or involved in attaining a desired outcome, wherein the model of the applicable biological system includes at least one first or second element representing at least one agent or its interaction with the biological system or a biomarker for the desired outcome in said biological system.

33. The method of claim 32, wherein the virtual model and program instructions are applied to identifying any number of first or second elements which are downstream of the at least one first or second element representing in said virtual model at least one agent or its interaction with the biological system, and thereby identifying pools of entities or processes in said biological system which are putatively effected by said at least one agent acting upon said biological system.

34. The method of claim 32, wherein the virtual model and program instructions are applied to: i) selecting a set of two or more of said first or second elements representing two or more agents or their interactions with their targets, ii) identifying a shared set of any number of first or second elements which are shared by the pathways downstream from the first or second elements of the selected set, and iii) identifying any outcome which would be affected by changes in the pools of entities or processes represented by the shared set as a result from manipulating the pools of entities or processes represented by the selected set, and thereby identifying or characterizing putative combined therapy regimes or harmful side effects of the combination of two or more selected agents.

35. The method of claim 32, wherein the virtual model and program instructions are applied to identifying any number of first and second elements in said virtual model which are upstream of the at least one first or second element representing in said virtual model at least one pool of entities or process which are biomarkers for a desired outcome, and thereby identifying upstream candidate target entities or processes which when targeted by an agent would influence said desired outcome in said biological system.

36. The method of claim 32, wherein the virtual model and program instructions are applied to identifying common first or second elements in said virtual model which are upstream of a plurality of first or second elements representing pools of entities or processes which are biomarkers for at least one desired outcome, and thereby identifying upstream candidate target entities or processes which when targeted by an agent would simultaneously influence the plurality of biomarkers for the at least one desired outcome.

37. A method for identifying putative effects of an agent or combination of agents on a human or other living organism, or any part thereof, the agents including environmental agents, drugs or any combination thereof, comprising applying the virtual model and program instructions of the computer readable medium or media of claim 27 in a computer system to identify downstream pools of entities or processes which could be affected by exposing said human or other living organism, or any part thereof, to said agent or combination of agents, wherein the reference set of one or more first or second elements represents the agent or combination of agents to be tested and the interactions of the agents with their targets in said human or other living organism, or any part thereof.

38. The computer readable medium or media of claim 25, wherein: a) a plurality of said first elements comprise first variables, representing the quantities or concentrations of the entities of said pools; and b) said program instructions comprise simulation functions to infer or compute, or any combination thereof, the values of said first variables when simulating the quantitative behavior of said complex system.

39. The computer readable medium or media of claim 38, wherein: a) a plurality of said second elements comprise second variables representing the rates of conversion of inputs into outputs represented by said input and output references or links; and b) said program instructions comprise simulation functions to infer or compute, or any combination thereof, the values of said second variables when simulating the quantitative behavior of said complex system.

40. The computer readable medium or media of claim 39, the virtual model further comprising a plurality of organizing elements representing compartments, including space, time-interval, or function compartments, organized in one or more levels of a hierarchy, each level representing a respective level of complexity, wherein said first and second elements have relationships with their corresponding organizing elements in the hierarchy.

41. The computer readable medium or media of claim 40, wherein said organizing elements comprise one or more elements to represent compartments of biological organization at the molecular assembly, reaction cascade, subcellular, cellular or multi-cellular levels, or any combination thereof, in one or more levels of a hierarchy.

42. The computer readable medium or media of claim 40, wherein said organizing elements comprise a plurality of elements representing different stages of the cell, including phases of the cell cycle, apoptosis, differentiation, disease or life cycle, or any combination thereof, in one or more levels of a hierarchy.

43. A method for simulating physiological or pathological states of a cell by using the computer readable medium or media of claim 40 in a computer system, comprising:
   a) implementing a virtual model of the cell comprising one or more first or second elements representing biomarkers for one or more phenotypes of one or more states of the cell, wherein one or more of said elements have a relationship with one or more of said organizing elements;
   b) setting the values of one or more sets of parameters or initial conditions of said virtual model; and
   c) executing the simulation functions over the variables of said virtual model to simulate a state or a succession of states of the cell.

44. The computer readable medium or media of claim 39 applicable to testing different model scenarios, wherein said program instructions comprise functions to assign to at least one selected variable or parameter of said virtual model a plurality of initial values representative of different model scenarios.

45. The computer readable medium or media of claim 39, wherein said program instructions comprise query functions for finding an upstream set of any number of said elements representing entities or processes of said biological system which are putative targets for manipulation to achieve any desired outcome, including affecting the expression of any gene(s) or receptor(s), or the secretion of any substance(s), the pools of entities or processes which are biomarkers for the outcome represented by a reference query set of any number of said elements.

46. The computer readable medium or media of claim 39, wherein said program instructions comprise query functions for finding a downstream set of any number of said elements representing entities or processes of said complex system which are putatively affected by the manipulation of entities or processes represented by a reference query set of any number of said elements.

47. A method for predicting putative beneficial or toxic effects of an agent or combination of agents on a human or other living organism, or any part thereof, the agents including drugs or any other preventive, diagnostic, prognostic or therapeutic agents or procedures, by applying the virtual model and program instructions of the computer readable medium or media of claim 39 in a computer system, comprising:
   a) implementing a virtual model representing said human or other living organism, or any part thereof, which comprises one or more sets of first and second elements representing the agent or combination of agents to be tested and the interactions of the agents with their targets in said human or other living organism, or any part thereof;
   b) executing said virtual model under various sets of conditions to simulate the effects of manipulating the agent or combination of agents on the quantitative behavior of said human or other living organism, or any part thereof; and
   c) identifying a set of any number of said first or second elements of said virtual model which represent pools of entities or processes of said human or other living organism, or any part thereof, which are putatively affected by exposing said human or other living organism, or any part thereof, to said agent or combination of agents, thereby identifying the beneficial or toxic effects of the agent or combination of agents.

48. A method for predicting putative targets for manipulation for the prevention or treatment of adverse conditions on a human or any other living organism, or any part thereof, by applying the virtual model and program instructions of the computer readable medium or media of claim 39 in a computer system to, comprising:
   a) implementing in said computer system a virtual model of said human or other living organism, or any part thereof;
   b) identifying, in reference to a query set, an upstream set of any number of said first or second elements of said virtual model representing pools of entities or processes which are putative targets for manipulation to achieve any desired outcome in said human or other living organism, or any part thereof, known to affect the prevention or treatment of said adverse conditions, including affecting the expression of any gene(s) or receptor(s), or the secretion of any substance(s), wherein the reference query set of one or more of said first or second elements represents pools of entities or processes which are biomarkers for the desired outcome; and
   c) executing said virtual model under various sets of conditions to simulate the effects of manipulating the putative targets on achieving the desired outcome, and thereby characterizing the putative targets.

49. A method for identifying one or more components of a cell as putative targets for interaction with one or more agents, the agents including drugs or any other preventive, diagnostic, prognostic or therapeutic agent or procedure, by applying the virtual model and program instructions of the computer readable medium or media of claim 39 in a computer system, comprising:
a) implementing a virtual model of the cell comprising first and second elements representing components characteristic of a phenotype of the cell;
b) executing the simulation functions over the variables of said elements to simulate a first state of the cell;
c) perturbing the virtual model by deleting one or more elements thereof, changing the amount or concentration of one or more first elements thereof or modifying one or more simulation functions or the relationships between one or more elements thereof, or any combination thereof;
d) executing the simulation functions over the variables of said elements after said perturbation of the virtual model to simulate a second state of the cell; and
e) comparing said first and second simulated states of the virtual model to identify the effect of said perturbation on the state of the virtual model, and thereby identifying one or more components of said cell as desirable putative targets for interaction with one or more agents.

50. The computer readable medium or media of claim 1 further enabling quantitative, semi-quantitative or mixed type simulations of said virtual models in said computer system, wherein:
a) mathematical models characterizing the quantitative behavior of said complex system comprise a number of quantitative or semi-quantitative variables or parameters, or any combination thereof, distributed among said first and second elements, said variables or parameters representing characteristics of the components they represent; and
b) said program instructions further comprise inference or simulation functions, or any combination thereof, for computing the values of said variables during the execution of the model.

51. The computer readable medium or media of claim 50 applicable to testing different model scenarios, wherein said inference or simulation functions comprise functions for assigning to at least one of said variables or parameters of said model a plurality of initial values representative of different model scenarios.

52. The computer readable medium or media of claim 50 wherein said program instructions comprise functions to identify common upstream pools of entities or processes, or any combination thereof, which putatively exert influences on a plurality of selected pools of entities or processes, or any combination thereof, based on the sequential ordering of the first and second elements as defined by said references or links.

53. The computer readable medium or media of claim 50 wherein said program instructions comprise functions to identify downstream pools of entities or processes, or any combination thereof, influenced by one or more selected pools of entities or processes, or any combination thereof, based on the sequential ordering of the first and second elements as defined by said references or links.

54. The computer readable medium or media of claim 50 applicable in a computer system comprising monitoring capabilities for monitoring the operation of said complex system in conjunction with the virtual model, comprising means for mapping one or more monitored variables of any component of said complex system to the corresponding of said variables which represent them in said virtual model.

55. The computer readable medium or media of claim 50 applicable in a computer system further comprising controlling means to developing strategies or generating instructions for controlling the operation of said complex system based on the simulation of said virtual model by modifying any component of said complex-system represented by any of said variables of said elements of the model.

56. The computer readable medium or media of claim 50, wherein said complex system is a biological system and a plurality of the entities represented are of at least one of the following types: cell, gene, mRNA, protein or any assembly, complex or combination thereof.

57. A method for predicting a function of a component of a complex biological system, intrinsic or added to the system, comprising applying the virtual model and program instructions of the computer readable medium or media of claim 56 in a computer system to simulate perturbations of said component in said virtual model for testing the function of said component in said biological system, wherein the virtual model of the applicable biological system comprises at least one first or second elements representing the component or its interactions with one or more components of said biological system.

58. A method for identifying or characterizing candidates for agent development, including drugs or any other preventive, diagnostic, prognostic or therapeutic agents or procedures, or any combination thereof, comprising applying the virtual model and program instructions of the computer readable medium or media of claim 56 in a computer system to identify the pools of entities or processes which are putatively affected by applying at least one candidate agent or involved in attaining a desired outcome in said biological system, wherein the model of the applicable biological system includes at least one first or second element representing the at said least one agent or its interaction with the biological system or at said least one biomarker for the desired outcome in said biological system.

59. The method of claim 58 wherein the virtual model and program instructions are applied to simulating the effects of manipulating at least one first or second element in said virtual model, representing said at least one agent or its one or more interactions with its one or more targets on said biological system, on any number of downstream first or second elements, which represent the pools of entities or processes putatively affected by said at least one agent, and thereby predicting putative beneficial or harmful effects of said at least one agent.

60. The method of claim 58 wherein the virtual model and program instructions are applied to simulating the effects of manipulating any combination of two or more first or second elements in said virtual model, representing a plurality of agents or their interactions with their targets, on a downstream set of any number of first or second elements which are shared by the downstream pathways from said plurality of first or second elements, the downstream set representing the entities or processes of said complex system affected by said combination, and thereby predicting putative effects of combined therapy regimes or harmful side effects for said combination of agents.

61. A method for identifying or characterizing appropriate applications for an agent, including drugs or any other preventive, diagnostic, prognostic or therapeutic agents or procedures, or any combination thereof, comprising applying the virtual model and program instructions of the computer readable medium or media of claim 56 in a computer system to simulate and evaluate the effects of the agent on the biological system of interest at the subcellular, cellular, or multi-cellular level, or any combination thereof.

62. A method for identifying one or more components of a cell as putative targets for interaction with one or more agents, the agents including drugs or any other preventive, diagnostic, prognostic or therapeutic agent or procedure, by applying the virtual model and program instructions of the computer readable medium or media of claim 56 in a computer system, comprising:
 a) implementing a virtual model of the cell comprising first and second elements representing components characteristic of a phenotype of the cell;
 b) setting the parameters or initial conditions of said virtual model to correlate said phenotype to the state of the cell;
 c) perturbing the virtual model by deleting one or more elements thereof, changing the parameters or initial conditions of one or more elements thereof or modifying one or more simulation functions or the relationships between one or more elements thereof; and
 d) executing the simulation functions over the perturbed virtual model to determine whether said perturbation causes a desired transition of said cell from one phenotype to another, and thereby identifying one or more components of said cell as desirable putative targets for interaction with one or more agents.

63. A method for identifying one or more components of a cell as putative targets for interaction with one or more agents, the agents including drugs or any other preventive, diagnostic, prognostic or therapeutic agent or procedure, by applying the virtual model and program instructions of the computer readable medium or media of claim 56 in a computer system, comprising:
 a) implementing a virtual model of the cell comprising first and second elements representing components believed to be intrinsic to a phenotype of the cell;
 b) generating one or more expanded or perturbed virtual models by inferring new or modified first and second elements and their relationships to any of the elements of the virtual model subsystem using experimental data;
 c) determining parameter values or constraining the virtual models by (i) sampling a set of one or more initial, expanded or perturbed virtual models and parameter values, (ii) simulating said virtual models by executing the simulation functions over the variables of the virtual models, and (iii) determining the initial values of variables and parameters which optimally fit a given set or sets of experimental data; and
 d) comparing a plurality of simulated states of the initial or expanded or perturbed virtual models to identify the effect of said expansion or perturbation on the state of the virtual model, and thereby identifying the pertaining new or modified first or second elements representing the one or more targets for interaction with one or more agents.

64. A method for designing or implementing a strategy for controlling the expansion or further differentiation of progenitor or other precursor living cells in a cell culture or reactor to produce outcome cells of one or more types having characteristic phenotypes, comprising applying the virtual model and program instructions of the computer readable medium or media of claim 56 in a computer system to:
 a) implementing a virtual model of the cellular system which comprises at least one first or second element representing at least one putative inducing agent or its interaction with at least one target in said precursor cell, or at least one pool of entities or process which is to be induced or modified to embody a characteristic phenotype of at least one outcome cell type, or any combination thereof;
 b) executing said virtual model to simulate the putative effects of manipulating said one or more putative inducing agents in achieving said desired phenotypes of said outcome cell types; and
 c) designing or implementing a strategy for controlling the expansion or further differentiation of said precursor cells in said cell culture medium or reactor based on one or more of said manipulations which result in the desired phenotypes.

65. A method for designing or implementing a strategy for controlling the production in a living cellular system of one or more substances for preventive, therapeutic or diagnostic uses by applying the virtual model and program instructions of the computer readable medium or media of claim 56 in a computer system, wherein the living cellular system comprises the producing cells in a cell culture, reactor or a microorganism, plant or animal living environment, comprising:
 a) implementing a virtual model of the living cellular system which includes one or more first or second elements representing one or more pools of substances to be produced or their production processes within said producing cells;
 b) executing said virtual model and any number of perturbations of said virtual model to simulate the putative effectiveness of said living cellular system and any number of manipulations of said living cellular system in achieving the desired production of said substances by said living cellular system; and
 c) designing or implementing a strategy for controlling the production of said substances in said living cellular system based on the simulation of said virtual model or any number of said perturbations which result in the desired level of production of said one or more substances.

66. The computer readable medium or media of claim 1 wherein a plurality of said first elements comprise at least one input or output reference or link to second elements or their components, representing respectively an input to the represented pool of entities from the represented process or a contribution by the represented pool of entities to the represented process.

67. The computer readable medium or media of claim 66 wherein said first elements comprise state variables and said program instructions comprise simulation functions to infer or compute, or any combination thereof, the value of any of said state variables over said inputs or outputs, or both.

68. The computer readable medium or media of claim 67 wherein said second elements comprise rate variables representing the rate of conversion of said inputs into said outputs and said program instructions comprise simulation functions to infer or compute, or any combination thereof, the value of any of said rate variables.

69. A computer system for implementing the virtual model and instructions of the computer readable medium or media of claim 1.

70. A method for implementing a virtual model of a complex system in a computer system comprising defining or selecting, or any combination thereof:
 a) a plurality of first and second variables, the first variables representing quantitatively, semi-quantitatively, or any combination thereof, pools of any number of entities of a given type, state and/or compartment, and the different types of second variables representing quantitatively, semi-quantitative, or any combination thereof; the rates of different types of processes of said complex system where said entities participate;

b) a plurality of input, regulator and output relationships between a plurality of said first and second variables;

c) functions to integrate said variables and their relationships, resulting in a network of one or more pathways, a plurality of said variables acting as junctions where different pathways merge or different pathways branch, or both; and d) functions to compute the values of said variables, to simulate the behavior of said complex system during execution of said model.

71. The method of claim 70 further comprising defining or selecting, or any combination thereof, links between a plurality of said elements and a plurality of databases, thereby integrating data in said databases.

72. The method of claim 70 further comprising defining or selecting, or any combination thereof, functions associated with any of said variables enabling the successive interactive navigation between related variables.

73. The method of claim 70 further comprising defining or selecting, or any combination thereof, functions to generate visual representations of said network of pathways on the display means of said computer system.

74. The method of claim 70 further comprising defining or selecting, or any combination thereof, functions to generate on-the-fly visual representations of subsets of the networks of pathways which meet user-defined criteria, including selection of one or more of said variables as starting nodes or a direction upstream or downstream from said starting nodes, or any combination thereof.

75. The method of claim 70 further comprising defining or selecting, or any combination thereof, query functions in reference to one or more of said variables, including criteria based on the upstream or downstream position within said network of any first or second variable in relation to said reference one or more variables, or any combination thereof.

76. The method of claim 70 applied to test different model scenarios, further comprising assigning to at least one selected variable or parameter of said virtual model a plurality of initial values representative of different model scenarios.

77. The method of claim 70 wherein said computer system comprises monitoring capabilities applicable in conjunction with the virtual model, further comprising defining or selecting, or any combination thereof, program functions for i) mapping the one or more monitored variables of components of said complex system to their corresponding variables in said model, ii) comparing said monitored values to the simulated values of their corresponding variables; and iii) inferring or computing, or any combination thereof, any adjustments derived from said comparisons.

78. A computer readable medium or media comprising instructions for implementing in a computer system the method of claim 77.

79. The method of claim 70, wherein said computer system comprises controlling capabilities applicable in conjunction with the virtual model, further comprising defining or selecting, or any combination thereof, program functions to control the operation of said complex system by modifying any of its components based on the simulation of said model.

80. A computer readable medium or media comprising instructions for implementing in a computer system the method of claim 79.

81. The method of claim 70 further comprising defining or selecting, or any combination thereof, a plurality of organizing elements representing compartments, including space, time-interval, or function compartments, or any combination thereof, organized in one or more levels of a hierarchy, each level representing a respective level of complexity; and relationships between a plurality of said variables and their corresponding organizing elements in the hierarchy.

82. The method of claim 81 further comprising defining or selecting, or any combination thereof, query functions in reference to one or more of said variables, including criteria based on the upstream or downstream position within said network of any first or second variable in relation to said reference one or more variables or the relationships between said variable and any of said organizing elements, or any combination thereof.

83. The method of claim 70 wherein said regulator relationships comprise relationships of at least of the following types: activator, inhibitor, catalyst, ligand, agonist, antagonist, repressor or promoter.

84. The method of claim 70, wherein said complex system is a biological system and the model is applied to identifying putative targets for manipulation to achieve any desired outcome, including affecting the expression of any gene or receptor, or the secretion of any substance, or any combination thereof, in various types of applications, including treatment of disease, improvement of livestock or food crops, or improvement of the environment, further comprising defining or selecting, or any combination thereof, functions to identify a target set of first or second variables, or any combination thereof, representing the putative target pools of entities or processes, which are upstream of a reference query set of one or more first or second variables, or any combination thereof, representing the pools of entities or processes which are biomarkers for said outcome.

85. A computer readable medium or media comprising instructions for implementing in a computer system the method of claim 84.

86. The method of claim 70, wherein said complex system is a biological system and the model is applied to identifying the putative effects of manipulation strategies for said biological system in various types of applications, including treatment of disease, improvement of livestock or food crops, or improvement of the environment, further comprising defining or selecting, or any combination thereof, functions to identify a downstream set of first or second variables, or any combination thereof, representing the pools of entities or processes of said biological system which are putatively affected by manipulating the entities or processes represented by a reference query set of one or more of said first or second variables, or any combination thereof.

87. A computer readable medium or media comprising instructions for implementing in a computer system the method of claim 86.

88. A computer readable medium or media comprising instructions for implementing in a computer system the method of claim 70.

89. A method for implementing models of biological complex systems in a computer system comprising aggregating a plurality of modules representing components of a complex system, wherein: i) a plurality of the modules comprise one or more terminals allowing the module to exchange signals with other modules; ii) the modules include process modules representing different types of processes; iii) a plurality of the process modules comprise input, regulator and output terminals; iv) the aggregating comprises establishing references or links, or any combination thereof, between the terminals of different modules resulting in a network of one or more crossing pathways which describes the topology of the complex system.

90. The method of claim 89, further comprising defining or selecting links between a plurality of said modules and a plurality of databases, thereby integrating data in said databases.

91. The method of claim 89, further comprising applying libraries of predefined and reusable modules in at least one of the composition or extension of said models, the libraries comprising different types of said modules, their components, or any combination thereof.

92. The method of claim 89, wherein said modules have references to or containment relationships with at least one compartment module in a hierarchy of at least one level representing at least one physical or conceptual compartment of the complex system.

93. The method of claim 89 wherein the modules comprise first modules representing pools of any number of entities of a given type, state and/or compartment and the references or links are references or links between the terminals of said first modules and the terminals of said process modules.

94. The method of claim 93, further comprising applying chaining functions to establish downstream or upstream relationships between chains of first modules and process modules, or any combination thereof, identified based on the sequential order of said first modules and process modules as defined by said references or links.

95. The method of claim 93, further comprising generating visual representations of said model on the display means of said computer system, with nodes representing a plurality of said modules linked according to said references or links resulting in a network of crossing pathways.

96. The method of claim 93 wherein a plurality of the entities represented are of at least one of the following types: cell, gene, mRNA, protein or any assembly, complex or combination thereof.

97. The method of claim 96 applied to the development of agents, the agents including drugs or any other preventive, diagnostic, prognostic or therapeutic agents or procedures, further comprising:
  a) including in the model of the applicable biological system at least one first module or process module representing at least one putative agent or its interaction with at least one target in said biological system, or biomarker for a desired outcome in said biological system; and
  b) applying said model to identify any number of pools of entities or processes affected as a result of applying said at least one putative agent or involved in achieving said desired outcome in said biological system.

98. The method of claim 97, wherein the method is applied to identifying putative beneficial or harmful effects of at least one agent acting upon said biological system, comprising identifying any number of first modules or process modules in said virtual model which are downstream of the at least one first module or process module representing the at least one agent or its interaction with the at least one target in said biological system.

99. The method of claim 97, wherein the method is applied to characterizing putative combined therapy regimes or putative harmful side effects resulting from interactions between the effects of two or more agents, comprising identifying any number of first modules or process modules in said virtual model which are shared by the pathways downstream from the two or more of said first modules or process modules representing said two or more agents or their interactions with their targets in said biological system.

100. The method of claim 97, wherein the method is applied to characterizing candidate target pools of entities or processes applicable in the selection of agents to influence at least one desired outcome in said biological system, comprising identifying any number of first modules or process modules in said virtual model which are upstream of the at least one first module or process module representing at least one pool of entities or process which is a biomarker for said desired outcome, wherein said upstream elements represent pools of entities or processes which are putative targets for manipulation in said biological system to achieve said desired outcome.

101. A computer readable medium or media comprising instructions for implementing in a computer system the method of claim 97.

102. The method of claim 96 applied to designing a strategy for controlling the expansion or further differentiation of progenitor or other precursor living cell in a cell culture or reactor to produce outcome cells of one or more types having characteristic phenotypes, further comprising:
  a) including in the model of the applicable cellular system at least one first module or process module representing at least one pool of entities or process which is a biomarker to be induced or modified to embody a characteristic an outcome cell phenotype;
  b) defining or selecting functions to identify at least one candidate target for putative inducing agents represented by at least one first module or process module in said model which is upstream of the at least one first module or process module representing said phenotype biomarker; and
  c) designing a strategy for controlling the expansion or further differentiation of said precursor cells in said cell culture or reactor based on at least one of said identified candidate targets for putative inducing agents which would induce the desired outcome cell phenotype.

103. A computer readable medium or media comprising instructions for implementing in a computer system the method of claim 102.

104. The method of claim 93 further comprising the step of defining or selecting stoichiometric coefficients for said process modules which relate said inputs and outputs.

105. The method of claim 93 wherein a plurality of said modules comprise quantitative or semi-quantitative variables or parameters, or any combination thereof, and the aggregating comprises applying functions over said variables or parameters to infer or simulate the behavioral model of the complex system.

106. The method of claim 105 applied to the analysis, dynamic simulation, steady state simulation, or optimization of the biological complex models, or any combination thereof.

107. The method of claim 105 wherein at least one of said modules is implemented as lumped parameter system, black-box system, abstraction, encapsulation, aggregation, or any combination thereof.

108. The method of claim 105, wherein the variables of said process modules comprise rate variables representing the rate of conversion of said inputs into said outputs.

109. The method of claim 105 applied to modeling of a set of related biological complex systems or their states, further comprising creating one or more network topologies corresponding to models or submodels representing the biological system or its subsystems; wherein one of said network topologies of said set is a master network topology representing a base biological system or state; and the difference between any of two said biological systems or their states is described through changes in: i) the values of one, or more parameters, ii) the initial values of one or more variables, iii) the topology derived from the references or links, iv) the exclusion or additional inclusion of one or more modules of the master network topology, or v) any combination thereof.

110. The method of claim 109, wherein said network topologies are abstract modules which can be reused as submodels to compose a plurality of more complex models or alternative implementation models.

111. The method of claim 105 further comprising applying said model to designing manipulation strategies or for controlling the operation of said complex system based on the behavior of the simulated model.

112. The method of claim 105 applied to monitoring or controlling the operation of said complex system, further comprising:
- b) mapping one or more monitored or controlled variables of any component of said complex system to the corresponding of said variables which represent them in said model;
- c) executing the model and comparing the values of the said monitored or controlled variables to the corresponding simulated values of the variables which represent them in said model;
- c) inferring or computing any corrective adjustments derived from said comparisons; and
- b) applying any of said corrective adjustments to modify the corresponding simulated or controlled variables.

113. A computer readable medium or media comprising instructions for implementing in a computer system the method of claim 112.

114. The method of claim 105 applied to testing different model scenarios, further comprising assigning to at least one of said variables or parameters of said model a plurality of initial values representative of different model scenarios.

115. The method of claim 105 applied to studying the operation of said biological system or to design manipulation strategies to control said operation for various applications, including those in the areas of disease prevention or treatment, therapeutics, diagnostics, drug production, livestock, food crops, food production or the environment, wherein the model of the biological system is at the subcellular, cellular, or multi-cellular level, or any combination thereof.

116. The method of claim 105 applied to agent development, including drugs or any other preventive, diagnostic, prognostic or therapeutic agents or procedures, or any combination thereof, further comprising identifying the pools of entities or processes which are putatively affected by applying at least one candidate agent or involved in attaining a desired outcome in said biological system, wherein the model of the applicable biological system, at the subcellular, cellular or multi-cellular, or any combination thereof, includes at least one first or second element representing the at least one agent or its interaction with the biological system, or a biomarker for the desired outcome in said biological system.

117. The method of claim 105 applied to predicting in a computer system a behavior of a biochemical system, further comprising comparing two or more models of a biochemical system under different conditions, and identifying correlative changes of the values of one or more of said variables between said two models with said different conditions, wherein said correlative changes predict a behavior of said biochemical system.

118. A computer readable medium or media comprising instructions for implementing in a computer system the method of claim 105.

119. A computer readable medium or media comprising instructions for implementing in a computer system the method of claim 93.

* * * * *